(12) United States Patent
Goodman et al.

(10) Patent No.: US 12,109,243 B2
(45) Date of Patent: *Oct. 8, 2024

(54) BACTERIAL EXTRACELLULAR VESICLES

(71) Applicant: Evelo Biosciences, Inc., Cambridge, MA (US)

(72) Inventors: Brian Goodman, Jamaica Plain, MA (US); Baundauna Bose, Cambridge, MA (US); Christopher J. H. Davitt, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/074,122

(22) Filed: Dec. 2, 2022

(65) Prior Publication Data

US 2023/0210913 A1 Jul. 6, 2023

Related U.S. Application Data

(62) Division of application No. 16/645,019, filed as application No. PCT/US2018/050211 on Sep. 10, 2018, now Pat. No. 11,524,037.

(60) Provisional application No. 62/669,151, filed on May 9, 2018, provisional application No. 62/556,015, filed on Sep. 8, 2017.

(51) Int. Cl.
*A61K 35/74* (2015.01)
*A61P 35/00* (2006.01)

(52) U.S. Cl.
CPC .............. *A61K 35/74* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,674,733 A | 10/1997 | Salyers et al. | |
| 6,812,023 B1 | 11/2004 | Lamparski et al. | |
| 7,384,645 B2 | 6/2008 | Foster et al. | |
| 7,628,995 B2 | 12/2009 | Bos et al. | |
| 8,617,536 B2 | 12/2013 | Murray et al. | |
| 9,028,841 B2 | 5/2015 | Henn et al. | |
| 9,273,359 B2 | 3/2016 | Gho et al. | |
| 9,274,109 B2 | 3/2016 | Kim et al. | |
| 9,394,344 B2 | 7/2016 | DeLisa et al. | |
| 9,446,080 B2 | 9/2016 | McKenzie et al. | |
| 9,901,638 B2 | 2/2018 | Fathi et al. | |
| 11,524,037 B2 | 12/2022 | Goodman et al. | |
| 2003/0040492 A1 | 2/2003 | Haschke et al. | |
| 2005/0100559 A1 | 5/2005 | Myatt et al. | |
| 2006/0166344 A1 | 7/2006 | Pizza et al. | |
| 2006/0228351 A1 | 10/2006 | Masuyama et al. | |
| 2007/0087017 A1 | 4/2007 | Olivieri et al. | |
| 2008/0063665 A1 | 3/2008 | Oster et al. | |
| 2010/0015212 A1 | 1/2010 | Adu-Bobie et al. | |
| 2012/0159658 A1 | 6/2012 | Gho et al. | |
| 2012/0192295 A1 | 7/2012 | Kim et al. | |
| 2012/0213833 A1 | 8/2012 | Murray et al. | |
| 2012/0222142 A1 | 8/2012 | Kim et al. | |
| 2013/0017219 A1 | 1/2013 | Di Cioccio et al. | |
| 2013/0065861 A1 | 3/2013 | Wu et al. | |
| 2013/0195765 A1 | 8/2013 | Gho et al. | |
| 2013/0261078 A1 | 10/2013 | Zomer et al. | |
| 2016/0095941 A1 | 4/2016 | Brahmbhatt et al. | |
| 2016/0143961 A1 | 5/2016 | Berry et al. | |
| 2016/0158291 A1 | 6/2016 | Kreke et al. | |
| 2017/0087195 A1 | 3/2017 | Kim et al. | |
| 2017/0145061 A1 | 5/2017 | Lu et al. | |
| 2017/0216371 A1 | 8/2017 | Copeland | |
| 2020/0254028 A1 | 8/2020 | Goodman et al. | |
| 2023/0405058 A1 | 12/2023 | Goodman et al. | |

FOREIGN PATENT DOCUMENTS

| | | |
|---|---|---|
| DE | 2848965 A1 | 5/1980 |
| EP | 2494865 A2 | 9/2012 |
| ES | 2607955 T3 | 4/2017 |
| JP | 2011/188870 A | 9/2011 |
| JP | 2013/139471 A | 7/2013 |
| JP | 2016/507543 A | 3/2016 |
| KR | 2011/0082481 A | 7/2011 |
| KR | 101421779 B1 | 7/2014 |
| WO | WO-02/09643 A2 | 2/2002 |
| WO | WO-03/051379 A1 | 6/2003 |
| WO | WO-2011/027971 A2 | 3/2011 |
| WO | WO-2011/053653 A2 | 5/2011 |
| WO | WO-2012/002760 A2 | 1/2012 |
| WO | WO-2012/093754 A1 | 7/2012 |
| WO | WO-2012/093755 A1 | 7/2012 |
| WO | WO-2012/122478 A1 | 9/2012 |
| WO | WO-2014/122232 A1 | 8/2014 |
| WO | WO-2014/152484 A1 | 9/2014 |
| WO | WO-2014/196913 A1 | 12/2014 |
| WO | WO-16/137164 A2 | 9/2016 |
| WO | WO-16/144139 A2 | 9/2016 |
| WO | WO-2016/140540 A1 | 9/2016 |

(Continued)

OTHER PUBLICATIONS

Choi, E. B., et al. (2014). Decreased diversity of nasal microbiota and their secreted extracellular vesicles in patients with chronic rhinosinusitis based on a metagenomic analysis. Allergy, 69(4), 517-526.

Chutkan, H., et al. (2013). Quantitative and qualitative preparations of bacterial outer membrane vesicles. Methods in molecular biology (Clifton, N.J.), 966, 259-272.

Durand, G. A., et al. (2017). *Blautia massiliensis* sp. nov., isolated from a fresh human fecal sample and emended description of the genus *Blautia*. Anaerobe, 43, 47-55.

(Continued)

*Primary Examiner* — Brian Gangle

(74) *Attorney, Agent, or Firm* — Foley Hoag LLP; Brendan T. Jones; David E. Shore

(57) ABSTRACT

Provided herein are methods and compositions related to EVs useful as therapeutic agents.

19 Claims, 36 Drawing Sheets

(56) References Cited

FOREIGN PATENT DOCUMENTS

| WO | WO-2016/141454 A1 | 9/2016 |
|---|---|---|
| WO | WO-17/057882 A1 | 4/2017 |
| WO | WO-17/123025 A1 | 7/2017 |
| WO | WO-2017/148596 A1 | 9/2017 |

OTHER PUBLICATIONS

Kim, J. H., et al. (2015). Gram-negative and Gram-positive bacterial extracellular vesicles. Seminars in cell & developmental biology, 40, 97-104.

Klimentová, J., & Stulík, J. (2015). Methods of isolation and purification of outer membrane vesicles from gram-negative bacteria. Microbiological Research, 170, 1-9.

Labbé, S., & Grenier, D. (1995). Characterization of the human immunoglobulin G Fc-binding activity in Prevotella intermedia. Infection and immunity, 63(7), 2785-2789.

Macdonald, I. A., & Kuehn, M. J. (2013). Stress-induced outer membrane vesicle production by Pseudomonas aeruginosa. Journal of bacteriology, 195(13), 2971-2981.

McBroom, A. J., & Kuehn, M. J. (2007). Release of outer membrane vesicles by Gram-negative bacteria is a novel envelope stress response. Molecular microbiology, 63(2), 545-558.

Muraca, M., et al. (2015). Gut microbiota-derived outer membrane vesicles: under-recognized major players in health and disease?. Discovery medicine, 19(106), 343-348.

Poppleton, D. I., et al. (2017). Outer Membrane Proteome of Veillonella parvula: A Diderm Firmicute of the Human Microbiome. Frontiers in microbiology, 8, 1215.

Roier, S., et al. (2016). Bacterial outer membrane vesicle biogenesis: a new mechanism and its implications. Microbial cell (Graz, Austria), 3(6), 257-259.

Roier, S., et al. (2016). A novel mechanism for the biogenesis of outer membrane vesicles in Gram-negative bacteria. Nature communications, 7, 10515.

Schrempf, H., & Merling, P. (2015). Extracellular Streptomyces lividans vesicles: composition, biogenesis and antimicrobial activity. Microbial biotechnology, 8(4), 644-658.

Schwechheimer, C., et al. (2013). Envelope control of outer membrane vesicle production in Gram-negative bacteria. Biochemistry, 52(18), 3031-3040.

Al-Robaee et al., "IL-10 Implications in Psoriasis," International Journal of Health Sciences, Qassim University, 2(1): 53-58 (2008).

Anonymous, "Autoimmune Disease List," Global Autoimmune Institute, pp. 1-16, (2022).

Anonymous, "Cancer Types," National Cancer Institute, pp. 1-8, (2020).

Baart et al., "Scale-up for bulk production of vaccine against meningococcal disease", Vaccine, (2007).

Bitto et al., "The Theraputic Benefit of Bacterial Membrane Vesicles," International Journal of Molecular Sciences; 18: pp. 1-15, (2017).

Bouallagui et al., "Microbial monitoring by molecular tools of a two-phase anaerobic bioreactor treating fruit and vegetable wastes," Biotech Lett, 26(10):857-862 (2004).

Cabral et al., "Design of live attenuated bacterial vaccines based on D-glutamate auxotrophy," Nature Communications, 8:15480 (2017).

Chatterjee et al., "Vibrio cholerae O395 Outer Membrane Vesicles Modulate Intestinal Epithelial Cells in a NOD1 Protein-dependent Manner and Induce Dendritic Cell-mediated Th2/Th17 Cell Responses," J Biol Chem, 288(6):4299-4309 (2013).

Final Office Action for U.S. Appl. No. 16/126,463 dated Dec. 16, 2021.

Final Office Action for U.S. Appl. No. 16/126,463 dated Nov. 9, 2020.

Gupta et al., "Divergences in gene repertoire among the reference Prevotella genomes derived from distinct body sites of human," BMC Genomics, 16:153 (16 pages)(2015).

Hedberg et al., "Prevotella jejuni sp. nov., isolated from the small intestine of a child with coeliac disease," International Journal of Systematic and Evolutionary Microbiology, 63:4218-4223 (2013).

Hong et al., "Extracellular Vesicles Derived From Staphylococcus aureus Induce Atopic Dermatitis-like Skin Inflammation," Allergy, 66: 351-359, (2010).

International Search Report and Written Opinion for International Application No. PCT/US2018/050211 mailed Dec. 14, 2018.

International Search Report and Written Opinion for International Application No. PCT/US2018/050212 dated Feb. 26, 2019.

Kim, et al., "Bacterial outer membrane vesicles suppress tumor by interferon-γ-mediated antitumor response", Nat. Commun., 8: Article 626 (2017).

Larsen., "The immune response to Prevotella bacteria in chronic inflammatory disease", Immunology, 151(4): 363-374 (2017).

Li et al., "Antibiotic drug rifabutin is effective against lung cancer cells by targeting the eIF4E-β-catenin axis," Biochemical and Biophysical Research Communications, 472:299-305 (2016).

Lokeshwar et al., "Inhibition of Cell Proliferation, Invasion, Tumor Growth and Metastasis by an Oral Non-Antimicrobial Tetracycline Analog (col. 3) in a Metastatic Prostate Cancer Model," International Journal of Cancer, 98: 297-309, (2002).

MacDonald et al., "Stress-Induced Outer Membrane Vesicle Production by Pseudomonas aeruginosa," J Bacteriolgy, 195(13):2971-2981 (2013).

Madeira et al., "Biochemical and mutational analysis of a gingipain-like peptidase activity from Prevotella ruminicola B(1)4 and its role in ammonia production by ruminal bacteria", Applied and Environmental Microbiology, 63(2): 670-675 (1997).

Mangalam et al., ""Microbial monotherapy with Prevotella histicola for patients with multiple sclerosis,"" Expert Rev Neurother., 19(1): 45-53 (2019).

Mangalam et al., "Human Gut-Derived Commensal Bacteria Suppress CNS Inflammatory and Demyelinating Diseases," Cell Reports, 20: 1269-1277 (2017).

Non Final Office Action for U.S. Appl. No. 16/126,463 dated Aug. 23, 2021.

Non Final Office Action for U.S. Appl. No. 16/126,463 dated Jul. 16, 2020.

Non Final Office Action for U.S. Appl. No. 16/126,463 dated Mar. 14, 2022.

Non-Final Rejection for U.S. Appl. No. 16/126,463 dated Jul. 18, 2022.

Norheim et al., "An OMV Vaccine Derived from a Capsular Group B Meningococcus with Constitutive FetA Expression: Preclinical Evaluation of Immunogenicity and Toxicity," PLOS ONE, 10(9):e0134353 (2015).

Park et al., "Anti-tumor effect of bacterial outer membrane vesicles mediated by interferon-gamma" Journal of Extracellular Vesicles, 6 (1), p. 214 (2017).

Park et al., "Outer Membrane Vesicles as a Candidate Vaccine against Edwardsiellosis," PLOS ONE, 6(3):e17629 (2011).

Prado et al. "Protein content and activity of outer membrane vesicles produced by Prevotella ruminicola", Conference: Rowett-INRA 2014: pp. 115 (2014).

Pramod et al., "Exosomes Derived from M. Bovis BCG Infected Macrophages Activate Antigen-Specific CD4+ and CD8+ T Cells In Vitro and In Vivo," PLOS ONE, 3(6):e2461 (2008).

Sangshetti et al., "Quality by design approach: Regulatory need," Arabian Journal of Chemistry, 10: S3412-S3425 (2017).

Santos et al., "Susceptibility of Prevotella Intermedia/Prevotella Nigrescens (and Porphyromonas Gingivalis) to Propolis (Bee Glue) and other Antimicrobial Agents," Anaerobe, 9: 9-15, (2002).

Schorey et al., "Extracellular Vesicles and Infectious Diseases: New Complexity to an Old Story," The Journal of Clinical Investigation, 126(4): 1181-1189 (2016).

Stubbs et al., "Effect of environmental haemin upon the physiology and biochemistry of Prevotella intermedia R78," Lett App Microbiol, 29(1):31-36 (1999).

Suthanthiran et al., "Immunoregulatory Drugs: Mechanistic Basis for Use in Organ Transplantation," Pediatric Nephrology, 11: 651-657, (1997).

(56) References Cited

OTHER PUBLICATIONS

Takumi et al., "Oxygen induces mutation in a strict anaerobe, Prevotella melaninogenica", Free Radical Biology & Medicine, 44(10): 1857-1862 (2008).
Teles, "Production of outer membrane vesicles by the human pathogen Burkholderia cenocepacia: purification and preliminary characterization", R. F. B., (2016).
Waterbeemd et al., "Improved OMV vaccine against Neisseria meningitidis using genetically engineered strains and a detergent-free purification process", Vaccine, 28(30):4810-4816 (2010).
Beem et al., "Identification of hemolytic activity in Prevotella intermedia", *Oral microbiology and immunology* 13(2): 97-105 (1998).
Jinglu, "Modern Diagnosis and Treatment of Shock", Chinese Medicine Science and Technology Press, p. 150, (2001).
Matsushita et al., "Immunobiological activities of a 55-kilodalton cell surface protein of Prevotella intermedia ATCC 25611." *Infection and immunity* 62(6): 2459-2469 (1994).
Ping et al., "Advances in the study of exosomes and other extracellular vesicles in pathogenic microorganisms" Journal of Pathogen Biology, 12(4): 384-389 (2017).

Figure 20

BACTERIAL EXTRACELLULAR VESICLES

RELATED APPLICATIONS

This Application is a divisional of U.S. application Ser. No. 16/645,019, filed Mar. 6, 2020, which claims priority to national-stage application of International Application No. PCT/US2018/50211, filed Sep. 10, 2018, which claims the benefit of priority to U.S. Provisional Patent Applications having Ser. Nos. 62/556,015, filed Sep. 8, 2017, and 62/669,151, filed May 9, 2018, the contents of each of which are hereby incorporated herein by reference in their entirety.

SUMMARY

In certain aspects, provided herein are pharmaceutical compositions comprising bacterial extracellular vesicles (EVs) useful for the treatment and/or prevention of disease (e.g., cancer, autoimmune disease, inflammatory disease, metabolic disease), as well as methods of making and/or identifying such EVs, and methods of using such pharmaceutical compositions (e.g., for the treatment of cancers, autoimmune diseases, inflammatory diseases, metabolic diseases, either alone or in combination with other therapeutics). In some embodiments, the pharmaceutical compositions comprise both EVs and whole bacteria (e.g., live bacteria, killed bacteria, attenuated bacteria). In certain embodiments, provided herein are pharmaceutical compositions comprising bacteria in the absence of EVs. In some embodiments, the pharmaceutical compositions comprise EVs in the absence of bacteria. In some embodiments, the pharmaceutical compositions comprise EVs and/or bacteria from one or more of the bacteria strains or species listed in Table 1 and/or Table 2.

In certain embodiments, the pharmaceutical composition comprises a specific ratio of bacteria to EV particles. For example, in some embodiments, the pharmaceutical composition comprises at least 1 bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ EV particles. In some embodiments, the pharmaceutical composition comprises about 1 bacterium for every 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ EV particles. In some embodiments, the pharmaceutical composition comprises no more than 1 bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ EV particles. In some embodiments, the pharmaceutical composition comprises at least 1 EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ bacterium. In some embodiments, the pharmaceutical composition comprises about 1 EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ bacterium. In some embodiments, the pharmaceutical composition comprises no more than 1 EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ bacterium.

In certain aspects, the EVs are from an engineered bacteria that is modified to enhance certain desirable properties. For example, in some embodiments, the engineered bacteria are modified to increase production of EVs. In some embodiments, the engineered bacteria are modified to produce EVs with enhanced oral delivery (e.g., by improving acid resistance, muco-adherence and/or penetration and/or resistance to bile acids, resistance to anti-microbial peptides and/or antibody neutralization), to target desired cell types (e.g. M-cells, goblet cells, enterocytes, dendritic cells, macrophages) to improve bioavailability systemically or in an appropriate niche (e.g., mesenteric lymph nodes, Peyer's patches, lamina propria, tumor draining lymph nodes, and/or blood), to enhance the immunomodulatory and/or therapeutic effect of the EVs they produce (e.g., either alone or in combination with another therapeutic agent), to enhance immune activation by the EVs they produce and/or to improve bacterial and/or EV manufacturing (e.g., greater stability, improved freeze-thaw tolerance, shorter generation times). In some embodiments, provided herein are methods of making such EVs and bacteria.

In certain embodiments, provided herein are methods of treating a subject who has cancer comprising administering to the subject a pharmaceutical composition described herein. In certain embodiments, provided herein are methods of treating a subject who has an immune disorder (e.g., autoimmune disease, an inflammatory disease, an allergy) comprising administering to the subject a pharmaceutical composition described herein. In certain embodiments, provided herein are methods of treating a subject who has a metabolic disease comprising administering to the subject a pharmaceutical composition described herein.

In some embodiments, the method further comprises administering to the subject an antibiotic. In some embodiments, the method further comprises administering to the subject one or more other cancer therapies (e.g., surgical removal of a tumor, the administration of a chemotherapeutic agent, the administration of radiation therapy, and/or the administration of a cancer immunotherapy, such as an immune checkpoint inhibitor, a cancer-specific antibody, a cancer vaccine, a primed antigen presenting cell, a cancer-specific T cell, a cancer-specific chimeric antigen receptor (CAR) T cell, an immune activating protein, and/or an adjuvant). In some embodiments, the method further comprises the administration of another therapeutic bacterium and/or EV. In some embodiments, the method further comprises the administration of an immune suppressant and/or an anti-inflammatory agent. In some embodiments, the method further comprises the administration of a metabolic disease therapeutic agent.

BRIEF DESCRIPTION OF THE FIGURES

FIG. 20 shows the efficacy of *Burkholderia pseudomallei* EVs compared to intravenously (i.v.) administered anti-PD-1 or vehicle in a mouse colorectal carcinoma model.

DETAILED DESCRIPTION

Definitions

Figure 1:
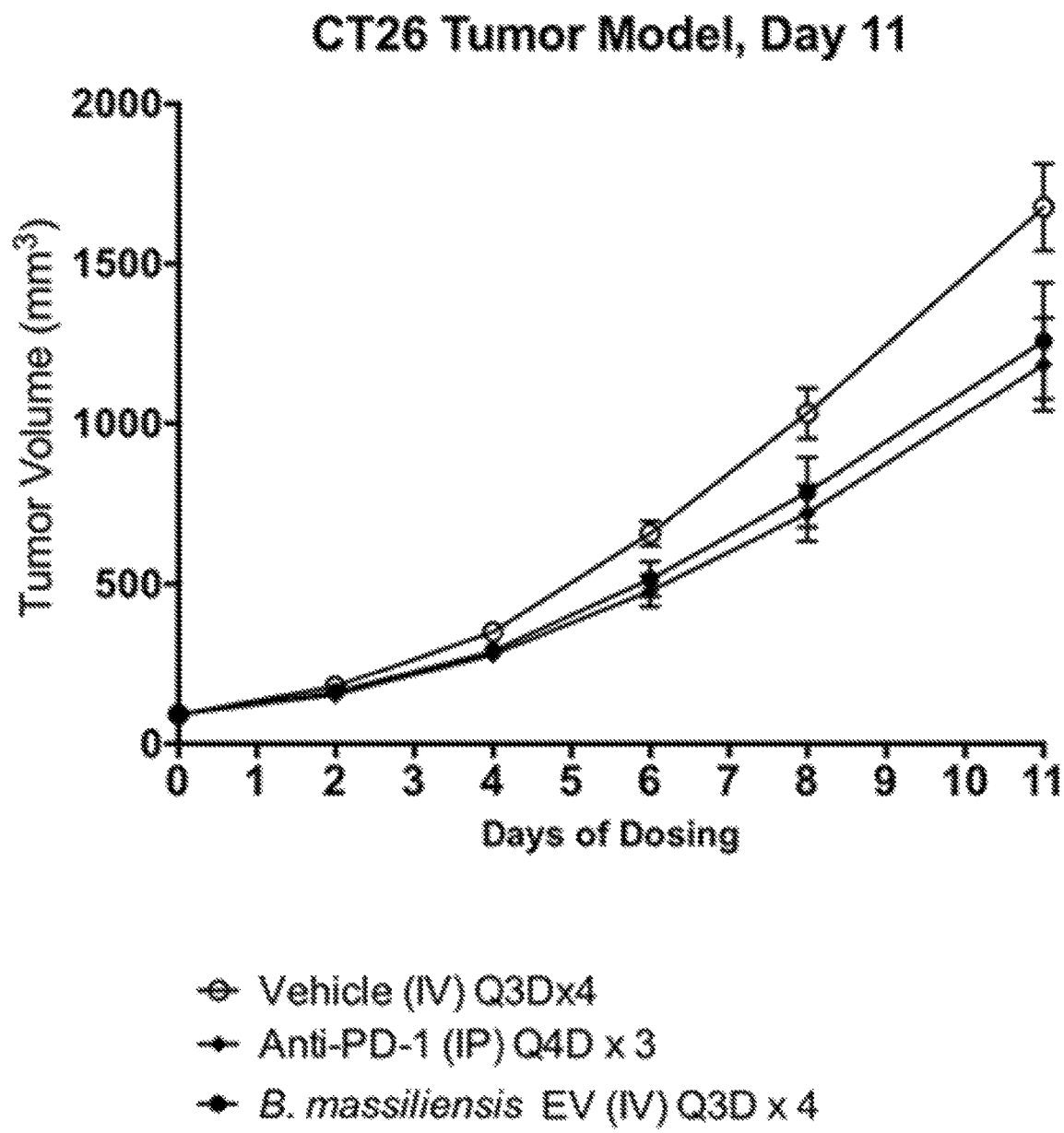
FIG. 1 shows the efficacy of iv administered *Blautia massiliensis* compared to that of intraperitoneally (i.p.) administered anti-PD-1 in a mouse colorectal carcinoma model.

"Adjuvant" or "Adjuvant therapy" broadly refers to an agent that affects an immunological or physiological response in a patient or subject. For example, an adjuvant might increase the presence of an antigen over time or to an area of interest like a tumor, help absorb an antigen presenting cell antigen, activate macrophages and lymphocytes and support the production of cytokines. By changing an immune response, an adjuvant might permit a smaller dose of an immune interacting agent to increase the effectiveness or safety of a particular dose of the immune interacting agent. For example, an adjuvant might prevent T cell exhaustion and thus increase the effectiveness or safety of a particular immune interacting agent.

"Administration" broadly refers to a route of administration of a composition to a subject. Examples of routes of administration include oral administration, rectal administration, topical administration, inhalation (nasal) or injection. Administration by injection includes intravenous (IV), intramuscular (IM), intratumoral (IT) and subcutaneous (SC) administration. The pharmaceutical compositions described herein can be administered in any form by any effective route, including but not limited to intratumoral, oral, parenteral, enteral, intravenous, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), implanted, intravesical, intrapulmonary, intraduodenal, intragastrical, and intrabronchial. In preferred embodiments, the pharmaceutical compositions described herein are administered orally, rectally, intratumorally, topically, intravesically, by injection into or adjacent to a draining lymph node, intravenously, by inhalation or aerosol, or subcutaneously.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable region (abbreviated herein as $V_H$) and a heavy chain constant region. Each light chain includes a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" includes, for example, monoclonal antibodies, polyclonal antibodies, chimeric antibodies, humanized antibodies, human antibodies, multispecific antibodies (e.g., bispecific antibodies), single-chain antibodies and antigen-binding antibody fragments.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')$_2$, Fv, scFv, disulfide linked Fv, Fd, diabodies, single-chain antibodies, NANOBODIES®, isolated CDRH3, and other antibody fragments that retain at least a portion of the variable region of an intact antibody. These antibody fragments can be obtained using conventional recombinant and/or enzymatic techniques and can be screened for antigen binding in the same manner as intact antibodies.

"Cancer" broadly refers to an uncontrolled, abnormal growth of a host's own cells leading to invasion of surrounding tissue and potentially tissue distal to the initial site of abnormal cell growth in the host. Major classes include carcinomas which are cancers of the epithelial tissue (e.g., skin, squamous cells); sarcomas which are cancers of the connective tissue (e.g., bone, cartilage, fat, muscle, blood vessels, etc.); leukemias which are cancers of blood forming tissue (e.g., bone marrow tissue); lymphomas and myelomas which are cancers of immune cells; and central nervous system cancers which include cancers from brain and spinal tissue. "Cancer(s)," "neoplasm(s)," and "tumor(s)" are used herein interchangeably. As used herein, "cancer" refers to all types of cancer or neoplasm or malignant tumors including leukemias, carcinomas and sarcomas, whether new or recurring. Specific examples of cancers are: carcinomas, sarcomas, myelomas, leukemias, lymphomas and mixed type tumors. Non-limiting examples of cancers are new or recurring cancers of the brain, melanoma, bladder, breast, cervix, colon, head and neck, kidney, lung, non-small cell lung, mesothelioma, ovary, prostate, sarcoma, stomach, uterus and medulloblastoma.

"Cellular augmentation" broadly refers to the influx of cells or expansion of cells in an environment that are not substantially present in the environment prior to administration of a composition and not present in the composition itself. Cells that augment the environment include immune cells, stromal cells, bacterial and fungal cells. Environments of particular interest are the microenvironments where cancer cells reside or locate. In some instances, the microenvironment is a tumor microenvironment or a tumor draining lymph node. In other instances, the microenvironment is a pre-cancerous tissue site or the site of local administration of a composition or a site where the composition will accumulate after remote administration.

"Clade" refers to the OTUs or members of a phylogenetic tree that are downstream of a statistically valid node in a phylogenetic tree. The clade comprises a set of terminal leaves in the phylogenetic tree that is a distinct monophyletic evolutionary unit and that share some extent of sequence similarity. "Operational taxonomic units," "OTU" (or plural, "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share ≥97% average nucleotide identity across the entire 16S or some variable region of the 16S are considered the same OTU (see e.g. Claesson M J. Wang Q, O'Sullivan O, Greene-Diniz R. Cole J R. Ros R P. and O'Toole P W. 2010. Comparison of two next-generation sequencing technologies for resolving highly complex microbiota composition using tandem variable 16S rRNA gene regions. *Nucleic Acids Res* 38: e200. Konstantinidis K T, Ramette A, and Tiedje J M. 2006. The bacterial species definition in the genomic era. *Philos Trans R Soc Lond B Biol Sci* 361. 1929-1940.) In embodiments involving the complete genome, MLSTs, specific genes, or sets of genes OTUs that share ≥95% average nucleotide identity are considered the same OTU (see e.g. Achtman M. and Wagner M. 2008. Microbial diversity and the genetic nature of microbial species. *Nat. Rev. Microbiol.* 6: 431-440. Konstantinidis K T, Ramette A, and Tiedje J M. 2006. The bacterial species definition in the genomic era. *Philos Trans R Soc Lond B Biol Sci* 361: 1929-1940.). OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Such characterization employs, e.g., WGS data or a whole genome sequence.

A "combination" of EVs from two or more microbial strains includes the physical co-existence of the two EVs, either in the same material or product or in physically connected products, as well as the temporal co-administration or co-localization of the EVs from the two strains.

The term "decrease" or "deplete" means a change, such that the difference is, depending on circumstances, at least 10%, 20%, 30%, 40%, 50%, 60%, 70%, 80%, 90%, 1/100, 1/1000, 1/10,000, 1/100,000, 1/1,000,000 or undetectable after treatment when compared to a pre-treatment state.

As used herein, the term "Dysbiosis" refers to a state in which the synergy between microbes and the tumor is broken such as the microbes no longer support the nucleation, maintenance, progression or spread or metastasis of a tumor.

The term "epitope" means a protein determinant capable of specific binding to an antibody or T cell receptor. Epitopes usually consist of chemically active surface groupings of molecules such as amino acids or sugar side chains. Certain epitopes can be defined by a particular sequence of amino acids to which an antibody is capable of binding.

As used herein, "engineered bacteria" are any bacteria that have been genetically altered from their natural state by human intervention and the progeny of any such bacteria. Engineered bacteria include, for example, the products of targeted genetic modification, the products of random mutagenesis screens and the products of directed evolution.

The term "gene" is used broadly to refer to any nucleic acid associated with a biological function. The term "gene" applies to a specific genomic sequence, as well as to a cDNA or an mRNA encoded by that genomic sequence.

"Identity" as between nucleic acid sequences of two nucleic acid molecules can be determined as a percentage of identity using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA Atschul, S. F., et al., J Molec Biol 215:403 (1990); Guide to Huge Computers, Mrtin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)).

As used herein, the term "immune disorder" refers to any disease, disorder or disease symptom caused by an activity of the immune system, including autoimmune diseases, inflammatory diseases and allergies. Immune disorders include, but are not limited to, autoimmune diseases (e.g., Lupus, Scleroderma, hemolytic anemia, vasculitis, type one diabetes, Grave's disease, rheumatoid arthritis, multiple sclerosis, Goodpasture's syndrome, pernicious anemia and/or myopathy), inflammatory diseases (e.g., acne vulgaris, asthma, celiac disease, chronic prostatitis, glomerulonephritis, inflammatory bowel disease, pelvic inflammatory disease, reperfusion injury, rheumatoid arthritis, sarcoidosis, transplant rejection, vasculitis and/or interstitial cystitis), and/or an allergies (e.g., food allergies, drug allergies and/or environmental allergies).

"Immunotherapy" is treatment that uses a subject's immune system to treat disease (e.g., immune disease, inflammatory disease, metabolic disease, cancer) and includes, for example, checkpoint inhibitors, cancer vaccines, cytokines, cell therapy, CAR-T cells, and dendritic cell therapy.

The term "increase" means a change, such that the difference is, depending on circumstances, at least 10%, 20%, 30%, 40%, 50%, 60%, 70%, 80%, 90%, 2-fold, 4-fold, 10-fold, 100-fold, $10^3$ fold, $10^4$ fold, $10^5$ fold, $10^6$ fold, and/or $10^7$ fold greater after treatment when compared to a pre-treatment state. Properties that may be increased include immune cells, bacterial cells, stromal cells, myeloid derived suppressor cells, fibroblasts, metabolites, and cytokines.

"Innate immune agonists" or "immuno-adjuvants" are small molecules, proteins, or other agents that specifically target innate immune receptors including Toll-Like Receptors (TLR), NOD receptors, RLRs, C-type lectin receptors, STING-cGAS Pathway components, inflammasome complexes. For example, LPS is a TLR-4 agonist that is bacterially derived or synthesized and aluminum can be used as an immune stimulating adjuvant. immuno-adjuvants are a specific class of broader adjuvant or adjuvant therapy. Examples of STING agonists include, but are not limited to, 2'3'-cGAMP, 3'3'-cGAMP, c-di-AMP, c-di-GMP, 2'2'-cGAMP, and 2'3'-cGAM(PS)2 (Rp/Sp) (Rp, Sp-isomers of the bis-phosphorothioate analog of 2'3'-cGAMP). Examples of TLR agonists include, but are not limited to, TLR1, TLR2, TLR3, TLR4, TLR5, TLR6, TLR7, TLR8, TLR9, TLR1O and TLR1 1. Examples of NOD agonists include, but are not limited to, N-acetylmuramyl-L-alanyl-D-isoglutamine (muramyldipeptide (MDP)), gamma-D-glutamyl-meso-diaminopimelic acid (iE-DAP), and desmuramylpeptides (DMP).

The "internal transcribed spacer" or "ITS" is a piece of non-functional RNA located between structural ribosomal RNAs (rRNA) on a common precursor transcript often used for identification of eukaryotic species in particular fungi. The rRNA of fungi that forms the core of the ribosome is transcribed as a signal gene and consists of the 8S, 5.8S and 28S regions with ITS4 and 5 between the 8S and 5.8S and 5.8S and 28S regions, respectively. These two intercistronic segments between the 18S and 5.8S and 5.8S and 28S regions are removed by splicing and contain significant variation between species for barcoding purposes as previously described (Schoch et al Nuclear ribosomal internal transcribed spacer (ITS) region as a universal DNA barcode marker for Fungi. PNAS 109:6241-6246. 2012). 18S rDNA is traditionally used for phylogenetic reconstruction however the ITS can serve this function as it is generally highly conserved but contains hypervariable regions that harbor sufficient nucleotide diversity to differentiate genera and species of most fungus.

The term "isolated" or "enriched" encompasses a microbe, EV or other entity or substance that has been (1) separated from at least some of the components with which it was associated when initially produced (whether in nature or in an experimental setting), and/or (2) produced, prepared, purified, and/or manufactured by the hand of man. Isolated microbes may be separated from at least about 10%, about 20%, about 30%, about 40%, about 50%, about 60%, about 70%, about 80%, about 90%, or more of the other components with which they were initially associated. In some embodiments, isolated microbes are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a microbe or other material that has been separated from at least some of the components with which it was associated either when initially produced or generated (e.g., whether in nature or in an experimental setting), or during any time after its initial production. A microbe or a microbial population may be considered purified if it is isolated at or after production, such as from a material or environment containing the microbe or microbial population, and a purified microbe or microbial population may contain other materials up to about 10%, about 20%, about 30%, about 40%, about 50%, about 60%, about 70%, about 80%, about 90%, or above about 90% and still be considered "isolated." In some embodiments, purified microbes or microbial population are more than about 80%, about 85%, about 90%, about 91%, about 92%, about 93%, about 94%, about 95%, about 96%, about 97%, about 98%, about 99%, or more than about 99% pure. In the instance of microbial compositions provided herein, the one or more microbial types present in the composition can be independently purified from one or more other microbes produced and/or present in the material or environment containing the microbial type. Microbial compositions and the microbial components thereof are generally purified from residual habitat products."

"Metabolite" as used herein refers to any and all molecular compounds, compositions, molecules, ions, co-factors, catalysts or nutrients used as substrates in any cellular or microbial metabolic reaction or resulting as product compounds, compositions, molecules, ions, co-factors, catalysts or nutrients from any cellular or microbial metabolic reaction.

"Microbe" refers to any natural or engineered organism characterized as a bacterium, fungus, microscopic alga, protozoan, and the stages of development or life cycle stages (e.g., vegetative, spore (including sporulation, dormancy, and germination), latent, biofilm) associated with the organism. Examples of gut microbes include: *Actinomyces graevenitzii, Actinomyces odontolyticus, Akkermansia muciniphila, Bacteroides caccae, Bacteroides fragilis, Bacteroides putredinis, Bacteroides thetaiotaomicron, Bacteroides vultagus, Bifidobacterium adolescentis, Bifidobacterium bifidum, Bilophila wadsworthia, Blautia, Butyrivibrio, Campylobacter gracilis*, Clostridia cluster III, Clostridia cluster IV, Clostridia cluster IX (Acidaminococcaceae group), Clostridia cluster XI, Clostridia cluster XIII (*Peptostreptococcus* group), Clostridia cluster XIV, Clostridia cluster XV, *Collinsella aerofaciens, Coprococcus, Corynebacterium sunsvallense, Desulfomonas pigra, Dorea formicigenerans, Dorea longicatena, Escherichia coli, Eubacterium hadrum, Eubacterium rectale, Faecalibacteria prausnitzii, Gemella, Lactococcus, Lanchnospira*, Mollicutes cluster XVI, Mollicutes cluster XVIII, *Prevotella, Rothia mucilaginosa, Ruminococcus callidus, Ruminococcus gnavus, Ruminococcus torques*, and *Streptococcus*.

"Microbiome" broadly refers to the microbes residing on or in body site of a subject or patient. Microbes in a microbiome may include bacteria, viruses, eukaryotic microorganisms, and/or viruses. Individual microbes in a microbiome may be metabolically active, dormant, latent, or exist as spores, may exist planktonically or in biofilms, or may be present in the microbiome in sustainable or transient manner. The microbiome may be a commensal or healthy-state microbiome or a disease-state microbiome. The microbiome may be native to the subject or patient, or components of the microbiome may be modulated, introduced, or depleted due to changes in health state (e.g., precancerous or cancerous state) or treatment conditions (e.g., antibiotic treatment, exposure to different microbes). In some aspects, the microbiome occurs at a mucosal surface. In some aspects, the microbiome is a gut microbiome. In some aspects, the microbiome is a tumor microbiome.

A "microbiome profile" or a "microbiome signature" of a tissue or sample refers to an at least partial characterization of the bacterial makeup of a microbiome. In some embodiments, a microbiome profile indicates whether at least 2, 3, 4, 5, 6, 7, 8, 9, 10, 15, 20, 25, 30, 35, 40, 45, 50, 55, 60, 65, 70, 75, 80, 85, 90, 95, 100 or more bacterial strains are present or absent in a microbiome. In some embodiments, a microbiome profile indicates whether at least 2, 3, 4, 5, 6, 7, 8, 9, 10, 15, 20, 25, 30, 35, 40, 45, 50, 55, 60, 65, 70, 75, 80, 85, 90, 95, 100 or more cancer-associated bacterial strains are present in a sample. In some embodiments, the microbiome profile indicates the relative or absolute amount of each bacterial strain detected in the sample. In some embodiments, the microbiome profile is a cancer-associated microbiome profile. A cancer-associated microbiome profile is a microbiome profile that occurs with greater frequency in a subject who has cancer than in the general population. In some embodiments, the cancer-associated microbiome profile comprises a greater number of or amount of cancer-associated bacteria than is normally present in a microbiome of an otherwise equivalent tissue or sample taken from an individual who does not have cancer.

"Modified" in reference to a bacteria broadly refers to a bacteria that has undergone a change from its wild-type form. Examples of bacterial modifications include genetic modification, gene expression, phenotype modification, formulation, chemical modification, and dose or concentration. Examples of improved properties are described throughout this specification and include, e.g., attenuation, auxotrophy, homing, or antigenicity. Phenotype modification might include, by way of example, bacteria growth in media that modify the phenotype of a bacterium that increase or decrease virulence.

As used herein, a gene is "overexpressed" in a bacteria if it is expressed at a higher level in an engineered bacteria under at least some conditions than it is expressed by a wild-type bacteria of the same species under the same conditions. Similarly, a gene is "underexpressed" in a bacteria if it is expressed at a lower level in an engineered bacteria under at least some conditions than it is expressed by a wild-type bacteria of the same species under the same conditions.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), micro RNA (miRNA), silencing RNA (siRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

An "oncobiome" as used herein comprises pathogenic, tumorigenic and/or cancer-associated microbiota, wherein the microbiota comprises one or more of a virus, a bacterium, a fungus, a protist, a parasite, or another microbe.

"Oncotrophic" or "oncophilic" microbes and bacteria are microbes that are highly associated or present in a cancer microenvironment. They may be preferentially selected for within the environment, preferentially grow in a cancer microenvironment or hone to a said environment.

"Operational taxonomic units" and "OTU(s)" refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. For 16S, OTUs that share ≥97% average nucleotide identity across the entire 16S or some variable region of the 16S are considered the same OTU. See e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940. For complete genomes, MLSTs, specific genes, other than 16S, or sets of genes OTUs that share ≥95% average nucleotide identity are considered the same OTU. See e.g., Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940. OTUs are frequently defined by comparing sequences between organisms.

Generally, sequences with less than 95% sequence identity are not considered to form part of the same OTU. OTUs may also be characterized by any combination of nucleotide markers or genes, in particular highly conserved genes (e.g., "house-keeping" genes), or a combination thereof. Operational Taxonomic Units (OTUs) with taxonomic assignments made to, e.g., genus, species, and phylogenetic clade are provided herein.

As used herein, the term "extracellular vesicle" or "EV" or refers to a composition derived from a bacteria that comprises bacterial lipids, and bacterial proteins and/or bacterial nucleic acids and/or carbohydrate moieties contained in a nanoparticle. These EVs may contain 1, 2, 3, 4, 5, 10, or more than 10 different lipid species. EVs may contain 1, 2, 3, 4, 5, 10, or more than 10 different protein species. EVs may contain 1, 2, 3, 4, 5, 10, or more than 10 different nucleic acid species. EVs may contain 1, 2, 3, 4, 5, 10, or more than 10 different carbohydrate species.

As used herein, a substance is "pure" if it is substantially free of other components. The terms "purify," "purifying" and "purified" refer to a EV or other material that has been separated from at least some of the components with which it was associated either when initially produced or generated (e.g., whether in nature or in an experimental setting), or during any time after its initial production. An EV may be considered purified if it is isolated at or after production, such as from one or more other bacterial components, and a purified microbe or microbial population may contain other materials up to about 10%, about 20%, about 30%, about 40%, about 50%, about 60%, about 70%, about 80%, about 90%, or above about 90% and still be considered "purified." In some embodiments, purified EVs are more than about 80%, about 85%, about 90%, about 91%, about 92%, about 93%, about 94%, about 95%, about 96%, about 97%, about 98%, about 99%, or more than about 99% pure. EV compositions and the microbial components thereof are, e.g., purified from residual habitat products.

As used herein, the term "purified EV composition" or "EV composition" refer to a preparation that includes EVs that have been separated from at least one associated substance found in a source material (e.g. separated from at least one other bacterial component) or any material associated with the EVs in any process used to produce the preparation. It also refers to a composition that has been significantly enriched or concentrated. In some embodiments the EVs are concentrated by 2 fold, 3-fold, 4-fold, 5-fold, 10-fold, 100-fold, 1000-fold, 10,000-fold or more than 10,000 fold.

"Residual habitat products" refers to material derived from the habitat for microbiota within or on a subject. For example, microbes live in feces in the gastrointestinal tract, on the skin itself, in saliva, mucus of the respiratory tract, or secretions of the genitourinary tract (i.e., biological matter associated with the microbial community). Substantially free of residual habitat products means that the microbial composition no longer contains the biological matter associated with the microbial environment on or in the human or animal subject and is 100% free, 99% free, 98% free, 97% free, 96% free, or 95% free of any contaminating biological matter associated with the microbial community. Residual habitat products can include abiotic materials (including undigested food) or it can include unwanted microorganisms. Substantially free of residual habitat products may also mean that the microbial composition contains no detectable cells from a human or animal and that only microbial cells are detectable. In one embodiment, substantially free of residual habitat products may also mean that the microbial composition contains no detectable viral (including microbial viruses (e.g., phage)), fungal, mycoplasmal contaminants. In another embodiment, it means that fewer than $1\times10^{-2}\%$, $1\times10^{-3}\%$, $1\times10^{-4}\%$, $1\times10^{-5}\%$, $1\times10^{-6}\%$, $1\times10^{-7}\%$, $1\times10^{-8}\%$ of the viable cells in the microbial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of $10^{-8}$ or $10^{-9}$), such as through multiple 10-fold serial dilutions. This can further be confirmed by showing that multiple isolated colonies have similar cell shapes and Gram staining behavior. Other methods for confirming adequate purity include genetic analysis (e.g., PCR, DNA sequencing), serology and antigen analysis, enzymatic and metabolic analysis, and methods using instrumentation such as flow cytometry with reagents that distinguish desired constituents from contaminants.

As used herein, "specific binding" refers to the ability of an antibody to bind to a predetermined antigen or the ability of a polypeptide to bind to its predetermined binding partner. Typically, an antibody or polypeptide specifically binds to its predetermined antigen or binding partner with an affinity corresponding to a $K_D$ of about $10^{-7}$ M or less, and binds to the predetermined antigen/binding partner with an affinity (as expressed by $K_D$) that is at least 10 fold less, at least 100 fold less or at least 1000 fold less than its affinity for binding to a non-specific and unrelated antigen/binding partner (e.g., BSA, casein). Alternatively, specific binding applies more broadly to a two component system where one component is a protein, lipid, or carbohydrate or combination thereof and engages with the second component which is a protein, lipid, carbohydrate or combination thereof in a specific way.

The terms "subject" or "patient" refers to any animal. A subject or a patient described as "in need thereof" refers to one in need of a treatment for a disease. Mammals (i.e., mammalian animals) include humans, laboratory animals (e.g., primates, rats, mice), livestock (e.g., cows, sheep, goats, pigs), and household pets (e.g., dogs, cats, rodents).

"Strain" refers to a member of a bacterial species with a genetic signature such that it may be differentiated from closely-related members of the same bacterial species. The genetic signature may be the absence of all or part of at least one gene, the absence of all or part of at least on regulatory region (e.g., a promoter, a terminator, a riboswitch, a ribosome binding site), the absence ("curing") of at least one native plasmid, the presence of at least one recombinant gene, the presence of at least one mutated gene, the presence of at least one foreign gene (a gene derived from another species), the presence at least one mutated regulatory region (e.g., a promoter, a terminator, a riboswitch, a ribosome binding site), the presence of at least one non-native plasmid, the presence of at least one antibiotic resistance cassette, or a combination thereof. Genetic signatures between different strains may be identified by PCR amplification optionally followed by DNA sequencing of the genomic region(s) of interest or of the whole genome. In the case in which one strain (compared with another of the same species) has gained or lost antibiotic resistance or gained or lost a biosynthetic capability (such as an auxotrophic strain), strains may be differentiated by selection or counter-selection using an antibiotic or nutrient/metabolite, respectively.

As used herein, the term "treating" a disease in a subject or "treating" a subject having or suspected of having a disease refers to subjecting the subject to a pharmaceutical treatment, e.g., the administration of one or more agents, such that at least one symptom of the disease is decreased or prevented from worsening. Thus, in one embodiment, "treating" refers inter alia to delaying progression, expediting remission, inducing remission, augmenting remission, speeding recovery, increasing efficacy of or decreasing resistance to alternative therapeutics, or a combination thereof.

Bacteria

In certain aspects, provided herein are pharmaceutical compositions that comprise bacteria and/or EVs made from bacteria.

In some embodiments, the bacteria from which the EVs are obtained are modified to enhance EV production, to enhance oral delivery of the produced EVs (e.g., by improving acid resistance, muco-adherence and/or penetration and/or resistance to bile acids, digestive enzymes, resistance to anti-microbial peptides and/or antibody neutralization), to target desired cell types (e.g. M-cells, goblet cells, enterocytes, dendritic cells, macrophages), to enhance their immunomodulatory and/or therapeutic effect of the produced EVs (e.g., either alone or in combination with another therapeutic agent), and/or to enhance immune activation or suppression by the produced EVs (e.g., through modified production of polysaccharides, pili, fimbriae, adhesins). In some embodiments, the engineered bacteria described herein are modified to improve bacterial and/or EV manufacturing (e.g., higher oxygen tolerance, stability, improved freeze-thaw tolerance, shorter generation times). For example, in some embodiments, the engineered bacteria described include bacteria harboring one or more genetic changes, such change being an insertion, deletion, translocation, or substitution, or any combination thereof, of one or more nucleotides contained on the bacterial chromosome or endogenous plasmid and/or one or more foreign plasmids, wherein the genetic change may results in the overexpression and/or underexpression of one or more genes. The engineered microbe(s) may be produced using any technique known in the art, including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, directed evolution, or any combination thereof.

As used herein, the term "bacteria" broadly refers to the domain of prokaryotic organisms, including Gram positive and Gram negative organisms. Examples of species and/or strains of bacteria that can be used to produce the EVs described herein are provided in Tables 1 and/or Table 2 and elsewhere throughout the specification. In some embodiments, the bacterial strain is a bacterial strain having a genome that has at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity to a strain listed in Table 1 and/or Table 2. In some embodiments, the EVs are from an oncotrophic bacteria. In some embodiments, the EVs are from an immunostimulatory bacteria. In some embodiments the EVs are from an immunosuppressive bacteria. In some embodiments, the EVs are from an immunomodulatory bacteria. In certain embodiments, EVs are generated from a combination of bacterial strains provided herein. In some embodiments, the combination is a combination of at least 2, 3, 4, 5, 6, 7, 8, 9, 10, 11, 12, 13, 14, 15, 20, 25, 30, 35, 40, 45 or 50 bacterial strains. In some embodiments combination includes EVs from bacterial strains listed in Table 1 and/or Table 2 and/or bacterial strains having a genome that has at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity to a strain listed in Table 1 and/or Table 2.

TABLE 1

Exemplary Bacterial Strains

| OTU | Public DB Accession |
| --- | --- |
| *Abiotrophia defectiva* | ACIN02000016 |
| *Abiotrophia para_adiacens* | AB022027 |
| *Abiotrophia* sp. oral clone P4PA_155 P1 | AY207063 |
| *Acetanaerobacterium elongatum* | NR_042930 |
| *Acetivibrio cellulolyticus* | NR_025917 |
| *Acetivibrio ethanolgignens* | FR749897 |
| *Acetobacter aceti* | NR_026121 |
| *Acetobacter fabarum* | NR_042678 |
| *Acetobacter lovaniensis* | NR_040832 |
| *Acetobacter malorum* | NR_025513 |
| *Acetobacter orientalis* | NR_028625 |
| *Acetobacter pasteurianus* | NR_026107 |
| *Acetobacter pomorum* | NR_042112 |
| *Acetobacter syzygii* | NR_040868 |
| *Acetobacter tropicalis* | NR_036881 |
| *Acetobacteraceae bacterium* AT_5844 | AGEZ01000040 |
| *Acholeplasma laidlawii* | NR_074448 |
| *Achromobacter denitrificans* | NR_042021 |
| *Achromobacter piechaudii* | ADMS01000149 |
| *Achromobacter xylosoxidans* | ACRC01000072 |
| *Acidaminococcus fermentans* | CP001859 |

TABLE 1-continued

Exemplary Bacterial Strains

| OTU | Public DB Accession |
|---|---|
| *Acidaminococcus intestini* | CP003058 |
| *Acidaminococcus* sp. D21 | ACGB01000071 |
| *Acidilobus saccharovorans* | AY350586 |
| *Acidithiobacillus ferrivorans* | NR_074660 |
| *Acidovorax* sp. 98_63833 | AY258065 |
| *Acinetobacter baumannii* | ACYQ01000014 |
| *Acinetobacter calcoaceticus* | AM157426 |
| *Acinetobacter* genomosp. C1 | AY278636 |
| *Acinetobacter haemolyticus* | ADMT01000017 |
| *Acinetobacter johnsonii* | ACPL01000162 |
| *Acinetobacter junii* | ACPM01000135 |
| *Acinetobacter lwoffii* | ACPN01000204 |
| *Acinetobacter parvus* | AIEB01000124 |
| *Acinetobacter radioresistens* | ACVR01000010 |
| *Acinetobacter schindleri* | NR_025412 |
| *Acinetobacter* sp. 56A1 | GQ178049 |
| *Acinetobacter* sp. CIP 101934 | JQ638573 |
| *Acinetobacter* sp. CIP 102143 | JQ638578 |
| *Acinetobacter* sp. CIP 53.82 | JQ638584 |
| *Acinetobacter* sp. M16_22 | HM366447 |
| *Acinetobacter* sp. RUH2624 | ACQF01000094 |
| *Acinetobacter* sp. SH024 | ADCH01000068 |
| *Actinobacillus actinomycetemcomitans* | AY362885 |
| *Actinobacillus minor* | ACFT01000025 |
| *Actinobacillus pleuropneumoniae* | NR_074857 |
| *Actinobacillus succinogenes* | CP000746 |
| *Actinobacillus ureae* | AEVG01000167 |
| *Actinobaculum massiliae* | AF487679 |
| *Actinobaculum schaalii* | AY957507 |
| *Actinobaculum* sp. BM#101342 | AY282578 |
| *Actinobaculum* sp. P2P_19 P1 | AY207066 |
| *Actinomyces cardiffensis* | GU470888 |
| *Actinomyces europaeus* | NR_026363 |
| *Actinomyces funkei* | HQ906497 |
| *Actinomyces* genomosp. C1 | AY278610 |
| *Actinomyces* genomosp. C2 | AY278611 |
| *Actinomyces* genomosp. P1 oral clone MB6_C03 | DQ003632 |
| *Actinomyces georgiae* | GU561319 |
| *Actinomyces israelii* | AF479270 |
| *Actinomyces massiliensis* | AB545934 |
| *Actinomyces meyeri* | GU561321 |
| *Actinomyces naeslundii* | X81062 |
| *Actinomyces nasicola* | AJ508455 |
| *Actinomyces neuii* | X71862 |
| *Actinomyces odontolyticus* | ACYT01000123 |
| *Actinomyces oricola* | NR_025559 |
| *Actinomyces orihominis* | AJ575186 |
| *Actinomyces oris* | BABV01000070 |
| *Actinomyces* sp. 7400942 | EU484334 |
| *Actinomyces* sp. c109 | AB167239 |
| *Actinomyces* sp. CCUG 37290 | AJ234058 |
| *Actinomyces* sp. ChDC B197 | AF543275 |
| *Actinomyces* sp. GEJ15 | GU561313 |
| *Actinomyces* sp. HKU31 | HQ335393 |
| *Actinomyces* sp. ICM34 | HQ616391 |
| *Actinomyces* sp. ICM41 | HQ616392 |
| *Actinomyces* sp. ICM47 | HQ616395 |
| *Actinomyces* sp. ICM54 | HQ616398 |
| *Actinomyces* sp. M2231_94_1 | AJ234063 |
| *Actinomyces* sp. oral clone GU009 | AY349361 |
| *Actinomyces* sp. oral clone GU067 | AY349362 |
| *Actinomyces* sp. oral clone IO076 | AY349363 |
| *Actinomyces* sp. oral clone IO077 | AY349364 |
| *Actinomyces* sp. oral clone IP073 | AY349365 |
| *Actinomyces* sp. oral clone IP081 | AY349366 |
| *Actinomyces* sp. oral clone JA063 | AY349367 |
| *Actinomyces* sp. oral taxon 170 | AFBL01000010 |
| *Actinomyces* sp. oral taxon 171 | AECW01000034 |
| *Actinomyces* sp. oral taxon 178 | AEUH01000060 |
| *Actinomyces* sp. oral taxon 180 | AEPP01000041 |
| *Actinomyces* sp. oral taxon 848 | ACUY01000072 |
| *Actinomyces* sp. oral taxon C55 | HM099646 |
| *Actinomyces* sp. TeJ5 | GU561315 |
| *Actinomyces urogenitalis* | ACFH01000038 |
| *Actinomyces viscosus* | ACRE01000096 |
| *Adlercreutzia equolifaciens* | AB306661 |
| *Aerococcus sanguinicola* | AY837833 |
| *Aerococcus urinae* | CP002512 |
| *Aerococcus urinaeequi* | NR_043443 |
| *Aerococcus viridans* | ADNT01000041 |
| *Aeromicrobium marinum* | NR_025681 |
| *Aeromicrobium* sp. JC14 | JF824798 |
| *Aeromonas allosaccharophila* | S39232 |
| *Aeromonas enteropelogenes* | X71121 |
| *Aeromonas hydrophila* | NC_008570 |
| *Aeromonas jandaei* | X60413 |
| *Aeromonas salmonicida* | NC_009348 |
| *Aeromonas trota* | X60415 |
| *Aeromonas veronii* | NR_044845 |
| *Afipia* genomosp. 4 | EU117385 |
| *Aggregatibacter actinomycetemcomitans* | CP001733 |
| *Aggregatibacter aphrophilus* | CP001607 |
| Aggregatibacter segnis | AEPS01000017 |
| *Agrobacterium radiobacter* | CP000628 |
| *Agrobacterium tumefaciens* | AJ389893 |
| *Agrococcus jenensis* | NR_026275 |
| *Akkermansia muciniphila* | CP001071 |
| *Alcaligenes faecalis* | AB680368 |
| *Alcaligenes* sp. CO14 | DQ643040 |
| *Alcaligenes* sp. S3 | HQ262549 |
| *Alicyclobacillus acidocaldarius* | NR_074721 |
| *Alicyclobacillus acidoterrestris* | NR_040844 |
| *Alicyclobacillus contaminans* | NR_041475 |
| *Alicyclobacillus cycloheptanicus* | NR_024754 |
| *Alicyclobacillus herbarius* | NR_024753 |
| *Alicyclobacillus pomorum* | NR_024801 |
| *Alicyclobacillus* sp. CCUG 53762 | HE613268 |
| *Alistipes finegoldii* | NR_043064 |
| *Alistipes indistinctus* | AB490804 |
| *Alistipes onderdonkii* | NR_043318 |
| *Alistipes putredinis* | ABFK02000017 |
| *Alistipes shahii* | FP929032 |
| *Alistipes* sp. HGB5 | AENZ01000082 |
| *Alistipes* sp. JC50 | JF824804 |
| *Alistipes* sp. RMA 9912 | GQ140629 |
| *Alkaliphilus metalliredigenes* | AY137848 |
| *Alkaliphilus oremlandii* | NR_043674 |
| *Alloscardovia omnicolens* | NR_042583 |
| *Alloscardovia* sp. OB7196 | AB425070 |
| *Anaerobaculum hydrogeniformans* | ACJX02000009 |
| *Anaerobiospirillum succiniciproducens* | NR_026075 |
| *Anaerobiospirillum thomasii* | AJ420985 |
| *Anaerococcus hydrogenalis* | ABXA01000039 |
| *Anaerococcus lactolyticus* | ABYO01000217 |
| *Anaerococcus octavius* | NR_026360 |
| *Anaerococcus prevotii* | CP001708 |
| *Anaerococcus* sp. 8404299 | HM587318 |
| *Anaerococcus* sp. 8405254 | HM587319 |
| *Anaerococcus* sp. 9401487 | HM587322 |
| *Anaerococcus* sp. 9403502 | HM587325 |
| *Anaerococcus* sp. gpac104 | AM176528 |
| *Anaerococcus* sp. gpac126 | AM176530 |
| *Anaerococcus* sp. gpac155 | AM176536 |
| *Anaerococcus* sp. gpac199 | AM176539 |
| *Anaerococcus* sp. gpac215 | AM176540 |
| *Anaerococcus tetradius* | ACGC01000107 |
| *Anaerococcus vaginalis* | ACXU01000016 |
| *Anaerofustis stercorihominis* | ABIL02000005 |
| *Anaeroglobus geminatus* | AGCJ01000054 |
| *Anaerosporobacter mobilis* | NR_042953 |
| *Anaerostipes caccae* | ABAX03000023 |
| *Anaerostipes* sp. 3_2_56FAA | ACWB01000002 |
| *Anaerotruncus colihominis* | ABGD02000021 |
| *Anaplasma marginale* | ABOR01000019 |
| *Anaplasma phagocytophilum* | NC_007797 |
| *Aneurinibacillus aneurinilyticus* | AB101592 |
| *Aneurinibacillus danicus* | NR_028657 |
| *Aneurinibacillus migulanus* | NR_036799 |
| *Aneurinibacillus terranovensis* | NR_042271 |
| *Aneurinibacillus thermoaerophilus* | NR_029303 |
| *Anoxybacillus contaminans* | NR_029006 |
| *Anoxybacillus flavithermus* | NR_074667 |

TABLE 1-continued

Exemplary Bacterial Strains

| OTU | Public DB Accession |
|---|---|
| *Arcanobacterium haemolyticum* | NR_025347 |
| *Arcanobacterium pyogenes* | GU585578 |
| *Arcobacter butzleri* | AEPT01000071 |
| *Arcobacter cryaerophilus* | NR_025905 |
| *Arthrobacter agilis* | NR_026198 |
| *Arthrobacter arilaitensis* | NR_074608 |
| *Arthrobacter bergerei* | NR_025612 |
| *Arthrobacter globiformis* | NR_026187 |
| *Arthrobacter nicotianae* | NR_026190 |
| *Atopobium minutum* | HM007583 |
| *Atopobium parvulum* | CP001721 |
| *Atopobium rimae* | ACFE01000007 |
| *Atopobium* sp. BS2 | HQ616367 |
| *Atopobium* sp. F0209 | EU592966 |
| *Atopobium* sp. ICM42b10 | HQ616393 |
| *Atopobium* sp. ICM57 | HQ616400 |
| *Atopobium vaginae* | AEDQ01000024 |
| *Aurantimonas coralicida* | AY065627 |
| *Aureimonas altamirensis* | FN658986 |
| *Auritibacter ignavus* | FN554542 |
| *Averyella dalhousiensis* | DQ481464 |
| *Bacillus aeolius* | NR_025557 |
| *Bacillus aerophilus* | NR_042339 |
| *Bacillus aestuarii* | GQ980243 |
| *Bacillus alcalophilus* | X76436 |
| *Bacillus amyloliquefaciens* | NR_075005 |
| *Bacillus anthracis* | AAEN01000020 |
| *Bacillus atrophaeus* | NR_075016 |
| *Bacillus badius* | NR_036893 |
| *Bacillus cereus* | ABDJ01000015 |
| *Bacillus circulans* | AB271747 |
| *Bacillus clausii* | FN397477 |
| *Bacillus coagulans* | DQ297928 |
| *Bacillus firmus* | NR_025842 |
| *Bacillus flexus* | NR_024691 |
| *Bacillus fordii* | NR_025786 |
| *Bacillus gelatini* | NR_025595 |
| *Bacillus halmapalus* | NR_026144 |
| *Bacillus halodurans* | AY144582 |
| *Bacillus herbersteinensis* | NR_042286 |
| *Bacillus horti* | NR_036860 |
| *Bacillus idriensis* | NR_043268 |
| *Bacillus lentus* | NR_040792 |
| *Bacillus licheniformis* | NC_006270 |
| *Bacillus megaterium* | GU252124 |
| *Bacillus nealsonii* | NR_044546 |
| *Bacillus niabensis* | NR_043334 |
| *Bacillus niacini* | NR_024695 |
| *Bacillus pocheonensis* | NR_041377 |
| *Bacillus pumilus* | NR_074977 |
| *Bacillus safensis* | JQ624766 |
| *Bacillus simplex* | NR_042136 |
| *Bacillus sonorensis* | NR_025130 |
| *Bacillus* sp. 10403023 MM10403188 | CAET01000089 |
| *Bacillus* sp. 2_A_57_CT2 | ACWD01000095 |
| *Bacillus* sp. 2008724126 | GU252108 |
| *Bacillus* sp. 2008724139 | GU252111 |
| *Bacillus* sp. 7_16AIA | FN397518 |
| *Bacillus* sp. 9_3AIA | FN397519 |
| *Bacillus* sp. AP8 | JX101689 |
| *Bacillus* sp. B27(2008) | EU362173 |
| Bacillus sp. BT1B_CT2 | ACWC01000034 |
| *Bacillus* sp. GB1.1 | FJ897765 |
| *Bacillus* sp. GB9 | FJ897766 |
| *Bacillus* sp. HU19.1 | FJ897769 |
| *Bacillus* sp. HU29 | FJ897771 |
| *Bacillus* sp. HU33.1 | FJ897772 |
| *Bacillus* sp. JC6 | JF824800 |
| *Bacillus* sp. oral taxon F26 | HM099642 |
| *Bacillus* sp. oral taxon F28 | HM099650 |
| *Bacillus* sp. oral taxon F79 | HM099654 |
| *Bacillus* sp. SRC_DSF1 | GU797283 |
| *Bacillus* sp. SRC_DSF10 | GU797292 |
| *Bacillus* sp. SRC_DSF2 | GU797284 |
| *Bacillus* sp. SRC_DSF6 | GU797288 |
| *Bacillus* sp. tc09 | HQ844242 |
| *Bacillus* sp. zh168 | FJ851424 |
| *Bacillus sphaericus* | DQ286318 |
| *Bacillus sporothermodurans* | NR_026010 |
| *Bacillus subtilis* | EU627588 |
| *Bacillus thermoamylovorans* | NR_029151 |
| *Bacillus thuringiensis* | NC_008600 |
| *Bacillus weihenstephanensis* | NR_074926 |
| *Bacteroidales* bacterium ph8 | JN837494 |
| *Bacteroidales* genomosp. P1 | AY341819 |
| *Bacteroidales* genomosp. P2 oral clone MB1_G13 | DQ003613 |
| *Bacteroidales* genomosp. P3 oral clone MB1_G34 | DQ003615 |
| *Bacteroidales* genomosp. P4 oral clone MB2_G17 | DQ003617 |
| *Bacteroidales* genomosp. P5 oral clone MB2_P04 | DQ003619 |
| *Bacteroidales* genomosp. P6 oral clone MB3_C19 | DQ003634 |
| *Bacteroidales* genomosp. P7 oral clone MB3_P19 | DQ003623 |
| *Bacteroidales* genomosp. P8 oral clone MB4_G15 | DQ003626 |
| *Bacteroides acidifaciens* | NR_028607 |
| *Bacteroides barnesiae* | NR_041446 |
| *Bacteroides caccae* | EU136686 |
| *Bacteroides cellulosilyticus* | ACCH01000108 |
| *Bacteroides clarus* | AFBM01000011 |
| *Bacteroides coagulans* | AB547639 |
| *Bacteroides coprocola* | ABIY02000050 |
| *Bacteroides coprophilus* | ACBW01000012 |
| *Bacteroides dorei* | ABWZ01000093 |
| *Bacteroides eggerthii* | ACWG01000065 |
| *Bacteroides faecis* | GQ496624 |
| *Bacteroides finegoldii* | AB222699 |
| *Bacteroides fluxus* | AFBN01000029 |
| *Bacteroides fragilis* | AP006841 |
| *Bacteroides galacturonicus* | DQ497994 |
| *Bacteroides helcogenes* | CP002352 |
| *Bacteroides heparinolyticus* | JN867284 |
| *Bacteroides intestinalis* | ABJL02000006 |
| *Bacteroides massiliensis* | AB200226 |
| *Bacteroides nordii* | NR_043017 |
| *Bacteroides oleiciplenus* | AB547644 |
| *Bacteroides ovatus* | ACWH01000036 |
| *Bacteroides pectinophilus* | ABVQ01000036 |
| *Bacteroides plebeius* | AB200218 |
| *Bacteroides pyogenes* | NR_041280 |
| *Bacteroides salanitronis* | CP002530 |
| *Bacteroides salyersiae* | EU136690 |
| *Bacteroides* sp. 1_1_14 | ACRP01000155 |
| *Bacteroides* sp. 1_1_30 | ADCL01000128 |
| *Bacteroides* sp. 1_1_6 | ACIC01000215 |
| *Bacteroides* sp. 2_1_22 | ACPQ01000117 |
| *Bacteroides* sp. 2_1_56FAA | ACWI01000065 |
| *Bacteroides* sp. 2_2_4 | ABZZ01000168 |
| *Bacteroides* sp. 20_3 | ACRQ01000064 |
| *Bacteroides* sp. 3_1_19 | ADCJ01000062 |
| *Bacteroides* sp. 3_1_23 | ACRS01000081 |
| *Bacteroides* sp. 3_1_33FAA | ACPS01000085 |
| *Bacteroides* sp. 3_1_40A | ACRT01000136 |
| *Bacteroides* sp. 3_2_5 | ACIB01000079 |
| *Bacteroides* sp. 315_5 | FJ848547 |
| *Bacteroides* sp. 31SF15 | AJ583248 |
| *Bacteroides* sp. 31SF18 | AJ583249 |
| *Bacteroides* sp. 35AE31 | AJ583244 |
| *Bacteroides* sp. 35AE37 | AJ583245 |
| *Bacteroides* sp. 35BE34 | AJ583246 |
| *Bacteroides* sp. 35BE35 | AJ583247 |
| *Bacteroides* sp. 4_1_36 | ACTC01000133 |
| *Bacteroides* sp. 4_3_47FAA | ACDR02000029 |
| *Bacteroides* sp. 9_1_42FAA | ACAA01000096 |
| *Bacteroides* sp. AR20 | AF139524 |
| *Bacteroides* sp. AR29 | AF139525 |
| *Bacteroides* sp. B2 | EU722733 |
| *Bacteroides* sp. D1 | ACAB02000030 |

TABLE 1-continued

Exemplary Bacterial Strains

| OTU | Public DB Accession |
|---|---|
| *Bacteroides* sp. D2 | ACGA01000077 |
| *Bacteroides* sp. D20 | ACPT01000052 |
| *Bacteroides* sp. D22 | ADCK01000151 |
| *Bacteroides* sp. F_4 | AB470322 |
| *Bacteroides* sp. NB_8 | AB117565 |
| *Bacteroides* sp. WH2 | AY895180 |
| *Bacteroides* sp. XB12B | AM230648 |
| *Bacteroides* sp. XB44A | AM230649 |
| *Bacteroides stercoris* | ABFZ02000022 |
| *Bacteroides thetaiotaomicron* | NR_074277 |
| *Bacteroides uniformis* | AB050110 |
| *Bacteroides ureolyticus* | GQ167666 |
| *Bacteroides vulgatus* | CP000139 |
| *Bacteroides xylanisolvens* | ADKP01000087 |
| *Bacteroidetes* bacterium oral taxon D27 | HM099638 |
| *Bacteroidetes* bacterium oral taxon F31 | HM099643 |
| *Bacteroidetes* bacterium oral taxon F44 | HM099649 |
| *Barnesiella intestinihominis* | AB370251 |
| *Barnesiella viscericola* | NR_041508 |
| *Bartonella bacilliformis* | NC_008783 |
| Bartonella *grahamii* | CP001562 |
| *Bartonella henselae* | NC_005956 |
| *Bartonella quintana* | BX897700 |
| *Bartonella tamiae* | EF672728 |
| *Bartonella washoensis* | FJ719017 |
| *Bdellovibrio* sp. MPA | AY294215 |
| *Bifidobacteriaceae* genomosp. C1 | AY278612 |
| *Bifidobacterium adolescentis* | AAXD02000018 |
| *Bifidobacterium angulatum* | ABYS02000004 |
| *Bifidobacterium animalis* | CP001606 |
| *Bifidobacterium bifidum* | ABQP01000027 |
| *Bifidobacterium breve* | CP002743 |
| *Bifidobacterium catenulatum* | ABXY01000019 |
| *Bifidobacterium dentium* | CP001750 |
| *Bifidobacterium gallicum* | ABXB03000004 |
| *Bifidobacterium infantis* | AY151398 |
| *Bifidobacterium kashiwanohense* | AB491757 |
| *Bifidobacterium longum* | ABQQ01000041 |
| *Bifidobacterium pseudocatenulatum* | ABXX02000002 |
| *Bifidobacterium pseudolongum* | NR_043442 |
| *Bifidobacterium scardovii* | AJ307005 |
| *Bifidobacterium* sp. HM2 | AB425276 |
| *Bifidobacterium* sp. HMLN12 | JF519685 |
| *Bifidobacterium* sp. M45 | HM626176 |
| *Bifidobacterium* sp. MSX5B | HQ616382 |
| *Bifidobacterium* sp. TM_7 | AB218972 |
| *Bifidobacterium thermophilum* | DQ340557 |
| *Bifidobacterium urinalis* | AJ278695 |
| *Bilophila wadsworthia* | ADCP01000166 |
| *Bisgaard* Taxon | AY683487 |
| *Bisgaard* Taxon | AY683489 |
| *Bisgaard* Taxon | AY683491 |
| *Bisgaard* Taxon | AY683492 |
| *Blastomonas natatoria* | NR_040824 |
| *Blautia coccoides* | AB571656 |
| *Blautia glucerasea* | AB588023 |
| *Blautia glucerasei* | AB439724 |
| *Blautia hansenii* | ABYU02000037 |
| *Blautia hydrogenotrophica* | ACBZ01000217 |
| *Blautia luti* | AB691576 |
| *Blautia producta* | AB600998 |
| *Blautia schinkii* | NR_026312 |
| *Blautia* sp. M25 | HM626178 |
| *Blautia stercoris* | HM626177 |
| *Blautia wexlerae* | EF036467 |
| *Bordetella bronchiseptica* | NR_025949 |
| *Bordetella holmesii* | AB683187 |
| *Bordetella parapertussis* | NR_025950 |
| *Bordetella pertussis* | BX640418 |
| *Borrelia afzelii* | ABCU01000001 |
| *Borrelia burgdorferi* | ABGI01000001 |
| *Borrelia crocidurae* | DQ057990 |
| *Borrelia duttonii* | NC_011229 |
| *Borrelia garinii* | ABJV01000001 |
| *Borrelia hermsii* | AY597657 |
| *Borrelia hispanica* | DQ057988 |
| *Borrelia persica* | HM161645 |
| *Borrelia recurrentis* | AF107367 |
| *Borrelia* sp. NE49 | AJ224142 |
| *Borrelia spielmanii* | ABKB01000002 |
| *Borrelia turicatae* | NC_008710 |
| *Borrelia valaisiana* | ABCY01000002 |
| *Brachybacterium alimentarium* | NR_026269 |
| *Brachybacterium conglomeratum* | AB537169 |
| *Brachybacterium tyrofermentans* | NR_026272 |
| *Brachyspira aalborgi* | FM178386 |
| *Brachyspira pilosicoli* | NR_075069 |
| *Brachyspira* sp. HIS3 | FM178387 |
| *Brachyspira* sp. HIS4 | FM178388 |
| *Brachyspira* sp. HIS5 | FM178389 |
| *Brevibacillus agri* | NR_040983 |
| *Brevibacillus brevis* | NR_041524 |
| *Brevibacillus centrosporus* | NR_043414 |
| *Brevibacillus choshinensis* | NR_040980 |
| *Brevibacillus invocatus* | NR_041836 |
| *Brevibacillus laterosporus* | NR_037005 |
| *Brevibacillus parabrevis* | NR_040981 |
| *Brevibacillus reuszeri* | NR_040982 |
| *Brevibacillus* sp. phR | JN837488 |
| *Brevibacillus thermoruber* | NR_026514 |
| *Brevibacterium aurantiacum* | NR_044854 |
| *Brevibacterium casei* | JF951998 |
| *Brevibacterium epidermidis* | NR_029262 |
| *Brevibacterium frigoritolerans* | NR_042639 |
| *Brevibacterium linens* | AJ315491 |
| *Brevibacterium mcbrellneri* | ADNU01000076 |
| *Brevibacterium paucivorans* | EU086796 |
| *Brevibacterium sanguinis* | NR_028016 |
| *Brevibacterium* sp. H15 | AB177640 |
| *Brevibacterium* sp. JC43 | JF824806 |
| *Brevundimonas subvibrioides* | CP002102 |
| *Brucella abortus* | ACBJ01000075 |
| *Brucella canis* | NR_044652 |
| *Brucella ceti* | ACJD01000006 |
| *Brucella melitensis* | AE009462 |
| *Brucella microti* | NR_042549 |
| *Brucella ovis* | NC_009504 |
| *Brucella* sp. 83_13 | ACBQ01000040 |
| *Brucella* sp. BO1 | EU053207 |
| *Brucella suis* | ACBK01000034 |
| *Bryantella formatexigens* | ACCL02000018 |
| *Buchnera aphidicola* | NR_074609 |
| *Bulleidia extructa* | ADFR01000011 |
| *Burkholderia ambifaria* | AAUZ01000009 |
| *Burkholderia cenocepacia* | AAHI01000060 |
| *Burkholderia cepacia* | NR_041719 |
| *Burkholderia mallei* | CP000547 |
| *Burkholderia multivorans* | NC_010086 |
| *Burkholderia oklahomensis* | DQ108388 |
| *Burkholderia pseudomallei* | CP001408 |
| *Burkholderia rhizoxinica* | HQ005410 |
| *Burkholderia* sp. 383 | CP000151 |
| *Burkholderia xenovorans* | U86373 |
| *Burkholderiales* bacterium 1_1_47 | ADCQ01000066 |
| *Butyricicoccus pullicaecorum* | HH793440 |
| *Butyricimonas virosa* | AB443949 |
| *Butyrivibrio crossotus* | ABWN01000012 |
| *Butyrivibrio fibrisolvens* | U41172 |
| *Caldimonas manganoxidans* | NR_040787 |
| *Caminicella sporogenes* | NR_025485 |
| *Campylobacter coli* | AAFL01000004 |
| *Campylobacter concisus* | CP000792 |
| *Campylobacter curvus* | NC_009715 |
| Campylobacter *fetus* | ACLG01001177 |
| *Campylobacter gracilis* | ACYG01000026 |
| *Campylobacter hominis* | NC_009714 |
| *Campylobacter jejuni* | AL139074 |
| *Campylobacter lari* | CP000932 |
| *Campylobacter rectus* | ACFU01000050 |
| *Campylobacter showae* | ACVQ01000030 |
| *Campylobacter* sp. FOBRC14 | HQ616379 |
| *Campylobacter* sp. FOBRC15 | HQ616380 |

TABLE 1-continued

Exemplary Bacterial Strains

| OTU | Public DB Accession |
|---|---|
| Campylobacter sp. oral clone BB120 | AY005038 |
| Campylobacter sputorum | NR_044839 |
| Campylobacter upsaliensis | AEPU01000040 |
| Candidatus Arthromitus sp. SFB_mouse_Yit | NR_074460 |
| Candidatus Sulcia muelleri | CP002163 |
| Capnocytophaga canimorsus | CP002113 |
| Capnocytophaga genomosp. C1 | AY278613 |
| Capnocytophaga gingivalis | ACLQ01000011 |
| Capnocytophaga granulosa | X97248 |
| Capnocytophaga ochracea | AEOH01000054 |
| Capnocytophaga sp. GEJ8 | GU561335 |
| Capnocytophaga sp. oral clone AH015 | AY005074 |
| Capnocytophaga sp. oral clone ASCH05 | AY923149 |
| Capnocytophaga sp. oral clone ID062 | AY349368 |
| Capnocytophaga sp. oral strain A47ROY | AY005077 |
| Capnocytophaga sp. oral strain S3 | AY005073 |
| Capnocytophaga sp. oral taxon 338 | AEXX01000050 |
| Capnocytophaga sp. S1b | U42009 |
| Capnocytophaga sputigena | ABZV01000054 |
| Cardiobacterium hominis | ACKY01000036 |
| Cardiobacterium valvarum | NR_028847 |
| Carnobacterium divergens | NR_044706 |
| Carnobacterium maltaromaticum | NC_019425 |
| Catabacter hongkongensis | AB671763 |
| Catenibacterium mitsuokai | AB030224 |
| Catonella genomosp. P1 oral clone MB5_P12 | DQ003629 |
| Catonella morbi | ACIL02000016 |
| Catonella sp. oral clone FL037 | AY349369 |
| Cedecea davisae | AF493976 |
| Cellulosimicrobium funkei | AY501364 |
| Cetobacterium somerae | AJ438155 |
| Chlamydia muridarum | AE002160 |
| Chlamydia psittaci | NR_036864 |
| Chlamydia trachomatis | U68443 |
| Chlamydiales bacterium NS11 | JN606074 |
| Chlamydiales bacterium NS13 | JN606075 |
| Chlamydiales bacterium NS16 | JN606076 |
| Chlamydophila pecorum | D88317 |
| Chlamydophila pneumoniae | NC_002179 |
| Chlamydophila psittaci | D85712 |
| Chloroflexi genomosp. P1 | AY331414 |
| Christensenella minuta | AB490809 |
| Chromobacterium violaceum | NC_005085 |
| Chryseobacterium anthropi | AM982793 |
| Chryseobacterium gleum | ACKQ02000003 |
| Chryseobacterium hominis | NR_042517 |
| Citrobacter amalonaticus | FR870441 |
| Citrobacter braakii | NR_028687 |
| Citrobacter farmeri | AF025371 |
| Citrobacter freundii | NR_028894 |
| Citrobacter gillenii | AF025367 |
| Citrobacter koseri | NC_009792 |
| Citrobacter murliniae | AF025369 |
| Citrobacter rodentium | NR_074903 |
| Citrobacter sedlakii | AF025364 |
| Citrobacter sp. 30_2 | ACDJ01000053 |
| Citrobacter sp. KMSI_3 | GQ468398 |
| Citrobacter werkmanii | AF025373 |
| Citrobacter youngae | ABWL02000011 |
| Cloacibacillus evryensis | GQ258966 |
| Clostridiaceae bacterium END_2 | EF451053 |
| Clostridiaceae bacterium JC13 | JF824807 |
| Clostridiales bacterium 1_7_47FAA | ABQR01000074 |
| Clostridiales bacterium 9400853 | HM587320 |
| Clostridiales bacterium 9403326 | HM587324 |
| Clostridiales bacterium oral clone P4PA_66 P1 | AY207065 |
| Clostridiales bacterium oral taxon 093 | GQ422712 |
| Clostridiales bacterium oral taxon F32 | HM099644 |
| Clostridiales bacterium ph2 | JN837487 |
| Clostridiales bacterium SY8519 | AB477431 |
| Clostridiales genomosp. BVAB3 | CP001850 |
| Clostridiales sp. SM4_1 | FP929060 |
| Clostridiales sp. SS3_4 | AY305316 |
| Clostridiales sp. SSC_2 | FP929061 |
| Clostridium acetobutylicum | NR_074511 |
| Clostridium aerotolerans | X76163 |
| Clostridium aldenense | NR_043680 |
| Clostridium aldrichii | NR_026099 |
| Clostridium algidicarnis | NR_041746 |
| Clostridium algidixylanolyticum | NR_028726 |
| Clostridium aminovalericum | NR_029245 |
| Clostridium amygdalinum | AY353957 |
| Clostridium argentinense | NR_029232 |
| Clostridium asparagiforme | ACCJ01000522 |
| Clostridium baratii | NR_029229 |
| Clostridium bartlettii | ABEZ02000012 |
| Clostridium beijerinckii | NR_074434 |
| Clostridium bifermentans | X73437 |
| Clostridium bolteae | ABCC02000039 |
| Clostridium botulinum | NC_010723 |
| Clostridium butyricum | ABDT01000017 |
| Clostridium cadaveris | AB542932 |
| Clostridium carboxidivorans | FR733710 |
| Clostridium carnis | NR_044716 |
| Clostridium celatum | X77844 |
| Clostridium celerecrescens | JQ246092 |
| Clostridium cellulosi | NR_044624 |
| Clostridium chauvoei | EU106372 |
| Clostridium citroniae | ADLJ01000059 |
| Clostridium clariflavum | NR_041235 |
| Clostridium clostridiiformes | M59089 |
| Clostridium clostridioforme | NR_044715 |
| Clostridium coccoides | EF025906 |
| Clostridium cochlearium | NR_044717 |
| Clostridium cocleatum | NR_026495 |
| Clostridium colicanis | FJ957863 |
| Clostridium colinum | NR_026151 |
| Clostridium difficile | NC_013315 |
| Clostridium disporicum | NR_026491 |
| Clostridium estertheticum | NR_042153 |
| Clostridium fallax | NR_044714 |
| Clostridium favososporum | X76749 |
| Clostridium felsineum | AF270502 |
| Clostridium frigidicarnis | NR_024919 |
| Clostridium gasigenes | NR_024945 |
| Clostridium ghonii | AB542933 |
| Clostridium glycolicum | FJ384385 |
| Clostridium glycyrrhizinilyticum | AB233029 |
| Clostridium haemolyticum | NR_024749 |
| Clostridium hathewayi | AY552788 |
| Clostridium hiranonis | AB023970 |
| Clostridium histolyticum | HF558362 |
| Clostridium hylemonae | AB023973 |
| Clostridium indolis | AF028351 |
| Clostridium innocuum | M23732 |
| Clostridium irregulare | NR_029249 |
| Clostridium isatidis | NR_026347 |
| Clostridium kluyveri | NR_074165 |
| Clostridium lactatifermentans | NR_025651 |
| Clostridium lavalense | EF564277 |
| Clostridium leptum | AJ305238 |
| Clostridium limosum | FR870444 |
| Clostridium magnum | X77835 |
| Clostridium malenominatum | FR749893 |
| Clostridium mayombei | FR733682 |
| Clostridium methylpentosum | ACEC01000059 |
| Clostridium nexile | X73443 |
| Clostridium novyi | NR_074343 |
| Clostridium orbiscindens | Y18187 |
| Clostridium oroticum | FR749922 |
| Clostridium paraputrificum | AB536771 |
| Clostridium perfringens | ABDW01000023 |
| Clostridium phytofermentans | NR_074652 |
| Clostridium piliforme | D14639 |
| Clostridium putrefaciens | NR_024995 |
| Clostridium quinii | NR_026149 |
| Clostridium ramosum | M23731 |
| Clostridium rectum | NR_029271 |
| Clostridium saccharogumia | DQ100445 |
| Clostridium saccharolyticum | CP002109 |
| Clostridium sardiniense | NR_041006 |
| Clostridium sartagoforme | NR_026490 |

TABLE 1-continued

Exemplary Bacterial Strains

| OTU | Public DB Accession |
|---|---|
| Clostridium scindens | AF262238 |
| Clostridium septicum | NR_026020 |
| Clostridium sordellii | AB448946 |
| Clostridium sp. 7_2_43FAA | ACDK01000101 |
| Clostridium sp. D5 | ADBG01000142 |
| Clostridium sp. HGF2 | AENW01000022 |
| Clostridium sp. HPB_46 | AY862516 |
| Clostridium sp. JC122 | CAEV01000127 |
| Clostridium sp. L2_50 | AAYW02000018 |
| Clostridium sp. LMG 16094 | X95274 |
| Clostridium sp. M62_1 | ACFX02000046 |
| Clostridium sp. MLG055 | AF304435 |
| Clostridium sp. MT4 E | FJ159523 |
| Clostridium sp. NMBHI_1 | JN093130 |
| Clostridium sp. NML 04A032 | EU815224 |
| Clostridium sp. SS2_1 | ABGC03000041 |
| Clostridium sp. SY8519 | AP012212 |
| Clostridium sp. TM_40 | AB249652 |
| Clostridium sp. YIT 12069 | AB491207 |
| Clostridium sp. YIT 12070 | AB491208 |
| Clostridium sphenoides | X73449 |
| Clostridium spiroforme | X73441 |
| Clostridium sporogenes | ABKW02000003 |
| Clostridium sporosphaeroides | NR_044835 |
| Clostridium stercorarium | NR_025100 |
| Clostridium sticklandii | L04167 |
| Clostridium straminisolvens | NR_024829 |
| Clostridium subterminale | NR_041795 |
| Clostridium sulfidigenes | NR_044161 |
| Clostridium symbiosum | ADLQ01000114 |
| Clostridium tertium | Y18174 |
| Clostridium tetani | NC_004557 |
| Clostridium thermocellum | NR_074629 |
| Clostridium tyrobutyricum | NR_044718 |
| Clostridium viride | NR_026204 |
| Clostridium xylanolyticum | NR_037068 |
| Collinsella aerofaciens | AAVN02000007 |
| Collinsella intestinalis | ABXH02000037 |
| Collinsella stercoris | ABXJ01000150 |
| Collinsella tanakaei | AB490807 |
| Comamonadaceae bacterium NML000135 | JN585335 |
| Comamonadaceae bacterium NML790751 | JN585331 |
| Comamonadaceae bacterium NML910035 | JN585332 |
| Comamonadaceae bacterium NML910036 | JN585333 |
| Comamonadaceae bacterium oral taxon F47 | HM099651 |
| Comamonas sp. NSP5 | AB076850 |
| Conchiformibius kuhniae | NR_041821 |
| Coprobacillus cateniformis | AB030218 |
| Coprobacillus sp. 29_1 | ADKX01000057 |
| Coprobacillus sp. D7 | ACDT01000199 |
| Coprococcus catus | EU266552 |
| Coprococcus comes | ABVR01000038 |
| Coprococcus eutactus | EF031543 |
| Coprococcus sp. ART55_1 | AY350746 |
| Coriobacteriaceae bacterium BV3Ac1 | JN809768 |
| Coriobacteriaceae bacterium JC110 | CAEM01000062 |
| Coriobacteriaceae bacterium phI | JN837493 |
| Corynebacterium accolens | ACGD01000048 |
| Corynebacterium ammoniagenes | ADNS01000011 |
| Corynebacterium amycolatum | ABZU01000033 |
| Corynebacterium appendicis | NR_028951 |
| Corynebacterium argentoratense | EF463055 |
| Corynebacterium atypicum | NR_025540 |
| Corynebacterium aurimucosum | ACLH01000041 |
| Corynebacterium bovis | AF537590 |
| Corynebacterium canis | GQ871934 |
| Corynebacterium casei | NR_025101 |
| Corynebacterium confusum | Y15886 |
| Corynebacterium coyleae | X96497 |
| Corynebacterium diphtheriae | NC_002935 |
| Corynebacterium durum | Z97069 |
| Corynebacterium efficiens | ACLI01000121 |
| Corynebacterium falsenii | Y13024 |
| Corynebacterium flavescens | NR_037040 |
| Corynebacterium genitalium | ACLJ01000031 |
| Corynebacterium glaucum | NR_028971 |
| Corynebacterium glucuronolyticum | ABYP01000081 |
| Corynebacterium glutamicum | BA000036 |
| Corynebacterium hansenii | AM946639 |
| Corynebacterium imitans | AF537597 |
| Corynebacterium jeikeium | ACYW01000001 |
| Corynebacterium kroppenstedtii | NR_026380 |
| Corynebacterium lipophiloflavum | ACHJ01000075 |
| Corynebacterium macginleyi | AB359393 |
| Corynebacterium mastitidis | AB359395 |
| Corynebacterium matruchotii | ACSH02000003 |
| Corynebacterium minutissimum | X82064 |
| Corynebacterium mucifaciens | NR_026396 |
| Corynebacterium propinquum | NR_037038 |
| Corynebacterium pseudodiphtheriticum | X84258 |
| Corynebacterium pseudogenitalium | ABYQ01000237 |
| Corynebacterium pseudotuberculosis | NR_037070 |
| Corynebacterium pyruviciproducens | FJ185225 |
| Corynebacterium renale | NR_037069 |
| Corynebacterium resistens | ADGN01000058 |
| Corynebacterium riegelii | EU848548 |
| Corynebacterium simulans | AF537604 |
| Corynebacterium singulare | NR_026394 |
| Corynebacterium sp. 1 ex sheep | Y13427 |
| Corynebacterium sp. L_2012475 | HE575405 |
| Corynebacterium sp. NML 93_0481 | GU238409 |
| Corynebacterium sp. NML 97_0186 | GU238411 |
| Corynebacterium sp. NML 99_0018 | GU238413 |
| Corynebacterium striatum | ACGE01000001 |
| Corynebacterium sundsvallense | Y09655 |
| Corynebacterium tuberculostearicum | ACVP01000009 |
| Corynebacterium tuscaniae | AY677186 |
| Corynebacterium ulcerans | NR_074467 |
| Corynebacterium urealyticum | X81913 |
| Corynebacterium ureicelerivorans | AM397636 |
| Corynebacterium variabile | NR_025314 |
| Corynebacterium xerosis | FN179330 |
| Coxiella burnetii | CP000890 |
| Cronobacter malonaticus | GU122174 |
| Cronobacter sakazakii | NC_009778 |
| Cronobacter turicensis | FN543093 |
| Cryptobacterium curtum | GQ422741 |
| Cupriavidus metallidurans | GU230889 |
| Cytophaga xylanolytica | FR733683 |
| Deferribacteres sp. oral clone JV001 | AY349370 |
| Deferribacteres sp. oral clone JV006 | AY349371 |
| Deferribacteres sp. oral clone JV023 | AY349372 |
| Deinococcus radiodurans | AE000513 |
| Deinococcus sp. R_43890 | FR682752 |
| Delftia acidovorans | CP000884 |
| Dermabacter hominis | FJ263375 |
| Dermacoccus sp. Ellin185 | AEIQ01000090 |
| Desmospora activa | AM940019 |
| Desmospora sp. 8437 | AFHT01000143 |
| Desulfitobacterium frappieri | AJ276701 |
| Desulfitobacterium hafniense | NR_074996 |
| Desulfobulbus sp. oral clone CH031 | AY005036 |
| Desulfotomaculum nigrificans | NR_044832 |
| Desulfovibrio desulfuricans | DQ092636 |
| Desulfovibrio fairfieldensis | U42221 |
| Desulfovibrio piger | AF192152 |
| Desulfovibrio sp. 3_1_syn3 | ADDR01000239 |
| Desulfovibrio vulgaris | NR_074897 |
| Dialister invisus | ACIM02000001 |
| Dialister micraerophilus | AFBB01000028 |
| Dialister microaerophilus | AENT01000008 |
| Dialister pneumosintes | HM596297 |
| Dialister propionicifaciens | NR_043231 |
| Dialister sp. oral taxon 502 | GQ422739 |
| Dialister succinatiphilus | AB370249 |
| Dietzia natronolimnaea | GQ870426 |
| Dietzia sp. BBDP51 | DQ337512 |
| Dietzia sp. CA149 | GQ870422 |
| Dietzia timorensis | GQ870424 |
| Dorea formicigenerans | AAXA02000006 |
| Dorea longicatena | AJ132842 |
| Dysgonomonas gadei | ADLV01000001 |

TABLE 1-continued

Exemplary Bacterial Strains

| OTU | Public DB Accession |
|---|---|
| Dysgonomonas mossii | ADLW01000023 |
| Edwardsiella tarda | CP002154 |
| Eggerthella lenta | AF292375 |
| Eggerthella sinensis | AY321958 |
| Eggerthella sp. 1_3_56FAA | ACWN01000099 |
| Eggerthella sp. HGA1 | AEXR01000021 |
| Eggerthella sp. YY7918 | AP012211 |
| Ehrlichia chaffeensis | AAIF01000035 |
| Eikenella corrodens | ACEA01000028 |
| Enhydrobacter aerosaccus | ACYI01000081 |
| Enterobacter aerogenes | AJ251468 |
| Enterobacter asburiae | NR_024640 |
| Enterobacter cancerogenus | Z96078 |
| Enterobacter cloacae | FP929040 |
| Enterobacter cowanii | NR_025566 |
| Enterobacter hormaechei | AFHR01000079 |
| Enterobacter sp. 247BMC | HQ122932 |
| Enterobacter sp. 638 | NR_074777 |
| Enterobacter sp. JC163 | JN657217 |
| Enterobacter sp. SCSS | HM007811 |
| Enterobacter sp. TSE38 | HM156134 |
| Enterobacteriaceae bacterium 9_2_54FAA | ADCU01000033 |
| Enterobacteriaceae bacterium CF01Ent_1 | AJ489826 |
| Enterobacteriaceae bacterium Smarlab 3302238 | AY538694 |
| Enterococcus avium | AF133535 |
| Enterococcus caccae | AY943820 |
| Enterococcus casseliflavus | AEWT01000047 |
| Enterococcus durans | AJ276354 |
| Enterococcus faecalis | AE016830 |
| Enterococcus faecium | AM157434 |
| Enterococcus gallinarum | AB269767 |
| Enterococcus gilvus | AY033814 |
| Enterococcus hawaiiensis | AY321377 |
| Enterococcus hirae | AF061011 |
| Enterococcus italicus | AEPV01000109 |
| Enterococcus mundtii | NR_024906 |
| Enterococcus raffinosus | FN600541 |
| Enterococcus sp. BV2CASA2 | JN809766 |
| Enterococcus sp. CCRI_16620 | GU457263 |
| Enterococcus sp. F95 | FJ463817 |
| Enterococcus sp. RfL6 | AJ133478 |
| Enterococcus thailandicus | AY321376 |
| Eremococcus coleocola | AENN01000008 |
| Erysipelothrix inopinata | NR_025594 |
| Erysipelothrix rhusiopathiae | ACLK01000021 |
| Erysipelothrix tonsillarum | NR_040871 |
| Erysipelotrichaceae bacterium 3_1_53 | ACTJ01000113 |
| Erysipelotrichaceae bacterium 5_2_54FAA | ACZW01000054 |
| Escherichia albertii | ABKX01000012 |
| Escherichia coli | NC_008563 |
| Escherichia fergusonii | CU928158 |
| Escherichia hermannii | HQ407266 |
| Escherichia sp. 1_1_43 | ACID01000033 |
| Escherichia sp. 4_1_40B | ACDM02000056 |
| Escherichia sp. B4 | EU722735 |
| Escherichia vulneris | NR_041927 |
| Ethanoligenens harbinense | AY675965 |
| Eubacteriaceae bacterium P4P_50 P4 | AY207060 |
| Eubacterium barkeri | NR_044661 |
| Eubacterium biforme | ABYT01000002 |
| Eubacterium brachy | U13038 |
| Eubacterium budayi | NR_024682 |
| Eubacterium callanderi | NR_026330 |
| Eubacterium cellulosolvens | AY178842 |
| Eubacterium contortum | FR749946 |
| Eubacterium coprostanoligenes | HM037995 |
| Eubacterium cylindroides | FP929041 |
| Eubacterium desmolans | NR_044644 |
| Eubacterium dolichum | L34682 |
| Eubacterium eligens | CP001104 |
| Eubacterium fissicatena | FR749935 |
| Eubacterium hadrum | FR749933 |
| Eubacterium hallii | L34621 |
| Eubacterium infirmum | U13039 |
| Eubacterium limosum | CP002273 |
| Eubacterium moniliforme | HF558373 |
| Eubacterium multiforme | NR_024683 |
| Eubacterium nitritogenes | NR_024684 |
| Eubacterium nodatum | U13041 |
| Eubacterium ramulus | AJ011522 |
| Eubacterium rectale | FP929042 |
| Eubacterium ruminantium | NR_024661 |
| Eubacterium saburreum | AB525414 |
| Eubacterium saphenum | NR_026031 |
| Eubacterium siraeum | ABCA03000054 |
| Eubacterium sp. 3_1_31 | ACTL01000045 |
| Eubacterium sp. AS15b | HQ616364 |
| Eubacterium sp. OBRC9 | HQ616354 |
| Eubacterium sp. oral clone GI038 | AY349374 |
| Eubacterium sp. oral clone IR009 | AY349376 |
| Eubacterium sp. oral clone JH012 | AY349373 |
| Eubacterium sp. oral clone JI012 | AY349379 |
| Eubacterium sp. oral clone JN088 | AY349377 |
| Eubacterium sp. oral clone JS001 | AY349378 |
| Eubacterium sp. oral clone OH3A | AY947497 |
| Eubacterium sp. WAL 14571 | FJ687606 |
| Eubacterium tenue | M59118 |
| Eubacterium tortuosum | NR_044648 |
| Eubacterium ventriosum | L34421 |
| Eubacterium xylanophilum | L34628 |
| Eubacterium yurii | AEES01000073 |
| Ewingella americana | JN175329 |
| Exiguobacterium acetylicum | FJ970034 |
| Facklamia hominis | Y10772 |
| Faecalibacterium prausnitzii | ACOP02000011 |
| Filifactor alocis | CP002390 |
| Filifactor villosus | NR_041928 |
| Finegoldia magna | ACHM02000001 |
| Flavobacteriaceae genomosp. C1 | AY278614 |
| Flavobacterium sp. NF2_1 | FJ195988 |
| Flavonifractor plautii | AY724678 |
| Flexispira rappini | AY126479 |
| Flexistipes sinusarabici | NR_074881 |
| Francisella novicida | ABSS01000002 |
| Francisella philomiragia | AY928394 |
| Francisella tularensis | ABAZ01000082 |
| Fulvimonas sp. NML 060897 | EF589680 |
| Fusobacterium canifelinum | AY162222 |
| Fusobacterium genomosp. C1 | AY278616 |
| Fusobacterium genomosp. C2 | AY278617 |
| Fusobacterium gonidiaformans | ACET01000043 |
| Fusobacterium mortiferum | ACDB02000034 |
| Fusobacterium naviforme | HQ223106 |
| Fusobacterium necrogenes | X55408 |
| Fusobacterium necrophorum | AM905356 |
| Fusobacterium nucleatum | ADVK01000034 |
| Fusobacterium periodonticum | ACJY01000002 |
| Fusobacterium russii | NR_044687 |
| Fusobacterium sp. 1_1_41FAA | ADGG01000053 |
| Fusobacterium sp. 11_3_2 | ACUO01000052 |
| Fusobacterium sp. 12_1B | AGWJ01000070 |
| Fusobacterium sp. 2_1_31 | ACDC02000018 |
| Fusobacterium sp. 3_1_27 | ADGF01000045 |
| Fusobacterium sp. 3_1_33 | ACQE01000178 |
| Fusobacterium sp. 3_1_36A2 | ACPU01000044 |
| Fusobacterium sp. 3_1_5R | ACDD01000078 |
| Fusobacterium sp. AC18 | HQ616357 |
| Fusobacterium sp. ACB2 | HQ616358 |
| Fusobacterium sp. AS2 | HQ616361 |
| Fusobacterium sp. CM1 | HQ616371 |
| Fusobacterium sp. CM21 | HQ616375 |
| Fusobacterium sp. CM22 | HQ616376 |
| Fusobacterium sp. D12 | ACDG02000036 |
| Fusobacterium sp. oral clone ASCF06 | AY923141 |
| Fusobacterium sp. oral clone ASCF11 | AY953256 |
| Fusobacterium ulcerans | ACDH01000090 |
| Fusobacterium varium | ACIE01000009 |
| Gardnerella vaginalis | CP001849 |
| Gemella haemolysans | ACDZ02000012 |
| Gemella morbillorum | NR_025904 |
| Gemella morbillorum | ACRX01000010 |
| Gemella sanguinis | ACRY01000057 |

TABLE 1-continued

Exemplary Bacterial Strains

| OTU | Public DB Accession |
|---|---|
| *Gemella* sp. oral clone ASCE02 | AY923133 |
| *Gemella* sp. oral clone ASCF04 | AY923139 |
| *Gemella* sp. oral clone ASCF12 | AY923143 |
| *Gemella* sp. WAL 1945J | EU427463 |
| *Gemmiger formicilis* | GU562446 |
| *Geobacillus kaustophilus* | NR_074989 |
| *Geobacillus* sp. E263 | DQ647387 |
| *Geobacillus* sp. WCH70 | CP001638 |
| *Geobacillus stearothermophilus* | NR_040794 |
| *Geobacillus thermocatenulatus* | NR_043020 |
| *Geobacillus thermodenitrificans* | NR_074976 |
| *Geobacillus thermoglucosidasius* | NR_043022 |
| *Geobacillus thermoleovorans* | NR_074931 |
| *Geobacter bemidjiensis* | CP001124 |
| *Gloeobacter violaceus* | NR_074282 |
| *Gluconacetobacter azotocaptans* | NR_028767 |
| *Gluconacetobacter diazotrophicus* | NR_074292 |
| *Gluconacetobacter entanii* | NR_028909 |
| *Gluconacetobacter europaeus* | NR_026513 |
| *Gluconacetobacter hansenii* | NR_026133 |
| *Gluconacetobacter johannae* | NR_024959 |
| *Gluconacetobacter oboediens* | NR_041295 |
| *Gluconacetobacter xylinus* | NR_074338 |
| *Gordonia bronchialis* | NR_027594 |
| *Gordonia polyisoprenivorans* | DQ385609 |
| *Gordonia* sp. KTR9 | DQ068383 |
| *Gordonia sputi* | FJ536304 |
| *Gordonia terrae* | GQ848239 |
| *Gordonibacter pamelaeae* | AM886059 |
| *Gordonibacter pamelaeae* | FP929047 |
| *Gracilibacter thermotolerans* | NR_043559 |
| *Gramella forsetii* | NR_074707 |
| *Granulicatella adiacens* | ACKZ01000002 |
| *Granulicatella elegans* | AB252689 |
| *Granulicatella paradiacens* | AY879298 |
| *Granulicatella* sp. M658_99_3 | AJ271861 |
| *Granulicatella* sp. oral clone ASC02 | AY923126 |
| *Granulicatella* sp. oral clone ASCA05 | DQ341469 |
| *Granulicatella* sp. oral clone ASCB09 | AY953251 |
| *Granulicatella* sp. oral clone ASCG05 | AY923146 |
| *Grimontia hollisae* | ADAQ01000013 |
| *Haematobacter* sp. BC14248 | GU396991 |
| *Haemophilus aegyptius* | AFBC01000053 |
| *Haemophilus ducreyi* | AE017143 |
| *Haemophilus* genomosp. P2 oral clone MB3_C24 | DQ003621 |
| *Haemophilus* genomosp. P3 oral clone MB3_C38 | DQ003635 |
| *Haemophilus haemolyticus* | JN175335 |
| *Haemophilus influenzae* | AADP01000001 |
| *Haemophilus parahaemolyticus* | GU561425 |
| *Haemophilus parainfluenzae* | AEWU01000024 |
| *Haemophilus paraphrophaemolyticus* | M75076 |
| *Haemophilus parasuis* | GU226366 |
| *Haemophilus somnus* | NC_008309 |
| *Haemophilus* sp. 70334 | HQ680854 |
| *Haemophilus* sp. HK445 | FJ685624 |
| *Haemophilus* sp. oral clone ASCA07 | AY923117 |
| *Haemophilus* sp. oral clone ASCG06 | AY923147 |
| *Haemophilus* sp. oral clone BJ021 | AY005034 |
| *Haemophilus* sp. oral clone BJ095 | AY005033 |
| *Haemophilus* sp. oral clone JM053 | AY349380 |
| *Haemophilus* sp. oral taxon 851 | AGRK01000004 |
| *Haemophilus sputorum* | AFNK01000005 |
| *Hafnia alvei* | DQ412565 |
| *Halomonas elongata* | NR_074782 |
| *Halomonas johnsoniae* | FR775979 |
| *Halorubrum lipolyticum* | AB477978 |
| *Helicobacter bilis* | ACDN01000023 |
| *Helicobacter canadensis* | ABQS01000108 |
| *Helicobacter cinaedi* | ABQT01000054 |
| *Helicobacter pullorum* | ABQU01000097 |
| *Helicobacter pylori* | CP000012 |
| *Helicobacter* sp. None | U44756 |
| *Helicobacter winghamensis* | ACDO01000013 |
| *Heliobacterium modesticaldum* | NR_074517 |
| *Herbaspirillum seropedicae* | CP002039 |
| *Herbaspirillum* sp. JC206 | JN657219 |
| *Histophilus somni* | AF549387 |
| *Holdemania filiformis* | Y11466 |
| *Hydrogenoanaerobacterium saccharovorans* | NR_044425 |
| *Hyperthermus butylicus* | CP000493 |
| *Hyphomicrobium sulfonivorans* | AY468372 |
| *Hyphomonas neptunium* | NR_074092 |
| *Ignatzschineria indica* | HQ823562 |
| *Ignatzschineria* sp. NML 95_0260 | HQ823559 |
| *Ignicoccus islandicus* | X99562 |
| *Inquilinus limosus* | NR_029046 |
| *Janibacter limosus* | NR_026362 |
| *Janibacter melonis* | EF063716 |
| *Janthinobacterium* sp. SY12 | EF455530 |
| *Johnsonella ignava* | X87152 |
| *Jonquetella anthropi* | ACOO02000004 |
| *Kerstersia gyiorum* | NR_025669 |
| *Kingella denitrificans* | AEWV01000047 |
| *Kingella* genomosp. P1 oral cone MB2_C20 | DQ003616 |
| *Kingella kingae* | AFHS01000073 |
| *Kingella oralis* | ACJW02000005 |
| *Kingella* sp. oral clone ID059 | AY349381 |
| *Klebsiella oxytoca* | AY292871 |
| *Klebsiella pneumoniae* | CP000647 |
| *Klebsiella* sp. AS10 | HQ616362 |
| *Klebsiella* sp. Co9935 | DQ068764 |
| *Klebsiella* sp. enrichment culture clone SRC_DSD25 | HM195210 |
| *Klebsiella* sp. OBRC7 | HQ616353 |
| *Klebsiella* sp. SP_BA | FJ999767 |
| *Klebsiella* sp. SRC_DSD1 | GU797254 |
| *Klebsiella* sp. SRC_DSD11 | GU797263 |
| *Klebsiella* sp. SRC_DSD12 | GU797264 |
| *Klebsiella* sp. SRC_DSD15 | GU797267 |
| *Klebsiella* sp. SRC_DSD2 | GU797253 |
| *Klebsiella* sp. SRC_DSD6 | GU797258 |
| *Klebsiella variicola* | CP001891 |
| *Kluyvera ascorbata* | NR_028677 |
| *Kluyvera cryocrescens* | NR_028803 |
| *Kocuria marina* | GQ260086 |
| *Kocuria palustris* | EU333884 |
| *Kocuria rhizophila* | AY030315 |
| *Kocuria rosea* | X87756 |
| *Kocuria varians* | AF542074 |
| *Lachnobacterium bovis* | GU324407 |
| *Lachnospira multipara* | FR733699 |
| *Lachnospira pectinoschiza* | L14675 |
| *Lachnospiraceae* bacterium 1_1_57FAA | ACTM01000065 |
| *Lachnospiraceae* bacterium 1_4_56FAA | ACTN01000028 |
| *Lachnospiraceae* bacterium 2_1_46FAA | ADLB01000035 |
| *Lachnospiraceae* bacterium 2_1_58FAA | ACTO01000052 |
| *Lachnospiraceae* bacterium 3_1_57FAA_CT1 | ACTP01000124 |
| *Lachnospiraceae* bacterium 4_1_37FAA | ADCR01000030 |
| *Lachnospiraceae* bacterium 5_1_57FAA | ACTR01000020 |
| *Lachnospiraceae* bacterium 5_1_63FAA | ACTS01000081 |
| *Lachnospiraceae* bacterium 6_1_63FAA | ACTV01000014 |
| *Lachnospiraceae* bacterium 8_1_57FAA | ACWQ01000079 |
| *Lachnospiraceae* bacterium 9_1_43BFAA | ACTX01000023 |
| *Lachnospiraceae* bacterium A4 | DQ789118 |
| *Lachnospiraceae* bacterium DJF VP30 | EU728771 |
| *Lachnospiraceae* bacterium ICM62 | HQ616401 |
| *Lachnospiraceae* bacterium MSX33 | HQ616384 |
| *Lachnospiraceae* bacterium oral taxon 107 | ADDS01000069 |
| *Lachnospiraceae* bacterium oral taxon F15 | HM099641 |
| *Lachnospiraceae* genomosp. C1 | AY278618 |
| *Lactobacillus acidipiscis* | NR_024718 |
| *Lactobacillus acidophilus* | CP000033 |
| *Lactobacillus alimentarius* | NR_044701 |
| *Lactobacillus amylolyticus* | ADNY01000006 |
| *Lactobacillus amylovorus* | CP002338 |
| *Lactobacillus antri* | ACLL01000037 |
| *Lactobacillus brevis* | EU194349 |
| *Lactobacillus buchneri* | ACGH01000101 |
| *Lactobacillus casei* | CP000423 |
| *Lactobacillus catenaformis* | M23729 |

TABLE 1-continued

Exemplary Bacterial Strains

| OTU | Public DB Accession |
|---|---|
| *Lactobacillus coleohominis* | ACOH01000030 |
| *Lactobacillus coryniformis* | NR_044705 |
| *Lactobacillus crispatus* | ACOG01000151 |
| *Lactobacillus curvatus* | NR_042437 |
| *Lactobacillus delbrueckii* | CP002341 |
| *Lactobacillus dextrinicus* | NR_036861 |
| *Lactobacillus farciminis* | NR_044707 |
| *Lactobacillus fermentum* | CP002033 |
| *Lactobacillus gasseri* | ACOZ01000018 |
| *Lactobacillus gastricus* | AICN01000060 |
| *Lactobacillus* genomosp. C1 | AY278619 |
| *Lactobacillus* genomosp. C2 | AY278620 |
| *Lactobacillus helveticus* | ACLM01000202 |
| *Lactobacillus hilgardii* | ACGP01000200 |
| *Lactobacillus hominis* | FR681902 |
| *Lactobacillus iners* | AEKJ01000002 |
| *Lactobacillus jensenii* | ACQD01000066 |
| *Lactobacillus johnsonii* | AE017198 |
| *Lactobacillus kalixensis* | NR_029083 |
| *Lactobacillus kefiranofaciens* | NR_042440 |
| *Lactobacillus kefiri* | NR_042230 |
| *Lactobacillus kimchii* | NR_025045 |
| *Lactobacillus leichmannii* | JX986966 |
| *Lactobacillus mucosae* | FR693800 |
| *Lactobacillus murinus* | NR_042231 |
| *Lactobacillus nodensis* | NR_041629 |
| *Lactobacillus oeni* | NR_043095 |
| *Lactobacillus oris* | AEKL01000077 |
| *Lactobacillus parabrevis* | NR_042456 |
| *Lactobacillus parabuchneri* | NR_041294 |
| *Lactobacillus paracasei* | ABQV01000067 |
| *Lactobacillus parakefiri* | NR_029039 |
| *Lactobacillus pentosus* | JN813103 |
| *Lactobacillus perolens* | NR_029360 |
| *Lactobacillus plantarum* | ACGZ02000033 |
| *Lactobacillus pontis* | HM218420 |
| *Lactobacillus reuteri* | ACGW02000012 |
| *Lactobacillus rhamnosus* | ABWJ01000068 |
| *Lactobacillus rogosae* | GU269544 |
| *Lactobacillus ruminis* | ACGS02000043 |
| *Lactobacillus sakei* | DQ989236 |
| *Lactobacillus salivarius* | AEBA01000145 |
| *Lactobacillus saniviri* | AB602569 |
| *Lactobacillus senioris* | AB602570 |
| *Lactobacillus* sp. 66c | FR681900 |
| *Lactobacillus* sp. BT6 | HQ616370 |
| *Lactobacillus* sp. KLDS 1.0701 | EU600905 |
| *Lactobacillus* sp. KLDS 1.0702 | EU600906 |
| *Lactobacillus* sp. KLDS 1.0703 | EU600907 |
| *Lactobacillus* sp. KLDS 1.0704 | EU600908 |
| *Lactobacillus* sp. KLDS 1.0705 | EU600909 |
| *Lactobacillus* sp. KLDS 1.0707 | EU600911 |
| *Lactobacillus* sp. KLDS 1.0709 | EU600913 |
| *Lactobacillus* sp. KLDS 1.0711 | EU600915 |
| *Lactobacillus* sp. KLDS 1.0712 | EU600916 |
| *Lactobacillus* sp. KLDS 1.0713 | EU600917 |
| *Lactobacillus* sp. KLDS 1.0716 | EU600921 |
| *Lactobacillus* sp. KLDS 1.0718 | EU600922 |
| *Lactobacillus* sp. KLDS 1.0719 | EU600923 |
| *Lactobacillus* sp. oral clone HT002 | AY349382 |
| *Lactobacillus* sp. oral clone HT070 | AY349383 |
| *Lactobacillus* sp. oral taxon 052 | GQ422710 |
| *Lactobacillus tucceti* | NR_042194 |
| *Lactobacillus ultunensis* | ACGU01000081 |
| Lactobacillus *vaginalis* | ACGV01000168 |
| *Lactobacillus* vini | NR_042196 |
| *Lactobacillus vitulinus* | NR_041305 |
| *Lactobacillus zeae* | NR_037122 |
| *Lactococcus garvieae* | AF061005 |
| *Lactococcus lactis* | CP002365 |
| *Lactococcus raffinolactis* | NR_044359 |
| *Lactonifactor longoviformis* | DQ100449 |
| *Laribacter hongkongensis* | CP001154 |
| *Lautropia mirabilis* | AEQP01000026 |
| *Lautropia* sp. oral clone AP009 | AY005030 |
| *Legionella hackeliae* | M36028 |
| *Legionella longbeachae* | M36029 |
| *Legionella pneumophila* | NC_002942 |
| *Legionella* sp. D3923 | JN380999 |
| *Legionella* sp. D4088 | JN381012 |
| *Legionella* sp. H63 | JF831047 |
| *Legionella* sp. NML 93L054 | GU062706 |
| *Legionella steelei* | HQ398202 |
| *Leminorella grimontii* | AJ233421 |
| *Leminorella richardii* | HF558368 |
| *Leptospira borgpetersenii* | NC_008508 |
| *Leptospira broomii* | NR_043200 |
| *Leptospira interrogans* | NC_005823 |
| *Leptospira licerasiae* | EF612284 |
| *Leptotrichia buccalis* | CP001685 |
| *Leptotrichia* genomosp. C1 | AY278621 |
| *Leptotrichia goodfellowii* | ADAD01000110 |
| *Leptotrichia hofstadii* | ACVB02000032 |
| *Leptotrichia shahii* | AY029806 |
| *Leptotrichia* sp. neutropenicPatient | AF189244 |
| *Leptotrichia* sp. oral clone GT018 | AY349384 |
| *Leptotrichia* sp. oral clone GT020 | AY349385 |
| *Leptotrichia* sp. oral clone HE012 | AY349386 |
| *Leptotrichia* sp. oral clone IK040 | AY349387 |
| *Leptotrichia* sp. oral clone P2PB_51 P1 | AY207053 |
| *Leptotrichia* sp. oral taxon 223 | GU408547 |
| *Leuconostoc carnosum* | NR_040811 |
| *Leuconostoc citreum* | AM157444 |
| *Leuconostoc gasicomitatum* | FN822744 |
| *Leuconostoc inhae* | NR_025204 |
| *Leuconostoc kimchii* | NR_075014 |
| *Leuconostoc lactis* | NR_040823 |
| *Leuconostoc mesenteroides* | ACKV01000113 |
| *Leuconostoc pseudomesenteroides* | NR_040814 |
| *Listeria grayi* | ACCR02000003 |
| *Listeria innocua* | JF967625 |
| *Listeria ivanovii* | X56151 |
| *Listeria monocytogenes* | CP002003 |
| *Listeria welshimeri* | AM263198 |
| *Luteococcus sanguinis* | NR_025507 |
| *Lutispora thermophila* | NR_041236 |
| *Lysinibacillus fusiformis* | FN397522 |
| *Lysinibacillus sphaericus* | NR_074883 |
| *Macrococcus caseolyticus* | NR_074941 |
| *Mannheimia haemolytica* | ACZX01000102 |
| *Marvinbryantia formatexigens* | AJ505973 |
| *Massilia* sp. CCUG 43427A | FR773700 |
| *Megamonas funiformis* | AB300988 |
| *Megamonas hypermegale* | AJ420107 |
| *Megasphaera elsdenii* | AY038996 |
| *Megasphaera* genomosp. C1 | AY278622 |
| *Megasphaera* genomosp. type_1 | ADGP01000010 |
| *Megasphaera micronuciformis* | AECS01000020 |
| *Megasphaera* sp. BLPYG_07 | HM990964 |
| *Megasphaera* sp. UPII 199_6 | AFIJ01000040 |
| *Metallosphaera sedula* | D26491 |
| *Methanobacterium formicicum* | NR_025028 |
| *Methanobrevibacter acididurans* | NR_028779 |
| *Methanobrevibacter arboriphilus* | NR_042783 |
| *Methanobrevibacter curvatus* | NR_044796 |
| *Methanobrevibacter cuticularis* | NR_044776 |
| *Methanobrevibacter filiformis* | NR_044801 |
| *Methanobrevibacter gottschalkii* | NR_044789 |
| *Methanobrevibacter millerae* | NR_042785 |
| *Methanobrevibacter olleyae* | NR_043024 |
| *Methanobrevibacter oralis* | HE654003 |
| *Methanobrevibacter ruminantium* | NR_042784 |
| *Methanobrevibacter smithii* | ABYV02000002 |
| *Methanobrevibacter thaueri* | NR_044787 |
| *Methanobrevibacter woesei* | NR_044788 |
| *Methanobrevibacter wolinii* | NR_044790 |
| *Methanosphaera stadtmanae* | AY196684 |
| *Methylobacterium extorquens* | NC_010172 |
| *Methylobacterium podarium* | AY468363 |
| *Methylobacterium radiotolerans* | GU294320 |
| *Methylobacterium* sp. 1sub | AY468371 |
| *Methylobacterium* sp. MM4 | AY468370 |

TABLE 1-continued

Exemplary Bacterial Strains

| OTU | Public DB Accession |
|---|---|
| *Methylocella silvestris* | NR_074237 |
| *Methylophilus* sp. ECd5 | AY436794 |
| *Microbacterium chocolatum* | NR_037045 |
| *Microbacterium flavescens* | EU714363 |
| *Microbacterium gubbeenense* | NR_025098 |
| *Microbacterium lacticum* | EU714351 |
| *Microbacterium oleivorans* | EU714381 |
| *Microbacterium oxydans* | EU714348 |
| *Microbacterium paraoxydans* | AJ491806 |
| *Microbacterium phyllosphaerae* | EU714359 |
| *Microbacterium schleiferi* | NR_044936 |
| *Microbacterium* sp. 768 | EU714378 |
| *Microbacterium* sp. oral strain C24KA | AF287752 |
| *Microbacterium testaceum* | EU714365 |
| *Micrococcus antarcticus* | NR_025285 |
| *Micrococcus luteus* | NR_075062 |
| *Micrococcus lylae* | NR_026200 |
| *Micrococcus* sp. 185 | EU714334 |
| *Microcystis aeruginosa* | NC_010296 |
| *Mitsuokella jalaludinii* | NR_028840 |
| *Mitsuokella multacida* | ABWK02000005 |
| *Mitsuokella* sp. oral taxon 521 | GU413658 |
| *Mitsuokella* sp. oral taxon G68 | GU432166 |
| *Mobiluncus curtisii* | AEPZ01000013 |
| *Mobiluncus mulieris* | ACKW01000035 |
| *Moellerella wisconsensis* | JN175344 |
| *Mogibacterium diversum* | NR_027191 |
| *Mogibacterium neglectum* | NR_027203 |
| *Mogibacterium pumilum* | NR_028608 |
| *Mogibacterium timidum* | Z36296 |
| *Mollicutes* bacterium pACH93 | AY297808 |
| *Moorella thermoacetica* | NR_075001 |
| *Moraxella catarrhalis* | CP002005 |
| *Moraxella lincolnii* | FR822735 |
| *Moraxella osloensis* | JN175341 |
| Moraxella sp. 16285 | JF682466 |
| *Moraxella* sp. GM2 | JF837191 |
| *Morganella morganii* | AJ301681 |
| *Morganella* sp. JB_T16 | AJ781005 |
| *Morococcus cerebrosus* | JN175352 |
| *Moryella indoligenes* | AF527773 |
| *Mycobacterium abscessus* | AGQU01000002 |
| *Mycobacterium africanum* | AF480605 |
| *Mycobacterium alsiensis* | AJ938169 |
| *Mycobacterium avium* | CP000479 |
| *Mycobacterium chelonae* | AB548610 |
| *Mycobacterium colombiense* | AM062764 |
| *Mycobacterium elephantis* | AF385898 |
| *Mycobacterium gordonae* | GU142930 |
| *Mycobacterium intracellulare* | GQ153276 |
| *Mycobacterium kansasii* | AF480601 |
| *Mycobacterium lacus* | NR_025175 |
| *Mycobacterium leprae* | FM211192 |
| *Mycobacterium lepromatosis* | EU203590 |
| *Mycobacterium mageritense* | FR798914 |
| *Mycobacterium mantenii* | FJ042897 |
| *Mycobacterium marinum* | NC_010612 |
| *Mycobacterium microti* | NR_025234 |
| *Mycobacterium neoaurum* | AF268445 |
| *Mycobacterium parascrofulaceum* | ADNV01000350 |
| *Mycobacterium paraterrae* | EU919229 |
| *Mycobacterium phlei* | GU142920 |
| *Mycobacterium seoulense* | DQ536403 |
| *Mycobacterium smegmatis* | CP000480 |
| *Mycobacterium* sp. 1761 | EU703150 |
| *Mycobacterium* sp. 1776 | EU703152 |
| *Mycobacterium* sp. 1781 | EU703147 |
| *Mycobacterium* sp. 1791 | EU703148 |
| *Mycobacterium* sp. 1797 | EU703149 |
| *Mycobacterium* sp. AQIGA4 | HM210417 |
| *Mycobacterium* sp. B10_07.09.0206 | HQ174245 |
| *Mycobacterium* sp. GN_10546 | FJ497243 |
| *Mycobacterium* sp. GN_10827 | FJ497247 |
| *Mycobacterium* sp. GN_11124 | FJ652846 |
| *Mycobacterium* sp. GN_9188 | FJ497240 |
| *Mycobacterium* sp. GR_2007_210 | FJ555538 |
| *Mycobacterium* sp. HE5 | AJ012738 |
| *Mycobacterium* sp. NLA001000736 | HM627011 |
| *Mycobacterium* sp. W | DQ437715 |
| *Mycobacterium tuberculosis* | CP001658 |
| *Mycobacterium ulcerans* | AB548725 |
| *Mycobacterium vulneris* | EU834055 |
| *Mycoplasma agalactiae* | AF010477 |
| *Mycoplasma amphoriforme* | AY531656 |
| *Mycoplasma arthritidis* | NC_011025 |
| *Mycoplasma bovoculi* | NR_025987 |
| *Mycoplasma faucium* | NR_024983 |
| *Mycoplasma fermentans* | CP002458 |
| *Mycoplasma flocculare* | X62699 |
| *Mycoplasma genitalium* | L43967 |
| *Mycoplasma hominis* | AF443616 |
| *Mycoplasma orale* | AY796060 |
| *Mycoplasma ovipneumoniae* | NR_025989 |
| *Mycoplasma penetrans* | NC_004432 |
| *Mycoplasma pneumoniae* | NC_000912 |
| *Mycoplasma putrefaciens* | U26055 |
| *Mycoplasma salivarium* | M24661 |
| *Mycoplasmataceae* genomosp. P1 oral clone MB1_G23 | DQ003614 |
| *Myroides odoratimimus* | NR_042354 |
| *Myroides* sp. MY15 | GU253339 |
| *Neisseria bacilliformis* | AFAY01000058 |
| *Neisseria cinerea* | ACDY01000037 |
| *Neisseria elongata* | ADBF01000003 |
| *Neisseria flavescens* | ACQV01000025 |
| *Neisseria* genomosp. P2 oral clone MB5_P15 | DQ003630 |
| *Neisseria gonorrhoeae* | CP002440 |
| *Neisseria lactamica* | ACEQ01000095 |
| *Neisseria macacae* | AFQE01000146 |
| *Neisseria meningitidis* | NC_003112 |
| *Neisseria mucosa* | ACDX01000110 |
| *Neisseria pharyngis* | AJ239281 |
| *Neisseria polysaccharea* | ADBE01000137 |
| *Neisseria sicca* | ACKO02000016 |
| *Neisseria* sp. KEM232 | GQ203291 |
| *Neisseria* sp. oral clone AP132 | AY005027 |
| *Neisseria* sp. oral clone JC012 | AY349388 |
| *Neisseria* sp. oral strain B33KA | AY005028 |
| *Neisseria* sp. oral taxon 014 | ADEA01000039 |
| *Neisseria* sp. SMC_A9199 | FJ763637 |
| *Neisseria* sp. TM10_1 | DQ279352 |
| *Neisseria subflava* | ACEO01000067 |
| *Neorickettsia risticii* | CP001431 |
| *Neorickettsia sennetsu* | NC_007798 |
| *Nocardia brasiliensis* | AIHV01000038 |
| *Nocardia cyriacigeorgica* | HQ009486 |
| *Nocardia farcinica* | NC_006361 |
| *Nocardia puris* | NR_028994 |
| *Nocardia* sp. 01_Je_025 | GU574059 |
| *Nocardiopsis dassonvillei* | CP002041 |
| *Novosphingobium aromaticivorans* | AAAV03000008 |
| *Oceanobacillus caeni* | NR_041533 |
| *Oceanobacillus* sp. Ndiop | CAER01000083 |
| *Ochrobactrum anthropi* | NC_009667 |
| *Ochrobactrum intermedium* | ACQA01000001 |
| *Ochrobactrum pseudintermedium* | DQ365921 |
| *Odoribacter laneus* | AB490805 |
| *Odoribacter splanchnicus* | CP002544 |
| *Okadaella gastrococcus* | HQ699465 |
| *Oligella ureolytica* | NR_041998 |
| *Oligella urethralis* | NR_041753 |
| *Olsenella* genomosp. C1 | AY278623 |
| *Olsenella profusa* | FN178466 |
| *Olsenella* sp. F0004 | EU592964 |
| *Olsenella* sp. oral taxon 809 | ACVE01000002 |
| *Olsenella uli* | CP002106 |
| *Opitutus terrae* | NR_074978 |
| *Oribacterium sinus* | ACKX01000142 |
| *Oribacterium* sp. ACB1 | HM120210 |
| *Oribacterium* sp. ACB7 | HM120211 |
| *Oribacterium* sp. CM12 | HQ616374 |
| *Oribacterium* sp. ICM51 | HQ616397 |

TABLE 1-continued

Exemplary Bacterial Strains

| OTU | Public DB Accession |
|---|---|
| Oribacterium sp. OBRC12 | HQ616355 |
| Oribacterium sp. oral taxon 078 | ACIQ02000009 |
| Oribacterium sp. oral taxon 102 | GQ422713 |
| Oribacterium sp. oral taxon 108 | AFIH01000001 |
| Orientia tsutsugamushi | AP008981 |
| Ornithinibacillus bavariensis | NR_044923 |
| Ornithinibacillus sp. 7_10AIA | FN397526 |
| Oscillibacter sp. G2 | HM626173 |
| Oscillibacter valericigenes | NR_074793 |
| Oscillospira guilliermondii | AB040495 |
| Oxalobacter formigenes | ACDQ01000020 |
| Paenibacillus barcinonensis | NR_042272 |
| Paenibacillus barengoltzii | NR_042756 |
| Paenibacillus chibensis | NR_040885 |
| Paenibacillus cookii | NR_025372 |
| Paenibacillus durus | NR_037017 |
| Paenibacillus glucanolyticus | D78470 |
| Paenibacillus lactis | NR_025739 |
| Paenibacillus lautus | NR_040882 |
| Paenibacillus pabuli | NR_040853 |
| Paenibacillus polymyxa | NR_037006 |
| Paenibacillus popilliae | NR_040888 |
| Paenibacillus sp. CIP 101062 | HM212646 |
| Paenibacillus sp. HGF5 | AEXS01000095 |
| Paenibacillus sp. HGF7 | AFDH01000147 |
| Paenibacillus sp. JC66 | JF824808 |
| Paenibacillus sp. oral taxon F45 | HM099647 |
| Paenibacillus sp. R_27413 | HE586333 |
| Paenibacillus sp. R_27422 | HE586338 |
| Paenibacillus timonensis | NR_042844 |
| Pantoea agglomerans | AY335552 |
| Pantoea ananatis | CP001875 |
| Pantoea brenneri | EU216735 |
| Pantoea citrea | EF688008 |
| Pantoea conspicua | EU216737 |
| Pantoea septica | EU216734 |
| Papillibacter cinnamivorans | NR_025025 |
| Parabacteroides distasonis | CP000140 |
| Parabacteroides goldsteinii | AY974070 |
| Parabacteroides gordonii | AB470344 |
| Parabacteroides johnsonii | ABYH01000014 |
| Parabacteroides merdae | EU136685 |
| Parabacteroides sp. D13 | ACPW01000017 |
| Parabacteroides sp. NS31_3 | JN029805 |
| Parachlamydia sp. UWE25 | BX908798 |
| Paracoccus denitrificans | CP000490 |
| Paracoccus marcusii | NR_044922 |
| Paraprevotella clara | AFFY01000068 |
| Paraprevotella xylaniphila | AFBR01000011 |
| Parascardovia denticolens | ADEB01000020 |
| Parasutterella excrementihominis | AFBP01000029 |
| Parasutterella secunda | AB491209 |
| Parvimonas micra | AB729072 |
| Parvimonas sp. oral taxon 110 | AFII01000002 |
| Pasteurella bettyae | L06088 |
| Pasteurella dagmatis | ACZR01000003 |
| Pasteurella multocida | NC_002663 |
| Pediococcus acidilactici | ACXB01000026 |
| Pediococcus pentosaceus | NR_075052 |
| Peptococcus niger | NR_029221 |
| Peptococcus sp. oral clone JM048 | AY349389 |
| Peptococcus sp. oral taxon 167 | GQ422727 |
| Peptoniphilus asaccharolyticus | D14145 |
| Peptoniphilus duerdenii | EU526290 |
| Peptoniphilus harei | NR_026358 |
| Peptoniphilus indolicus | AY153431 |
| Peptoniphilus ivorii | Y07840 |
| Peptoniphilus lacrimalis | ADDO01000050 |
| Peptoniphilus sp. gpac007 | AM176517 |
| Peptoniphilus sp. gpac018A | AM176519 |
| Peptoniphilus sp. gpac077 | AM176527 |
| Peptoniphilus sp. gpac148 | AM176535 |
| Peptoniphilus sp. JC140 | JF824803 |
| Peptoniphilus sp. oral taxon 386 | ADCS01000031 |
| Peptoniphilus sp. oral taxon 836 | AEAA01000090 |
| Peptostreptococcaceae bacterium phl | JN837495 |
| Peptostreptococcus anaerobius | AY326462 |
| Peptostreptococcus micros | AM176538 |
| Peptostreptococcus sp. 9succ1 | X90471 |
| Peptostreptococcus sp. oral clone AP24 | AB175072 |
| Peptostreptococcus sp. oral clone FJ023 | AY349390 |
| Peptostreptococcus sp. P4P_31 P3 | AY207059 |
| Peptostreptococcus stomatis | ADGQ01000048 |
| Phascolarctobacterium faecium | NR_026111 |
| Phascolarctobacterium sp. YIT 12068 | AB490812 |
| Phascolarctobacterium succinatutens | AB490811 |
| Phenylobacterium zucineum | AY628697 |
| Photorhabdus asymbiotica | Z76752 |
| Pigmentiphaga daeguensis | JN585327 |
| Planomicrobium koreense | NR_025011 |
| Plesiomonas shigelloides | X60418 |
| Porphyromonadaceae bacterium NML 060648 | EF184292 |
| Porphyromonas asaccharolytica | AENO01000048 |
| Porphyromonas endodontalis | ACNN01000021 |
| Porphyromonas gingivalis | AE015924 |
| Porphyromonas levii | NR_025907 |
| Porphyromonas macacae | NR_025908 |
| Porphyromonas somerae | AB547667 |
| Porphyromonas sp. oral clone BB134 | AY005068 |
| Porphyromonas sp. oral clone F016 | AY005069 |
| Porphyromonas sp. oral clone P2PB_52 P1 | AY207054 |
| Porphyromonas sp. oral clone P4GB_100 P2 | AY207057 |
| Porphyromonas sp. UQD 301 | EU012301 |
| Porphyromonas uenonis | ACLR01000152 |
| Prevotella albensis | NR_025300 |
| Prevotella amnii | AB547670 |
| Prevotella bergensis | ACKS01000100 |
| Prevotella bivia | ADFO01000096 |
| Prevotella brevis | NR_041954 |
| Prevotella buccae | ACRB01000001 |
| Prevotella buccalis | JN867261 |
| Prevotella copri | ACBX02000014 |
| Prevotella corporis | L16465 |
| Prevotella dentalis | AB547678 |
| Prevotella denticola | CP002589 |
| Prevotella disiens | AEDO01000026 |
| Prevotella genomosp. C1 | AY278624 |
| Prevotella genomosp. C2 | AY278625 |
| Prevotella genomosp. P7 oral clone MB2_P31 | DQ003620 |
| Prevotella genomosp. P8 oral clone MB3_P13 | DQ003622 |
| Prevotella genomosp. P9 oral clone MB7_G16 | DQ003633 |
| Prevotella heparinolytica | GQ422742 |
| Prevotella histicola | JN867315 |
| Prevotella intermedia | AF414829 |
| Prevotella loescheii | JN867231 |
| Prevotella maculosa | AGEK01000035 |
| Prevotella marshii | AEEI01000070 |
| Prevotella melaninogenica | CP002122 |
| Prevotella micans | AGWK01000061 |
| Prevotella multiformis | AEWX01000054 |
| Prevotella multisaccharivorax | AFJE01000016 |
| Prevotella nanceiensis | JN867228 |
| Prevotella nigrescens | AFPX01000069 |
| Prevotella oralis | AEPE01000021 |
| Prevotella oris | ADDV01000091 |
| Prevotella oulorum | L16472 |
| Prevotella pallens | AFPY01000135 |
| Prevotella ruminicola | CP002006 |
| Prevotella salivae | AB108826 |
| Prevotella sp. BI_42 | AJ581354 |
| Prevotella sp. CM38 | HQ610181 |
| Prevotella sp. ICM1 | HQ616385 |
| Prevotella sp. ICM55 | HQ616399 |
| Prevotella sp. JCM 6330 | AB547699 |
| Prevotella sp. oral clone AA020 | AY005057 |
| Prevotella sp. oral clone ASCG10 | AY923148 |
| Prevotella sp. oral clone ASCG12 | DQ272511 |
| Prevotella sp. oral clone AU069 | AY005062 |
| Prevotella sp. oral clone CY006 | AY005063 |
| Prevotella sp. oral clone DA058 | AY005065 |
| Prevotella sp. oral clone FL019 | AY349392 |
| Prevotella sp. oral clone FU048 | AY349393 |

TABLE 1-continued

Exemplary Bacterial Strains

| OTU | Public DB Accession |
|---|---|
| Prevotella sp. oral clone FW035 | AY349394 |
| Prevotella sp. oral clone GI030 | AY349395 |
| Prevotella sp. oral clone GI032 | AY349396 |
| Prevotella sp. oral clone GI059 | AY349397 |
| Prevotella sp. oral clone GU027 | AY349398 |
| Prevotella sp. oral clone HF050 | AY349399 |
| Prevotella sp. oral clone ID019 | AY349400 |
| Prevotella sp. oral clone IDR_CEC_0055 | AY550997 |
| Prevotella sp. oral clone IK053 | AY349401 |
| Prevotella sp. oral clone IK062 | AY349402 |
| Prevotella sp. oral clone P4PB_83 P2 | AY207050 |
| Prevotella sp. oral taxon 292 | GQ422735 |
| Prevotella sp. oral taxon 299 | ACWZ01000026 |
| Prevotella sp. oral taxon 300 | GU409549 |
| Prevotella sp. oral taxon 302 | ACZK01000043 |
| Prevotella sp. oral taxon 310 | GQ422737 |
| Prevotella sp. oral taxon 317 | ACQH01000158 |
| Prevotella sp. oral taxon 472 | ACZS01000106 |
| Prevotella sp. oral taxon 781 | GQ422744 |
| Prevotella sp. oral taxon 782 | GQ422745 |
| Prevotella sp. oral taxon F68 | HM099652 |
| Prevotella sp. oral taxon G60 | GU432133 |
| Prevotella sp. oral taxon G70 | GU432179 |
| Prevotella sp. oral taxon G71 | GU432180 |
| Prevotella sp. SEQ053 | JN867222 |
| Prevotella sp. SEQ065 | JN867234 |
| Prevotella sp. SEQ072 | JN867238 |
| Prevotella sp. SEQ116 | JN867246 |
| Prevotella sp. SG12 | GU561343 |
| Prevotella sp. sp24 | AB003384 |
| Prevotella sp. sp34 | AB003385 |
| Prevotella stercorea | AB244774 |
| Prevotella tannerae | ACIJ02000018 |
| Prevotella timonensis | ADEF01000012 |
| Prevotella veroralis | ACVA01000027 |
| Prevotella jejuni, Prevotella aurantiaca, Prevotella baroniae, Prevotella colorans, Prevotella corporis, Prevotella dentasini, Prevotella enoeca, Prevotella falsenii, Prevotella fusca, Prevotella heparinolytica, Prevotella loescheii, Prevotella multisaccharivorax, Prevotella nanceiensis, Prevotella oryzae, Prevotella paludivivens, Prevotella pleuritidis, Prevotella ruminicola, Prevotella saccharolytica, Prevotella scopos, Prevotella shahii, Prevotella zoogleoformans | |
| Prevotellaceae bacterium P4P_62 P1 | AY207061 |
| Prochlorococcus marinus | CP000551 |
| Propionibacteriaceae bacterium NML 02_0265 | EF599122 |
| Propionibacterium acidipropionici | NC_019395 |
| Propionibacterium acnes | ADJM01000010 |
| Propionibacterium avidum | AJ003055 |
| Propionibacterium freudenreichii | NR_036972 |
| Propionibacterium granulosum | FJ785716 |
| Propionibacterium jensenii | NR_042269 |
| Propionibacterium propionicum | NR_025277 |
| Propionibacterium sp. 434_HC2 | AFIL01000035 |
| Propionibacterium sp. H456 | AB177643 |
| Propionibacterium sp. LG | AY354921 |
| Propionibacterium sp. oral taxon 192 | GQ422728 |
| Propionibacterium sp. S555a | AB264622 |
| Propionibacterium thoenii | NR_042270 |
| Proteus mirabilis | ACLE01000013 |
| Proteus penneri | ABVP01000020 |
| Proteus sp. HS7514 | DQ512963 |
| Proteus vulgaris | AJ233425 |
| Providencia alcalifaciens | ABXW01000071 |
| Providencia rettgeri | AM040492 |
| Providencia rustigianii | AM040489 |
| Providencia stuartii | AF008581 |
| Pseudoclavibacter sp. Timone | FJ375951 |
| Pseudoflavonifractor capillosus | AY136666 |
| Pseudomonas aeruginosa | AABQ07000001 |
| Pseudomonas fluorescens | AY622220 |
| Pseudomonas gessardii | FJ943496 |
| Pseudomonas mendocina | AAUL01000021 |
| Pseudomonas monteilii | NR_024910 |
| Pseudomonas poae | GU188951 |
| Pseudomonas pseudoalcaligenes | NR_037000 |
| Pseudomonas putida | AF094741 |
| Pseudomonas sp. 2_1_26 | ACWU01000257 |
| Pseudomonas sp. G1229 | DQ910482 |
| Pseudomonas sp. NP522b | EU723211 |
| Pseudomonas stutzeri | AM905854 |
| Pseudomonas tolaasii | AF320988 |
| Pseudomonas viridiflava | NR_042764 |
| Pseudoramibacter alactolyticus | AB036759 |
| Psychrobacter arcticus | CP000082 |
| Psychrobacter cibarius | HQ698586 |
| Psychrobacter cryohalolentis | CP000323 |
| Psychrobacter faecalis | HQ698566 |
| Psychrobacter nivimaris | HQ698587 |
| Psychrobacter pulmonis | HQ698582 |
| Psychrobacter sp. 13983 | HM212668 |
| Pyramidobacter piscolens | AY207056 |
| Ralstonia pickettii | NC_010682 |
| Ralstonia sp. 5_7_47FAA | ACUF01000076 |
| Raoultella ornithinolytica | AB364958 |
| Raoultella planticola | AF129443 |
| Raoultella terrigena | NR_037085 |
| Rhodobacter sp. oral taxon C30 | HM099648 |
| Rhodobacter sphaeroides | CP000144 |
| Rhodococcus corynebacterioides | X80615 |
| Rhodococcus equi | ADNW01000058 |
| Rhodococcus erythropolis | ACNO01000030 |
| Rhodococcus fascians | NR_037021 |
| Rhodopseudomonas palustris | CP000301 |
| Rickettsia akari | CP000847 |
| Rickettsia conorii | AE008647 |
| Rickettsia prowazekii | M21789 |
| Rickettsia rickettsii | NC_010263 |
| Rickettsia slovaca | L36224 |
| Rickettsia typhi | AE017197 |
| Robinsoniella peoriensis | AF445258 |
| Roseburia cecicola | GU233441 |
| Roseburia faecalis | AY804149 |
| Roseburia faecis | AY305310 |
| Roseburia hominis | AJ270482 |
| Roseburia intestinalis | FP929050 |
| Roseburia inulinivorans | AJ270473 |
| Roseburia sp. 11SE37 | FM954975 |
| Roseburia sp. 11SE38 | FM954976 |
| Roseiflexus castenholzii | CP000804 |
| Roseomonas cervicalis | ADVL01000363 |
| Roseomonas mucosa | NR_028857 |
| Roseomonas sp. NML94_0193 | AF533357 |
| Roseomonas sp. NML97_0121 | AF533359 |
| Roseomonas sp. NML98_0009 | AF533358 |
| Roseomonas sp. NML98_0157 | AF533360 |
| Rothia aeria | DQ673320 |
| Rothia dentocariosa | ADDW01000024 |
| Rothia mucilaginosa | ACVO01000020 |
| Rothia nasimurium | NR_025310 |
| Rothia sp. oral taxon 188 | GU470892 |
| Ruminobacter amylophilus | NR_026450 |
| Ruminococcaceae bacterium D16 | ADDX01000083 |
| Ruminococcus albus | AY445600 |
| Ruminococcus bromii | EU266549 |
| Ruminococcus callidus | NR_029160 |
| Ruminococcus champanellensis | FP929052 |
| Ruminococcus flavefaciens | NR_025931 |
| Ruminococcus gnavus | X94967 |
| Ruminococcus hansenii | M59114 |
| Ruminococcus lactaris | ABOU02000049 |
| Ruminococcus obeum | AY169419 |
| Ruminococcus sp. 18P13 | AJ515913 |
| Ruminococcus sp. 5_1_39BFAA | ACII01000172 |
| Ruminococcus sp. 9SE51 | FM954974 |
| Ruminococcus sp. ID8 | AY960564 |
| Ruminococcus sp. K_1 | AB222208 |
| Ruminococcus torques | AAVP02000002 |
| Saccharomonospora viridis | X54286 |

TABLE 1-continued

Exemplary Bacterial Strains

| OTU | Public DB Accession |
|---|---|
| *Salmonella bongori* | NR_041699 |
| *Salmonella enterica* | NC_011149 |
| *Salmonella enterica* | NC_011205 |
| *Salmonella enterica* | DQ344532 |
| *Salmonella enterica* | ABEH02000004 |
| *Salmonella enterica* | ABAK02000001 |
| *Salmonella enterica* | NC_011080 |
| *Salmonella enterica* | EU118094 |
| *Salmonella enterica* | NC_011094 |
| *Salmonella enterica* | AE014613 |
| *Salmonella enterica* | ABFH02000001 |
| *Salmonella enterica* | ABEM01000001 |
| *Salmonella enterica* | ABAM02000001 |
| *Salmonella typhimurium* | DQ344533 |
| *Salmonella typhimurium* | AF170176 |
| *Sarcina ventriculi* | NR_026146 |
| *Scardovia inopinata* | AB029087 |
| *Scardovia wiggsiae* | AY278626 |
| *Segniliparus rotundus* | CP001958 |
| *Segniliparus rugosus* | ACZI01000025 |
| *Selenomonas artemidis* | HM596274 |
| *Selenomonas dianae* | GQ422719 |
| *Selenomonas flueggei* | AF287803 |
| *Selenomonas* genomosp. C1 | AY278627 |
| *Selenomonas* genomosp. C2 | AY278628 |
| *Selenomonas* genomosp. P5 | AY341820 |
| *Selenomonas* genomosp. P6 oral clone MB3_C41 | DQ003636 |
| *Selenomonas* genomosp. P7 oral clone MB5_C08 | DQ003627 |
| *Selenomonas* genomosp. P8 oral clone MB5_P06 | DQ003628 |
| *Selenomonas infelix* | AF287802 |
| *Selenomonas noxia* | GU470909 |
| *Selenomonas ruminantium* | NR_075026 |
| *Selenomonas* sp. FOBRC9 | HQ616378 |
| *Selenomonas* sp. oral clone FT050 | AY349403 |
| Selenomonas sp. oral clone GI064 | AY349404 |
| *Selenomonas* sp. oral clone GT010 | AY349405 |
| *Selenomonas* sp. oral clone HU051 | AY349406 |
| *Selenomonas* sp. oral clone IK004 | AY349407 |
| *Selenomonas* sp. oral clone IQ048 | AY349408 |
| *Selenomonas* sp. oral clone JI021 | AY349409 |
| *Selenomonas* sp. oral clone JS031 | AY349410 |
| *Selenomonas* sp. oral clone OH4A | AY947498 |
| *Selenomonas* sp. oral clone P2PA_80 P4 | AY207052 |
| *Selenomonas* sp. oral taxon 137 | AENV01000007 |
| *Selenomonas* sp. oral taxon 149 | AEEJ01000007 |
| *Selenomonas sputigena* | ACKP02000033 |
| *Serratia fonticola* | NR_025339 |
| *Serratia liquefaciens* | NR_042062 |
| *Serratia marcescens* | GU826157 |
| *Serratia odorifera* | ADBY01000001 |
| *Serratia proteamaculans* | AAUN01000015 |
| *Shewanella putrefaciens* | CP002457 |
| *Shigella boydii* | AAKA01000007 |
| *Shigella dysenteriae* | NC_007606 |
| *Shigella flexneri* | AE005674 |
| *Shigella sonnei* | NC_007384 |
| *Shuttleworthia satelles* | ACIP02000004 |
| *Shuttleworthia* sp. MSX8B | HQ616383 |
| *Shuttleworthia* sp. oral taxon G69 | GU432167 |
| *Simonsiella muelleri* | ADCY01000105 |
| *Slackia equolifaciens* | EU377663 |
| *Slackia exigua* | ACUX01000029 |
| *Slackia faecicanis* | NR_042220 |
| *Slackia heliotrinireducens* | NR_074439 |
| *Slackia isoflavoniconvertens* | AB566418 |
| *Slackia piriformis* | AB490806 |
| *Slackia* sp. NATTS | AB505075 |
| *Solobacterium moorei* | AECQ01000039 |
| *Sphingobacterium faecium* | NR_025537 |
| *Sphingobacterium mizutaii* | JF708889 |
| *Sphingobacterium multivorum* | NR_040953 |
| *Sphingobacterium spiritivorum* | ACHA02000013 |
| *Sphingomonas echinoides* | NR_024700 |
| *Sphingomonas* sp. oral clone FI012 | AY349411 |
| *Sphingomonas* sp. oral clone FZ016 | AY349412 |
| *Sphingomonas* sp. oral taxon A09 | HM099639 |
| *Sphingomonas* sp. oral taxon F71 | HM099645 |
| *Sphingopyxis alaskensis* | CP000356 |
| *Spiroplasma insolitum* | NR_025705 |
| *Sporobacter termitidis* | NR_044972 |
| *Sporolactobacillus inulinus* | NR_040962 |
| *Sporolactobacillus nakayamae* | NR_042247 |
| *Sporosarcina newyorkensis* | AFPZ01000142 |
| *Sporosarcina* sp. 2681 | GU994081 |
| *Staphylococcaceae* bacterium NML 92_0017 | AY841362 |
| *Staphylococcus aureus* | CP002643 |
| *Staphylococcus auricularis* | JQ624774 |
| *Staphylococcus capitis* | ACFR01000029 |
| *Staphylococcus caprae* | ACRH01000033 |
| *Staphylococcus carnosus* | NR_075003 |
| *Staphylococcus cohnii* | JN175375 |
| *Staphylococcus condimenti* | NR_029345 |
| *Staphylococcus epidermidis* | ACHE01000056 |
| *Staphylococcus equorum* | NR_027520 |
| *Staphylococcus fleurettii* | NR_041326 |
| *Staphylococcus haemolyticus* | NC_007168 |
| *Staphylococcus hominis* | AM157418 |
| *Staphylococcus lugdunensis* | AEQA01000024 |
| *Staphylococcus pasteuri* | FJ189773 |
| *Staphylococcus pseudintermedius* | CP002439 |
| *Staphylococcus saccharolyticus* | NR_029158 |
| *Staphylococcus saprophyticus* | NC_007350 |
| *Staphylococcus sciuri* | NR_025520 |
| *Staphylococcus* sp. clone bottae7 | AF467424 |
| *Staphylococcus* sp. H292 | AB177642 |
| *Staphylococcus* sp. H780 | AB177644 |
| *Staphylococcus succinus* | NR_028667 |
| *Staphylococcus vitulinus* | NR_024670 |
| *Staphylococcus warneri* | ACPZ01000009 |
| *Staphylococcus xylosus* | AY395016 |
| *Stenotrophomonas maltophilia* | AAVZ01000005 |
| *Stenotrophomonas* sp. FG_6 | EF017810 |
| *Streptobacillus moniliformis* | NR_027615 |
| *Streptococcus agalactiae* | AAJO01000130 |
| *Streptococcus alactolyticus* | NR_041781 |
| *Streptococcus anginosus* | AECT01000011 |
| *Streptococcus australis* | AEQR01000024 |
| *Streptococcus bovis* | AEEL01000030 |
| *Streptococcus canis* | AJ413203 |
| *Streptococcus constellatus* | AY277942 |
| *Streptococcus cristatus* | AEVC01000028 |
| *Streptococcus downei* | AEKN01000002 |
| *Streptococcus dysgalactiae* | AP010673 |
| *Streptococcus equi* | CP001129 |
| *Streptococcus equinus* | AEVB01000043 |
| *Streptococcus gallolyticus* | FR824043 |
| *Streptococcus* genomosp. C1 | AY278629 |
| *Streptococcus* genomosp. C2 | AY278630 |
| *Streptococcus* genomosp. C3 | AY278631 |
| *Streptococcus* genomosp. C4 | AY278632 |
| *Streptococcus* genomosp. C5 | AY278633 |
| *Streptococcus* genomosp. C6 | AY278634 |
| *Streptococcus* genomosp. C7 | AY278635 |
| *Streptococcus* genomosp. C8 | AY278609 |
| *Streptococcus gordonii* | NC_009785 |
| *Streptococcus infantarius* | ABJK02000017 |
| *Streptococcus infantis* | AFNN01000024 |
| *Streptococcus intermedius* | NR_028736 |
| *Streptococcus lutetiensis* | NR_037096 |
| *Streptococcus massiliensis* | AY769997 |
| *Streptococcus milleri* | X81023 |
| *Streptococcus mitis* | AM157420 |
| *Streptococcus mutans* | AP010655 |
| *Streptococcus oligofermentans* | AY099095 |
| *Streptococcus oralis* | ADMV01000001 |
| *Streptococcus parasanguinis* | AEKM01000012 |
| *Streptococcus pasteurianus* | AP012054 |
| *Streptococcus peroris* | AEVF01000016 |
| *Streptococcus pneumoniae* | AE008537 |

TABLE 1-continued

Exemplary Bacterial Strains

| OTU | Public DB Accession |
|---|---|
| *Streptococcus porcinus* | EF121439 |
| *Streptococcus pseudopneumoniae* | FJ827123 |
| *Streptococcus pseudoporcinus* | AENS01000003 |
| *Streptococcus pyogenes* | AE006496 |
| *Streptococcus ratti* | X58304 |
| Streptococcus *salivarius* | AGBV01000001 |
| *Streptococcus sanguinis* | NR_074974 |
| *Streptococcus sinensis* | AF432857 |
| *Streptococcus* sp. 16362 | JN590019 |
| *Streptococcus* sp. 2_1_36FAA | ACOI01000028 |
| *Streptococcus* sp. 2285_97 | AJ131965 |
| *Streptococcus* sp. 69130 | X78825 |
| *Streptococcus* sp. AC15 | HQ616356 |
| *Streptococcus* sp. ACS2 | HQ616360 |
| *Streptococcus* sp. AS20 | HQ616366 |
| *Streptococcus* sp. BS35a | HQ616369 |
| *Streptococcus* sp. C150 | ACRI01000045 |
| *Streptococcus* sp. CM6 | HQ616372 |
| *Streptococcus* sp. CM7 | HQ616373 |
| *Streptococcus* sp. ICM10 | HQ616389 |
| *Streptococcus* sp. ICM12 | HQ616390 |
| *Streptococcus* sp. ICM2 | HQ616386 |
| *Streptococcus* sp. ICM4 | HQ616387 |
| *Streptococcus* sp. ICM45 | HQ616394 |
| *Streptococcus* sp. M143 | ACRK01000025 |
| *Streptococcus* sp. M334 | ACRL01000052 |
| *Streptococcus* sp. OBRC6 | HQ616352 |
| *Streptococcus* sp. oral clone ASB02 | AY923121 |
| *Streptococcus* sp. oral clone ASCA03 | DQ272504 |
| *Streptococcus* sp. oral clone ASCA04 | AY923116 |
| *Streptococcus* sp. oral clone ASCA09 | AY923119 |
| *Streptococcus* sp. oral clone ASCB04 | AY923123 |
| *Streptococcus* sp. oral clone ASCB06 | AY923124 |
| *Streptococcus* sp. oral clone ASCC04 | AY923127 |
| *Streptococcus* sp. oral clone ASCC05 | AY923128 |
| *Streptococcus* sp. oral clone ASCC12 | DQ272507 |
| *Streptococcus* sp. oral clone ASCD01 | AY923129 |
| *Streptococcus* sp. oral clone ASCD09 | AY923130 |
| *Streptococcus* sp. oral clone ASCD10 | DQ272509 |
| *Streptococcus* sp. oral clone ASCE03 | AY923134 |
| *Streptococcus* sp. oral clone ASCE04 | AY953253 |
| *Streptococcus* sp. oral clone ASCE05 | DQ272510 |
| *Streptococcus* sp. oral clone ASCE06 | AY923135 |
| *Streptococcus* sp. oral clone ASCE09 | AY923136 |
| *Streptococcus* sp. oral clone ASCE10 | AY923137 |
| *Streptococcus* sp. oral clone ASCE12 | AY923138 |
| *Streptococcus* sp. oral clone ASCF05 | AY923140 |
| *Streptococcus* sp. oral clone ASCF07 | AY953255 |
| *Streptococcus* sp. oral clone ASCF09 | AY923142 |
| *Streptococcus* sp. oral clone ASCG04 | AY923145 |
| *Streptococcus* sp. oral clone BW009 | AY005042 |
| *Streptococcus* sp. oral clone CH016 | AY005044 |
| *Streptococcus* sp. oral clone GK051 | AY349413 |
| *Streptococcus* sp. oral clone GM006 | AY349414 |
| *Streptococcus* sp. oral clone P2PA_41 P2 | AY207051 |
| *Streptococcus* sp. oral clone P4PA_30 P4 | AY207064 |
| *Streptococcus* sp. oral taxon 071 | AEEP01000019 |
| *Streptococcus* sp. oral taxon G59 | GU432132 |
| *Streptococcus* sp. oral taxon G62 | GU432146 |
| *Streptococcus* sp. oral taxon G63 | GU432150 |
| *Streptococcus* sp. SHV515 | Y07601 |
| *Streptococcus suis* | FM252032 |
| *Streptococcus thermophilus* | CP000419 |
| *Streptococcus uberis* | HQ391900 |
| *Streptococcus urinalis* | DQ303194 |
| *Streptococcus vestibularis* | AEKO01000008 |
| *Streptococcus viridans* | AF076036 |
| *Streptomyces albus* | AJ697941 |
| *Streptomyces griseus* | NR_074787 |
| *Streptomyces* sp. 1 AIP_2009 | FJ176782 |
| *Streptomyces* sp. SD 511 | EU544231 |
| *Streptomyces* sp. SD 524 | EU544234 |
| *Streptomyces* sp. SD 528 | EU544233 |
| *Streptomyces* sp. SD 534 | EU544232 |
| *Streptomyces thermoviolaceus* | NR_027616 |
| *Subdoligranulum* variabile | AJ518869 |
| *Succinatimonas hippei* | AEVO01000027 |
| *Sutterella morbirenis* | AJ832129 |
| *Sutterella parvirubra* | AB300989 |
| *Sutterella sanguinus* | AJ748647 |
| *Sutterella* sp. YIT 12072 | AB491210 |
| *Sutterella stercoricanis* | NR_025600 |
| *Sutterella wadsworthensis* | ADMF01000048 |
| *Synergistes* genomosp. C1 | AY278615 |
| *Synergistes* sp. RMA 14551 | DQ412722 |
| *Synergistetes* bacterium ADV897 | GQ258968 |
| *Synergistetes* bacterium LBVCM1157 | GQ258969 |
| *Synergistetes* bacterium oral taxon 362 | GU410752 |
| *Synergistetes* bacterium oral taxon D48 | GU430992 |
| *Syntrophococcus sucromutans* | NR_036869 |
| *Syntrophomonadaceae* genomosp. P1 | AY341821 |
| *Tannerella forsythia* | CP003191 |
| *Tannerella* sp. 6_1_58FAA_CTI | ACWX01000068 |
| *Tatlockia micdadei* | M36032 |
| *Tatumella ptyseos* | NR_025342 |
| *Tessaracoccus* sp. oral taxon F04 | HM099640 |
| *Tetragenococcus halophilus* | NR_075020 |
| *Tetragenococcus koreensis* | NR_043113 |
| *Thermoanaerobacter pseudethanolicus* | CP000924 |
| *Thermobifida fusca* | NC_007333 |
| *Thermofilum pendens* | X14835 |
| *Thermus aquaticus* | NR_025900 |
| *Tissierella praeacuta* | NR_044860 |
| *Trabulsiella guamensis* | AY373830 |
| *Treponema denticola* | ADEC01000002 |
| *Treponema* genomosp. P1 | AY341822 |
| *Treponema* genomosp. P4 oral clone MB2_G19 | DQ003618 |
| *Treponema* genomosp. P5 oral clone MB3_P23 | DQ003624 |
| *Treponema* genomosp. P6 oral clone MB4_G11 | DQ003625 |
| *Treponema lecithinolyticum* | NR_026247 |
| *Treponema pallidum* | CP001752 |
| *Treponema parvum* | AF302937 |
| *Treponema phagedenis* | AEFH01000172 |
| *Treponema putidum* | AJ543428 |
| *Treponema refringens* | AF426101 |
| *Treponema socranskii* | NR_024868 |
| *Treponema* sp. 6:H:D15A_4 | AY005083 |
| *Treponema* sp. clone DDKL_4 | Y08894 |
| *Treponema* sp. oral clone JU025 | AY349417 |
| *Treponema* sp. oral clone JU031 | AY349416 |
| *Treponema* sp. oral clone P2PB_53P3 | AY207055 |
| *Treponema* sp. oral taxon 228 | GU408580 |
| *Treponema* sp. oral taxon 230 | GU408603 |
| *Treponema* sp. oral taxon 231 | GU408631 |
| *Treponema* sp. oral taxon 232 | GU408646 |
| *Treponema* sp. oral taxon 235 | GU408673 |
| *Treponema* sp. oral taxon 239 | GU408738 |
| *Treponema* sp. oral taxon 247 | GU408748 |
| *Treponema* sp. oral taxon 250 | GU408776 |
| *Treponema* sp. oral taxon 251 | GU408781 |
| *Treponema* sp. oral taxon 254 | GU408803 |
| *Treponema* sp. oral taxon 265 | GU408850 |
| *Treponema* sp. oral taxon 270 | GQ422733 |
| *Treponema* sp. oral taxon 271 | GU408871 |
| *Treponema* sp. oral taxon 508 | GU413616 |
| *Treponema* sp. oral taxon 518 | GU413640 |
| *Treponema* sp. oral taxon G85 | GU432215 |
| *Treponema* sp. ovine footrot | AJ010951 |
| *Treponema vincentii* | ACYH01000036 |
| *Tropheryma whipplei* | BX251412 |
| *Trueperella pyogenes* | NR_044858 |
| *Tsukamurella paurometabola* | X80628 |
| *Tsukamurella tyrosinosolvens* | AB478958 |
| *Turicibacter sanguinis* | AF349724 |
| *Ureaplasma parvum* | AE002127 |
| *Ureaplasma urealyticum* | AAYN01000002 |
| *Ureibacillus composti* | NR_043746 |
| *Ureibacillus suwonensis* | NR_043232 |
| *Ureibacillus terrenus* | NR_025394 |
| *Ureibacillus thermophilus* | NR_043747 |
| *Ureibacillus thermosphaericus* | NR_040961 |
| *Vagococcus fluvialis* | NR_026489 |

TABLE 1-continued

Exemplary Bacterial Strains

| OTU | Public DB Accession |
|---|---|
| *Veillonella atypica* | AEDS01000059 |
| *Veillonella dispar* | ACIK02000021 |
| *Veillonella* genomosp. P1 oral clone MB5_P17 | DQ003631 |
| *Veillonella montpellierensis* | AF473836 |
| *Veillonella parvula* | ADFU01000009 |
| *Veillonella* sp. 3_1_44 | ADCV01000019 |
| *Veillonella* sp. 6_1_27 | ADCW01000016 |
| *Veillonella* sp. ACP1 | HQ616359 |
| *Veillonella* sp. AS16 | HQ616365 |
| *Veillonella* sp. BS32b | HQ616368 |
| *Veillonella* sp. ICM51a | HQ616396 |
| *Veillonella* sp. MSA12 | HQ616381 |
| *Veillonella* sp. NVG 100cf | EF108443 |
| *Veillonella* sp. OK11 | JN695650 |
| *Veillonella* sp. oral clone ASCA08 | AY923118 |
| *Veillonella* sp. oral clone ASCB03 | AY923122 |
| *Veillonella* sp. oral clone ASCG01 | AY923144 |
| *Veillonella* sp. oral clone ASCG02 | AY953257 |
| *Veillonella* sp. oral clone OH1A | AY947495 |
| *Veillonella* sp. oral taxon 158 | AENU01000007 |
| *Veillonellaceae* bacterium oral taxon 131 | GU402916 |
| *Veillonellaceae* bacterium oral taxon 155 | GU470897 |
| *Vibrio cholerae* | AAUR01000095 |
| *Vibrio fluvialis* | X76335 |
| *Vibrio furnissii* | CP002377 |
| *Vibrio mimicus* | ADAF01000001 |
| *Vibrio parahaemolyticus* | AAWQ01000116 |
| *Vibrio* sp. RC341 | ACZT01000024 |
| *Vibrio vulnificus* | AE016796 |
| *Victivallaceae* bacterium NML 080035 | FJ394915 |
| *Victivallis vadensis* | ABDE02000010 |
| *Virgibacillus proomii* | NR_025308 |
| *Weissella beninensis* | EU439435 |
| *Weissella cibaria* | NR_036924 |
| *Weissella confusa* | NR_040816 |
| *Weissella hellenica* | AB680902 |
| *Weissella kandleri* | NR_044659 |
| *Weissella koreensis* | NR_075058 |
| *Weissella paramesenteroides* | ACKU01000017 |
| *Weissella* sp. KLDS 7.0701 | EU600924 |
| *Wolinella succinogenes* | BX571657 |
| *Xanthomonadaceae* bacterium NML 03_0222 | EU313791 |
| *Xanthomonas campestris* | EF101975 |
| *Xanthomonas* sp. kmd_489 | EU723184 |
| *Xenophilus aerolatus* | JN585329 |
| *Yersinia aldovae* | AJ871363 |
| *Yersinia aleksiciae* | AJ627597 |
| *Yersinia bercovieri* | AF366377 |
| *Yersinia enterocolitica* | FR729477 |
| *Yersinia frederiksenii* | AF366379 |
| *Yersinia intermedia* | AF366380 |
| *Yersinia kristensenii* | ACCA01000078 |
| *Yersinia mollaretii* | NR_027546 |
| *Yersinia pestis* | AE013632 |
| *Yersinia pseudotuberculosis* | NC_009708 |
| *Yersinia rohdei* | ACCD01000071 |
| *Yokenella regensburgei* | AB273739 |
| *Zimmermannella bifida* | AB012592 |
| *Zymomonas mobilis* | NR_074274 |

TABLE 2

Exemplary Oncophilic Bacteria

| Genera | Species | Tumor Association |
|---|---|---|
| *Mycoplasma* | *hyorhinis* | Gastric Carcinoma |
| *Propionibacterium* | *Acnes* | Prostate Cancer |
| *Mycoplasma* | *genitalium* | Prostate Cancer |
| *Methylophilus* | sp. | Prostate Cancer |
| *Chlamydia* | *trachomatis* | Prostate Cancer |
| *Helicobacter* | *pylori* | Gastric MALT |
| *Listeria* | *welshimeri* | Renal Cancer |

TABLE 2-continued

Exemplary Oncophilic Bacteria

| Genera | Species | Tumor Association |
|---|---|---|
| *Streptococcus* | *pneumoniae* | Lymphoma and Leukemia |
| *Haemophilus* | *influenzae* | Lymphoma and Leukemia |
| *Staphylococcus* | *aureus* | Breast Cancer |
| *Listeria* | *monocytogenes* | Breast Cancer |
| *Methylobacterium* | *radiotolerans* | Breast Cancer |
| *Shingomonas* | *yanoikuyae* | breast Cancer |
| *Fusobacterium* | sp | Larynx cancer |
| *Provetelis* | sp | Larynx cancer |
| *streptococcus* | *pneumoniae* | Larynx cancer |
| *Gemella* | sp | Larynx cancer |
| *Bordetella* | *Pertussis* | Larynx cancer |
| *Corumebacterium* | *tuberculostearicum* | Oral squamous cell carcinoma |
| *Micrococcus* | *luteus* | Oral squamous cell carcinoma |
| *Prevotella* | *melaninogenica* | Oral squamous cell carcinoma |
| *Exiguobacterium* | *oxidotolerans* | Oral squamous cell carcinoma |
| *Fusobacterium* | *naviforme* | Oral squamous cell carcinoma |
| *Veillonella* | *parvula* | Oral squamous cell carcinoma |
| *Streptococcus* | *salivarius* | Oral squamous cell carcinoma |
| *Streptococcus* | *mitis/oralis* | Oral squamous cell carcinoma |
| *veillonella* | *dispar* | Oral squamous cell carcinoma |
| *Peptostreptococcus* | *stomatis* | Oral squamous cell carcinoma |
| *Streptococcus* | *gordonii* | Oral squamous cell carcinoma |
| *Gemella* | *Haemolysans* | Oral squamous cell carcinoma |
| *Gemella* | *morbillorum* | Oral squamous cell carcinoma |
| *Johnsonella* | *ignava* | Oral squamous cell carcinoma |
| *Streptococcus* | *parasanguins* | Oral squamous cell carcinoma |
| *Granulicatella* | *adiacens* | Oral squamous cell carcinoma |
| *Mycobacteria* | *marinum* | lung infection |
| *Campylobacter* | *concisus* | Barrett's Esophagus |
| *Campylobacter* | *rectus* | Barrett's Esophagus |
| *Oribacterium* | sp | Esophageal adenocarcinoma |
| *Catonella* | sp | Esophageal adenocarcinoma |
| *Peptostreptococcus* | sp | Esophageal adenocarcinoma |
| *Eubacterium* | sp | Esophageal adenocarcinoma |
| *Dialister* | sp | Esophageal adenocarcinoma |
| *Veillonella* | sp | Esophageal adenocarcinoma |
| *Anaeroglobus* | sp | Esophageal adenocarcinoma |
| *Megasphaera* | sp | Esophageal adenocarcinoma |
| *Atoppbium* | sp | Esophageal adenocarcinoma |
| *Solobacterium* | sp | Esophageal adenocarcinoma |
| *Rothia* | sp | Esophageal adenocarcinoma |
| *Actinomyces* | sp | Esophageal adenocarcinoma |
| *Fusobacterium* | sp | Esophageal adenocarcinoma |
| *Sneathia* | sp | Esophageal adenocarcinoma |
| *Leptotrichia* | sp | Esophageal adenocarcinoma |
| *Capnocytophaga* | sp | Esophageal adenocarcinoma |
| *Prevotella* | sp | Esophageal adenocarcinoma |
| *Porphyromonas* | sp | Esophageal adenocarcinoma |
| *Campylobacter* | sp | Esophageal adenocarcinoma |
| *Haemophilus* | sp | Esophageal adenocarcinoma |
| *Neisseria* | sp | Esophageal adenocarcinoma |
| TM7 | sp | Esophageal adenocarcinoma |
| *Granulicatella* | sp | Esophageal adenocarcinoma |
| *Variovorax* | sp | Psuedomyxoma Peritonei |
| *Escherichia* | *Shigella* | Psuedomyxoma Peritonei |
| *Pseudomonas* | sp | Psuedomyxoma Peritonei |
| *Tessaracoccus* | sp | Psuedomyxoma Peritonei |
| *Acinetobacter* | sp | Psuedomyxoma Peritonei |
| *Helicobacter* | *hepaticus* | Breast cancer |
| *Chlamydia* | *psittaci* | MALT lymphoma |
| *Borrelia* | *burgdorferi* | B cell lymphoma skin |
| *Escherichia* | *Coli* NC101 | Colorectal Cancer |
| *Salmonella* | *typhimurium* | Tool |
| *Eterococcus* | *faecalis* | blood |
| *Streptococcus* | *mitis* | blood |
| *Streptococcus* | *sanguis* | blood |
| *Streptococcus* | *anginosus* | blood |
| *Streptococcus* | *salvarius* | blood |
| *Staphylococcus* | *epidermidis* | blood |
| *Streptococcus* | *gallolyticus* | Colorectal Cancer |
| *Campylobacter* | *showae* CC57C | Colorectal Cancer |
| *Leptotrichia* | sp | Colorectal Cancer |

In certain embodiments the EVs described herein areobtained from obligate anaerobic bacteria. Examples of obligate anaerobic bacteria include gram-negative rods (including the genera of *Bacteroides, Prevotella, Porphyromonas, Fusobacterium*, Bilophila and Sutterella spp.), gram-positive cocci (primarily *Peptostreptococcus* spp.), gram-positive spore-forming (*Clostridium* spp.), non-spore-forming bacilli (*Actinomyces, Propionibacterium, Eubacterium, Lactobacillus* and *Bifidobacterium* spp.), and gram-negative cocci (mainly *Veillonella* spp.). In some embodiments, the obligate anearoic bacteria are of a genus selected from Agathobaculum, Atopobium, *Blautia, Burkholderia*, Dielma, Longicatena, *Paraclostridium*, Turicibacter, and Tyzzerella.

In some embodiments, the EVs described herein are obtained from bacterium of a genus selected from *Escherichia, Klebsiella, Lactobacillus, Shigella*, and Staphylococcusa.

In some embodiments, the bacteria and/or EVs described herein are of a species selected from *Blautia massiliensis, Paraclostridium benzoelyticum, Dielma fastidiosa, Longicatena caecimuris, Veillonella tobetsuensis*.

In some embodiments, the EVs and/or bacteria described herein are modified such that they comprise, are linked to, and/or are bound by a therapeutic moiety. In some embodiments, the therapeutic moiety is a cancer-specific moiety. In some embodiments, the cancer-specific moiety has binding specificity for a cancer cell (e.g., has binding specificity for a cancer-specific antigen). In some embodiments, the cancer-specific moiety comprises an antibody or antigen binding fragment thereof. In some embodiments, the cancer-specific moiety comprises a T cell receptor or a chimeric antigen receptor (CAR). In some embodiments, the cancer-specific moiety comprises a ligand for a receptor expressed on the surface of a cancer cell or a receptor-binding fragment thereof. In some embodiments, the cancer-specific moiety is a bipartite fusion protein that has two parts: a first part that binds to and/or is linked to the bacterium and a second part that is capable of binding to a cancer cell (e.g., by having binding specificity for a cancer-specific antigen). In some embodiments, the first part is a fragment of or a full-length peptidoglycan recognition protein, such as PGRP. In some embodiments the first part has binding specificity for the EV (e.g., by having binding specificity for a bacterial antigen). In some embodiments, the first and/or second part comprises an antibody or antigen binding fragment thereof. In some embodiments, the first and/or second part comprises a T cell receptor or a chimeric antigen receptor (CAR). In some embodiments, the first and/or second part comprises a ligand for a receptor expressed on the surface of a cancer cell or a receptor-binding fragment thereof. In certain embodiments, co-administration of the cancer-specific moiety with the EVs (either in combination or in separate administrations) increases the targeting of the EVs to the cancer cells.

In some embodiments, the EVs described herein is modified such that they comprise, are linked to, and/or are bound by a magnetic and/or paramagnetic moiety (e.g., a magnetic bead). In some embodiments, the magnetic and/or paramagnetic moiety is comprised by and/or directly linked to the bacteria. In some embodiments, the magnetic and/or paramagnetic moiety is linked to and/or a part of an EV-binding moiety that that binds to the EV. In some embodiments, the EV-binding moiety is a fragment of or a full-length peptidoglycan recognition protein, such as PGRP. In some embodiments the EV-binding moiety has binding specificity for the EV (e.g., by having binding specificity for a bacterial antigen). In some embodiments, the EV-binding moiety comprises an antibody or antigen binding fragment thereof. In some embodiments, the EV-binding moiety comprises a T cell receptor or a chimeric antigen receptor (CAR). In some embodiments, the EV-binding moiety comprises a ligand for a receptor expressed on the surface of a cancer cell or a receptor-binding fragment thereof. In certain embodiments, co-administration of the magnetic and/or paramagnetic moiety with the EVs (either together or in separate administrations) can be used to increase the targeting of the EVs to cancer calls and/or a part of a subject where cancer cells are present.

Production of EVs

In certain aspects, the EVs described herein can be prepared using any method known in the art.

In some embodiments, the EVs are prepared without an EV purification step. For example, in some embodiments, bacteria comprising the EVs described herein are killed using a method that leaves the bacterial EVs intact and the resulting bacterial components, including the EVs, are used in the methods and compositions described herein. In some embodiments, the bacteria are killed using an antibiotic (e.g., using an antibiotic described herein). In some embodiments, the bacteria are killed using UV irradiation.

In some embodiments, the EVs described herein are purified from one or more other bacterial components. Methods for purifying EVs from bacteria are known in the art. In some embodiments EVs are prepared from bacterial cultures using methods described in S. Bin Park, et al. PLOS ONE. 6(3):e17629 (2011) or G. Norheim, et al. PLOS ONE. 10(9): e0134353 (2015), each of which is hereby incorporated by reference in its entirety. In some embodiments, the bacteria are cultured to high optical density and then centrifuged to pellet bacteria (e.g., at 10,000×g for 30 min at 4° C.). In some embodiments, the culture supernatants are then passed through filter to exclude intact bacterial cells (e.g., a 0.22 µm filter). In some embodiments, filtered supernatants are centrifuged to pellet bacterial EVs (e.g., at 100,000-150,000×g for 1-3 hours at 4° C.). In some embodiments, the EVs are further purified by resuspending the resulting EV pellets (e.g., in PBS), and applying the resuspended EVs to sucrose gradient (e.g., a 30-60% discontinuous sucrose gradient), followed by centrifugation (e.g., at 200,000×g for 20 hours at 4° C.). EV bands can be collected, washed with (e.g., with PBS), and centrifuged to pellet the EVs (e.g., at 150,000×g for 3 hours at 4° C.). The purified EVs can be stored, for example, at −80° C. until use. In some embodiments, the EVs are further purified by treatment with DNase and/or proteinase K For example, in some embodiments, cultures of bacteria disclosed herein can be centrifuged at 11,000×g for 20-40 min at 4° C. to pellet bacteria. Culture supernatants may be passed through a 0.22 µm filter to exclude intact bacterial cells. Filtered supernatants may then be concentrated using methods that may include, but are not limited to, ammonium sulfate precipitation, ultracentrifugation, or filtration. For example, for ammonium sulfate precipitation, 1.5-3 M ammonium sulfate can be added to filtered supernatant slowly, while stirring at 4° C. Precipitations can be incubated at 4° C. for 8-48 hours and then centrifuged at 11,000×g for 20-40 min at 4° C. The resulting pellets contain bacterial EVs and other debris. Using ultracentrifugation, filtered supernatants can be centrifuged at 100,000-200,000×g for 1-16 hours at 4° ° C. The pellet of this centrifugation contains bacterial EVs and other debris. In some embodiments, using a filtration technique, such as through the use of an Amicon Ultra spin filter or by tangential flow filtration, supernatants can be filtered so as to retain species of molecular weight>50 or 100 kDa.

Alternatively, EVs can be obtained from bacterial cultures continuously during growth, or at selected time points during growth, by connecting a bioreactor to an alternating tangential flow (ATF) system (e.g., XCell ATF from Repligen). The ATF system retains intact cells (>0.22 um) in the bioreactor, and allows smaller components (e.g., EVs, free proteins) to pass through a filter for collection. For example, the system may be configured so that the <0.22 um filtrate is then passed through a second filter of 100 kDa, allowing species such as EVs between 0.22 um and 100 kDa to be collected, and species smaller than 100 kDa to be pumped back into the bioreactor. Alternatively, the system may be configured to allow for medium in the bioreactor to be replenished and/or modified during growth of the culture. EVs collected by this method may be further purified and/or concentrated by ultracentrifugation or filtration as described above for filtered supernatants.

EVs obtained by methods provided herein may be further purified by size based column chromatography, by affinity chromatography, and by gradient ultracentrifugation, using methods that may include, but are not limited to, use of a sucrose gradient or Optiprep gradient. Briefly, using a sucrose gradient method, if ammonium sulfate precipitation or ultracentrifugation were used to concentrate the filtered supernatants, pellets are resuspended in 60% sucrose, 30 mM Tris, pH 8.0. If filtration was used to concentrate the filtered supernatant, the concentrate is buffer exchanged into 60% sucrose, 30 mM Tris, pH 8.0, using an Amicon Ultra column. Samples are applied to a 35-60% discontinuous sucrose gradient and centrifuged at 200,000×g for 3-24 hours at 4° ° C. Briefly, using an Optiprep gradient method, if ammonium sulfate precipitation or ultracentrifugation were used to concentrate the filtered supernatants, pellets are resuspended in 35% Optiprep in PBS. In some embodiments, if filtration was used to concentrate the filtered supernatant, the concentrate is diluted using 60% Optiprep to a final concentration of 35% Optiprep. Samples are applied to a 35-60% discontinuous sucrose gradient and centrifuged at 200,000×g for 3-24 hours at 4° C.

In some embodiments, to confirm sterility and isolation of the EV preparations, EVs are serially diluted onto agar medium used for routine culture of the bacteria being tested, and incubated using routine conditions. Non-sterile preparations are passed through a 0.22 um filter to exclude intact cells. To further increase purity, isolated EVs may be DNase or proteinase K treated.

In some embodiments, for preparation of EVs used for in vivo injections, purified EVs are processed as described previously (G. Norheim, et al. PLOS ONE. 10(9): e0134353 (2015)). Briefly, after sucrose gradient centrifugation, bands containing EVs are resuspended to a final concentration of 50 g/mL in a solution containing 3% sucrose or other solution suitable for in vivo injection known to one skilled in the art. This solution may also contain adjuvant, for example aluminum hydroxide at a concentration of 0-0.5% (w/v).

In certain embodiments, to make samples compatible with further testing (e.g. to remove sucrose prior to TEM imaging or in vitro assays), samples are buffer exchanged into PBS or 30 mM Tris, pH 8.0 using filtration (e.g. Amicon Ultra columns), dialysis, or ultracentrifugation (200,000×g, ≥3 hours, 4° C.) and resuspension.

In some embodiments, the sterility of the EV preparations can be confirmed by plating a portion of the EVs onto agar medium used for standard culture of the bacteria used in the generation of the EVs and incubating using standard conditions.

In some embodiments select EVs are isolated and enriched by chromatography and binding surface moieties on EVs. In other embodiments, select EVs are isolated and/or enriched by fluorescent cell sorting by methods using affinity reagents, chemical dyes, recombinant proteins or other methods known to one skilled in the art.

Pharmaceutical Compositions

In certain embodiments, the methods provided herein are pharmaceutical compositions comprising EVs and/or bacteria provided herein (e.g., an EV composition). In some embodiments, the EV composition comprises an EV and/or a combination of EVs described herein and a pharmaceutically acceptable carrier.

In some embodiments, the pharmaceutical compositions comprise EVs substantially or entirely free of bacteria. In some embodiments, the pharmaceutical compositions comprise both EVs and whole bacteria (e.g., live bacteria, killed bacteria, attenuated bacteria). In certain embodiments, the pharmaceutical compositions comprise bacteria that is substantially or entirely free of EVs. In some embodiments, the pharmaceutical compositions comprise EVs and/or bacteria from one or more (e.g., 1, 2, 3, 4, 5, 6, 7, 8, 9, 10 or more) of the bacteria strains or species listed in Table 1 and/or Table 2.

In some embodiments, the pharmaceutical composition comprises at least 1 bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, and/or $1 \times 10^{12}$ EV particles.

In some embodiments, the pharmaceutical composition comprises about 1 bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, 5×10$^6$, 6×10$^6$, 7×10$^6$, 8×10$^6$, 9×10$^6$, 1×10$^7$, 2×10$^7$, 3×10$^7$, 4×10$^7$, 5×10$^7$, 6×10$^7$, 7×10$^7$, 8×10$^7$, 9×10$^7$, 1×10$^8$, 2×10$^8$, 3×10$^8$, 4×10$^8$, 5×10$^8$, 6×10$^8$, 7×10$^8$, 8×10$^8$, 9×10$^8$, 1×10$^9$, 2×10$^9$, 3×10$^9$, 4×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$, 6×10$^{10}$, 7×10$^{10}$, 8×10$^{10}$, 9×10$^{10}$, 1×10$^{11}$, 2×10$^{11}$, 3×10$^{11}$, 4×10$^{11}$, 5×10$^{11}$, 6×10$^{11}$, 7×10$^{11}$, 8×10$^{11}$, 9×10$^{11}$, and/or 1×10$^{12}$ EV particles.

In certain embodiments, the pharmaceutical composition comprises a certain ratio of bacteria particles to EV particles. The number of bacteria particles can be based on actual particle number or (if the bacteria is live) the number of CFUs. The particle number can be established by combining a set number of purified EVs with a set number of purified bacterium, by modifying the growth conditions under which the bacteria are cultured, or by modifying the bacteria itself to produce more or fewer EVs.

In some embodiments, to quantify the numbers of EVs and/or bacteria present in a bacterial sample, electron microscopy (e.g., EM of ultrathin frozen sections) can be used to visualize the vesicles and bacteria and count their relative numbers. Alternatively, combinations of nanoparticle tracking analysis (NTA), Coulter counting, and dynamic light scattering (DLS) or a combination of these techniques can be used. NTA and the Coulter counter count particles and show their sizes. DLS gives the size distribution of particles, but not the concentration. Bacteria frequently have diameters of 1-2 μm. The full range is 0.2-20 um. Combined results from Coulter counting and NTA can reveal the numbers of bacteria in a given sample. Coulter counting reveals the numbers of particles with diameters of 0.7-10 um. NTA reveals the numbers of particles with diameters of 50-1400 nm. For most bacterial samples, the Coulter counter alone can reveal the number of bacteria in a sample. EVs are 20-250 nm in diameter. NTA will allow us to count the numbers of particles that are 50-250 nm in diameter. DLS reveals the distribution of particles of different diameters within an approximate range of 1 nm-3 um.

In some embodiments, the pharmaceutical composition comprises no more than 1 bacterium for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, 1×10$^3$, 2×10$^3$, 3×10$^3$, 4×10$^3$, 5×10$^3$, 6×10$^3$, 7×10$^3$, 8×10$^3$, 9×10$^3$, 1×10$^4$, 2×10$^4$, 3×10$^4$, 4×10$^4$, 5×10$^4$, 6×10$^4$, 7×10$^4$, 8×10$^4$, 9×10$^4$, 1×10$^5$, 2×10$^5$, 3×10$^5$, 4×10$^5$, 5×10$^5$, 6×10$^5$, 7×10$^5$, 8×10$^5$, 9×10$^5$, 1×10$^6$, 2×10$^6$, 3×10$^6$, 4×10$^6$, 5×10$^6$, 6×10$^6$, 7×10$^6$, 8×10$^6$, 9×10$^6$, 1×10$^7$, 2×10$^7$, 3×10$^7$, 4×10$^7$, 5×10$^7$, 6×10$^7$, 7×10$^7$, 8×10$^7$, 9×10$^7$, 1×10$^8$, 2×10$^8$, 3×10$^8$, 4×10$^8$, 5×10$^8$, 6×10$^8$, 7×10$^8$, 8×10$^8$, 9×10$^8$, 1×10$^9$, 2×10$^9$, 3×10$^9$, 4×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$, 6×10$^{10}$, 7×10$^{10}$, 8×10$^{10}$, 9×10$^{10}$, 1×10$^{11}$, 2×10$^{11}$, 3×10$^{11}$, 4×10$^{11}$, 5×10$^{11}$, 6×10$^{11}$, 7×10$^{11}$, 8×10$^{11}$, 9×10$^{11}$, and/or 1×10$^{12}$ EV particles.

In some embodiments, the pharmaceutical composition comprises at least 1 EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, 1×10$^3$, 2×10$^3$, 3×10$^3$, 4×10$^3$, 5×10$^3$, 6×10$^3$, 7×10$^3$, 8×10$^3$, 9×10$^3$, 1×10$^4$, 2×10$^4$, 3×10$^4$, 4×10$^4$, 5×10$^4$, 6×10$^4$, 7×10$^4$, 8×10$^4$, 9×10$^4$, 1×10$^5$, 2×10$^5$, 3×10$^5$, 4×10$^5$, 5×10$^5$, 6×10$^5$, 7×10$^5$, 8×10$^5$, 9×10$^5$, 1×10$^6$, 2×10$^6$, 3×10$^6$, 4×10$^6$, 5×10$^6$, 6×10$^6$, 7×10$^6$, 8×10$^6$, 9×10$^6$, 1×10$^7$, 2×10$^7$, 3×10$^7$, 4×10$^7$, 5×10$^7$, 6×10$^7$, 7×10$^7$, 8×10$^7$, 9×10$^7$, 1×10$^8$, 2×10$^8$, 3×10$^8$, 4×10$^8$, 5×10$^8$, 6×10$^8$, 7×10$^8$, 8×10$^8$, 9×10$^8$, 1×10$^9$, 2×10$^9$, 3×10$^9$, 4×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$, 6×10$^{10}$, 7×10$^{10}$, 8×10$^{10}$, 9×10$^{10}$, 1×10$^{11}$, 2×10$^{11}$, 3×10$^{11}$, 4×10$^{11}$, 5×10$^{11}$, 6×10$^{11}$, 7×10$^{11}$, 8×10$^{11}$, 9×10$^{11}$, and/or 1×10$^{12}$ bacterium.

In some embodiments, the pharmaceutical composition comprises about 1 EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, 1×10$^3$, 2×10$^3$, 3×10$^3$, 4×10$^3$, 5×10$^3$, 6×10$^3$, 7×10$^3$, 8×10$^3$, 9×10$^3$, 1×10$^4$, 2×10$^4$, 3×10$^4$, 4×10$^4$, 5×10$^4$, 6×10$^4$, 7×10$^4$, 8×10$^4$, 9×10$^4$, 1×10$^5$, 2×10$^5$, 3×10$^5$, 4×10$^5$, 5×10$^5$, 6×10$^5$, 7×10$^5$, 8×10$^5$, 9×10$^5$, 1×10$^6$, 2×10$^6$, 3×10$^6$, 4×10$^6$, 5×10$^6$, 6×10$^6$, 7×10$^6$, 8×10$^6$, 9×10$^6$, 1×10$^7$, 2×10$^7$, 3×10$^7$, 4×10$^7$, 5×10$^7$, 6×10$^7$, 7×10$^7$, 8×10$^7$, 9×10$^7$, 1×10$^8$, 2×10$^8$, 3×10$^8$, 4×10$^8$, 5×10$^8$, 6×10$^8$, 7×10$^8$, 8×10$^8$, 9×10$^8$, 1×10$^9$, 2×10$^9$, 3×10$^9$, 4×10$^9$, 5×10$^9$, 6×10$^9$, 7×10$^9$, 8×10$^9$, 9×10$^9$, 1×10$^{10}$, 2×10$^{10}$, 3×10$^{10}$, 4×10$^{10}$, 5×10$^{10}$, 6×10$^{10}$, 7×10$^{10}$, 8×10$^{10}$, 9×10$^{10}$, 1×10$^{11}$, 2×10$^{11}$, 3×10$^{11}$, 4×10$^{11}$, 5×10$^{11}$, 6×10$^{11}$, 7×10$^{11}$, 8×10$^{11}$, 9×10$^{11}$, and/or 1×10$^{12}$ bacterium.

In some embodiments, the pharmaceutical composition comprises no more than 1 EV particle for every 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8. 2.9, 3, 3.1, 3.2, 3.3, 3.4, 3.5, 3.6, 3.7, 3.8. 3.9, 4, 4.1, 4.2, 4.3, 4.4, 4.5, 4.6, 4.7, 4.8. 4.9, 5, 5.1, 5.2, 5.3, 5.4, 5.5, 5.6, 5.7, 5.8. 5.9, 6, 6.1, 6.2, 6.3, 6.4, 6.5, 6.6, 6.7, 6.8. 6.9, 7, 7.1, 7.2, 7.3, 7.4, 7.5, 7.6, 7.7, 7.8. 7.9, 8, 8.1, 8.2, 8.3, 8.4, 8.5, 8.6, 8.7, 8.8. 8.9, 9, 9.1, 9.2, 9.3, 9.4, 9.5, 9.6, 9.7, 9.8. 9.9, 10, 11, 12, 13, 14, 15, 16, 17, 18. 19, 20, 21, 22, 23, 24, 25, 26, 27, 28. 29, 30, 31, 32, 33, 34, 35, 36, 37, 38. 39, 40, 41, 42, 43, 44, 45, 46, 47, 48. 49, 50, 51, 52, 53, 54, 55, 56, 57, 58. 59, 60, 61, 62, 63, 64, 65, 66, 67, 68. 69, 70, 71, 72, 73, 74, 75, 76, 77, 78. 79, 80, 81, 82, 83, 84, 85, 86, 87, 88. 89, 90, 91, 92, 93, 94, 95, 96, 97, 98. 99, 100, 150, 200, 250, 300, 350, 400, 450, 500, 550, 600, 650, 700, 750, 800, 850, 900, 950, 1×10$^3$, 2×10$^3$, 3×10$^3$, 4×10$^3$, 5×10$^3$, 6×10$^3$, 7×10$^3$, 8×10$^3$, 9×10$^3$, 1×10$^4$, 2×10$^4$, 3×10$^4$, 4×10$^4$, 5×10$^4$, 6×10$^4$, 7×10$^4$, 8×10$^4$, 9×10$^4$, 1×10$^5$, 2×10$^5$, 3×10$^5$, 4×10$^5$, 5×10$^5$, 6×10$^5$, 7×10$^5$, 8×10$^5$, 9×10$^5$, 1×10$^6$, 2×10$^6$, 3×10$^6$, 4×10$^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, and/or $1\times10^{12}$ bacterium.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are EVs.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are bacteria.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are EVs.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are bacteria.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are EVs.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the particles in the pharmaceutical composition are bacteria.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is EV protein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is bacteria protein.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is EV protein.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is bacteria protein.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is EV protein.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the protein in the pharmaceutical composition is bacteria protein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are EV lipids.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are bacteria lipids.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are EV lipids.

In some embodiments, no more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are bacteria lipids.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are EV lipids.

In some embodiments, about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the lipids in the pharmaceutical composition are bacteria lipids.

In some embodiments, the EVs in the pharmaceutical composition are purified from one or more other bacterial components. In some embodiments, the pharmaceutical composition further comprises other bacterial components. In some embodiments, the pharmaceutical composition comprise bacteria cells.

In certain aspects, provided are pharmaceutical compositions for administration subjects. In some embodiments, the pharmaceutical compositions are combined with additional active and/or inactive materials in order to produce a final product, which may be in single dosage unit or in a multi-dose format. In some embodiments, the the pharmaceutical compositions is combined with an adjuvant such as an immuno-adjuvant (e.g., STING agonists, TLR agonists, NOD agonists).

In some embodiments the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments the composition comprises at least one lipid. As used herein a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments the excipient is a buffering agent. Non-limiting examples of suitable buffering agents include sodium citrate, magnesium carbonate, magnesium bicarbonate, calcium carbonate, and calcium bicarbonate.

In some embodiments the excipient comprises a preservative. Non-limiting examples of suitable preservatives include antioxidants, such as alpha-tocopherol and ascorbate, and antimicrobials, such as parabens, chlorobutanol, and phenol.

In some embodiments the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

In some embodiments the composition is a food product for animals, including humans. The animals, other than humans, are not particularly limited, and the composition can be used for various livestock, poultry, pets, experimental animals, and the like. Specific examples of the animals include pigs, cattle, horses, sheep, goats, chickens, wild ducks, ostriches, domestic ducks, dogs, cats, rabbits, hamsters, mice, rats, monkeys, and the like, but the animals are not limited thereto.

Therapeutic Agents

In certain aspects, the methods provided herein include the administration to a subject of a pharmaceutical composition described herein either alone or in combination with an additional therapeutic. In some embodiments, the additional therapeutic is an immunosuppressant, a steroid, cancer therapeutic.

In some embodiments the EV is administered to the subject before the therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments the EV is administered to the subject after the therapeutic is administered (e.g., at least 1, 2, 3, 4, 5, 6, 7, 8, 9, 10, 11, 12, 13, 14, 15, 16, 17, 18, 19, 20, 21, 22, 23 or 24 hours after or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the EV and the therapeutic are administered to the subject simultaneously or nearly simultaneously (e.g., administrations occur within an hour of each other). In some embodiments, the subject is administered an antibiotic before the EV is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days before). In some embodiments, the subject is administered an antibiotic after the EV is administered to the subject (e.g., at least 1, 2, 3, 4, 5, 6, 7, 8, 9, 10, 11, 12, 13, 14, 15, 16, 17, 18, 19, 20, 21, 22, 23 or 24 hours before or at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after). In some embodiments, the EV and the antibiotic are administered to the subject simultaneously or nearly simultaneously (e.g., administrations occur within an hour of each other).

In some embodiments, the additional therapeutic is a cancer therapeutic. In some embodiments, the cancer therapeutic is a chemotherapeutic agent. Examples of such chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In some embodiments, the cancer therapeutic is a cancer immunotherapy agent. Immunotherapy refers to a treatment that uses a subject's immune system to treat cancer, e.g., checkpoint inhibitors, cancer vaccines, cytokines, cell therapy, CAR-T cells, and dendritic cell therapy. Non-limiting examples of immunotherapies are checkpoint inhibitors include Nivolumab (BMS, anti-PD-1), Pembrolizumab (Merck, anti-PD-1), Ipilimumab (BMS, anti-CTLA-4), MEDI4736 (AstraZeneca, anti-PD-L1), and MPDL3280A (Roche, anti-PD-L1). Other immunotherapies may be tumor vaccines, such as Gardail, CERVARIX® (Human Papillomavirus Bivalent (Types 16 and 18) Vaccine, Recombinant), BCG, sipulencel-T, Gp100:209-217, AGS-003, DCVax-L, Algenpantucel-L, Tergenpantucel-L, TG4010, ProstAtak® (aglatimagene besadenovec), PROSTVAC® (PSA-TRICOM or PROSTVAC®-V/R-TRICOM (rilimogene-galvacirepvec), Rindopepimul, E75 peptide acetate, IMA901, POL-103A, Belagenpumatucel-L, GSK1572932A, MDX-1279, GV1001, and Tecemotide. Immunotherapy may be administered via injection (e.g., intravenously, intratumorally, subcutaneously, or into lymph nodes), but may also be administered orally, topically, or via aerosol. Immunotherapies may comprise adjuvants such as cytokines.

In some embodiments, the immunotherapy agent is an immune checkpoint inhibitor. Immune checkpoint inhibition broadly refers to inhibiting the checkpoints that cancer cells can produce to prevent or downregulate an immune response. Examples of immune checkpoint proteins include, but are not limited to, CTLA4, PD-1, PD-L1, PD-L2, A2AR, B7-H3, B7-H4, BTLA, KIR, LAG3, TIM-3 or VISTA. Immune checkpoint inhibitors can be antibodies or antigen binding fragments thereof that bind to and inhibit an immune checkpoint protein. Examples of immune checkpoint inhibitors include, but are not limited to, nivolumab, pembrolizumab, pidilizumab, AMP-224, AMP-514, STI- A1110, TSR-042, RG-7446, BMS-936559, MEDI-4736, MSB-0020718C, AUR-012 and STI-A1010.

In some embodiments, the methods provided herein include the administration of a pharmaceutical composition described herein in combination with one or more additional therapeutic. In some embodiments, the methods disclosed herein include the administration of two additional immunotherapy agents (e.g., immune checkpoint inhibitor). For example, the methods provided herein include the administration of a pharmaceutical composition described herein in combination with a PD-1 inhibitor and a CLTA-4 inhibitor or a PD-L1 inhibitor and a CTLA-4 inhibitor.

In some embodiments, the immunotherapy agent is an antibody or antigen binding fragment thereof that, for example, binds to a cancer-associated antigen. Examples of cancer-associated antigens include, but are not limited to, adipophilin, AIM-2, ALDHIA1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNKIA1, CTAG1, CTAG2, cyclin D1, Cyclin-A1, dek-can fusion protein, DKK1, EFTUD2, Elongation factor 2, ENAH (hMena), Ep-CAM, EpCAM, EphA3, epithelial tumor antigen ("ETA"), ETV6-AMLI fusion protein, EZH2, FGF5, FLT3-ITD, FN1, G250/MN/CAIX, GAGE-1,2,8, GAGE-3,4,5,6,7, GAS7, glypican-3, GnTV, gp100/Pme117, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHNI also known as CCDC110, LAGE-1, LDLR-fucosyltransferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MCIR, MCSP, mdm-2, ME1, Melan-A/MART-1, Meloe, Midkine, MMP-2, MMP-7, MUCI, MUC5AC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAX5, PBF, pml-RARalpha fusion protein, polymorphic epithelial mucin ("PEM"), PPPIR3B, PRAME, PRDX5, PSA, PSMA, PTPRK, RAB38/NY-MEL-1, RAGE-1, RBAF600, RGS5, RhoC, RNF43, RU2AS, SAGE, secernin 1, SIRT2, SNRPD1, SOX10, Sp17, SPA17, SSX-2, SSX-4, STEAPI, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen.

In some embodiments, the immunotherapy agent is a cancer vaccine and/or a component of a cancer vaccine (e.g., an antigenic peptide and/or protein). The cancer vaccine can be a protein vaccine, a nucleic acid vaccine or a combination thereof. For example, in some embodiments, the cancer vaccine comprises a polypeptide comprising an epitope of a cancer-associated antigen. In some embodiments, the cancer vaccine comprises a nucleic acid (e.g., DNA or RNA, such as mRNA) that encodes an epitope of a cancer-associated antigen. Examples of cancer-associated antigens include, but are not limited to, adipophilin, AIM-2, ALDH1A1, alpha-actinin-4, alpha-fetoprotein ("AFP"), ARTC1, B-RAF, BAGE-1, BCLX (L), BCR-ABL fusion protein b3a2, beta-catenin, BING-4, CA-125, CALCA, carcinoembryonic antigen ("CEA"), CASP-5, CASP-8, CD274, CD45, Cdc27, CDK12, CDK4, CDKN2A, CEA, CLPP, COA-1, CPSF, CSNKIA1, CTAG1, CTAG2, cyclin D1, Cyclin-A1,dek-can fusion protein, DKK1, EFTUD2, Elongation factor 2, ENAH (hMena), Ep-CAM, EpCAM, EphA3, epithelial tumor antigen ("ETA"), ETV6-AMLI fusion protein, EZH2, FGFS, FLT3-ITD, FN1, G250/MN/CAIX, GAGE-1,2,8, GAGE-3,4,5,6,7, GAS7, glypican-3, GnTV, gp100/Pme117, GPNMB, HAUS3, Hepsin, HER-2/neu, HERV-K-MEL, HLA-A11, HLA-A2, HLA-DOB, hsp70-2, IDO1, IGF2B3, IL13Ralpha2, Intestinal carboxyl esterase, K-ras, Kallikrein 4, KIF20A, KK-LC-1, KKLC1, KM-HN-1, KMHNI also known as CCDC110, LAGE-1, LDLR-fucosyltranferaseAS fusion protein, Lengsin, M-CSF, MAGE-A1, MAGE-A10, MAGE-A12, MAGE-A2, MAGE-A3, MAGE-A4, MAGE-A6, MAGE-A9, MAGE-C1, MAGE-C2, malic enzyme, mammaglobin-A, MART2, MATN, MCIR, MCSP, mdm-2, MEL Melan-A/MART-1, Meloe, Midkine, MMP-2, MMP-7, MUCI, MUCSAC, mucin, MUM-1, MUM-2, MUM-3, Myosin, Myosin class I, N-raw, NA88-A, neo-PAP, NFYC, NY-BR-1, NY-ESO-1/LAGE-2, OA1, OGT, OS-9, P polypeptide, p53, PAP, PAXS, PBF, pm1-RARalpha fusion protein, polymorphic epithelial mucin ("PEM"), PPPIR3B, PRAME, PRDXS, PSA, PSMA, PTPRK, RAB38/NY-MEL-1, RAGE-1, RBAF600, RGSS, RhoC, RNF43, RU2AS, SAGE, secernin 1, SIRT2, SNRPD1, SOX10, Sp17, SPA17, SSX-2, SSX-4, STEAPI, survivin, SYT-SSX1 or -SSX2 fusion protein, TAG-1, TAG-2, Telomerase, TGF-betaRII, TPBG, TRAG-3, Triosephosphate isomerase, TRP-1/gp75, TRP-2, TRP2-INT2, tyrosinase, tyrosinase ("TYR"), VEGF, WT1, XAGE-1b/GAGED2a. In some embodiments, the antigen is a neo-antigen. In some embodiments, the cancer vaccine is administered with an adjuvant. Examples of adjuvants include, but are not limited to, an immune modulatory protein, Adjuvant 65, α-GalCer, aluminum phosphate, aluminum hydroxide, calcium phosphate, β-Glucan Peptide, CpG ODN DNA, GPI-0100, lipid A, lipopolysaccharide, Lipovant, MONTANIDE®, N-acetyl-muramyl-L-alanyl-D-isoglutamine, Pam3CSK4, quil A, cholera toxin (CT) and heat-labile toxin from enterotoxigenic *Escherichia coli* (LT) including derivatives of these (CTB, mmCT, CTA1-DD, LTB, LTK63, LTR72, dmLT) and trehalose dimycolate.

In some embodiments, the immunotherapy agent is an immune modulating protein to the subject. In some embodiments, the immune modulatory protein is a cytokine or chemokine. Examples of immune modulating proteins include, but are not limited to, B lymphocyte chemoattractant ("BLC"), C-C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon alpha ("IFN-alpha"), Interferon beta ("IFN-beta") Interferon gamma ("IFN-gamma"), Interlukin-1 alpha ("IL-1 alpha"), Interlukin-1 beta ("IL-1 beta"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit beta of Interleukin-12 ("IL-12 p40" or "IL-12 p70"), Interleukin-13 ("IL-13"), Interleukin-15 ("IL-15"), Interleukin-16 ("IL-16"), Interleukin-17A-F ("IL-17A-F"), Interleukin-18 ("IL-18"), Interleukin-21 ("IL-21"), Interleukin-22 ("IL-22"), Interleukin-23 ("IL-23"), Interleukin-33 ("IL-33"), Chemokine (C-C motif) Ligand 2 ("MCP-1"), Macrophage colony-stimulating factor ("M-CSF"), Monokine induced by gamma interferon ("MIG"), Chemokine (C-C motif) ligand 2 ("MIP-1 alpha"), Chemokine (C-C motif) ligand 4 ("MIP-1 beta"), Macrophage inflammatory protein-1-delta ("MIP-1 delta"), Platelet-derived growth factor subunit B ("PDGF-BB"), Chemokine (C-C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-alpha ("TNF alpha"), Tumor necrosis factor, lymphotoxin-beta ("TNF beta"), Soluble TNF receptor type 1 ("sTNFRI"), sTNFRIIAR, Brain-derived neurotrophic factor ("BDNF"), Basic fibroblast growth factor ("bFGF"), Bone morphogenetic protein 4 ("BMP-4"), Bone morphogenetic protein 5 ("BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing complex ("SCF"), Stem cell factor receptor ("SCF R"), Transforming growth factor alpha ("TGFalpha"), Transforming growth factor beta-1 ("TGF beta 1"), Transforming growth factor beta-3 ("TGF beta 3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C-C motif) ligand 27 ("CTACK"), Chemokine (C-X-C motif) ligand 16 ("CXCL16"), C—X—C motif chemokine 5 ("ENA-78"), Chemokine (C-C motif) ligand 26 ("Eotaxin-3"), Granulocyte chemotactic protein 2 ("GCP-2"), GRO, Chemokine (C-C motif) ligand 14 ("HCC-1"), Chemokine (C-C motif) ligand 16 ("HCC-4"), Interleukin-9 ("IL-9"), Interleukin-17 F ("IL-17F"), Interleukin-18-binding protein ("IL-18 BPa"), Interleukin-28 A ("IL-28A"), Interleukin 29 ("IL-29"), Interleukin 31 ("IL-31"), C—X—C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C-C motif) ligand 20 ("MIP-3 alpha"), C-C motif chemokine 19 ("MIP-3 beta"), Chemokine (C-C motif) ligand 23 ("MPIF-1"), Macrophage stimulating protein alpha chain ("MSPalpha"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 alpha ("SDF-1 alpha"), Chemokine (C-C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-10 Rbeta, IL-17R, IL-2Rgamma, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRGI-betal, Beta-type platelet-derived growth factor receptor ("PDGF Rbeta"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDARActivin A, Agouti-related protein ("AgRP"), Ribonuclease 5 ("Angiogenin"), Angiopoietin 1, Angiostatin, Cathepsin S, CD40, Cryptic family protein IB ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 RI, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 beta"), sgp130, Secreted frizzled-related protein 2 ("ShhN"), Sialic acid-binding immunoglobulin-type lectins ("Siglec-5"), ST2, Transforming growth factor-beta 2 ("TGF beta 2"), Tie-2, Thrombopoietin ("TPO"), Tumor necrosis factor receptor superfamily member 10D ("TRAIL R4"), Triggering receptor expressed on myeloid cells 1 ("TREM-1"), Vascular endothelial growth factor C ("VEGF-C"), VEGFRIAdiponectin, Adipsin ("AND"), Alpha-fetoprotein ("AFP"), Angiopoietin-like 4 ("ANGPTL4"), Beta-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C-X-C motif) ligand 1 ("GRO alpha"), human chorionic gonadotropin ("beta HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF-19"), Galectin-3, Hepatocyte growth factor receptor ("HGF R"), IFN-gammalpha/beta R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33", Kallikrein 14, Asparaginyl endopeptidase ("Legumain"), Oxidized low-density lipoprotein receptor 1 ("LOX-1"), Mannose-binding lectin ("MBL"), Neprilysin ("NEP"), Notch homolog 1, translocation-associated (*Drosophila*) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Tolllike receptor 2 ("TLR2"), Tumor necrosis factor receptor superfamily member 10A ("TRAIL RI"), Transferrin ("TRF"), WIF-IACE-2, Albumin, AMICA, Angiopoietin 4, B-cell activating factor ("BAFF"), Carbohydrate antigen 19-9 ("CA19-9"), CD 163, Clusterin, CRT AM, Chemokine (C-X-C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor alpha ("FOLR1"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNTI-inducible-signaling pathway protein 1 ("WISP-1"), and Receptor Activator of Nuclear Factor κ B ("RANK").

In some embodiments, the cancer therapeutic agent is an anti-cancer compound. Exemplary anti-cancer compounds include, but are not limited to, Alemtuzumab (Campath®), Alitretinoin (Panretin®), Anastrozole (Arimidex®), Bevacizumab (Avastin®), Bexarotene (Targretin®), Bortezomib (Velcade®), Bosutinib (Bosulif®), Brentuximab vedotin (Adcetris®), Cabozantinib (Cometriq™), Carfilzomib (Kyprolis™), Cetuximab (Erbitux®), Crizotinib (Xalkori®), Dasatinib (Sprycel®), Denileukin diftitox (Ontak®), Erlotinib hydrochloride (Tarceva®), Everolimus (Afinitor®), Exemestane (Aromasin®), Fulvestrant (Faslodex®), Gefitinib (Iressa®), Ibritumomab tiuxetan (Zevalin®), Imatinib mesylate (Gleevec®), Ipilimumab (Yervoy™), Lapatinib ditosylate (Tykerb®), Letrozole (Femara®), Nilotinib (Tasigna®), Ofatumumab (Arzerra®), Panitumumab (Vectibix®), Pazopanib hydrochloride (Votrient®), Pertuzumab (Perjeta™), Pralatrexate (Folotyn®), Regorafenib (Stivarga®), Rituximab (Rituxan®), Romidepsin (Istodax®), Sorafenib tosylate (Nexavar®), Sunitinib malate (Sutent®), Tamoxifen, Temsirolimus (Torisel®), Toremifene (Fareston®), Tositumomab and 131I-tositumomab (Bexxar®), Trastuzumab (Herceptin®), Tretinoin (Vesanoid®), Vandetanib (Caprelsa®), Vemurafenib (Zelboraf®), Vorinostat (Zolinza®), and Ziv-aflibercept (Zaltrap®).

Exemplary anti-cancer compounds that modify the function of proteins that regulate gene expression and other cellular functions (e.g., HDAC inhibitors, retinoid receptor ligands) are Vorinostat (Zolinza®), Bexarotene (Targretin®) and Romidepsin (Istodax®), Alitretinoin (Panretin®), and Tretinoin (Vesanoid®).

Exemplary anti-cancer compounds that induce apoptosis (e.g., proteasome inhibitors, antifolates) are Bortezomib (Velcade®), Carfilzomib (Kyprolis™), and Pralatrexate (Folotyn®).

Exemplary anti-cancer compounds that increase anti-tumor immune response (e.g., anti CD20, anti CD52; anti-cytotoxic T-lymphocyte-associated antigen-4) are Rituximab (Rituxan®), Alemtuzumab (Campath®), Ofatumumab (Arzerra®), and Ipilimumab (Yervoy™).

Exemplary anti-cancer compounds that deliver toxic agents to cancer cells (e.g., anti-CD20-radionuclide fusions; IL-2-diphtheria toxin fusions; anti-CD30-monomethylauristatin E (MMAE)-fusions) are Tositumomab and 131I-tositumomab (Bexxar®) and Ibritumomab tiuxetan (Zevalin®), Denileukin diftitox (Ontak®), and Brentuximab vedotin (Adcetris®).

Other exemplary anti-cancer compounds are small molecule inhibitors and conjugates thereof of, e.g., Janus kinase, ALK, Bcl-2, PARP, PI3K, VEGF receptor, Braf, MEK, CDK, and HSP90.

Exemplary platinum-based anti-cancer compounds include, for example, cisplatin, carboplatin, oxaliplatin, satraplatin, picoplatin, Nedaplatin, Triplatin, and Lipoplatin. Other metal-based drugs suitable for treatment include, but are not limited to ruthenium-based compounds, ferrocene derivatives, titanium-based compounds, and gallium-based compounds.

In some embodiments, the cancer therapeutic is a radioactive moiety that comprises a radionuclide. Exemplary radionuclides include, but are not limited to Cr-51, Cs-131, Ce-134, Se-75, Ru-97, I-125, Eu-149, Os-189m, Sb-119, I-123, Ho-161, Sb-117, Ce-139, In-111, Rh-103m, Ga-67, Tl-201, Pd-103, Au-195, Hg-197, Sr-87m, Pt-191, P-33, Er-169, Ru-103, Yb-169, Au-199, Sn-121, Tm-167, Yb-175, In-113m, Sn-113, Lu-177, Rh-10$^5$, Sn-117m, Cu-67, Sc-47, Pt-195m, Ce-141, I-131, Tb-161, As-77, Pt-197, Sm-153, Gd-159, Tm-173, Pr-143, Au-198, Tm-170, Re-186, Ag-111, Pd-109, Ga-73, Dy-165, Pm-149, Sn-123, Sr-89, Ho-166, P-32, Re-188, Pr-142, Ir-194, In-114m/In-114, and Y-90.

In some embodiments, the cancer therapeutic is an antibiotic. For example, if the presence of a cancer-associated bacteria and/or a cancer-associated microbiome profile is detected according to the methods provided herein, antibiotics can be administered to eliminate the cancer-associated bacteria from the subject. "Antibiotics" broadly refers to compounds capable of inhibiting or preventing a bacterial infection. Antibiotics can be classified in a number of ways, including their use for specific infections, their mechanism of action, their bioavailability, or their spectrum of target microbe (e.g., Gram-negative vs. Gram-positive bacteria, aerobic vs. anaerobic bacteria, etc.) and these may be used to kill specific bacteria in specific areas of the host ("niches") (Leekha, et al 2011. General Principles of Antimicrobial Therapy. Mayo Clin Proc. 86(2): 156-167). In certain embodiments, antibiotics can be used to selectively target bacteria of a specific niche. In some embodiments, antibiotics known to treat a particular infection that includes a cancer niche may be used to target cancer-associated microbes, including cancer-associated bacteria in that niche. In other embodiments, antibiotics are administered after the bacterial treatment. In some embodiments, antibiotics are administered after the bacterial treatment to remove the engraftment.

In some aspects, antibiotics can be selected based on their bactericidal or bacteriostatic properties. Bactericidal antibiotics include mechanisms of action that disrupt the cell wall (e.g., β-lactams), the cell membrane (e.g., daptomycin), or bacterial DNA (e.g., fluoroquinolones). Bacteriostatic agents inhibit bacterial replication and include sulfonamides, tetracyclines, and macrolides, and act by inhibiting protein synthesis. Furthermore, while some drugs can be bactericidal in certain organisms and bacteriostatic in others, knowing the target organism allows one skilled in the art to select an antibiotic with the appropriate properties. In certain treatment conditions, bacteriostatic antibiotics inhibit the activity of bactericidal antibiotics. Thus, in certain embodiments, bactericidal and bacteriostatic antibiotics are not combined.

Antibiotics include, but are not limited to aminoglycosides, ansamycins, carbacephems, carbapenems, cephalosporins, glycopeptides, lincosamides, lipopeptides, macrolides, monobactams, nitrofurans, oxazolidonones, penicillins, polypeptide antibiotics, quinolones, fluoroquinolone, sulfonamides, tetracyclines, and anti-mycobacterial compounds, and combinations thereof.

Aminoglycosides include, but are not limited to Amikacin, Gentamicin, Kanamycin, Neomycin, Netilmicin, Tobramycin, Paromomycin, and Spectinomycin. Aminoglycosides are effective, e.g., against Gram-negative bacteria, such as *Escherichia coli, Klebsiella, Pseudomonas aeruginosa,* and *Francisella tularensis*, and against certain aerobic bacteria but less effective against obligate/facultative anaerobes. Aminoglycosides are believed to bind to the bacterial 30S or 50S ribosomal subunit thereby inhibiting bacterial protein synthesis.

Ansamycins include, but are not limited to, Geldanamycin, Herbimycin, Rifamycin, and Streptovaricin. Geldanamycin and Herbimycin are believed to inhibit or alter the function of Heat Shock Protein 90.

Carbacephems include, but are not limited to, Loracarbef. Carbacephems are believed to inhibit bacterial cell wall synthesis.

Carbapenems include, but are not limited to, Ertapenem, Doripenem, Imipenem/Cilastatin, and Meropenem. Carbapenems are bactericidal for both Gram-positive and Gram-negative bacteria as broad-spectrum antibiotics. Carbapenems are believed to inhibit bacterial cell wall synthesis.

Cephalosporins include, but are not limited to, Cefadroxil, Cefazolin, Cefalotin, Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, and Ceftobiprole. Selected Cephalosporins are effective, e.g., against Gram-negative bacteria and against Gram-positive bacteria, including *Pseudomonas*, certain Cephalosporins are effective against methicillin-resistant *Staphylococcus aureus* (MRSA). Cephalosporins are believed to inhibit bacterial cell wall synthesis by disrupting synthesis of the peptidoglycan layer of bacterial cell walls.

Glycopeptides include, but are not limited to, Teicoplanin, Vancomycin, and Telavancin. Glycopeptides are effective, e.g., against aerobic and anaerobic Gram-positive bacteria including MRSA and *Clostridium difficile*. Glycopeptides are believed to inhibit bacterial cell wall synthesis by disrupting synthesis of the peptidoglycan layer of bacterial cell walls.

Lincosamides include, but are not limited to, Clindamycin and Lincomycin. Lincosamides are effective, e.g., against anaerobic bacteria, as well as *Staphylococcus*, and *Streptococcus*. Lincosamides are believed to bind to the bacterial 50S ribosomal subunit thereby inhibiting bacterial protein synthesis.

Lipopeptides include, but are not limited to, Daptomycin. Lipopeptides are effective, e.g., against Gram-positive bacteria. Lipopeptides are believed to bind to the bacterial membrane and cause rapid depolarization.

Macrolides include, but are not limited to, Azithromycin, Clarithromycin, Dirithromycin, Erythromycin, Roxithromycin, Troleandomycin, Telithromycin, and Spiramycin. Macrolides are effective, e.g., against *Streptococcus* and *Mycoplasma*. Macrolides are believed to bind to the bacterial or 50S ribosomal subunit, thereby inhibiting bacterial protein synthesis.

Monobactams include, but are not limited to, Aztreonam. Monobactams are effective, e.g., against Gram-negative bacteria. Monobactams are believed to inhibit bacterial cell wall synthesis by disrupting synthesis of the peptidoglycan layer of bacterial cell walls.

Nitrofurans include, but are not limited to, Furazolidone and Nitrofurantoin.

Oxazolidonones include, but are not limited to, Linezolid, Posizolid, Radezolid, and Torezolid. Oxazolidonones are believed to be protein synthesis inhibitors.

Penicillins include, but are not limited to, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin and Ticarcillin. Penicillins are effective, e.g., against Gram-positive bacteria, facultative anaerobes, e.g., *Streptococcus, Borrelia,* and *Treponema*. Penicillins are believed to inhibit bacterial cell wall synthesis by disrupting synthesis of the peptidoglycan layer of bacterial cell walls.

Penicillin combinations include, but are not limited to, Amoxicillin/clavulanate, Ampicillin/sulbactam, Piperacillin/tazobactam, and Ticarcillin/clavulanate.

Polypeptide antibiotics include, but are not limited to, Bacitracin, Colistin, and Polymyxin B and E. Polypeptide Antibiotics are effective, e.g., against Gram-negative bacteria. Certain polypeptide antibiotics are believed to inhibit isoprenyl pyrophosphate involved in synthesis of the peptidoglycan layer of bacterial cell walls, while others destabilize the bacterial outer membrane by displacing bacterial counter-ions.

Quinolones and Fluoroquinolone include, but are not limited to, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, and Temafloxacin. Quinolones/Fluoroquinolone are effective, e.g., against *Streptococcus* and *Neisseria*. Quinolones/Fluoroquinolone are believed to inhibit the bacterial DNA gyrase or topoisomerase IV, thereby inhibiting DNA replication and transcription.

Sulfonamides include, but are not limited to, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole), and Sulfonamidochrysoidine. Sulfonamides are believed to inhibit folate synthesis by competitive inhibition of dihydropteroate synthetase, thereby inhibiting nucleic acid synthesis.

Tetracyclines include, but are not limited to, Demeclocycline, Doxycycline, Minocycline, Oxytetracycline, and Tetracycline. Tetracyclines are effective, e.g., against Gram-negative bacteria. Tetracyclines are believed to bind to the bacterial 30S ribosomal subunit thereby inhibiting bacterial protein synthesis.

Anti-mycobacterial compounds include, but are not limited to, Clofazimine, Dapsone, Capreomycin, Cycloserine, Ethambutol, Ethionamide, Isoniazid, Pyrazinamide, Rifampicin, Rifabutin, Rifapentine, and Streptomycin.

Suitable antibiotics also include arsphenamine, chloramphenicol, fosfomycin, fusidic acid, metronidazole, mupirocin, platensimycin, quinupristin/dalfopristin, tigecycline, tinidazole, trimethoprim amoxicillin/clavulanate, ampicillin/sulbactam, amphomycin ristocetin, azithromycin, bacitracin, buforin II, carbomycin, cecropin Pl, clarithromycin, erythromycins, furazolidone, fusidic acid, Na fusidate, gramicidin, imipenem, indolicidin, josamycin, magainan II, metronidazole, nitroimidazoles, mikamycin, mutacin B-Ny266, mutacin B-JH1 140, mutacin J-T8, nisin, nisin A, novobiocin, oleandomycin, ostreogrycin, piperacillin/tazobactam, pristinamycin, ramoplanin, ranalexin, reuterin, rifaximin, rosamicin, rosaramicin, spectinomycin, spiramycin, staphylomycin, streptogramin, streptogramin A, synergistin, taurolidine, teicoplanin, telithromycin, ticarcillin/clavulanic acid, triacetyloleandomycin, tylosin, tyrocidin, tyrothricin, vancomycin, vemamycin, and virginiamycin.

In some embodiments, the additional therapeutic is an immunosuppressive agent, a DMARD, a pain-control drug, a steroid, a non-steroidal antiinflammatory drug (NSAID), or a cytokine antagonist, and combinations thereof. Representative agents include, but are not limited to, cyclosporin, retinoids, corticosteroids, propionic acid derivative, acetic acid derivative, enolic acid derivatives, fenamic acid derivatives, Cox-2 inhibitors, lumiracoxib, ibuprophen, cholin magnesium salicylate, fenoprofen, salsalate, difunisal, tolmetin, ketoprofen, flurbiprofen, oxaprozin, indomethacin, sulindac, etodolac, ketorolac, nabumetone, naproxen, valdecoxib, etoricoxib, MK0966; rofecoxib, acetominophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib, methotrexate (MTX), antimalarial drugs (e.g., hydroxychloroquine and chloroquine), sulfasalazine, Leflunomide, azathioprine, cyclosporin, gold salts, minocycline, cyclophosphamide, D-penicillamine, minocycline, auranofin, tacrolimus, myocrisin, chlorambucil, TNF alpha antagonists (e.g., TNF alpha antagonists or TNF alpha receptor antagonists), e.g., ADALIMUMAB (Humira®), ETANERCEPT (Enbrel®), INFLIXIMAB (Remicade®; TA-650), CERTOLIZUMAB PEGOL (Cimzia®; CDP870), GOLIMUMAB (Simpom®; CNTO 148), ANAKINRA (Kineret®), RITUXIMAB (Rituxan®; MabThera®), ABATACEPT (Orencia®), TOCILIZUMAB (RoActemra/Actemra®), integrin antagonists (TYSABRI® (natalizumab)), IL-1 antagonists (ACZ885 (Ilaris)), Anakinra (Kineret®)), CD4 antagonists, IL-23 antagonists, IL-20 antagonists, IL-6 antagonists, BLyS antagonists (e.g., Ataci-cept, Benlysta®/LymphoStat-B® (belimumab)), p38 Inhibitors, CD20 antagonists (Ocrelizumab, Ofatumumab (Arzerra®)), interferon gamma antagonists (Fontolizumab), prednisolone, Prednisone, dexamethasone, Cortisol, cortisone, hydrocortisone, methylprednisolone, betamethasone, triamcinolone, beclometasone, fludrocortisone, deoxycorticosterone, aldosterone, Doxycycline, vancomycin, pioglitazone, SBI-087, SCIO-469, Cura-100, Oncoxin+Viusid, TwHF, Methoxsalen, Vitamin D—ergocalciferol, Milnacipran, Paclitaxel, rosig tazone, Tacrolimus (Prograf®), RADOOI, rapamune, rapamycin, fostamatinib, Fentanyl, XOMA 052, Fostamatinib disodium, rosightazone, Curcumin (Longvida™), Rosuvastatin, Maraviroc, ramipnl, Milnacipran, Cobiprostone, somatropin, tgAAC94 gene therapy vector, MK0359, GW856553, esomeprazole, everolimus, trastuzumab, JAK1 and JAK2 inhibitors, pan JAK inhibitors, e.g., tetracyclic pyridone 6 (P6), 325, PF-956980, denosumab, IL-6 antagonists, CD20 antagonistis, CTLA4 antagonists, IL-8 antagonists, IL-21 antagonists, IL-22 antagonist, integrin antagonists (Tysarbri® (natalizumab)), VGEF antagnosits, CXCL antagonists, MMP antagonists, defensin antagonists, IL-1 antagonists (including IL-1 beta antagonsits), and IL-23 antagonists (e.g., receptor decoys, antagonistic antibodies, etc.).

In some embodiments, the agent is an immunosuppressive agent. Examples of immunosuppressive agents include, but are not limited to, corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, TLR antagonists, inflammasome inhibitors, anti-cholinergic decongestants, mast-cell stabilizers, monoclonal anti-IgE antibodies, vaccines (e.g., vaccines used for vaccination where the amount of an allergen is gradually increased), cytokine inhibitors, such as anti-IL-6 antibodies, TNF inhibitors such as infliximab, adalimumab, certolizumab pegol, golimumab, or etanercept, iand combinations thereof.

Administration

In certain aspects, provided herein is a method of delivering a pharmaceutical composition described herein to a subject. In some embodiments of the methods provided herein, the pharmaceutical composition is administered in conjunction with the administration of an additional therapeutic. In some embodiments, the pharmaceutical composition comprises EVs and/or bacteria co-formulated with the additional therapeutic. In some embodiments, the pharmaceutical composition is co-administered with the additional therapeutic. In some embodiments, the additional therapeutic is administered to the subject before administration of the pharmaceutical composition (e.g., about 1, 2, 3, 4, 5, 6, 7, 8, 9, 10, 15, 20, 25, 30, 35, 40, 45, 50 or 55 minutes before, about 1, 2, 3, 4, 5, 6, 7, 8, 9, 10, 11, 12, 13, 14, 15, 16, 17, 18, 19, 20, 21, 22 or 23 hours before, or about 1, 2, 3, 4, 5, 6, 7, 8, 9, 10, 11, 12, 13 or 14 days before). In some embodiments, the additional therapeutic is administered to the subject after administration of the pharmaceutical composition (e.g., about 1, 2, 3, 4, 5, 6, 7, 8, 9, 10, 15, 20, 25, 30, 35, 40, 45, 50 or 55 minutes after, about 1, 2, 3, 4, 5, 6, 7, 8, 9, 10, 11, 12, 13, 14, 15, 16, 17, 18, 19, 20, 21, 22 or 23 hours after, or about 1, 2, 3, 4, 5, 6, 7, 8, 9, 10, 11, 12, 13 or 14 days after). In some embodiments the same mode of delivery are used to deliver both the pharmaceutical composition and the additional therapeutic. In some embodiments different modes of delivery are used to administer the pharmaceutical composition and the additional therapeutic.

For example, in some embodiments the pharmaceutical composition is administered orally while the additional therapeutic is administered via injection (e.g., an intravenous, intramuscular and/or intratumoral injection).

In certain embodiments, the pharmaceutical compositions, dosage forms, and kits described herein can be administered in conjunction with any other conventional anticancer treatment, such as, for example, radiation therapy and surgical resection of the tumor. These treatments may be applied as necessary and/or as indicated and may occur before, concurrent with or after administration of the pharmaceutical compositions, dosage forms, and kits described herein.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, tumor size, and other compounds such as drugs being administered concurrently. In addition to the above factors, such levels can be affected by the infectivity of the microorganism, and the nature of the microorganism, as can be determined by one skilled in the art. In the present methods, appropriate minimum dosage levels of microorganisms can be levels sufficient for the microorganism to survive, grow and replicate. The dose of the pharmaceutical compositions described herein may be appropriately set or adjusted in accordance with the dosage form, the route of administration, the degree or stage of a target disease, and the like. For example, the general effective dose of the agents may range between 0.01 mg/kg body weight/day and 1000 mg/kg body weight/day, between 0.1 mg/kg body weight/day and 1000 mg/kg body weight/day, 0.5 mg/kg body weight/day and 500 mg/kg body weight/day, 1 mg/kg body weight/day and 100 mg/kg body weight/day, or between 5 mg/kg body weight/day and 50 mg/kg body weight/day. The effective dose may be 0.01, 0.05, 0.1, 0.5, 1, 2, 3, 5, 10, 20, 30, 40, 50, 60, 70, 80, 90, 100, 200, 500, or 1000 mg/kg body weight/day or more, but the dose is not limited thereto.

In some embodiments, the dose administered to a subject is sufficient to prevent disease (e.g., autoimmune disease, inflammatory disease, metabolic disease, cancer), delay its onset, or slow or stop its progression. One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the active agents used in accordance with the invention vary depending on the active agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and most preferably causing complete regression of the cancer.

Separate administrations can include any number of two or more administrations, including two, three, four, five or six administrations. One skilled in the art can readily determine the number of administrations to perform or the desirability of performing one or more additional administrations according to methods known in the art for monitoring therapeutic methods and other monitoring methods provided herein. Accordingly, the methods provided herein include methods of providing to the subject one or more administrations of an pharmaceutical composition, where the number of administrations can be determined by monitoring the subject, and, based on the results of the monitoring, determining whether or not to provide one or more additional administrations. Deciding on whether or not to provide one or more additional administrations can be based on a variety of monitoring results.

The time period between administrations can be any of a variety of time periods. The time period between administrations can be a function of any of a variety of factors, including monitoring steps, as described in relation to the number of administrations, the time period for a subject to mount an immune response and/or the time period for a subject to clear the EV from normal tissue. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the EV from normal tissue; for example, the time period can be more than the time period for a subject to clear the EV from normal tissue, such as more than about a day, more than about two days, more than about three days, more than about five days, or more than about a week.

In some embodiments, the delivery of an additional therapeutic in combination with the pharmaceutical composition described herein reduces the adverse effects and/or improves the efficacy of the additional therapeutic.

The effective dose of an additional therapeutic described herein is the amount of the therapeutic agent that is effective to achieve the desired therapeutic response for a particular patient, composition, and mode of administration, with the least toxicity to the patient. The effective dosage level can be identified using the methods described herein and will depend upon a variety of pharmacokinetic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose of an additional therapy will be the amount of the therapeutic agent which is the lowest dose effective to produce a therapeutic effect. Such an effective dose will generally depend upon the factors described above.

The toxicity of an additional therapy is the level of adverse effects experienced by the subject during and following treatment. Adverse events associated with additional therapy toxicity include, but are not limited to, abdominal pain, acid indigestion, acid reflux, allergic reactions, alopecia, anaphylasix, anemia, anxiety, lack of appetite, arthralgias, asthenia, ataxia, azotemia, loss of balance, bone pain, bleeding, blood clots, low blood pressure, elevated blood pressure, difficulty breathing, bronchitis, bruising, low white blood cell count, low red blood cell count, low platelet count, cardiotoxicity, cystitis, hemorrhagic cystitis, arrhythmias, heart valve disease, cardiomyopathy, coronary artery disease, cataracts, central neurotoxicity, cognitive impairment, confusion, conjunctivitis, constipation, coughing, cramping, cystitis, deep vein thrombosis, dehydration, depression, diarrhea, dizziness, dry mouth, dry skin, dyspepsia, dyspnea, edema, electrolyte imbalance, esophagitis, fatigue, loss of fertility, fever, flatulence, flushing, gastric reflux, gastroesophageal reflux disease, genital pain, granulocytopenia, gynecomastia, glaucoma, hair loss, hand-foot syndrome, headache, hearing loss, heart failure, heart palpitations, heartburn, hematoma, hemorrhagic cystitis, hepatotoxicity, hyperamylasemia, hypercalcemia, hyperchloremia, hyperglycemia, hyperkalemia, hyperlipasemia, hypermagnesemia, hypernatremia, hyperphosphatemia, hyperpigmentation, hypertriglyceridemia, hyperuricemia, hypoalbuminemia, hypocalcemia, hypochloremia, hypoglycemia, hypokalemia, hypomagnesemia, hyponatremia, hypophosphatemia, impotence, infection, injection site reactions, insomnia, iron deficiency, itching, joint pain, kidney failure, leukopenia, liver dysfunction, memory loss, menopause, mouth sores, mucositis, muscle pain, myalgias, myelosuppression, myocarditis, neutropenic fever, nausea, nephrotoxicity, neutropenia, nosebleeds, numbness, ototoxicity, pain, palmar-plantar erythrodysesthesia, pancytopenia, pericarditis, peripheral neuropathy, pharyngitis, photophobia, photosensitivity, pneumonia, pneumonitis, proteinuria, pulmonary embolus, pulmonary fibrosis, pulmonary toxicity, rash, rapid heart beat, rectal bleeding, restlessness, rhinitis, seizures, shortness of breath, sinusitis, thrombocytopenia, tinnitus, urinary tract infection, vaginal bleeding, vaginal dryness, vertigo, water retention, weakness, weight loss, weight gain, and xerostomia. In general, toxicity is acceptable if the benefits to the subject achieved through the therapy outweigh the adverse events experienced by the subject due to the therapy.

Immune Disorders

In some embodiments, the methods and compositions described herein relate to the treatment or prevention a disease or disorder associated a pathological immune response, such as an autoimmune disease, an allergic reaction and/or an inflammatory disease. In some embodiments, the disease or disorder is an inflammatory bowel disease (e.g., Crohn's disease or ulcerative colitis).

The methods described herein can be used to treat any subject in need thereof. As used herein, a "subject in need thereof" includes any subject that has a disease or disorder associated with a pathological immune response (e.g., an inflammatory bowel disease), as well as any subject with an increased likelihood of acquiring a such a disease or disorder.

The compositions described herein can be used, for example, as a pharmaceutical composition for preventing or treating (reducing, partially or completely, the adverse effects of) an autoimmune disease, such as chronic inflammatory bowel disease, systemic lupus erythematosus, psoriasis, muckle-wells syndrome, rheumatoid arthritis, multiple sclerosis, or Hashimoto's disease; an allergic disease, such as a food allergy, pollenosis, or asthma; an infectious disease, such as an infection with *Clostridium difficile*; an inflammatory disease such as a TNF-mediated inflammatory disease (e.g., an inflammatory disease of the gastrointestinal tract, such as pouchitis, a cardiovascular inflammatory condition, such as atherosclerosis, or an inflammatory lung disease, such as chronic obstructive pulmonary disease); a pharmaceutical composition for suppressing rejection in organ transplantation or other situations in which tissue rejection might occur; a supplement, food, or beverage for improving immune functions; or a reagent for suppressing the proliferation or function of immune cells.

In some embodiments, the methods provided herein are useful for the treatment of inflammation. In certain embodiments, the inflammation of any tissue and organs of the body, including musculoskeletal inflammation, vascular inflammation, neural inflammation, digestive system inflammation, ocular inflammation, inflammation of the reproductive system, and other inflammation, as discussed below.

Immune disorders of the musculoskeletal system include, but are not limited, to those conditions affecting skeletal joints, including joints of the hand, wrist, elbow, shoulder, jaw, spine, neck, hip, knew, ankle, and foot, and conditions affecting tissues connecting muscles to bones such as tendons. Examples of such immune disorders, which may be treated with the methods and compositions described herein include, but are not limited to, arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular immune disorders refers to a immune disorder that affects any structure of the eye, including the eye lids. Examples of ocular immune disorders which may be treated with the methods and compositions described herein include, but are not limited to, blepharitis, blepharochalasis, conjunctivitis, dacryoadenitis, keratitis, keratoconjunctivitis sicca (dry eye), scleritis, trichiasis, and uveitis Examples of nervous system immune disorders which may be treated with the methods and compositions described herein include, but are not limited to, encephalitis, Guillain-Barre syndrome, meningitis, neuromyotonia, narcolepsy, multiple sclerosis, myelitis and schizophrenia. Examples of inflammation of the vasculature or lymphatic system which may be treated with the methods and compositions described herein include, but are not limited to, arthrosclerosis, arthritis, phlebitis, vasculitis, and lymphangitis.

Examples of digestive system immune disorders which may be treated with the methods and compositions described herein include, but are not limited to, cholangitis, cholecystitis, enteritis, enterocolitis, gastritis, gastroenteritis, inflammatory bowel disease, ileitis, and proctitis. Inflammatory bowel diseases include, for example, certain art-recognized forms of a group of related conditions. Several major forms of inflammatory bowel diseases are known, with Crohn's disease (regional bowel disease, e.g., inactive and active forms) and ulcerative colitis (e.g., inactive and active forms) the most common of these disorders. In addition, the inflammatory bowel disease encompasses irritable bowel syndrome, microscopic colitis, lymphocytic-plasmocytic enteritis, coeliac disease, collagenous colitis, lymphocytic colitis and eosinophilic enterocolitis. Other less common forms of IBD include indeterminate colitis, pseudomembranous colitis (necrotizing colitis), ischemic inflammatory bowel disease, Behcet's disease, sarcoidosis, scleroderma, IBD-associated dysplasia, dysplasia associated masses or lesions, and primary sclerosing cholangitis.

Examples of reproductive system immune disorders which may be treated with the methods and compositions described herein include, but are not limited to, cervicitis, chorioamnionitis, endometritis, epididymitis, omphalitis, oophoritis, orchitis, salpingitis, tubo-ovarian abscess, urethritis, vaginitis, vulvitis, and vulvodynia.

The methods and compositions described herein may be used to treat autoimmune conditions having an inflammatory component. Such conditions include, but are not limited to, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, Muckle-Wells syndrome, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, and vitiligo.

The methods and compositions described herein may be used to treat T-cell mediated hypersensitivity diseases having an inflammatory component. Such conditions include, but are not limited to, contact hypersensitivity, contact dermatitis (including that due to poison ivy), uticaria, skin allergies, respiratory allergies (hay fever, allergic rhinitis, house dustmite allergy) and gluten-sensitive enteropathy (Celiac disease).

Other immune disorders which may be treated with the methods and compositions include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatitis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopeniaurpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic obstructive pulmonary disease, and inflammation accompanying infectious conditions (e.g., sepsis).

Metabolic Disorders

The methods and compositions described herein may be used to treat metabolic disorders and metabolic syndromes. Such conditions include, but are not limited to, Type II Diabetes, Encephalopathy, Tay-Sachs disease, Krabbe disease, Galactosemia, Phenylketonuria (PKU), and Maple syrup urine disease. Accordingly, in certain embodiments provided herein are methods of treating metabolic diseases comprising administering to a subject a composition provided herein. In certain embodiments the metabolic disease is Type II Diabetes, Encephalopathy, Tay-Sachs disease, Krabbe disease, Galactosemia, Phenylketonuria (PKU), or Maple syrup urine disease.

Cancer

In some embodiments, the methods and compositions described herein relate to the treatment of cancer. In some embodiments, any cancer can be treated using the methods described herein. Examples of cancers that may treated by methods and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the methods and compositions provided herein relate to the treatment of a leukemia. The term "leukemia" is meant broadly progressive, malignant diseases of the hematopoietic organs/systems and is generally characterized by a distorted proliferation and development of leukocytes and their precursors in the blood and bone marrow. Non-limiting examples of leukemia diseases include, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemia.

In some embodiments, the methods and compositions provided herein relate to the treatment of a carcinoma. The term "carcinoma" refers to a malignant growth made up of epithelial cells tending to infiltrate the surrounding tissues, and/or resist physiological and non-physiological cell death signals and gives rise to metastases. Non-limiting exemplary types of carcinomas include, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti.

In some embodiments, the methods and compositions provided herein relate to the treatment of a sarcoma. The term "sarcoma" generally refers to a tumor which is made up of a substance like the embryonic connective tissue and is generally composed of closely packed cells embedded in a fibrillar, heterogeneous, or homogeneous substance. Sarcomas include, but are not limited to, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Additional exemplary neoplasias that can be treated using the methods and compositions described herein include Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, plasmacytoma, colorectal cancer, rectal cancer, and adrenal cortical cancer.

In some embodiments, the cancer treated is a melanoma. The term "melanoma" is taken to mean a tumor arising from the melanocytic system of the skin and other organs. Non-limiting examples of melanomas are Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

Particular categories of tumors that can be treated using methods and compositions described herein include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, pulmonary squamous cell carcinoma, basal cell carcinoma, adenocarcinoma (well differentiated, moderately differentiated, poorly differentiated or undifferentiated), bronchioloalveolar carcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, plasmacytoma, colorectal cancer, and rectal cancer.

Cancers treated in certain embodiments also include pre-cancerous lesions, e.g., actinic keratosis (solar keratosis), moles (dysplastic nevi), acitinic chelitis (farmer's lip), cutaneous horns, Barrett's esophagus, atrophic gastritis, dyskeratosis congenita, sideropenic dysphagia, lichen planus, oral submucous fibrosis, actinic (solar) elastosis and cervical dysplasia.

Cancers treated in some embodiments include non-cancerous or benign tumors, e.g., of endodermal, ectodermal or mesenchymal origin, including, but not limited to cholangioma, colonic polyp, adenoma, papilloma, cystadenoma, liver cell adenoma, hydatidiform mole, renal tubular adenoma, squamous cell papilloma, gastric polyp, hemangioma, osteoma, chondroma, lipoma, fibroma, lymphangioma, leiomyoma, rhabdomyoma, astrocytoma, nevus, meningioma, and ganglioneuroma.

Other Diseases and Disorders

In some embodiments, the methods and compositions described herein relate to the treatment of Nonalcoholic Fatty Liver Disease (NAFLD) and Nonalcoholic Steatohepatitis (NASH).

In some embodiments, the methods and compositions described herein relate to the treatment of liver diseases. Such diseases include, but are not limited to, Alagille Syndrome, Alcohol-Related Liver Disease, Alpha-1 Antitrypsin Deficiency, Autoimmune Hepatitis, Benign Liver Tumors, Biliary Atresia, Cirrhosis, Galactosemia, Gilbert Syndrome, Hemochromatosis, Hepatitis A, Hepatitis B, Hepatitis C, Hepatic Encephalopathy, Intrahepatic Cholestasis of Pregnancy (ICP), Lysosomal Acid Lipase Deficiency (LAL-D), Liver Cysts, Liver Cancer, Newborn Jaundice, Non-Alcoholic Fatty Liver Disease, Primary Biliary Cholangitis (PBC), Primary Sclerosing Cholangitis (PSC), Reye Syndrome, Type I Glycogen Storage Disease, and Wilson Disease The methods and compositions described herein may be used to treat neurodegenerative and neurological diseases. In certain embodiments, the neurodegenerative and/or neurological disease is Parkinson's disease, Alzheimer's disease, prion disease, Huntington's disease, motor neurone diseases (MND), spinocerebellar ataxia, spinal muscular atrophy, dystonia, idiopathicintracranial hypertension, epilepsy, nervous system disease, central nervous system disease, movement disorders, multiple sclerosis, encephalopathy, peripheral neuropathy or post-operative cognitive dysfunction.

Methods of Making Enhanced Bacteria

In certain aspects, provided herein are methods of making engineered bacteria for the production of the EVs described herein. In some embodiments, the engineered bacteria are modified to enhance certain desirable properties. For example, in some embodiments, the engineered bacteria are modified to increase production of EVs by the bacteria. In some embodiments, the engineered bacteria are modified to produce EVs with enhanced oral delivery (e.g., by improving acid resistance and/or resistance to bile acids), to enhance the immunomodulatory and/or therapeutic effect of the EVs they produce (e.g., either alone or in combination with another therapeutic agent), to enhance immune activation by the EVs they produce and/or to improve bacterial and/or EV manufacturing (e.g., higher oxygen tolerance, improved freeze-thaw tolerance, shorter generation times). The engineered bacteria may be produced using any technique known in the art, including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, directed evolution, CRISPR/Cas9, or any combination thereof.

In some embodiments of the methods provided herein, the bacterium is modified by directed evolution. In some embodiments, the directed evolution comprises exposure of the bacterium to an environmental condition and selection of bacterium with improved survival and/or growth under the environmental condition. In some embodiments, the method comprises a screen of mutagenized bacteria using an assay that identifies enhanced bacterium. In some embodiments, the method further comprises mutagenizing the bacteria (e.g., by exposure to chemical mutagens and/or UV radiation) followed by an assay to detect bacteria having the desired phenotype (e.g., an in vivo assay, an ex vivo assay, or an in vitro assay).

In some embodiments, the bacterium provided herein are modified by exposure to a stress-inducing environment (e.g., an environment that induces envelope stress). In some embodiments, growth under such growth conditions increase production of EVs by the bacterium. For example, in some embodiments, the bacterium is grown in the presence of subinhibitory concentrations of an antibiotic described herein (e.g., 0.1-1 µg/mL chloramphenicol, or 0.1-0.3 µg/mL gentamicin). In some embodiments, host antimicrobial peptides (e.g., lysozyme, defensins, and Reg proteins) are used in place of or in combination with antibiotics. In some embodiments, bacterially-produced antimicrobial peptides (e.g., bacteriocins and microcins) are used. In some embodiments, the stress is temperature stress (e.g., growth at 37-50° C.). In some embodiments, the stress is carbon limitation stress (e.g., growth in a media comprising limited carbon sources, such as media with carbon source restricted below 1% (w/v)). In some embodiments, the stress is salt stress (e.g., growth in a medium containing 0.5M NaCl). In some embodiments, the stress is UV stress (e.g., growth under a UV lamp, either throughout the entire cultivation period or only during a portion of the cultivation period). In some embodiments, the stress is reactive oxygen stress (e.g., growth in media containing subinhibitory concentrations of hydrogen peroxide, such as 250-1,000 µM hydrogen peroxide). In some embodiments, a combination of the stresses disclosed herein are applied to the bacterium.

EXAMPLES

Example 1: Preparation and Purification of EVs from Bacteria

Extracellular vesicles (EVs) are prepared from bacterial cultures using methods known to those skilled in the art (S. Bin Park, et al. PLOS ONE. 6(3): e17629 (2011)).

For example, bacterial cultures are centrifuged at 11,000×g for 20-40 min at 4° C. to pellet bacteria. Culture supernatants are then passed through a 0.22 µm filter to exclude intact bacterial cells. Filtered supernatants are concentrated using methods that may include, but are not limited to, ammonium sulfate precipitation, ultracentrifugation, or filtration. Briefly, for ammonium sulfate precipitation, 1.5-3 M ammonium sulfate is added to filtered supernatant slowly, while stirring at 4° C. Precipitations are incubated at 4° C. for 8-48 hours and then centrifuged at 11,000×g for 20-40 min at 4° C. The pellets contain bacterial EVs and other debris. Briefly, using ultracentrifugation, filtered supernatants are centrifuged at 100,000-200,000×g for 1-16 hours at 4° C. The pellet of this centrifugation contains bacterial EVs and other debris. Briefly, using a filtration technique, using an Amicon Ultra spin filter or by tangential flow filtration, supernatants are filtered so as to retain species of molecular weight>50 or 100 kDa.

Alternatively, EVs are obtained from bacterial cultures continuously during growth, or at selected time points during growth, by connecting a bioreactor to an alternating tangential flow (ATF) system (e.g., XCell ATF from Repligen) according to manufacturer's instructions. The ATF system retains intact cells (>0.22 um) in the bioreactor, and allows smaller components (e.g., EVs, free proteins) to pass through a filter for collection. For example, the system may be configured so that the <0.22 um filtrate is then passed through a second filter of 100 kDa, allowing species such as EVs between 0.22 um and 100 kDa to be collected, and species smaller than 100 kDa to be pumped back into the bioreactor. Alternatively, the system may be configured to allow for medium in the bioreactor to be replenished and/or modified during growth of the culture. EVs collected by this method may be further purified and/or concentrated by ultracentrifugation or filtration as described above for filtered supernatants.

EVs obtained by methods described above may be further purified by gradient ultracentrifugation, using methods that may include, but are not limited to, use of a sucrose gradient or Optiprep gradient. Briefly, using a sucrose gradient method, if ammonium sulfate precipitation or ultracentrifugation were used to concentrate the filtered supernatants, pellets are resuspended in 60% sucrose, 30 mM Tris, pH 8.0. If filtration was used to concentrate the filtered supernatant, the concentrate is buffer exchanged into 60% sucrose, 30 mM Tris, pH 8.0, using an Amicon Ultra column. Samples are applied to a 35-60% discontinuous sucrose gradient and centrifuged at 200,000×g for 3-24 hours at 4° C. Briefly, using an Optiprep gradient method, if ammonium sulfate precipitation or ultracentrifugation were used to concentrate the filtered supernatants, pellets are resuspended in 35% Optiprep in PBS. If filtration was used to concentrate the filtered supernatant, the concentrate is diluted using 60% Optiprep to a final concentration of 35% Optiprep. Samples are applied to a 35-60% discontinuous sucrose gradient and centrifuged at 200,000×g for 3-24 hours at 4° C.

To confirm sterility and isolation of the EV preparations, EVs are serially diluted onto agar medium used for routine culture of the bacteria being tested, and incubated using routine conditions. Non-sterile preparations are passed through a 0.22 um filter to exclude intact cells. To further increase purity, isolated EVs may be DNase or proteinase K treated.

Alternatively, for preparation of EVs used for in vivo injections, purified EVs are processed as described previously (G. Norheim, et al. PLOS ONE. 10(9): e0134353 (2015)). Briefly, after sucrose gradient centrifugation, bands containing EVs are resuspended to a final concentration of 50 µg/mL in a solution containing 3% sucrose or other solution suitable for in vivo injection known to one skilled in the art. This solution may also contain adjuvant, for example aluminum hydroxide at a concentration of 0-0.5% (w/v).

To make samples compatible with further testing (e.g. to remove sucrose prior to TEM imaging or in vitro assays), samples are buffer exchanged into PBS or 30 mM Tris, pH 8.0 using filtration (e.g. Amicon Ultra columns), dialysis, or ultracentrifugation (200,000×g, ≥3 hours, 4° C.) and resuspension.

Example 2: Labeling Bacterial EVs

In order to track their biodistribution in vivo and to quantify and localize them in vitro in various preparations and in assays conducted with mammalian cells, EVs are labeled as previously described (N. Kesty, et al. *EMBO Journal*. 23: 4538-4549 (2004)).

For example, purified EVs are incubated with fluorescein isothiocyanate (FITC) (Sigma-Aldrich, USA), Cy7, or any other fluorochrome suitable for flow cytometry, 1:1 for 1 hour at 25° C. The incubation step may be extended overnight at 4° ° C. To remove extra fluorochrome, EVs are then either (1) pelleted by centrifugation at 200,000×g for 3 hr-overnight, washed, and resuspended in PBS or another appropriate buffer for downstream applications; or (2) buffer exchanged into PBS or another appropriate buffer for downstream applications by dialysis or by filtration (e.g., using an Amicon Ultra column).

Alternatively, EVs are obtained from bacteria cultured in medium containing 0.8 mM 3-azido-D-alanine or HADA. EVs are resuspended or buffer exchanged into PBS and a portion is further labeled with 10 uM Dibenzo-aza-cyclooctyne (DIBAC)-fluorescent dye in 1% BSA/PBS (dyes include Cy5, TAMRA, Rhodamine-green, and Cy7) if grown with 3-azido-D-alanine. Unincorporated dye is removed as described above, by (1) ultracentrifugation, washing, and resuspension; or (2) buffer exchange by dialysis or filtration.

Labeled EVs may also be generated from bacteria expressing green-fluorescent protein (GFP), or any other fluorescent protein. For Gram negative bacteria, periplasmic targeting sequences are appended to the fluorescent proteins, so that they are appropriately localized to be internalized by EVs as they form.

Quantum dots may be used to label EVs for non-invasive in vivo imaging studies (K. Kikushima, et al. *Scientific Reports*. 3(1913) (2013)). Quantum dots are conjugated to an antibody confirmed to be present in the EV membrane. Isolated EVs are incubated with quantum dot conjugates, and extra conjugates are removed as described above, by (1) ultracentrifugation, washing, and resuspension; or (2) buffer exchange by dialysis or filtration.

Fluorescently labeled EVs are detected in in vitro and ex vivo samples by confocal microscopy, nanoparticle tracking analysis, and/or flow cytometry. Additionally, fluorescently labeled EVs are detected in whole animals and/or dissected organs and tissues using an instrument such as the IVIS spectrum CT (Perkin Elmer), as in H-I. Choi, et al. *Experimental & Molecular Medicine*. 49: e330 (2017).

Additionally, EVs may be radiolabeled as previously described (Z. Varga et al., Cancer Biother Radiopharm. 2016 June; 31(5):168-73).

For example, purified EVs are radiolabeled with the $^{99m}$Tc-tricarbonyl complex $[^{99m}Tc(CO)_3(H_2O)_3]^+$ using a commercial kit (Isolink®; Mallinckrodt Medical B.V.), according to the manufacturer's instructions.

Example 3: Transmission Electron Microscopy to Visualize Bacterial Production of EVs and Purified Bacterial EVs Transmission electron microscopy (TEM) is used to visualize bacteria as they produce EVs or purified bacterial EVs (S. Bin Park, et al. PLOS ONE. 6(3): e17629 (2011). EVs are prepared from bacteria batch culture as described in Example 1. EVs are mounted onto 300- or 400-mesh-size carbon-coated copper grids (Electron Microscopy Sciences, USA) for 2 min and washed with deionized water. EVs are negatively stained using 2% (w/v) uranyl acetate for 20 sec-1 min. Copper grids are washed with sterile water and dried. Images are acquired using a transmission electron microscope with 100-120 kV acceleration voltage. Stained EVs appear between 20-250 nm in diameter and are electron dense. 10-50 fields on each grid are screened.

Example 4: Profiling EV Composition and Content

EVs may be characterized by any one of various methods including, but not limited to, NanoSight characterization, SDS-PAGE gel electrophoresis, Western blot, ELISA, liquid chromatography-mass spectrometry and mass spectrometry, dynamic light scattering, lipid levels, total protein, lipid to protein ratios, nucleic acid analysis and zeta potential.

NanoSight Characterization of EVs

Nanoparticle tracking analysis (NTA) is used to characterize the size distribution of purified bacterial EVs. Purified EV preps are run on a NanoSight machine (Malvern Instruments) to assess EV size and concentration.

SDS-PAGE Gel Electrophoresis

To identify the protein components of purified EVs (Example 1), samples are run on a Bolt Bis-Tris Plus 4-12% gel (Thermo-Fisher Scientific) using standard techniques. Samples are boiled in 1×SDS sample buffer for 10 min, cooled to 4° C., and then centrifuged at 16,000×g for 1 min. Samples are then run on a SDS-PAGE gel and stained using one of several standard techniques (e.g., Silver staining, Coomassie Blue, Gel Code Blue) for visualization of bands.

Western Blot Analysis

To identify and quantify specific protein components of purified EVs, EV proteins are separated by SDS-PAGE as described above and subjected to Western blot analysis (Cvjetkovic et al., Sci. Rep. 6, 36338 (2016) and are quantified via ELISA.

Liquid Chromatography-Mass Spectrometry (LC-MS MS) and Mass Spectrometry (MS)

Proteins present in EVs are identified and quantified by Mass Spectrometry techniques. Additionally, metabolic content is ascertained using liquid chromatography techniques combined with mass spectrometry. A variety of techniques exist to determine metabolomic content of various samples and are known to one skilled in the art involving solvent extraction, chromatographic separation and a variety of ionization techniques coupled to mass determination (Roberts et al 2012 Targeted Metabolomics. Curr Protoc Mol Biol. 30: 1-24; Dettmer et al 2007, Mass spectrometry-based metabolomics. Mass Spectrom Rev. 26(1):51-78). As a non-limiting example, a LC-MS system includes a 4000 QTRAP triple quadrupole mass spectrometer (AB SCIEX) combined with 1100 Series pump (Agilent) and an HTS PAL autosampler (Leap Technologies). Media samples or other complex metabolic mixtures (~10 µL) are extracted using nine volumes of 74.9:24.9:0.2 (v/v/v) acetonitrile/methanol/formic acid containing stable isotope-labeled internal standards (valine-d8, Isotec; and phenylalanine-d8, Cambridge Isotope Laboratories). Standards may be adjusted or modified depending on the metabolites of interest. The samples are centrifuged (10 min, 9,000 g, 4° C.), and the supernatants (10 µL) are submitted to LCMS by injecting the solution onto the HILIC column (150×2.1 mm, 3 µm particle size). The column is eluted by flowing a 5% mobile phase [10 mM ammonium formate, 0.1% formic acid in water] for 1 min at a rate of 250 µL/min followed by a linear gradient over 10 min to a solution of 40% mobile phase [acetonitrile with 0.1% formic acid]. The ion spray voltage is set to 4.5 kV and the source temperature is 450° C.

The data are analyzed using commercially available software like Multiquant 1.2 from AB SCIEX for mass spectrum peak integration. Peaks of interest should be manually curated and compared to standards to confirm the identity of the peak. Quantitation with appropriate standards is performed to determine the number of metabolites present in the initial media, after bacterial conditioning and after tumor cell growth.

Dynamic Light Scattering (DLS)

DLS measurements, including the distribution of particles of different sizes in different EV preps are taken using instruments such as the DynaPro NanoStar (Wyatt Technology) and the Zetasizer Nano ZS (Malvern Instruments).

Lipid Levels

Lipid levels are quantified using FM4-64 (Life Technologies), by methods similar to those described by A. J. McBroom et al. *J Bacteriol* 188:5385-5392. and A. Frias, et al. *Microb Ecol.* 59:476-486 (2010). Samples are incubated with FM4-64 (3.3 µg/mL in PBS for 10 min at 37° C. in the dark). After excitation at 515 nm, emission at 635 nm is measured using a Spectramax M5 plate reader (Molecular Devices). Absolute concentrations are determined by comparison of unknown samples to standards (such as palmitoyloleoylphosphatidylglycerol (POPG) vesicles) of known concentrations.

Total Protein

Protein levels are quantified by standard assays such as the Bradford and BCA assays. The Bradford assays are run using Quick Start Bradford 1× Dye Reagent (Bio-Rad), according to manufacturer's protocols. BCA assays are run using the Pierce BCA Protein Assay Kit (Thermo-Fisher Scientific). Absolute concentrations are determined by comparison to a standard curve generated from BSA of known concentrations.

Lipid:Protein Ratios

Lipid:protein ratios are generated by dividing lipid concentrations by protein concentrations. These provide a measure of the purity of vesicles as compared to free protein in each preparation.

Nucleic Acid Analysis

Nucleic acids are extracted from EVs and quantified using a Qubit fluorometer. Size distribution is assessed using a BioAnalyzer and the material is sequenced.

Zeta Potential

The zeta potential of different preparations are measured using instruments such as the Zetasizer ZS (Malvern Instruments).

Example 5: Manipulating Bacteria Through Stress to Produce Various Amounts of EVs and/or to Vary Content of EVs Stress, and in particular envelope stress, has been shown to increase production of EVs by some bacterial strains (I. MacDonald, M. Kuehn. *J Bacteriol* 195(13): doi: 10/1128/JB.02267-12). In order to vary production of EVs by bacteria, bacteria are stressed using various methods.

Bacteria may be subjected to single stressors or stressors in combination. The effects of different stressors on different bacteria is determined empirically by varying the stress condition and determining the IC50 value (the conditions required to inhibit cell growth by 50%). EV purification, quantification, and characterization occurs as detailed in Examples 1-4. EV production is quantified (1) in complex samples of bacteria and EVs by nanoparticle tracking analysis (NTA) or transmission electron microscopy (TEM); or (2) following EV purification by NTA, lipid quantification, or protein quantification. EV content is assessed following purification by methods described above.

Antibiotic Stress

Bacteria are cultivated under standard growth conditions with the addition of subinhibitory concentrations of antibiotics. This may include 0.1-1 µg/mL chloramphenicol, or 0.1-0.3 µg/mL gentamicin, or similar concentrations of other antibiotics (e.g., ampicillin, polymyxin B). Host antimicrobial products such as lysozyme, defensins, and Reg proteins may be used in place of antibiotics. Bacterially-produced antimicrobial peptides, including bacteriocins and microcins may also be used.

Temperature Stress

Bacteria are cultivated under standard growth conditions, but at higher or lower temperatures than are typical for their growth. Alternatively, bacteria are grown under standard conditions, and then subjected to cold shock or heat shock by incubation for a short period of time at low or high temperatures respectively. For example, bacteria grown at 37° C. are incubated for 1 hour at 4° C.-18° C. for cold shock or 42° C.-50° C. for heat shock.

Starvation and Nutrient Limitation

To induce nutritional stress, bacteria are cultivated under conditions where one or more nutrients are limited. Bacteria may be subjected to nutritional stress throughout growth or shifted from a rich medium to a poor medium. Some examples of media components that are limited are carbon, nitrogen, iron, and sulfur. An example medium is M9 minimal medium (Sigma-Aldrich), which contains low glucose as the sole carbon source. Particularly for *Prevotella* spp., iron availability is varied by altering the concentration of hemin in media and/or by varying the type of porphyrin or other iron carrier present in the media, as cells grown in low hemin conditions were found to produce greater numbers of EVs (S. Stubbs et al. *Letters in Applied Microbiology.* 29:31-36 (1999). Media components are also manipulated by the addition of chelators such as EDTA and deferoxamine.

Saturation

Bacteria are grown to saturation and incubated past the saturation point for various periods of time. Alternatively, conditioned media is used to mimic saturating environments during exponential growth. Conditioned media is prepared by removing intact cells from saturated cultures by centrifugation and filtration, as described in Example 1, and conditioned media may be further treated to concentrate or remove specific components.

Salt Stress

Bacteria are cultivated in or exposed for brief periods to medium containing NaCl, bile salts, or other salts.

UV Stress

UV stress is achieved by cultivating bacteria under a UV lamp or by exposing bacteria to UV using an instrument such as a Stratalinker (Agilent). UV may be administered throughout the entire cultivation period, in short bursts, or for a single defined period following growth.

Reactive Oxygen Stress

Bacteria are cultivated in the presence of subinhibitory concentrations of hydrogen peroxide (250-1,000 µM) to induce stress in the form of reactive oxygen species. Anaerobic bacteria are cultivated in or exposed to concentrations of oxygen that are toxic to them.

Detergent Stress

Bacteria are cultivated in or exposed to detergent, such as sodium dodecyl sulfate (SDS) or deoxycholate.

pH Stress

Bacteria are cultivated in or exposed for limited times to media of different pH.

Example 6: Preparation of EV-Free Bacteria

Bacterial samples containing minimal amounts of EVs are prepared. EV production is quantified (1) in complex samples of bacteria and extracellular components by NTA or TEM; or (2) following EV purification from bacterial samples, by NTA, lipid quantification, or protein quantification.
  a. Centrifugation and washing: Bacterial cultures are centrifuged at 11,000×g to separate intact cells from supernatant (including free proteins and vesicles). The pellet is washed with buffer, such as PBS, and stored in a stable way (e.g., mixed with glycerol, flash frozen, and stored at)−80° ° C.
  b. ATF: Bacteria and EVs are separated by connection of a bioreactor to an ATF system. EV-free bacteria are retained within the bioreactor, and may be further separated from residual EVs by centrifugation and washing, as described above.
  c. Bacteria are grown under conditions that are found to limit production of EVs. Conditions that may be varied include those listed for Example 5.

Example 7: In Vitro Screening of EVs for Enhanced Activation of Dendritic Cells The ability of *Vibrio cholerae* EVs to activate dendritic cells indirectly through epithelial cells is one nonlimiting mechanism by which they stimulate an immune response in mammalian hosts (D. Chatterjee, K. Chadhuri. *J Biol Chem*. 288(6):4299-309. (2013)). As this EV activity is likely shared with other bacteria that stimulate pro-inflammatory cascades in vivo, in vitro methods to assay DC activation by bacterial EVs are disclosed herein. Briefly, PBMCs are isolated from heparinized venous blood from CMs by gradient centrifugation using Lymphoprep (Nycomed, Oslo, Norway) or from mouse spleens or bone marrow using the magnetic bead-based Human Blood Dendritic cell isolation kit (Miltenyi Biotech, Cambridge, MA). Using anti-human CD14 mAb, the monocytes are purified by Moflo and cultured in cRPMI at a cell density of 5e5 cells/ml in a 96-well plate (Costar Corp) for 7 days at 37° C. For maturation of dendritic cells, the culture is stimulated with 0.2 ng/ml IL-4 and 1000 U/ml GM-CSF at 37° ° C. for one week. Alternatively, maturation is achieved through incubation with recombinant GM-CSF alone for a week. Mouse DCs can be harvested directly from spleens using bead enrichment or differentiated from haematopheotic stem cells. Briefly, bone marrow is obtained from the femurs of mice. Cells are recovered and red blood cells lysed. Stem cells are cultured in cell culture medium together with 20 ng/ml mouse GMCSF for 4 days. Additional medium containing 20 ng/ml mouse GM-CSF is added. On day 6 the medium and non-adherent cells are removed and replaced with fresh cell culture medium containing 20 ng/ml GMCSF. A final addition of cell culture medium with 20 ng/ml GM-CSF is added on day 7. On day 10 non-adherent cells are harvested and seeded into cell culture plates overnight and stimulated as required. Dendritic cells are then treated with 25-75 μg/mL EVs for 24 hours with antibiotics. EV compositions tested may include a EVs from a single bacterial species or strain. EV compositions tested may also include a mixture of EVs from bacterial genera, species within a genus, or strains within a species. PBS and EVs from *Lactobacillus* are included as negative controls and LPS, anti-CD40 antibodies, and EVs from *Bifidobacterium* spp. are used as positive controls. Following incubation, DCs are stained with anti CD11b, CD11c, CD103, CD8a, CD40, CD80, CD83, CD86, MHCI and MHCII, and analyzed by flow cytometry. DCs that are significantly increased in CD40, CD80, CD83, and CD86 as compared to negative controls are considered to be activated by the associated bacterial EV composition. These experiments are repeated three times at minimum.

To screen for the ability of EV-activated epithelial cells to stimulate DCs, the above protocol is followed with the addition of a 24-hour epithelial cell EV co-culture prior to incubation with DCs. Epithelial cells are washed after incubation with EVs and are then co-cultured with DCs in an absence of EVs for 24 hours before being processed as above. Epithelial cell lines may include Int407, HEL293, HT29, T84 and CACO2.

As an additional measure of DC activation, 100 μl of culture supernatant is removed from wells following 24 hour incubation of DCs with EVs or EV-treated epithelial cells and is analyzed for secreted cytokines, chemokines, and growth factors using the multiplexed Luminex Magpix. Kit (EMD Millipore, Darmstadt, Germany). Briefly, the wells are pre-wet with buffer, and 25 μl of 1× antibody-coated magnetic beads are added and 2×200 μl of wash buffer are performed in every well using the magnet. 50 μl of Incubation buffer, 50 μl of diluent and 50 μl of samples are added and mixed via shaking for 2 hrs at room temperature in the dark. The beads are then washed twice with 200 μl wash buffer. 100 μl of 1× biotinylated detector antibody is added and the suspension is incubated for 1 hr with shaking in the dark. Two, 200 μl washes are then performed with wash buffer. 100 μl of 1×SAV-RPE reagent is added to each well and is incubated for 30 min at RT in the dark. Three 200 μl washes are performed and 125 μl of wash buffer is added with 2-3 min shaking occurs. The wells are then submitted for analysis in the Luminex xMAP system.

Standards allow for careful quantitation of the cytokines including GM-CSF, IFN-g, IFN-a, IFN-B, IL-1a, IL-1B, IL-2, IL-4, IL-5, IL-6, IL-8, IL-10, IL-13, IL-12 (p40/p70), IL-17A, IL-17F, IL-21, IL-22 IL-23, IL-25, IP-10, KC, MCP-1, MIG, MIP1a, TNFa, and VEGF. These cytokines are assessed in samples of both mouse and human origin. Increases in these cytokines in the bacterial treated samples indicate enhanced production of proteins and cytokines from the host. Other variations on this assay examining specific cell types ability to release cytokines are assessed by acquiring these cells through sorting methods and are recognized by one of ordinary skill in the art. Furthermore, cytokine mRNA is also assessed to address cytokine release in response to a EV composition. These changes in the cells of the host stimulate an immune response similarly to in vivo response in a cancer microenvironment.

This DC stimulation protocol may be repeated using combinations of purified EVs and live bacterial strains to maximize immune stimulation potential.

Example 8: In Vitro Screening of EVs for Enhanced Activation of CD8+ T Cell Killing when Incubated with Tumor Cells In vitro methods for screening for EVs that can activate CD8+ T cell killing of tumor cells are described. Briefly, DCs are isolated from human PBMCs or mouse spleens and incubated with single-strain EVs, mixtures of EVs, and appropriate controls as described in Example 12. In addition, CD8+ T cells are obtained from human PBMCs or mouse spleens using the magnetic bead-based Mouse CD8a+ T Cell Isolation Kit and the magnetic bead-based Human CD8+ T Cell Isolation Kit (both from Miltenyi Biotech, Cambridge, MA). After the 24 hour incubation of DCs with EVs, or DCs with EV-stimulated epithelial cells (detailed in Example 12), EVs are removed from cells with PBS washes, 100 µl of fresh media with antibiotics is added to each well, and 200,000 T cells are added to each experimental well in the 96-well plate. Anti-CD3 antibody is added at a final concentration of 2 µg/ml. Co-cultures are then allowed to incubate at 37° ° C. for 96 hours under normal oxygen conditions.

72 hours into the coculture incubation, 50,000 tumor cells/well are plated per well in new 96-well plates. Mouse tumor cell lines used include B16.F10, SIY+B16.F10, and others. Human tumor cell lines are HLA-matched to donor, and can include PANC-1, UNKPC960/961, UNKC, and HELA cell lines. After completion of the 96 hour co-culture, 100 µl of the CD8+ T cell and DC mixture is transferred to wells containing tumor cells. Plates are incubated for 24 hours at 37° C. under normal oxygen conditions. Staurospaurine is used as negative control to account for cell death.

Following this incubation, flow cytometry is used to measure tumor cell death and characterize immune cell phenotype. Briefly, tumor cells are stained with viability dye. FACS analysis is used to gate specifically on tumor cells and measure the percentage of dead (killed) tumor cells. Data are also displayed as the absolute number of dead tumor cells per well. Cytotoxic CD8+ T cell phenotype may be characterized by the following methods: a) concentration of supernatant granzyme B, IFNy and TNFa in the culture supernatant as described below, b) CD8+ T cell surface expression of activation markers such as DC69, CD25, CD154, PD-1, gamma/delta TCR, Foxp3, T-bet, granzyme B, c) intracellular cytokine staining of IFNy, granzyme B, TNFa in CD8+ T cells. CD4+ T cell phenotype may also be assessed by intracellular cytokine staining in addition to supernatant cytokine concentration including INFy, TNFa, IL-12, IL-4, IL-5, IL-17, IL-10, chemokines etc.

As an additional measure of CD8+ T cell activation, 100 µl of culture supernatant is removed from wells following the 96 hour incubation of T cells with DCs and is analyzed for secreted cytokines, chemokines, and growth factors using the multiplexed Luminex Magpix. Kit (EMD Millipore, Darmstadt, Germany). Briefly, the wells are pre-wet with buffer, and 25 µl of 1× antibody-coated magnetic beads are added and 2×200 µl of wash buffer are performed in every well using the magnet. 50 µl of Incubation buffer, 50 µl of diluent and 50 µl of samples are added and mixed via shaking for 2 hrs at room temperature in the dark. The beads are then washed twice with 200 µl wash buffer. 100 µl of 1× biotinylated detector antibody is added and the suspension is incubated for 1 hr with shaking in the dark. Two, 200 µl washes are then performed with wash buffer. 100 µl of 1×SAV-RPE reagent is added to each well and is incubated for 30 min at RT in the dark. Three 200 µl washes are performed and 125 µl of wash buffer is added with 2-3 min shaking occurs. The wells are then submitted for analysis in the Luminex xMAP system.

Standards allow for careful quantitation of the cytokines including GM-CSF, IFN-g, IFN-a, IFN-B IL-1a, IL-1B, IL-2, IL-4, IL-5, IL-6, IL-8, IL-10, IL-13, IL-12 (p40/p70), IL-17, IL-23, IP-10, KC, MCP-1, MIG, MIP1a, TNFa, and VEGF. These cytokines are assessed in samples of both mouse and human origin. Increases in these cytokines in the bacterial treated samples indicate enhanced production of proteins and cytokines from the host. Other variations on this assay examining specific cell types ability to release cytokines are assessed by acquiring these cells through sorting methods and are recognized by one of ordinary skill in the art. Furthermore, cytokine mRNA is also assessed to address cytokine release in response to an EV composition. These changes in the cells of the host stimulate an immune response similarly to in vivo response in a cancer microenvironment.

This CD8+ T cell stimulation protocol may be repeated using combinations of purified EVs and live bacterial strains to maximize immune stimulation potential.

Example 9: In Vitro Screening of EVs for Enhanced Tumor Cell Killing by PBMCs

Methods to screen EVs for the ability to stimulate PBMCs, which in turn activate CD8+ T cells to kill tumor cells are included. PBMCs are isolated from heparinized venous blood from CMs by ficoll-paque gradient centrifugation for mouse or human blood, or with Lympholyte Cell Separation Media (Cedarlane Labs, Ontario, Canada) from mouse blood. PBMCs are incubated with single-strain EVs, mixtures of EVs, and appropriate controls as described in Example 12. In addition, CD8+ T cells are obtained from human PBMCs or mouse spleens as in Example 12. After the 24 hour incubation of PBMCs with EVs, EVs are removed from cells with PBS washes, 100 µl of fresh media with antibiotics is added to each well, and 200,000 T cells are added to each experimental well in the 96-well plate. Anti-CD3 antibody is added at a final concentration of 2 µg/ml. Co-cultures are then allowed to incubate at 37° C. for 96 hours under normal oxygen conditions.

72 hours into the coculture incubation, 50,000 tumor cells/well are plated per well in new 96-well plates. Mouse tumor cell lines used include B16.F10, SIY+B16.F10, and others. Human tumor cell lines are HLA-matched to donor, and can include PANC-1, UNKPC960/961, UNKC, and HELA cell lines. After completion of the 96 hour co-culture, 100 µl of the CD8+T cell and PBMC mixture is transferred to wells containing tumor cells. Plates are incubated for 24 hours at 37° C. under normal oxygen conditions. Staurospaurine is used as negative control to account for cell death.

Following this incubation, flow cytometry is used to measure tumor cell death and characterize immune cell phenotype. Briefly, tumor cells are stained with viability dye. FACS analysis is used to gate specifically on tumor cells and measure the percentage of dead (killed) tumor cells. Data are also displayed as the absolute number of dead tumor cells per well. Cytotoxic CD8+ T cell phenotype may be characterized by the following methods: a) concentration of supernatant granzyme B, IFNy and TNFa in the culture supernatant as described below, b) CD8+ T cell surface expression of activation markers such as DC69, CD25, CD154, PD-1, gamma/delta TCR, Foxp3, T-bet, granzyme B, c) intracellular cytokine staining of IFNy, granzyme B, TNFa in CD8+ T cells. CD4+ T cell phenotype may also be assessed by intracellular cytokine staining in addition to supernatant cytokine concentration including INFy, TNFa, IL-12, IL-4, IL-5, IL-17, IL-10, chemokines etc.

As an additional measure of CD8+ T cell activation, 100 µl of culture supernatant is removed from wells following the 96 hour incubation of T cells with DCs and is analyzed for secreted cytokines, chemokines, and growth factors using the multiplexed Luminex Magpix. Kit (EMD Millipore, Darmstadt, Germany). Briefly, the wells are pre-wet with buffer, and 25 µl of 1× antibody-coated magnetic beads are added and 2×200 µl of wash buffer are performed in every well using the magnet. 50 µl of Incubation buffer, 50 µl of diluent and 50 µl of samples are added and mixed via shaking for 2 hrs at room temperature in the dark. The beads are then washed twice with 200 µl wash buffer. 100 µl of 1× biotinylated detector antibody is added and the suspension is incubated for 1 hr with shaking in the dark. Two, 200 µl washes are then performed with wash buffer. 100 µl of 1×SAV-RPE reagent is added to each well and is incubated for 30 min at RT in the dark. Three 200 µl washes are performed and 125 µl of wash buffer is added with 2-3 min shaking occurs. The wells are then submitted for analysis in the Luminex xMAP system.

Standards allow for careful quantitation of the cytokines including GM-CSF, IFN-g, IFN-a, IFN-B IL-1a, IL-1B, IL-2, IL-4, IL-5, IL-6, IL-8, IL-10, IL-13, IL-12 (p40/p70), IL-17, IL-23, IP-10, KC, MCP-1, MIG, MIP1a, TNFa, and VEGF. These cytokines are assessed in samples of both mouse and human origin. Increases in these cytokines in the bacterial treated samples indicate enhanced production of proteins and cytokines from the host. Other variations on this assay examining specific cell types ability to release cytokines are assessed by acquiring these cells through sorting methods and are recognized by one of ordinary skill in the art. Furthermore, cytokine mRNA is also assessed to address cytokine release in response to an EV composition. These changes in the cells of the host stimulate an immune response similarly to in vivo response in a cancer microenvironment.

This PBMC stimulation protocol may be repeated using combinations of purified EVs and live bacterial strains to maximize immune stimulation potential.

Example 10. In Vitro Detection of EVs in Antigen-Presenting Cells

Dendritic cells in the lamina propria constantly sample live bacteria, dead bacteria, and microbial products in the gut lumen by extending their dendrites across the gut epithelium, which is one way that EVs produced by bacteria in the intestinal lumen may directly stimulate dendritic cells. The following methods represent a way to assess the differential uptake of EVs by antigen-presenting cells. Optionally, these methods may be applied to assess immunomodulatory behavior of EVs administered to a patient.

Dendritic cells (DCs) are isolated from human or mouse bone marrow, blood, or spleens according to standard methods or kit protocols (e.g., Inaba K, Swiggard W J, Steinman RM, Romani N, Schuler G, 2001. Isolation of dendritic cells. Current Protocols in Immunology. Chapter 3: Unit3.7) and as discussed in Example 12.

To evaluate EV entrance into and/or presence in DCs, 250,000 DCs are seeded on a round cover slip in complete RPMI-1640 medium and are then incubated with EVs from single bacterial strains or combinations EVs at a multiplicity of infection (MOI) between 1:1 and 1:10. Purified EVs have been labeled with fluorochromes or fluorescent proteins as described in Example 2. After 1 hour of incubation, the cells are washed twice with ice-cold PBS, detached from the plate using trypsin. Cells are either allowed to remain intact or are lysed. Samples are then processed for flow cytometry. Total internalized EVs are quantified from lysed samples, and percentage of cells that uptake EVs is measured by counting fluorescent cells. The methods described above may also be performed in substantially the same manner using macrophages or epithelial cell lines (obtained from the ATCC) in place of DCs.

Example 11: In Vitro Screening of EVs with an Enhanced Ability to Activate NK Cell Killing when Incubated with Target Cells To demonstrate the ability of the selected EV compositions to elicit potent NK cell cytotoxicity to tumor cells when incubated with the tumor cells, the following in vitro assay is used. Briefly, mononuclear cells from heparinized blood are obtained from healthy human donors. Optionally, an expansion step to increase the numbers of NK cells is performed as previously described (e.g. see Somanschi et al 2011 J Vis Exp.). They are adjusted to a concentration of 1e6 cells/ml in RPMI-1640 medium containing 5% human serum. The PMNC cells are then labeled with appropriate antibodies and NK cells are isolated through FACS as CD3−/CD56+ cells and are ready for the subsequent cytotoxicity assay. Alternatively, NK cells are isolated using the autoMACs instrument and NK cell isolation kit following manufacturer's instructions (Miltenyl Biotec).

NK cells are counted, and plated in a 96 well format with 5000 cells per well, and incubated with single-strain EVs, EVs from mixtures of bacterial strains, and appropriate controls as described in Example 12. As an additional negative control, this assay is run with EVs from *Fusobacterium nucleatum*. *F. nucleatum* is known to be inhibitory to NK cell activity (see e.g. Gur et al 2005 Immunity 42:1-12). After 5-24 hours incubation of NK cells with EVs, EVs are removed from cells with PBS washes, NK cells are resuspended in 10 fresh media with antibiotics, and are added to 96-well plates containing 50,000 target tumor cells/well. Mouse tumor cell lines used include B16.F10, SIY+ B16.F10, and others. Human tumor cell lines are HLA-matched to donor, and can include PANC-1, UNKPC960/961, UNKC, and HELA cell lines. Plates are incubated for 24 hours at 37° C. under normal oxygen conditions. Staurospaurine is used as negative control to account for cell death.

Following this incubation, flow cytometry is used to measure tumor cell death. Briefly, tumor cells are stained with viability dye. FACS analysis is used to gate specifically on tumor cells and measure the percentage of dead (killed) tumor cells. Data are also displayed as the absolute number of dead tumor cells per well.

This NK cell stimulation protocol may be repeated using combinations of purified EVs and live bacterial strains to maximize immune stimulation potential.

Example 12: Using In Vitro Immune Activation Assays to Predict In Vivo Cancer Immunotherapy Efficacy of EV Compositions In vitro immune activation assays identify EVs that are able to stimulate dendritic cells, which in turn activate CD8+ T cell killing. Work by A. Sivan, et al, Science 350(6264): 1084-1089 (2015) has suggested that enhanced killing of tumor cells by CD8+ T cells in response to oral ingestion of *Bifidobacterium* spp. is an effective cancer immunotherapy in mice. Therefore, the in vitro assays described above are used as a predictive, fast screen of a large number of candidate EVs for potential immunotherapy activity. EVs that display enhanced stimulation of dendritic cells, enhanced stimulation of CD8+ T cell killing, enhanced stimulation of PBMC killing, and/or enhanced stimulation of NK cell killing, are preferentially chosen for in vivo cancer immunotherapy efficacy studies.

Example 13: Determining the Biodistribution of EVs when Delivered Orally to Mice Wild-type mice (e.g., C57BL/6 or BALB/c) are orally inoculated with the EV composition of interest to determine the in vivo biodistribution profile of purified EVs (Example 1). EVs are labeled as in Example 2 to aide in downstream analyses.

Mice can receive a single dose of the EV (25-100 µg) or several doses over a defined time course (25-100 µg). Mice are housed under specific pathogen-free conditions following approved protocols. Alternatively, mice may be bred and maintained under sterile, Germ-free conditions. Blood and stool samples can be taken at appropriate time points.

The mice are humanely sacrificed at various time points (i.e., hours to days) post inoculation with the EV compositions and a full necropsy under sterile conditions is performed. Following standard protocols, lymph nodes, adrenal glands, liver, colon, small intestine, cecum, stomach, spleen, kidneys, bladder, pancreas, heart, skin, lungs, brain, and other tissue of interest are harvested and are used directly or snap frozen for further testing. The tissue samples are dissected and homogenized to prepare single-cell suspensions following standard protocols known to one skilled in the art. The number of EVs present in the sample is then quantified through flow cytometry (Example 17). Quantification may also proceed with use of fluorescence microscopy after appropriate processing of whole mouse tissue (Vankelecom H., Fixation and paraffin-embedding of mouse tissues for GFP visualization, Cold Spring Harb. Protoc., 2009). Alternatively, the animals may be analyzed using live-imaging according to the EV labeling technique.

Example 14: Administering EV Compositions with Enhanced Immune Activation In Vitro to Treat Syngeneic Mouse Tumor Models A mouse model of cancer is generated by subcutaneously injecting a tumor cell line or patient derived tumor sample and allowing it to engraft into C57BL/6, female mice at ages 6-8 weeks old. The methods provided herein are replicated using several tumor cell lines including: B16-F10 or B16-F10-SIY cells as an orthotopic model of melanoma, Panc02 cells as an orthotopic model of pancreatic cancer, injected at a concentration of $1\times10^6$ cells into the right flank (Maletzki et al 2008. Gut 57:483-491), LLC1 cells as an orthotopic model of lung cancer, CT-26 as an orthotopic model of colorectal cancer, and RM-1 as an orthotopic model of prostate cancer. As an example, methods for the B16-F10 model are provided in depth herein.

A syngeneic mouse model of spontaneous melanoma with a very high metastatic frequency is used to test the ability of bacteria to reduce tumor growth and the spread of metastases. The EVs chosen for this assay are compositions that display enhanced activation of immune cell subsets and stimulate enhanced killing of tumor cells in vitro (Examples 12-16). The mouse melanoma cell line B16-F10 is obtained from ATCC. The cells are cultured in vitro as a monolayer in RPMI medium, supplemented with 10% heat-inactivated fetal bovine serum and 1% penicillin/streptomycin at 37° C. in an atmosphere of 5% CO2 in air. The exponentially growing tumor cells are harvested by trypsinization, washed three times with cold 1×PBS, and a suspension of 5E6 cells/ml is prepared for administration. Female C57BL/6 mice are used for this experiment. The mice are 6-8 weeks old and weigh approximately 16-20 g. For tumor development, each mouse is injected SC into the flank with 100 µl of the B16-F10 cell suspension. The mice are anesthetized by ketamine and xylazine prior to the cell transplantation. The animals used in the experiment may be started on an antibiotic treatment via instillation of a cocktail of kanamycin (0.4 mg/ml), gentamicin, (0.035 mg/ml), colistin (850 U/ml), metronidazole (0.215 mg/ml) and vancomycin (0.045 mg/ml) in the drinking water from day 2 to 5 and an intraperitoneal injection of clindamycin (10 mg/kg) on day 7 after tumor injection.

The size of the primary flank tumor is measured with a caliper every 2-3 days and the tumor volume is calculated using the following formula: tumor volume=the tumor width2×tumor length×0.5. After the primary tumor reaches approximately 100 mm3, the animals are sorted into several groups based on their body weight. The mice are then randomly taken from each group and assigned to a treatment group. EV compositions are prepared as described in Example 1. The mice are orally inoculated by gavage with either 25-100 µg EV to be tested, 25-100 µg EV from *Lactobacillus* (negative control), PBS, or 25-100 µg EV from *Bifidobacterium* spp. (positive control). Mice are orally gavaged with the same amount of EVs daily, weekly, bi-weekly, monthly, bi-monthly, or on any other dosing schedule throughout the treatment period. Mice are IV injected in the tail vein or directly injected into the tumor. Mice can be injected with 10 ng-1 ug of EVs, bacteria and EVs or inactivated bacteria and EVs. Mice can be injected weekly or once a month. Mice may also receive combinations of purified EVs and live bacteria to maximize tumor-killing potential. All mice are housed under specific pathogen-free conditions following approved protocols. Tumor size, mouse weight, and body temperature are monitored every 3-4 days and the mice are humanely sacrificed 6 weeks after the B16-F10 mouse melanoma cell injection or when the volume of the primary tumor reaches 1000 mm3. Blood draws are taken weekly and a full necropsy under sterile conditions is performed at the termination of the protocol.

Cancer cells can be easily visualized in the mouse B16-F10 melanoma model due to their melanin production. Following standard protocols, tissue samples from lymph nodes and organs from the neck and chest region are collected and the presence of micro- and macro-metastases is analyzed using the following classification rule. An organ is classified as positive for metastasis if at least two micro-metastatic and one macro-metastatic lesion per lymph node or organ are found. Micro-metastases are detected by staining the paraffin-embedded lymphoid tissue sections with hematoxylin-eosin following standard protocols known to one skilled in the art. The total number of metastases is correlated to the volume of the primary tumor and it is found that the tumor volume correlates significantly with tumor growth time and the number of macro- and micro-metastases in lymph nodes and visceral organs and also with the sum of all observed metastases. Twenty-five different metastatic sites are identified as previously described (Bobek V., et al., Syngeneic lymph-node-targeting model of green fluorescent protein-expressing Lewis lung carcinoma, Clin. Exp. Metastasis, 2004; 21(8):705-8).

The tumor tissue samples are further analyzed for tumor infiltrating lymphocytes. The CD8+ cytotoxic T cells can be isolated by FACS (see Example 17) and can then be further analyzed using customized p/MHC class I microarrays to reveal their antigen specificity (see e.g. Deviren G., et al., Detection of antigen-specific T cells on p/MHC microarrays, J. Mol. Recognit., 2007 January-February; 20(1):32-8). CD4+ T cells can be analyzed using customized p/MHC class II microarrays.

The same experiment is also performed with a mouse model of multiple pulmonary melanoma metastases. The mouse melanoma cell line B16-BL6 is obtained from ATCC and the cells are cultured in vitro as described above. Female C57BL/6 mice are used for this experiment. The mice are 6-8 weeks old and weigh approximately 16-20 g. For tumor development, each mouse is injected into the tail vein with 100 μl of a 2E6 cells/ml suspension of B16-BL6 cells. The tumor cells that engraft upon IV injection end up in the lungs.

The mice are humanely killed after 9 days. The lungs are weighed and analyzed for the presence of pulmonary nodules on the lung surface. The extracted lungs are bleached with Fekete's solution, which does not bleach the tumor nodules because of the melanin in the B16 cells though a small fraction of the nodules is amelanotic (i.e. white). The number of tumor nodules is carefully counted to determine the tumor burden in the mice. Typically, 200-250 pulmonary nodules are found on the lungs of the control group mice (i.e. PBS gavage).

The percentage tumor burden is calculated for the three treatment groups. This measure is defined as the mean number of pulmonary nodules on the lung surfaces of mice that belong to a treatment group divided by the mean number of pulmonary nodules on the lung surfaces of the control group mice.

Determining Metabolic Content with H-NMRI

Biological triplicates of media and spent media samples after bacterial conditioning and after growth of the tumor are deproteinized using Sartorius Centrisart I filters (cutoff 10 kDa). Before use, the filter is washed twice by centrifugation of water to remove glycerol and a small volume (20 μl) of 20.2 mM trimethylsilyl-2,2,3,3-tetradeuteropropionic acid (TSP, sodium salt) in D2O is added to 700 μl of the ultrafiltrate, providing a chemical shift reference (0.00 ppm) and a deuterium lock signal. 650 μl of the sample is placed in a 5 mm NMR tube. Single pulse 1H-NMR spectra (500 MHZ) are obtained on a Bruker DMX-500 spectrometer or comparable instrument as described previously (by Engelke et al. 2006 NMR spectroscopic studies on the late onset form of 3-methylutaconic aciduria type I and other defects in leucine metabolism. NMR Biomed. 19: 271-278). Phase and baseline are corrected manually. All spectra are scaled to TSP and metabolite signals are fitted semi-automatically with a Lorentzian line shape. Metabolite concentrations in the spent media are calculated relative to the known concentration in the standard medium and correspondingly expressed in units of mM. The concentration of a particular metabolite was calculated by the area of the corresponding peak to the area of the valine doublet at 1.04 ppm or an appropriate standard.

Determining Metabolic Content with LCMS

Metabolic content of a sample is ascertained using liquid chromatography techniques combined with mass spectrometry. A variety of techniques exist to determine metabolomic content of various samples and are known to one skilled in the art involving solvent extraction, chromatographic separation and a variety of ionization techniques coupled to mass determination (Roberts et al 2012 Targeted Metabolomics. Curr Protoc Mol Biol. 30: 1-24; Dettmer et al 2007, Mass spectrometry-based metabolomics. Mass Spectrom Rev. 26(1):51-78). As a non-limiting example, a LC-MS system includes a 4000 QTRAP triple quadrupole mass spectrometer (AB SCIEX) combined with 1100 Series pump (Agilent) and an HTS PAL autosampler (Leap Technologies). Media samples or other complex metabolic mixtures (~10 μL) are extracted using nine volumes of 74.9:24.9:0.2 (v/v/v) acetonitrile/methanol/formic acid containing stable isotope-labeled internal standards (valine-d8, Isotec; and phenylalanine-d8, Cambridge Isotope Laboratories). Standards may be adjusted or modified depending on the metabolites of interest. The samples are centrifuged (10 min, 9,000 g, 4° C.), and the supernatants (10 μL) are submitted to LCMS by injecting the solution onto the HILIC column (150×2.1 mm, 3 μm particle size). The column is eluted by flowing a 5% mobile phase [10 mM ammonium formate, 0.1% formic acid in water] for 1 min at a rate of 250 μL/min followed by a linear gradient over 10 min to a solution of 40% mobile phase [acetonitrile with 0.1% formic acid]. The ion spray voltage is set to 4.5 kV and the source temperature is 450° C.

The data are analyzed using commercially available software such as Multiquant 1.2 from AB SCIEX for mass spectrum peak integration. Peaks of interest are manually curated and compared to standards to confirm the identity of the peak. Quantitation with appropriate standards is performed to determine the amount of metabolites present in the initial media, after bacterial conditioning and after tumor cell growth.

The tumor biopsies and blood samples are submitted for metabolic analysis via LCMS techniques described herein. Differential levels of amino acids, sugars, lactate, among other metabolites, between test groups demonstrate the ability of the microbial composition to disrupt the tumor metabolic state.

RNA Seq to Determine Mechanism of Action

Dendritic cells are purified from tumors, Peyers patches, and mesenteric lymph nodes as described in Example 12. RNAseq analysis is carried out and analyzed according to standard techniques known to one skilled in the art (Z. Hou. Scientific Reports. 5(9570):doi: 10.1038/srep09570 (2015)). In the analysis, specific attention is placed on innate inflammatory pathway genes including TLRs, CLRs, NLRs, and STING, cytokines, chemokines, antigen processing and presentation pathways, cross presentation, and T cell co-stimulation.

Example 15: Administering EVs with Enhanced Immune Activation In Vitro to Treat Syngeneic Mouse Tumor Models in Combination with PD-1 or PD-L1 Inhibition To determine the efficacy of EVs in syngeneic tumor mouse models, colorectal cancer (CT-26) was used. Briefly, CT-26 (CAT #CRL-2638) tumor cells were cultured in vitro as a monolayer in RPMI-1640 or DMEM supplemented with 10% heat-inactivated fetal bovine serum at 37° C. in an atmosphere of 5% CO2 in air. The exponentially-growing cells were harvested and counted prior to tumor inoculation. 6-8 week old female BALB/c mice were used for this experiment. For tumor development, each mouse was injected subcutaneously in one or both rear flanks with $5\times10^5$ CT-26 tumor cells in 0.1 ml of 1×PBS. Some mice may receive antibiotic pre-treatment. Tumor size and mouse weight were monitored at least thrice weekly on nonconsecutive days.

Figure 2:
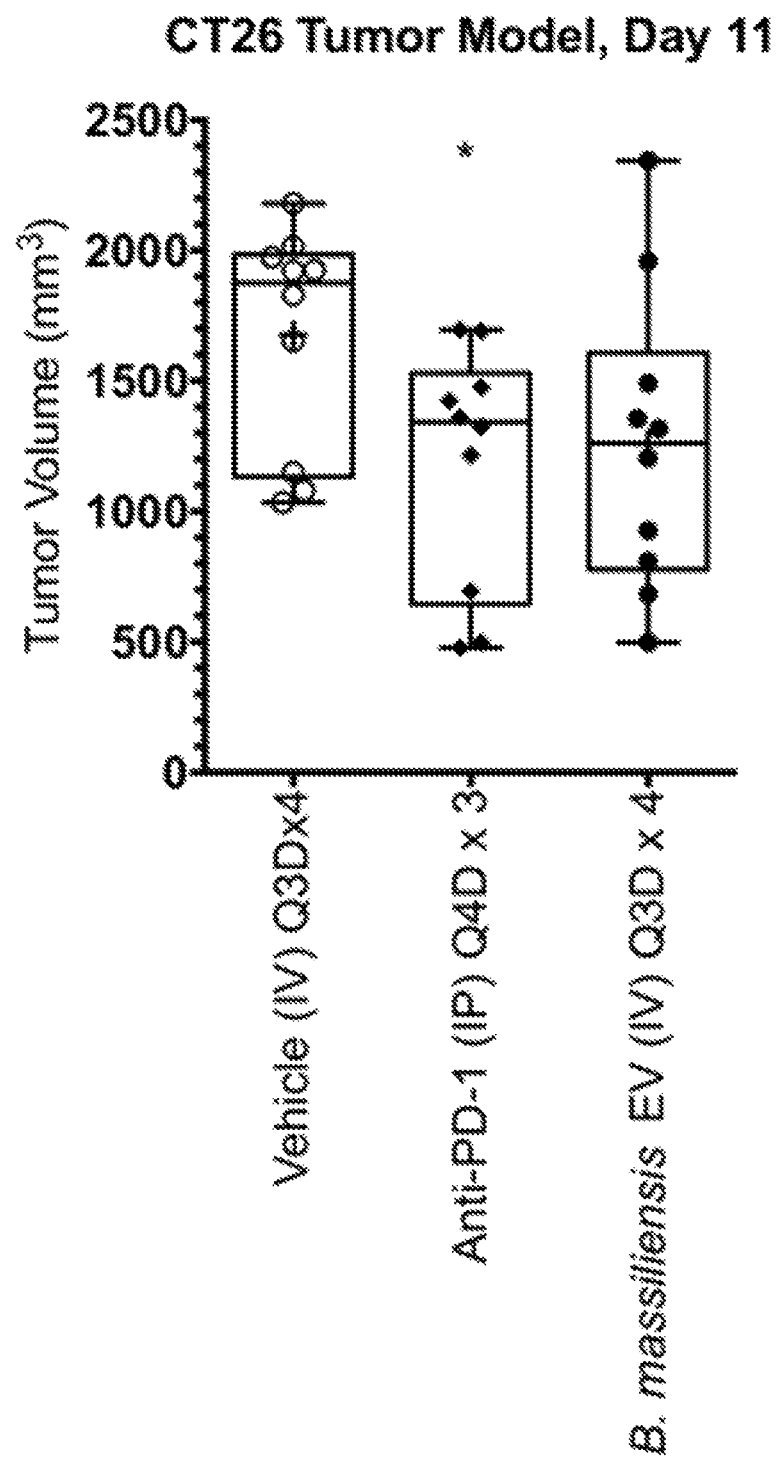
FIG. 2 shows inhibition of tumor growth (by volume) by the iv administration of *Blautia massiliensis* compared to intraperitoneally (i.p.) administered anti-PD-1 in a mouse colorectal carcinoma model.

EVs were tested for their efficacy in the mouse tumor model, either alone or in combination with whole bacterial cells and with or without anti-PD-1 or anti-PD-L1. EVs, bacterial cells, and/or anti-PD-1 or anti-PD-L1 were administered at varied time points and at varied doses. For example, on day 10 after tumor injection, or after the tumor volume reaches 100 mm³, the mice were treated with EVs alone or in combination with anti-PD-1 or anti-PD-L1. Dosing amount was administered according to table 3. The *Blautia massiliensis* group showed tumor growth inhibition comparable to that seen in the anti-PD-1 group (FIGS. 1 and 2).

TABLE 3

Dosing amount.

| Group | Treatment | Dose, route, schedule |
|---|---|---|
| 1 (n = 10) | IV Vehicle (PBS) | N/A, IV, Q3Dx4 |
| 2 (n = 10) | Anti-PD-1 | 200 ug, IP, Q4Dx3 |
| 3 (n = 10) | EV (IV) *Blautia massiliensis* | 5 ug, IV, Q3Dx4 |

For example, some mice are intravenously injected with EVs at 15, 20, or 15 ug/mouse. Other mice may receive 25, 50, or 100 mgs of EVs per mouse. While some mice receive EVs through i.v. injection, other mice may receive EVs through intraperitoneal (i.p.) injection, subcutaneous (s.c.) injection, nasal route administration, oral gavage, or other means of administration. Some mice may receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration. For example, some groups of mice may receive between $1 \times 10^4$ and $5 \times 10^9$ bacterial cells in an administration separate from, or comingled with, the EV administration. As with the EVs, bacterial cell administration may be varied by route of administration, dose, and schedule. This can include oral gavage, i.v. injection, i.p. injection, or nasal route injection. Some groups of mice are also injected with effective doses of checkpoint inhibitor. For example, mice receive 100 μg anti-PD-L1 mAB (clone 10f.9 g2, BioXCell) or another anti-PD-1 or anti-PD-L1 mAB in 100 μl PBS, and some mice receive vehicle and/or other appropriate control (e.g. control antibody). Mice are injected with mABs 3, 6, and 9 days after the initial injection. To assess whether checkpoint inhibition and EV immunotherapy have an additive, anti-tumor effect, control mice receiving anti-PD-1 or anti-PD-L1 mABs are included to the standard control panel. Primary (tumor size) and secondary (tumor infiltrating lymphocytes and cytokine analysis) endpoints are assessed, and some groups of mice are rechallenged with a subsequent tumor cell inoculation to assess the effect of treatment on memory response.

Example 16: EVs in a Mouse Model of Experimental Autoimmune Encephalomyelitis (EAE)

EAE is a well-studied animal model of multiple sclerosis, as reviewed by Constantinescu et al. (Experimental autoimmune encephalomyelitis (EAE) as a model for multiple sclerosis (MS). Br J Pharmacol. 2011 October; 164(4): 1079-1106). It can be induced in a variety of mouse and rat strains using different myelin-associated peptides, by the adoptive transfer of activated encephalitogenic T cells, or the use of TCR transgenic mice susceptible to EAE, as discussed in Mangalam et al. (Two discreet subsets of CD8+ T cells modulate PLP91-110 induced experimental autoimmune encephalomyelitis in HLA-DR3 transgenic mice. J Autoimmun. 2012 June; 38(4): 344-353).

EVs are tested for their efficacy in the rodent model of EAE, either alone or in combination with whole bacterial cells, with or without the addition of other anti-inflammatory treatments. For example, female 6-8 week old C57Bl/6 mice are obtained from Taconic (Germantown, NY). Groups of mice are administered two subcutaneous (s.c.) injections at two sites on the back (upper and lower) of 0.1 ml myelin oligodentrocyte glycoprotein 35-55 (MOG35-55; 100 ug per injection; 200 ug per mouse (total 0.2 ml per mouse)), emulsified in Complete Freund's Adjuvant (CFA; 2-5 mg killed *Mycobacterium tuberculosis* H37Ra/ml emulsion). Approximately 1-2 hours after the above, mice are intraperitoneally (i.p.) injected with 200 ng Pertussis toxin (PTx) in 0.1 ml PBS (2 ug/ml). An additional IP injection of PTx is administered on day 2. Alternatively, an appropriate amount of an alternative myelin peptide (e.g. proteolipid protein (PLP)) is used to induce EAE. Some animals serve as naïve controls. EAE severity is assessed and a disability score is assigned daily beginning on day 4 according to methods known in the art (Mangalam et al. 2012).

Treatment with EVs is initiated at some point, either around the time of immunization or following EAE immunization. For example, EVs may be administered at the same time as immunization (day 1), or they may be administered upon the first signs of disability (e.g. limp tail), or during severe EAE. EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through intraperitoneal (i.p.) injection, subcutaneous (s.c.) injection, nasal route administration, oral gavage, or other means of administration. Some mice may receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the EV administration. As with the EVs, bacterial cell administration may be varied by route of administration, dose, and schedule. This can include oral gavage, i.v. injection, i.p. injection, subcutaneous (s.c.) injection, or nasal route administration.

Some groups of mice may be treated with additional anti-inflammatory agent(s) or EAE therapeutic(s) (e.g. anti-CD154, blockade of members of the TNF family, Vitamin D, or other treatment), and/or an appropriate control (e.g. vehicle or control antibody) at various time points and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various timepoints, mice are sacrificed and sites of inflammation (e.g. brain and spinal cord), lymph nodes, or other tissues may be removed for ex vivo histological, cytokine and/or flow cytometric analysis using methods known in the art. For example, tissues are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ central nervous system (CNS)-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated encephalitogenic T cells or re-injection of EAE-inducing peptides). Mice are analyzed for susceptibility to disease and EAE severity following rechallenge.

Example 17: EVs in a Mouse Model of Collagen-Induced Arthritis (CIA)

Collagen-induced arthritis (CIA) is an animal model commonly used to study rheumatoid arthritis (RA), as described by Caplazi et al. (Mouse models of rheumatoid arthritis. Veterinary Pathology. Sep. 1, 2015. 52(5): 819-826) (see also Brand et al. Collagen-induced arthritis. Nature Protocols. 2007. 2: 1269-1275; Pietrosimone et al. Collagen-induced arthritis: a model for murine autoimmune arthritis. Bio Protoc. 2015 Oct. 20; 5(20): e1626).

Among other versions of the CIA rodent model, one model involves immunizing HLA-DQ8 Tg mice with chick type II collagen as described by Taneja et al. (J. Immunology. 2007. 56: 69-78; see also Taneja et al. J. Immunology 2008. 181: 2869-2877; and Taneja et al. Arthritis Rheum., 2007. 56: 69-78). Purification of chick CII has been described by Taneja et al. (Arthritis Rheum., 2007. 56: 69-78). Mice are monitored for CIA disease onset and progression following immunization, and severity of disease is evaluated and "graded" as described by Wooley, J. Exp. Med. 1981. 154: 688-700.

Mice are immunized for CIA induction and separated into various treatment groups. EVs are tested for their efficacy in CIA, either alone or in combination with whole bacterial cells, with or without the addition of other anti-inflammatory treatments.

Treatment with EVs is initiated either around the time of immunization with collagen or post-immunization. For example, in some groups, EVs may be administered at the same time as immunization (day 1), or EVs may be administered upon first signs of disease, or upon the onset of severe symptoms. EVs are administered at varied doses and at defined intervals.

For example, some mice are intravenously injected with EVs at 15, 20, or 15 ug/mouse. Other mice may receive 25, 50, or 100 mg of EVs per mouse. While some mice receive EVs through i.v. injection, other groups of mice may receive EVs through intraperitoneal (i.p.) injection, subcutaneous (s.c.) injection, nasal route administration, oral gavage, or other means of administration. Some mice may receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the EV administration. As with the EVs, bacterial cell administration may be varied by route of administration, dose, and schedule. This can include oral gavage, i.v. injection, i.p. injection, subcutaneous (s.c.) injection, intradermal (i.d.) injection, or nasal route administration.

Some groups of mice may be treated with additional anti-inflammatory agent(s) or CIA therapeutic(s) (e.g. anti-CD154, blockade of members of the TNF family, Vitamin D, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various timepoints, serum samples are obtained to assess levels of anti-chick and anti-mouse CII IgG antibodies using a standard ELISA (Batsalova et al. Comparative analysis of collagen type II-specific immune responses during development of collagen-induced arthritis in two B10 mouse strains. Arthritis Res Ther. 2012. 14(6): R237). Also, some mice are sacrificed and sites of inflammation (e.g. synovium), lymph nodes, or other tissues may be removed for ex vivo histological, cytokine and/or flow cytometric analysis using methods known in the art. The synovium and synovial fluid are analyzed for plasma cell infiltration and the presence of antibodies using techniques known in the art. In addition, tissues are dissociated using dissociation enzymes according to the manufacturer's instructions to examine the profiles of the cellular infiltrates. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+synovium-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger (e.g. activated re-injection with CIA-inducing peptides). Mice are analyzed for susceptibility to disease and CIA severity following rechallenge.

Example 18: EVs in a Mouse Model of Colitis

Dextran sulfate sodium (DSS)-induced colitis is a well-studied animal model of colitis, as reviewed by Randhawa et al. (A review on chemical-induced inflammatory bowel disease models in rodents. Korean J Physiol Pharmacol. 2014. 18(4): 279-288; see also Chassaing et al. Dextran sulfate sodium (DSS)-induced colitis in mice. Curr Protoc Immunol. 2014 Feb. 4; 104: Unit 15.25).

EVs are tested for their efficacy in a mouse model of DSS-induced colitis, either alone or in combination with whole bacterial cells, with or without the addition of other anti-inflammatory agents.

Groups of mice are treated with DSS to induce colitis as known in the art (Randhawa et al. 2014; Chassaing et al. 2014; see also Kim et al. Investigating intestinal inflammation in DSS-induced model of IBD. J Vis Exp. 2012. 60: 3678). For example, male 6-8 week old C57Bl/6 mice are obtained from Charles River Labs, Taconic, or other vendor. Colitis is induced by adding 3% DSS (MP Biomedicals, Cat. #0260110) to the drinking water. Some mice do not receive DSS in the drinking water and serve as naïve controls. Some mice receive water for five (5) days. Some mice may receive DSS for a shorter duration or longer than five (5) days. Mice are monitored and scored using a disability activity index known in the art based on weight loss (e.g. no weight loss (score 0); 1-5% weight loss (score 1); 5-10% weight loss (score 2)); stool consistency (e.g. normal (score 0); loose stool (score 2); diarrhea (score 4)); and bleeding (e.g. no blood (score 0), hemoccult positive (score 1); hemoccult positive and visual pellet bleeding (score 2); blood around anus, gross bleeding (score 4).

Treatment with EVs is initiated at some point, either on day 1 of DSS administration, or sometime thereafter. For example, EVs may be administered at the same time as DSS initiation (day 1), or they may be administered upon the first signs of disease (e.g. weight loss or diarrhea), or during the stages of severe colitis. Mice are observed daily for weight, morbidity, survival, presence of diarrhea and/or bloody stool.

EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through intraperitoneal (i.p.) injection, subcutaneous (s.c.) injection, nasal route administration, oral gavage, or other means of administration. Some mice may receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1 \times 10^4$ and $5 \times 10^9$ bacterial cells in an administration separate from, or comingled with, the EV administration. As with the EVs, bacterial cell administration may be varied by route of administration, dose, and schedule. This can include oral gavage, i.v. injection, i.p. injection, or nasal route administration.

Some groups of mice may be treated with additional anti-inflammatory agent(s) (e.g. anti-CD154, blockade of members of the TNF family, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some mice receive DSS without receiving antibiotics beforehand.

At various timepoints, mice undergo video endoscopy using a small animal endoscope (Karl Storz Endoskipe, Germany) under isoflurane anesthesia. Still images and video are recorded to evaluate the extent of colitis and the response to treatment. Colitis is scored using criteria known in the art. Fecal material is collected for study.

At various timepoints, mice are sacrificed and the colon, small intestine, spleen, and lymph nodes (e.g. mesenteric lymph nodes) are collected. Additionally, blood is collected into serum separation tubes. Tissue damage is assessed through histological studies that evaluate, but are not limited to, crypt architecture, degree of inflammatory cell infiltration, and goblet cell depletion.

The gastrointestinal (GI) tract, lymph nodes, and/or other tissues may be removed for ex vivo histological, cytokine and/or flow cytometric analysis using methods known in the art. For example, tissues are harvested and may be dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ GI tract-infiltrated immune cells obtained ex vivo. Finally, immunohistochemistry is carried out on various tissue sections to measure T cells, macrophages, dendritic cells, and checkpoint molecule protein expression.

In order to examine the impact and longevity of disease protection, rather than being sacrificed, some mice may be rechallenged with a disease trigger. Mice are analyzed for susceptibility to colitis severity following rechallenge.

Example 19: EVs in a Mouse Model of Delayed-Type Hypersensitivity (DTH)

Delayed-type hypersensitivity (DTH) is an animal model of atopic dermatitis (or allergic contact dermatitis), as reviewed by Petersen et al. (In vivo pharmacological disease models for psoriasis and atopic dermatitis in drug discovery. Basic & Clinical Pharm & Toxicology. 2006. 99(2): 104-115; see also Irving C. Allen (ed.) Mouse Models of Innate Immunity: Methods and Protocols, Methods in Molecular Biology, 2013. vol. 1031, DOI 10.1007/978-1-62703-481-4_13). It can be induced in a variety of mouse and rat strains using various haptens or antigens, for example an antigen emulsified with an adjuvant. DTH is characterized by sensitization as well as an antigen-specific T cell-mediated reaction that results in erythema, edema, and cellular infiltration—especially infiltration of antigen presenting cells (APCs), eosinophils, activated CD4+ T cells, and cytokine-expressing Th2 cells.

Generally, mice are primed with an antigen administered in the context of an adjuvant (e.g. Complete Freund's Adjuvant) in order to induce a secondary (or memory) immune response measured by swelling and antigen-specific antibody titer.

EVs are tested for their efficacy in the mouse model of DTH, either alone or in combination with whole bacterial cells, with or without the addition of other anti-inflammatory treatments. For example, 6-8 week old C57Bl/6 mice are obtained from Taconic (Germantown, NY), or other vendor. Groups of mice are administered four subcutaneous (s.c.) injections at four sites on the back (upper and lower) of antigen (e.g. Ovalbumin (OVA)) in an effective dose (50 µl total volume per site). For a DTH response, animals are injected intradermally (i.d.) in the ears under ketamine/xylazine anesthesia (approximately 50 mg/kg and 5 mg/kg, respectively). Some mice serve as control animals. Some groups of mice are challenged with 10 µl per ear (vehicle control (0.01% DMSO in saline) in the left ear and antigen (21.2 ug (12 nmol) in the right ear) on day 8. To measure ear inflammation, the ear thickness of manually restrained animals is measured using a Mitutoyo micrometer. The ear thickness is measured before intradermal challenge as the baseline level for each individual animal. Subsequently, the ear thickness is measured two times after intradermal challenge, at approximately 24 hours and 48 hours (i.e. days 9 and 10).

Treatment with EVs is initiated at some point, either around the time of priming or around the time of DTH challenge. For example, EVs may be administered at the same time as the subcutaneous injections (day 0), or they may be administered prior to, or upon, intradermal injection. EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through intraperitoneal (i.p.) injection, subcutaneous (s.c.) injection, nasal route administration, oral gavage, topical administration, intradermal (i.d.) injection, or other means of administration. Some mice may receive EVs every day (e.g. starting on day 0), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1\times10+$ and $5\times10^9$ bacterial cells in an administration separate from, or comingled with, the EV administration. As with the EVs, bacterial cell administration may be varied by route of administration, dose, and schedule. This can include oral gavage, i.v. injection, i.p. injection, i.d. injection, topical administration, or nasal route administration.

Figure 3A:
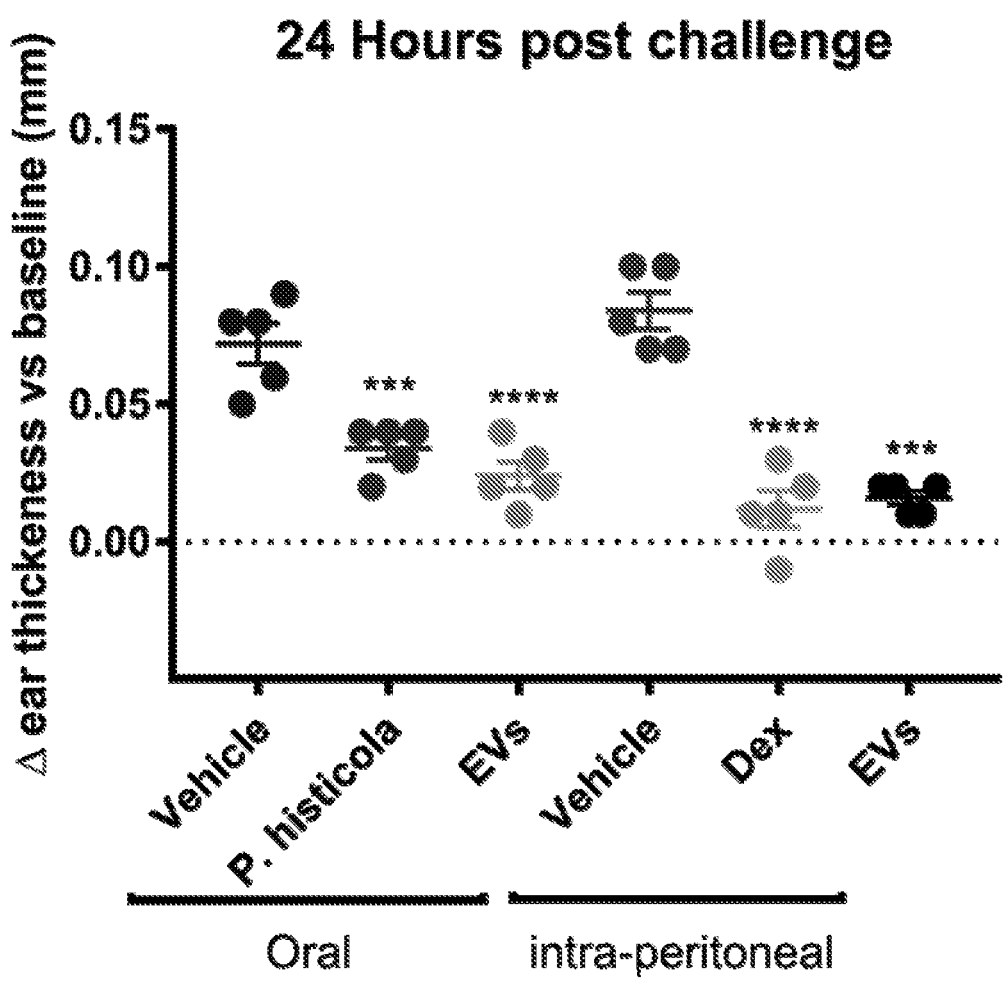
FIG. 3A shows the efficacy of orally or intra-peritoneally administered *Prevotella histicola* and *P. histicola*-derived EVs in reducing antigen-specific ear swelling (ear thickness) 24 hours after antigen challenge in a KLH-based delayed type hypersensitivity mouse model. Efficacy was seen in both the oral and i.p. administration groups.
Figure 3B:
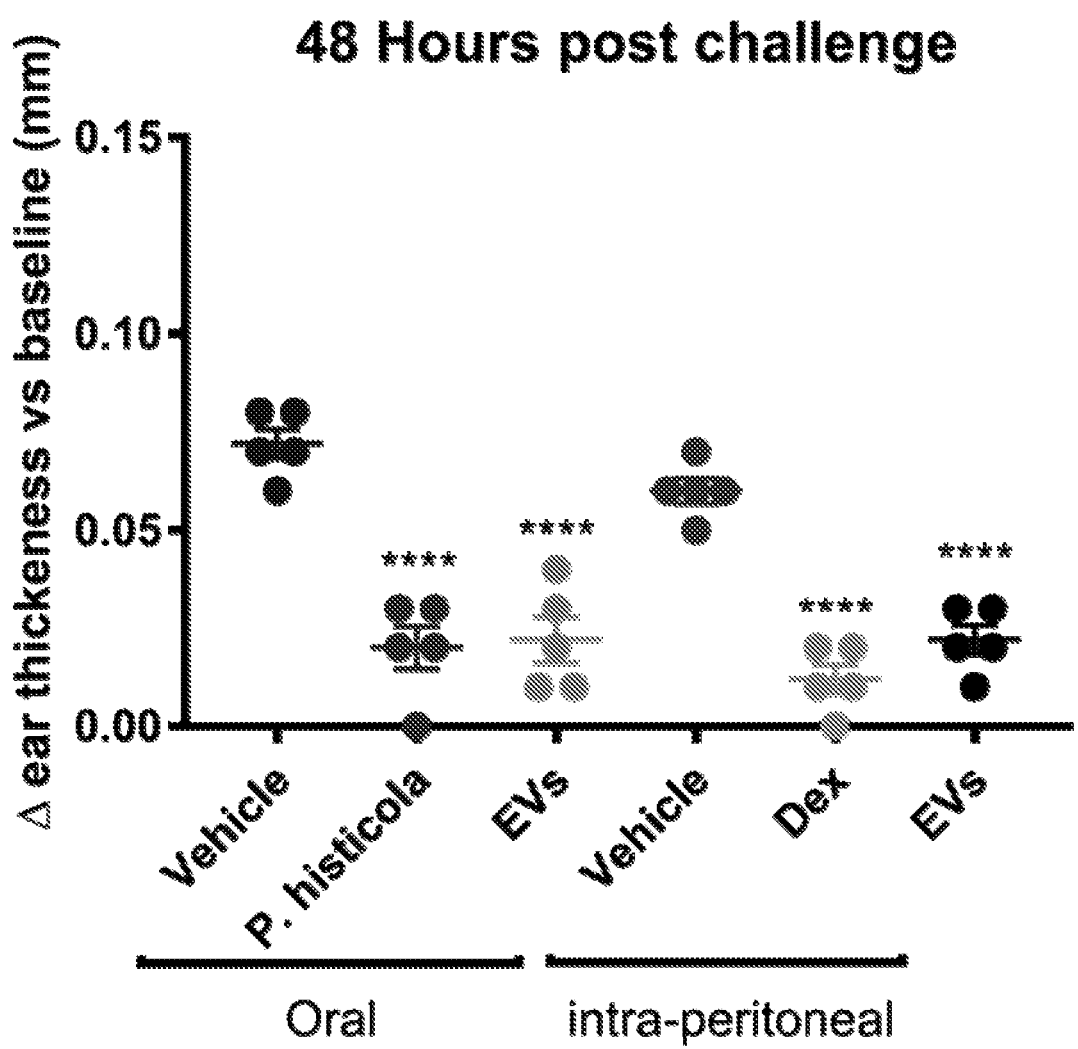
FIG. 3B shows the efficacy of orally or intra-peritoneally administered *Prevotella histicola* and *P. histicola*-derived EVs in reducing antigen-specific ear swelling (ear thickness) 48 hours after antigen challenge in a KLH-based delayed type hypersensitivity mouse model.
Figure 3C:
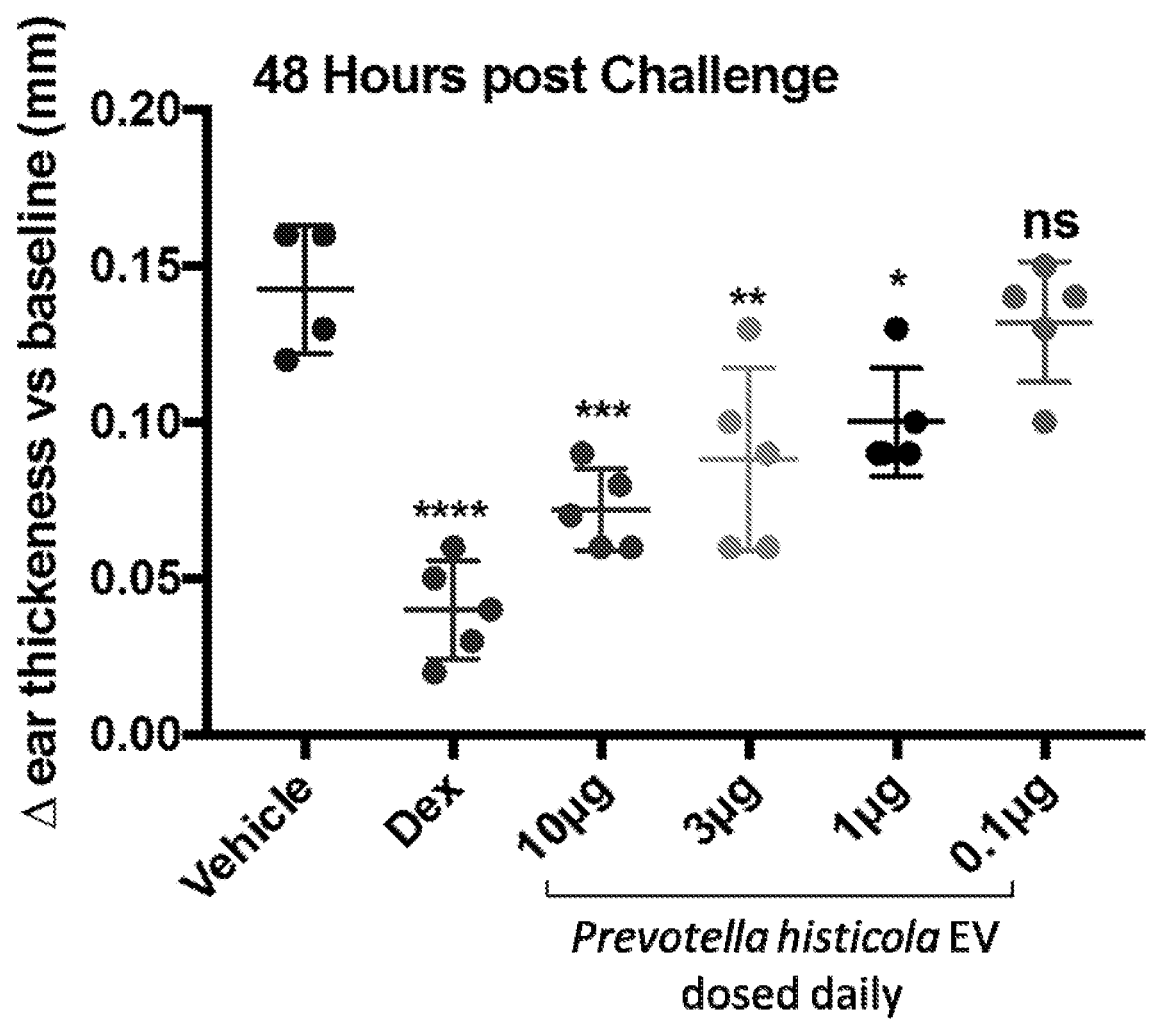
FIG. 3C shows the efficacy of intra-peritoneally administered *P. histicola*-derived EVs at the dose indicated (10 μg, 3 μg, 1 μg, and 0.1 μg) in reducing antigen-specific ear swelling (ear thickness) 48 hours after antigen challenge in a KLH-based delayed type hypersensitivity mouse model.

Mice were injected with KLH and CFA i.d at 4 locations along the back (50 ug per mouse of KLH prepared in a 1:1 ratio with CFA in a total volume of 50 µl per site). Mice were dosed for 9 days as follows; 1) oral administration of anaerobic PBS (vehicle); 2) oral administration of 10 mg *Prevotella histicola;* 3) oral administration of 100 ug *P. histicola*-derived EVs; 4) i.p. administration of PBS; 5) i.p. administration of Dexamethasone (positive control); and 6) i.p. administration of 10 ug *Prevotella histicola*-derived EVs. For the EVs, total protein was measured using Bio-rad assays (Cat #5000205) performed per manufacturer's instructions. At 24 and 48 hours post-challenge with 10 ug of KLH (10 µl volume), groups receiving *Prevotella histicola* (live cells) or *Prevotella histicola*-derived EVs, in both the oral and i.p administration groups, exhibited less inflammation than the vehicle groups (FIGS. 3A and 3B). A dose dependent DTH response following i.p. injection of *Prevotella histicola*-derived EVs at 10 µg, 3 µg, 1 µg, and 0.1 µg was observed in reducing antigen-specific ear swelling (ear thickness) 48 hours after antigen challenge in a KLH-based delayed type hypersensitivity mouse model (FIG. 3C).

Figure 8A:
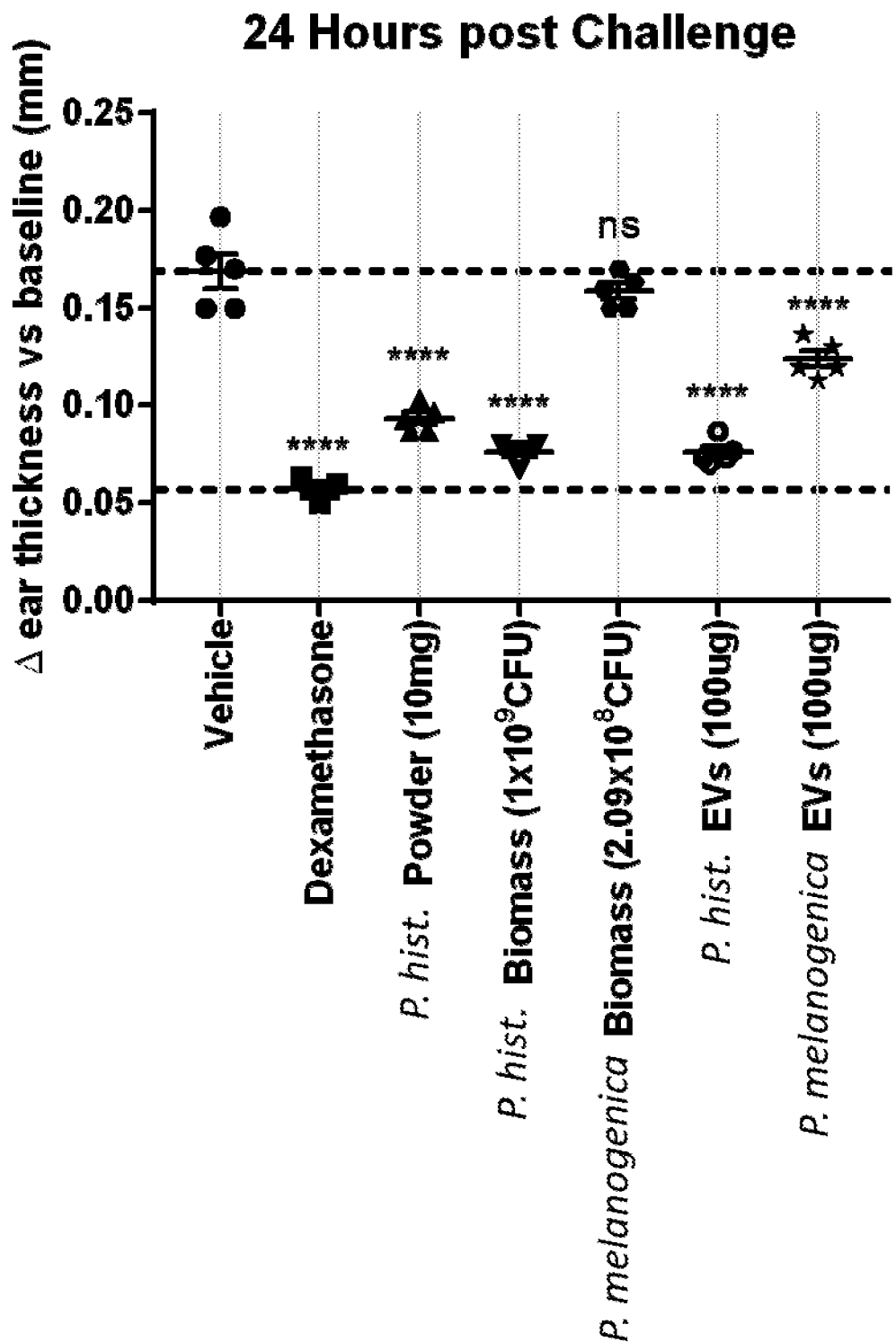
FIG. 8A shows the efficacy of administering *Prevotella histicola, P. melanogenica, P. histicola*-derived EVs, *P. melanogenica*-derived EVs in reducing antigen-specific ear swelling (ear thickness) 24 hours after antigen challenge in a KLH-based delayed type hypersensitivity mouse model. *P. melanogenica*-derived EVs is more effective than *P. melanogenica*.
Figure 8B:
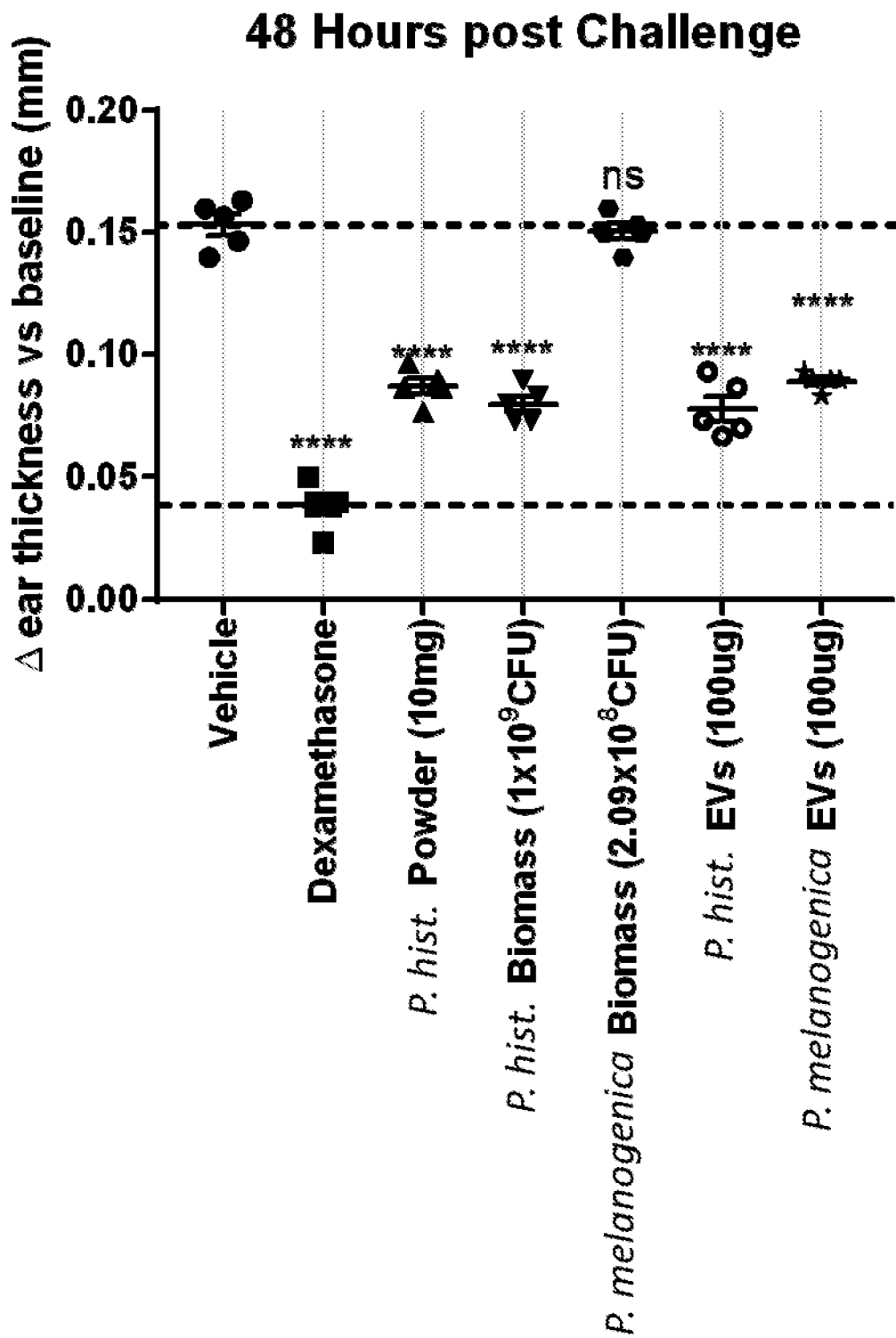
FIG. 8B shows the efficacy of administering *Prevotella histicola, P. melanogenica, P. histicola*-derived EVs, *P. melanogenica*-derived EVs in reducing antigen-specific ear swelling (ear thickness) 48 hours after antigen challenge in a KLH-based delayed type hypersensitivity mouse model. *P. melanogenica*-derived EVs is more effective than *P. melanogenica*.

Mice were injected with KLH and CFA i.d at 4 locations along the back (50 ug per mouse of KLH prepared in a 1:1 ratio with CFA in a total volume of 50 µl per site). Mice were dosed for 9 days as follows; 1) oral administration of anaerobic PBS (vehicle); 2) oral administration of 10 mg *Prevotella histicola;* 3) oral administration of $1\times10^9$ CFU *Prevotella histicola* biomass; 4) oral administration of $2.09\times10^8$ CFU *Prevotella melanogenica* biomass; 5) oral administration of 100 ug *P. histicola*-derived EVs; 6) oral administration of 100 ug *P. melanogenica*-derived EVs; and 7) i.p. administration of Dexamethasone (positive control). For the EVs, total protein was measured using Bio-rad assays (Cat #5000205) performed per manufacturer's instructions. At 24 and 48 hours post-challenge with 10 ug of KLH (10 µl volume), groups receiving *Prevotella histicola* (live cells) or *Prevotella histicola*-derived EVs exhibited less inflammation than the vehicle groups (FIGS. 8A and 8B). At 24 and 48 hours post-challenge with 10 ug of KLH (10 µl volume), the group receiving *Prevotella melanogenica*-derived EVs exhibited less inflammation than the vehicle groups and the group receiving *Prevotella melanogenica* (live cells) (FIGS. 8A and 8B).

The test formulations were prepared for KLH-based delayed type hypersensitivity model. The DTH model provides an in vivo mechanism to study the cell-mediated immune response, and resulting inflammation, following exposure to a specific antigen to which the mice have been sensitized. Several variations of the DTH model have been used and are well known in the art (Irving C. Allen (ed.). *Mouse Models of Innate Immunity: Methods and Protocols*, Methods in Molecular Biology. Vol. 1031, DOI 10.1007/978-1-62703-481-4_13, Springer Science+Business Media, LLC 2013). For example, the emulsion of Keyhole Limpet Hemocyanin (KLH) and Complete Freund's Adjuvant (CFA) are prepared freshly on the day of immunization (day 0). To this end, 8 mg of KLH powder is weighed and is thoroughly re-suspended in 16 mL saline. An emulsion is prepared by mixing the KLH/saline with an equal volume of CFA solution (e.g. 10 mL KLH/saline+10 mL CFA solution) using syringes and a luer lock connector. KLH and CFA is mixed vigorously for several minutes to form a white-colored emulsion to obtain maximum stability. A drop test is performed to check if a homogenous emulsion is obtained, mixing is continued until an intact drop remains visible in the water.

On day 0, C57Bl/6J female mice, approximately 7 weeks old, were primed with KLH antigen in CFA by subcutaneous immunization (4 sites, 50 µL per site).

Dexamethasone, a corticosteroid, is a known anti-inflammatory that ameliorates DTH reactions in mice, and serves as a positive control for suppressing inflammation in this model (Taube and Carlsten, Action of dexamethasone in the suppression of delayed-type hypersensitivity in reconstituted SCID mice. Inflamm Res. 2000. 49(10): 548-52). For the positive control group, a stock solution of 17 mg/mL of Dexamethasone was prepared on Day 0 by diluting 6.8 mg Dexamethasone in 400 μL 96% ethanol. For each day of dosing, a working solution is prepared by diluting the stock solution 100× in sterile PBS to obtain a final concentration of 0.17 mg/mL in a septum vial for intraperitoneal dosing. Dexamethasone-treated mice received 100 μL Dexamethasone i.p. (5 mL/kg of a 0.17 mg/mL solution). Frozen sucrose served as the negative control (vehicle). *Veillonella* Strains were dosed at $1\times10^{10}$ CFU p.o. daily. Dexamethasone (positive control), vehicle (negative control), and *Bifidobacterium animalis lactis* (10 mg powder) were dosed daily.

Figure 11:
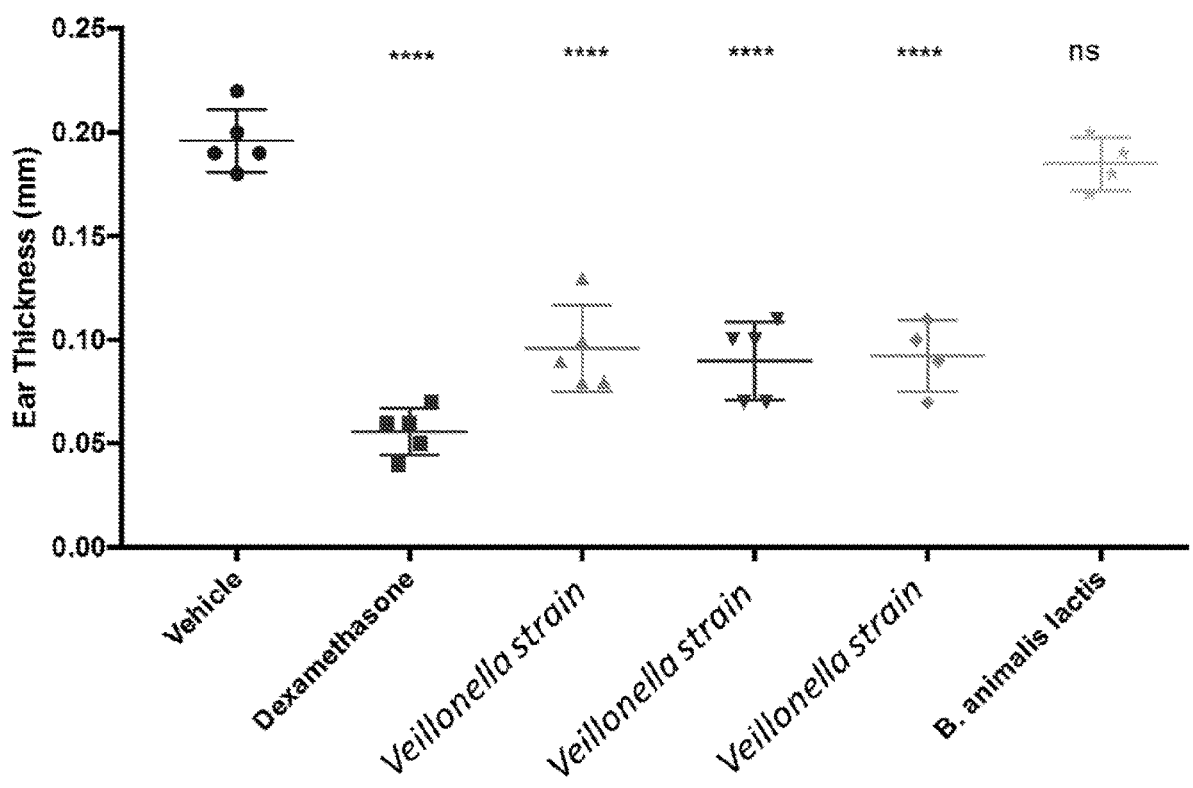
FIG. 11 shows the efficacy of orally administered *Veillonella tobetsuensis* and *Veillonella parvula* Strains in reducing antigen-specific ear swelling (ear thickness) at 24 hours compared to vehicle (negative control), anti-inflammatory Dexamethasone (positive control), and *Bifidobacterium animalis lactis* in a KLH-based delayed type hypersensitivity mouse model.

On day 8, mice were challenged intradermally (i.d.) with 10 μg KLH in saline (in a volume of 10 μL) in the left ear. Inflammatory responses were measured using methods known in the art. Ear pinna thickness was measured at 24 hours following antigen challenge (FIG. 11). As determined by ear thickness, *Veillonella* Strains were efficacious at suppressing inflammation compared to mice that received vehicle alone (comparable to Dexamethasone treatment).

The efficacy of *Veillonella* strains may be studied further using varied timing and varied doses. For instance, treatment with a *Veillonella* bacterial composition may be initiated at some point, either around the time of priming or around the time of DTH challenge. For example, *Veillonella* ($1\times10^9$ CFU per mouse per day) may be administered at the same time as the subcutaneous injections (day 0), or administered prior to, or upon, intradermal injection. *Veillonella* strains may be administered at varied doses and at defined intervals, and in various combinations. For example, some mice are intravenously injected with *Veillonella* at a range of between $1\times10^4$ and $5\times10^9$ bacterial cells per mouse. Some mice receive a mixture of Strains. While some mice will receive a *Veillonella* through i.v. injection, other mice may receive a *Veillonella* through intraperitoneal (i.p.) injection, subcutaneous (s.c.) injection, nasal route administration, oral gavage, topical administration, intradermal (i.d.) injection, or other means of administration. Some mice may receive a *Veillonella* every day (e.g. starting on day 0), while others may receive a *Veillonella* at alternative intervals (e.g. every other day, or once every three days). The bacterial cells may be live, dead, or weakened. The bacterial cells may be harvested fresh (or frozen) and administered, or they may be irradiated or heat-killed prior to administration.

Some groups of mice may be treated with anti-inflammatory agent(s) (e.g. anti-CD154, blockade of members of the TNF family, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various timepoints, serum samples are taken. Other groups of mice are sacrificed and lymph nodes, spleen, mesenteric lymph nodes (MLN), the small intestine, colon, and other tissues may be removed for histology studies, ex vivo histological, cytokine and/or flow cytometric analysis using methods known in the art. Some mice are exsanguinated from the orbital plexus under O2/CO2 anesthesia and ELISA assays performed.

Tissues may be dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+infiltrated immune cells obtained ex vivo. Finally, immunohistochemistry is carried out on various tissue sections to measure T cells, macrophages, dendritic cells, and checkpoint molecule protein expression.

Mice were primed and challenged with KLH as described above and, following measurement of the ear swelling at 48 hours, mice were sacrificed.

Figure 3D:
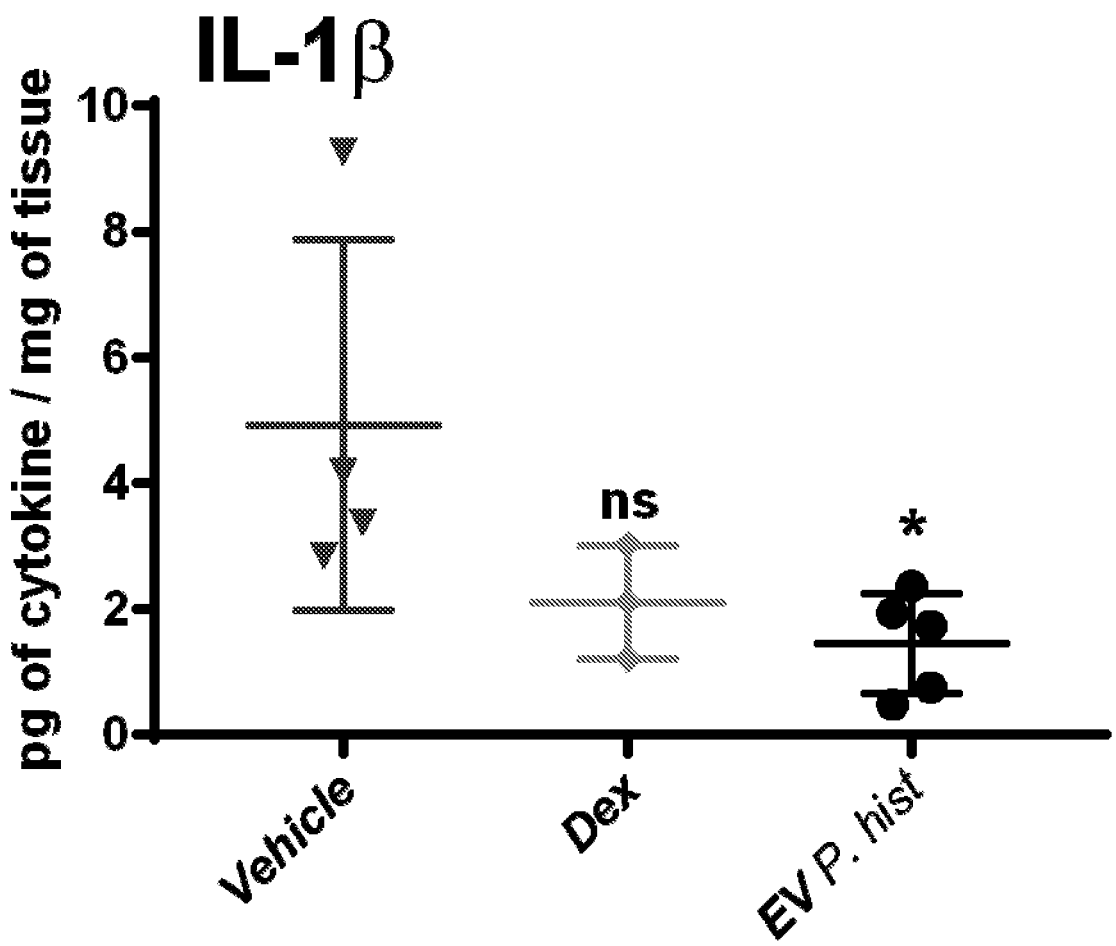
FIG. 3D shows the ability of intra-peritoneally administered *Prevotella histicola*-derived EVs to reduce expression of IL-1ß 48 hours after antigen challenge in a KLH-based delayed type hypersensitivity mouse model.

Ears were removed from the sacrificed animals and placed in cold EDTA-free protease inhibitor cocktail (Roche). Ears were homogenized using bead disruption and supernatants analyzed for IL-1ß by Luminex kit (EMD Millipore) as per manufacturer's instructions. Mice that were treated with 10 μg *P. histicola* EVs (i.p.) showed levels of IL-1B comparable to that seen in the Dexamethasone group (positive control). (FIG. 3D). *P. histicola*-derived EVs are capable of suppressing pro-inflammatory cytokines.

Figure 3E:
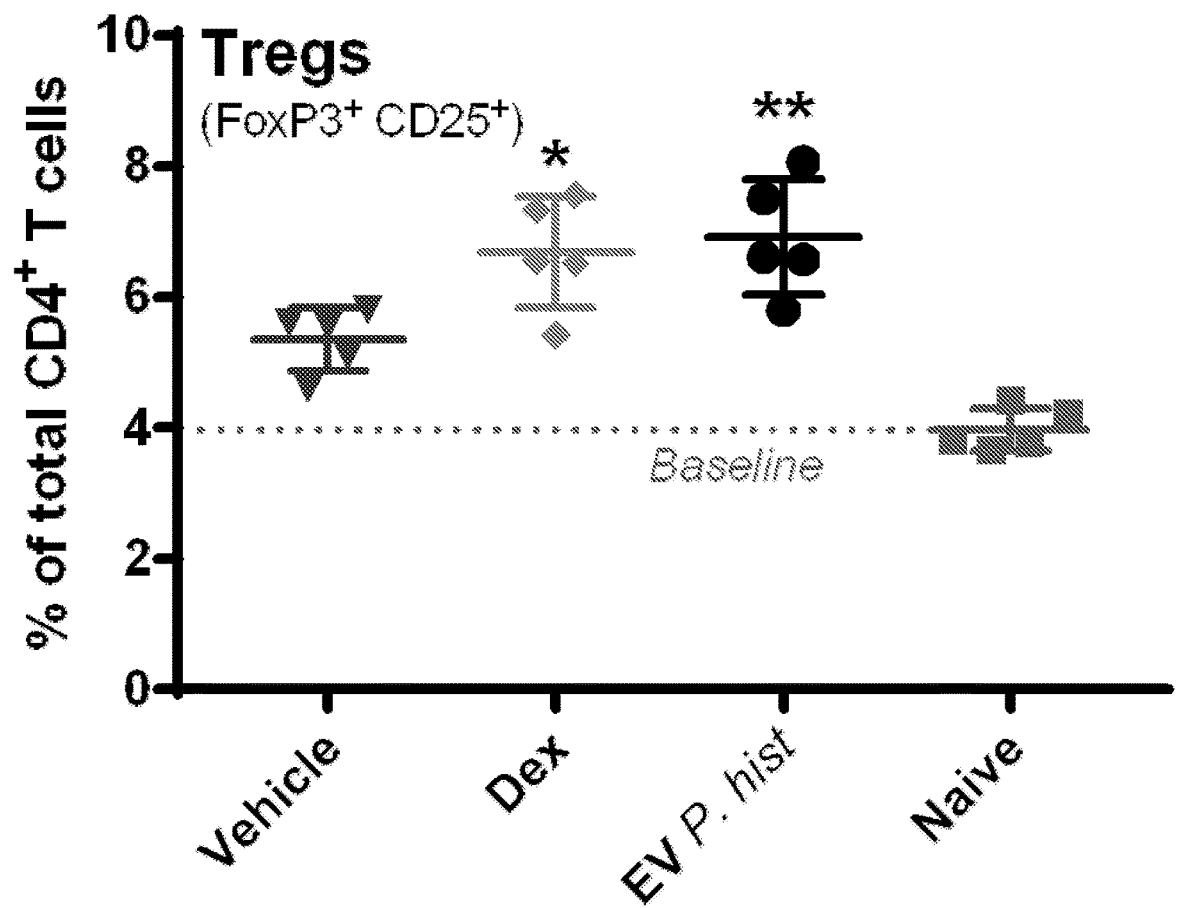
FIG. 3E shows the ability of intra-peritoneally administered *Prevotella histicola*-derived EVs to increase accumulation of Tregs in the cervical lymph nodes 48 hours after antigen challenge in a KLH-based delayed type hypersensitivity mouse model.

In addition, cervical lymph nodes were dissociated through a cell strainer, washed, and stained for FoxP3 (PE-FJK-16s) and CD25 (FITC-PC61.5) using methods known in the art (FIG. 3E). Mice that were treated with 10 μg *P. histicola* EVs (i.p.) showed an increase in Tregs in the cervical lymph nodes relative to naïve mice (negative control), and comparable to the Dexamethasone group (positive control). *P. histicola*-derived EVs are capable of inducing Tregs in draining lymph nodes of challenged mice.

In order to examine the impact and longevity of DTH protection, rather than being sacrificed, some mice may be rechallenged with the challenging antigen (e.g. OVA). Mice are analyzed for susceptibility to DTH and severity of response.

Example 20: EVs in a Mouse Model of Type 1 Diabetes (T1D)

Type 1 diabetes (T1D) is an autoimmune disease in which the immune system targets the islets of Langerhans of the pancreas, thereby destroying the body's ability to produce insulin.

There are various models of animal models of T1D, as reviewed by Belle et al. (Mouse models for type 1 diabetes. Drug Discov Today Dis Models. 2009; 6(2): 41-45; see also Aileen J F King. The use of animal models in diabetes research. Br J Pharmacol. 2012 June; 166(3): 877-894. There are models for chemically-induced T1D, pathogen-induced T1D, as well as models in which the mice spontaneously develop T1D.

EVs are tested for their efficacy in a mouse model of T1D, either alone or in combination with whole bacterial cells, with or without the addition of other anti-inflammatory treatments.

Depending on the method of T1D induction and/or whether T1D development is spontaneous, treatment with EVs is initiated at some point, either around the time of induction or following induction, or prior to the onset (or upon the onset) of spontaneously-occurring T1D. EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through intraperitoneal (i.p.) injection, subcutaneous (s.c.) injection, nasal route administration, oral gavage, or other means of administration. Some mice may receive EVs every day, while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1 \times 10+$ and $5 \times 10^9$ bacterial cells in an administration separate from, or comingled with, the EV administration. As with the EVs, bacterial cell administration may be varied by route of administration, dose, and schedule. This can include oral gavage, i.v. injection, i.p. injection, or nasal route administration.

Some groups of mice may be treated with additional treatments and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

Blood glucose is monitored biweekly prior to the start of the experiment. At various timepoints thereafter, nonfasting blood glucose is measured. At various timepoints, mice are sacrificed and site the pancreas, lymph nodes, or other tissues may be removed for ex vivo histological, cytokine and/or flow cytometric analysis using methods known in the art. For example, tissues are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified tissue-infiltrating immune cells obtained ex vivo. Finally, immunohistochemistry is carried out on various tissue sections to measure T cells, macrophages, dendritic cells, and checkpoint molecule protein expression. Antibody production may also be assessed by ELISA.

In order to examine the impact and longevity of disease protection, rather than being sacrificed, some mice may be rechallenged with a disease trigger, or assessed for susceptibility to relapse. Mice are analyzed for susceptibility to diabetes onset and severity following rechallenge (or spontaneously-occurring relapse).

Example 21: EVs in a Mouse Model of Primary Sclerosing Cholangitis (PSC)

Primary Sclerosing Cholangitis (PSC) is a chronic liver disease that slowly damages the bile ducts and leads to end-stage cirrhosis. It is associated with inflammatory bowel disease (IBD).

There are various animal models for PSC, as reviewed by Fickert et al. (Characterization of animal models for primary sclerosing cholangitis (PSC). J Hepatol. 2014 June 60(6): 1290-1303; see also Pollheimer and Fickert. Animal models in primary biliary cirrhosis and primary sclerosing cholangitis. Clin Rev Allergy Immunol. 2015 June 48(2-3): 207-17). Induction of disease in PSC models includes chemical induction (e.g. 3,5-diethoxycarbonyl-1,4-dihydrocollidine (DDC)-induced cholangitis), pathogen-induced (e.g. *Cryptosporidium parvum*), experimental biliary obstruction (e.g. common bile duct ligation (CBDL)), and transgenic mouse model of antigen-driven biliary injury (e.g. Ova-Bil transgenic mice). For example, bile duct ligation is performed as described by Georgiev et al. (Characterization of time-related changes after experimental bile duct ligation. Br J Surg. 2008. 95(5): 646-56), or disease is induced by DCC exposure as described by Fickert et al. (A new xenobiotic-induced mouse model of sclerosing cholangitis and biliary fibrosis. Am J Path. Vol 171(2): 525-536.

EVs are tested for their efficacy in a mouse model of PSC, either alone or in combination with whole bacterial cells, with or without the addition of some other therapeutic agent. DCC-Induced Cholangitis For example, 6-8 week old C57bl/6 mice are obtained from Taconic or other vendor. Mice are fed a 0.1% DCC-supplemented diet for various durations. Some groups receive DCC-supplement food for 1 week, others for 4 weeks, others for 8 weeks. Some groups of mice may receive a DCC-supplemented diet for a length of time and then be allowed to recover, thereafter receiving a normal diet. These mice may be studied for their ability to recover from disease and/or their susceptibility to relapse upon subsequent exposure to DCC. Treatment with EVs is initiated at some point, either around the time of DCC-feeding or subsequent to initial exposure to DCC. For example, EVs may be administered on day 1, or they may be administered sometime thereafter. EVs are administered at varied doses and at defined intervals. For example, some mice are intravenously injected with EVs at 15, 20, Or 15 ug/mouse. Other mice may receive 25, 50, 100 mg of EVs per mouse. While some mice receive EVs through i.v. injection, other mice may receive EVs through i.p. injection, subcutaneous (s.c.) injection, nasal route administration, oral gavage, or other means of administration. Some mice may receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen), and administered, or they may be irradiated or heat-killed prior to administration. For example, some groups of mice may receive between 1×10+ and 5×10⁹ bacterial cells in an administration separate from, or comingled with, the EV administration. As with EVs, bacterial cell administration may be varied by route of administration, dose, and schedule. This can include oral gavage, i.v. injection, i.p. injection, or nasal route administration. Some groups of mice may be treated with additional agents and/or an appropriate control (e.g. vehicle or antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics. At various timepoints, serum samples are analyzed for ALT, AP, bilirubin, and serum bile acid (BA) levels.

At various timepoints, mice are sacrificed, body and liver weight are recorded, and sites of inflammation (e.g. liver, small and large intestine, spleen), lymph nodes, or other tissues may be removed for ex vivo histolomorphological characterization, cytokine and/or flow cytometric analysis using methods known in the art (see Fickert et al. Characterization of animal models for primary sclerosing cholangitis (PSC)). J Hepatol. 2014. 60(6): 1290-1303). For example, bile ducts are stained for expression of ICAM-1, VCAM-1, MadCAM-1. Some tissues are stained for histological examination, while others are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80), as well as adhesion molecule expression (ICAM-1, VCAM-1, MadCAM-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+bile duct-infiltrated immune cells obtained ex vivo.

Liver tissue is prepared for histological analysis, for example, using Sirius-red staining followed by quantification of the fibrotic area. At the end of the treatment, blood is collected for plasma analysis of liver enzymes, for example, AST or ALT, and to determine Bilirubin levels. The hepatic content of Hydroxyproline can be measured using established protocols. Hepatic gene expression analysis of inflammation and fibrosis markers may be performed by qRT-PCR using validated primers. These markers may include, but are not limited to, MCP-1, alpha-SMA, Colla1, and TIMP-. Metabolite measurements may be performed in plasma, tissue and fecal samples using established metabolomics methods. Finally, immunohistochemistry is carried out on liver sections to measure neutrophils, T cells, macrophages, dendritic cells, or other immune cell infiltrates.

In order to examine the impact and longevity of disease protection, rather than being sacrificed, some mice may be rechallenged with DCC at a later time. Mice are analyzed for susceptibility to cholangitis and cholangitis severity following rechallenge.

BDL-Induced Cholangitis

Alternatively, EVs are tested for their efficacy in BDL-induced cholangitis. For example, 6-8 week old C57Bl/6J mice are obtained from Taconic or other vendor. After an acclimation period the mice are subjected to a surgical procedure to perform a bile duct ligation (BDL). Some control animals receive a sham surgery. The BDL procedure leads to liver injury, inflammation and fibrosis within 7-21 days.

Treatment with EVs is initiated at some point, either around the time of surgery or some time following the surgery. EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through i.p. injection, subcutaneous (s.c.) injection, nasal route administration, oral gavage, or other means of administration. Some mice receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. They bacterial cells may be harvested fresh (or frozen), and administered, or they may be irradiated or heat-killed prior to administration. For example, some groups of mice may receive between 1×10⁴ and 5×10⁹ bacterial cells in an administration separate from, or comingled with, the EV administration. As with EVs, bacterial cell administration may be varied by route of administration, dose, and schedule. This can include oral gavage, i.v. injection, i.p. injection, or nasal route administration. Some groups of mice may be treated with additional agents and/or an appropriate control (e.g. vehicle or antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics. At various timepoints, serum samples are analyzed for ALT, AP, bilirubin, and serum bile acid (BA) levels.

At various timepoints, mice are sacrificed, body and liver weight are recorded, and sites of inflammation (e.g. liver, small and large intestine, spleen), lymph nodes, or other tissues may be removed for ex vivo histolomorphological characterization, cytokine and/or flow cytometric analysis using methods known in the art (see Fickert et al. Characterization of animal models for primary sclerosing cholangitis (PSC)). J Hepatol. 2014. 60(6): 1290-1303). For example, bile ducts are stained for expression of ICAM-1, VCAM-1, MadCAM-1. Some tissues are stained for histological examination, while others are dissociated using dissociation enzymes according to the manufacturer's instructions. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1, F4/80), as well as adhesion molecule expression (ICAM-1, VCAM-1, MadCAM-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+bile duct-infiltrated immune cells obtained ex vivo.

Liver tissue is prepared for histological analysis, for example, using Sirius-red staining followed by quantification of the fibrotic area. At the end of the treatment, blood is collected for plasma analysis of liver enzymes, for example, AST or ALT, and to determine Bilirubin levels. The hepatic content of Hydroxyproline can be measured using established protocols. Hepatic gene expression analysis of inflammation and fibrosis markers may be performed by qRT-PCR using validated primers. These markers may include, but are not limited to, MCP-1, alpha-SMA, Col1la1, and TIMP-. Metabolite measurements may be performed in plasma, tissue and fecal samples using established metabolomics methods. Finally, immunohistochemistry is carried out on liver sections to measure neutrophils, T cells, macrophages, dendritic cells, or other immune cell infiltrates.

In order to examine the impact and longevity of disease protection, rather than being sacrificed, some mice may be analyzed for recovery.

Example 22: EVs in a Mouse Model of Nonalcoholic Steatohepatitis (NASH)

Nonalcoholic Steatohepatitis (NASH) is a severe form of Nonalcoholic Fatty Liver Disease (NAFLD), where buildup of hepatic fat (steatosis) and inflammation lead to liver injury and hepatocyte cell death (ballooning).

There are various animal models of NASH, as reviewed by Ibrahim et al. (Animal models of nonalcoholic steatohepatitis: Eat, Delete, and Inflame. Dig Dis Sci. 2016 May. 61(5): 1325-1336; see also Lau et al. Animal models of non-alcoholic fatty liver disease: current perspectives and recent advances 2017 January 241(1): 36-44).

EVs are tested for their efficacy in a mouse model of NASH, either alone or in combination with whole bacterial cells, with or without the addition of another therapeutic agent. For example, 8-10 week old C57Bl/6J mice, obtained from Taconic (Germantown, NY), or other vendor, are placed on a methionine choline deficient (MCD) diet for a period of 4-8 weeks during which NASH features develop, including steatosis, inflammation, ballooning and fibrosis.

*Prevotella histicola* bacterial cells and *P. histicola*-derived EVs are tested for their efficacy in a mouse model of NASH, either alone or in combination with each other, in varying proportions, with or without the addition of another therapeutic agent. For example, 8 week old C57Bl/6J mice, obtained from Charles River (France), or other vendor, were acclimated for a period of 5 days, randomized intro groups of 10 mice based on body weight, and placed on a methionine choline deficient (MCD) diet for example A02082002B from Research Diets (USA), for a period of 4 weeks during which NASH features developed, including steatosis, inflammation, ballooning and fibrosis. Control chow mice were fed a normal chow diet, for example RMI (E) 801492 from SDS Diets (UK). Control chow, MCD diet, and water were provided ad libitum.

Treatment with frozen, live *P. histicola* was initiated in day 1 of MCD diet for some mice and continued for 28 consecutive days. Some MCD diet mice were administered bacterial cells through daily oral gavage of 100 µl of a suspension containing $1.47 \times 10^9$ bacterial cells. Control chow and some MCD diet mice remained untreated, while some MCD diet mice were administered daily with a vehicle solution, through daily oral gavage, for 28 days. Some MCD diet mice were administered the reference compound and FXR agonist, obeticholic acid (OCA; positive control), at a dose of 30 mg/kg, through daily oral gavage, for 28 days. At the end of the treatment (day 28), mice are sacrificed and liver, small intestine, lumenal contents, blood, and feces, were removed for ex vivo histological, biochemical, molecular or cytokine and/or flow cytometry analysis using methods known in the art. For example, 0.5 cm³ liver samples were stored in formalin for 24 hours and then in ethanol at 4° C., prior to hematoxylin/eosin (H&E) and Sirius Red staining, and determination of NASH activity score (NAS). Histological analysis and scoring was conducted at Histalim (Montpelier, France) in a blinded manner. Slides containing one hepatic lobe section stained with either H&E or Sirius red were digitized using a NanoZoomer and visualized using NDP viewer, both from Hamamatsu (Japan). Each section was evaluated and scored individually. A NAS scoring system adapted from Kleiner et al. (Design and validation of a histological scoring system for nonalcoholic fatty liver disease. Hepatology. 2005 June 41(6): 1313-1321) was used to determine the degree of steatosis (scored 0-3), lobular inflammation (scored 0-3), hepatocyte ballooning (scored 0-3), and fibrosis (scored 0-4). An individual mouse NAS score was calculated by summing the score for steatosis, inflammation, ballooning, and fibrosis (scored 0-13). In addition, the levels of plasma AST and ALT were determined using a Pentra 400 instrument from Horiba (USA), according to manufacturer's instructions. The levels of hepatic total cholesterol, triglycerides, fatty acids, alanine aminotransferase, and aspartate aminotransferase were also determined using methods known in the art.

Figure 4:
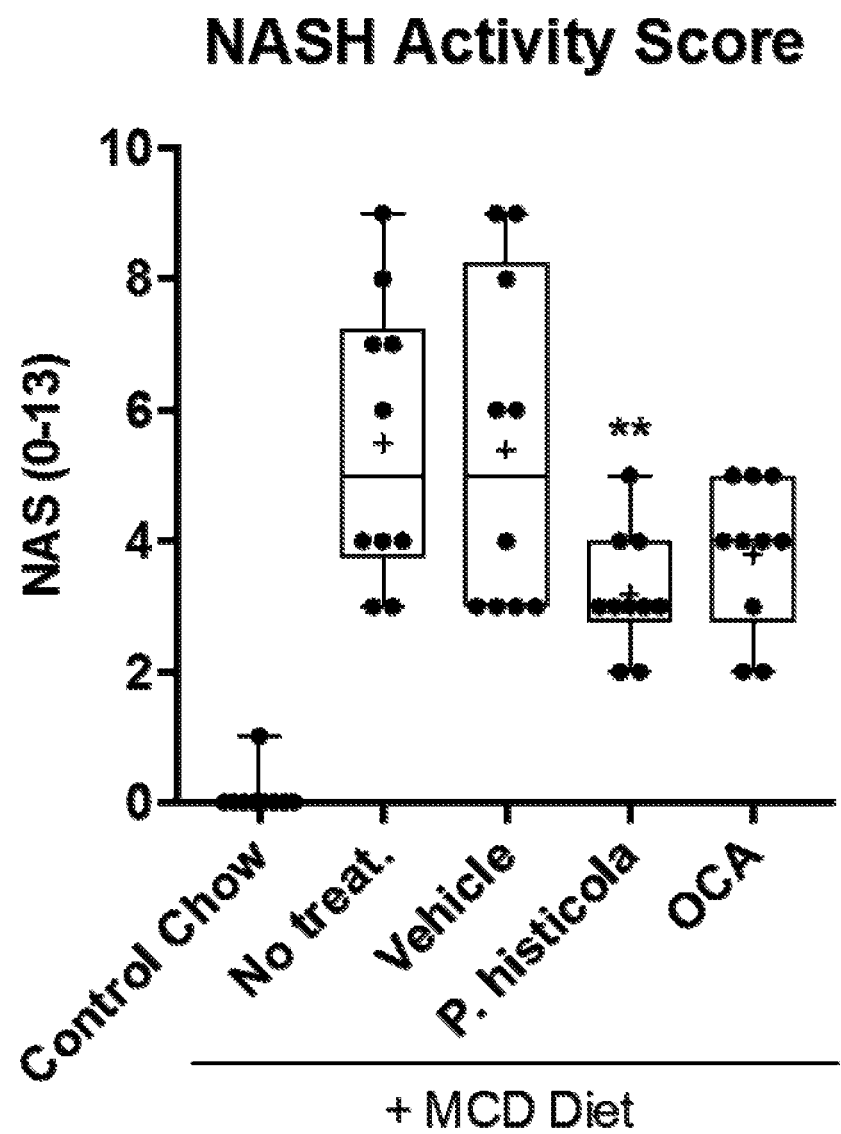
FIG. 4 shows that *P. histicola* was efficacious at reducing the NASH activity score (NAS) in mice receiving a methionine choline deficient (MCD) diet, which induces NASH symptoms.
Figure 5A:
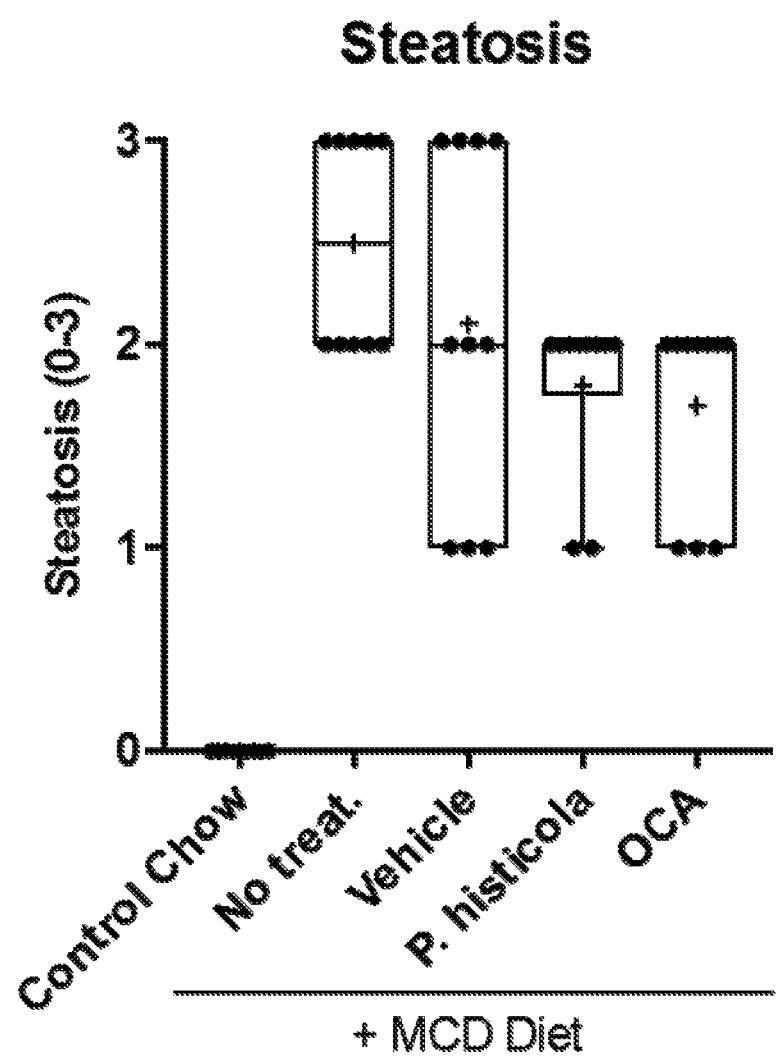
FIG. 5A shows that *P. histicola* reduced steatosis in mice that were fed an MCD diet.
Figure 5B:
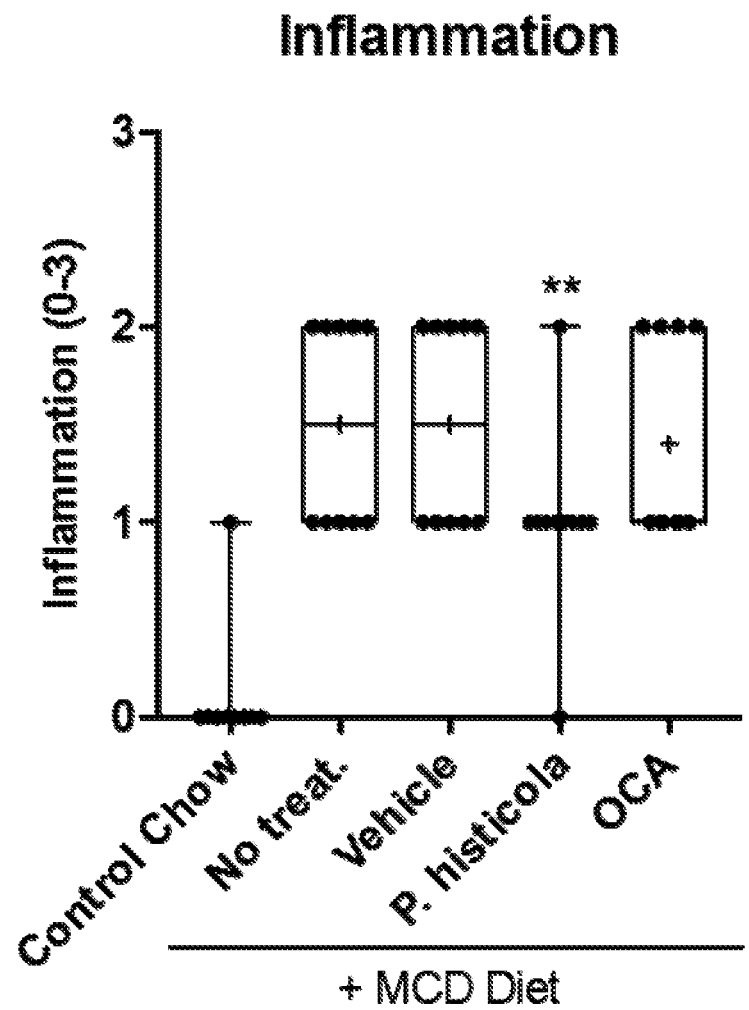
FIG. 5B and FIG. 5C show that *P. histicola* reduced inflammation in mice that were fed an MCD diet.
Figure 5C:
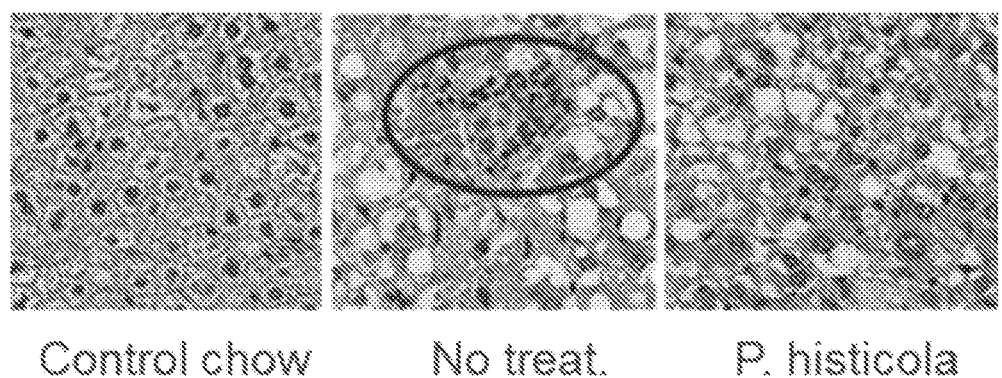
Figure 5D:
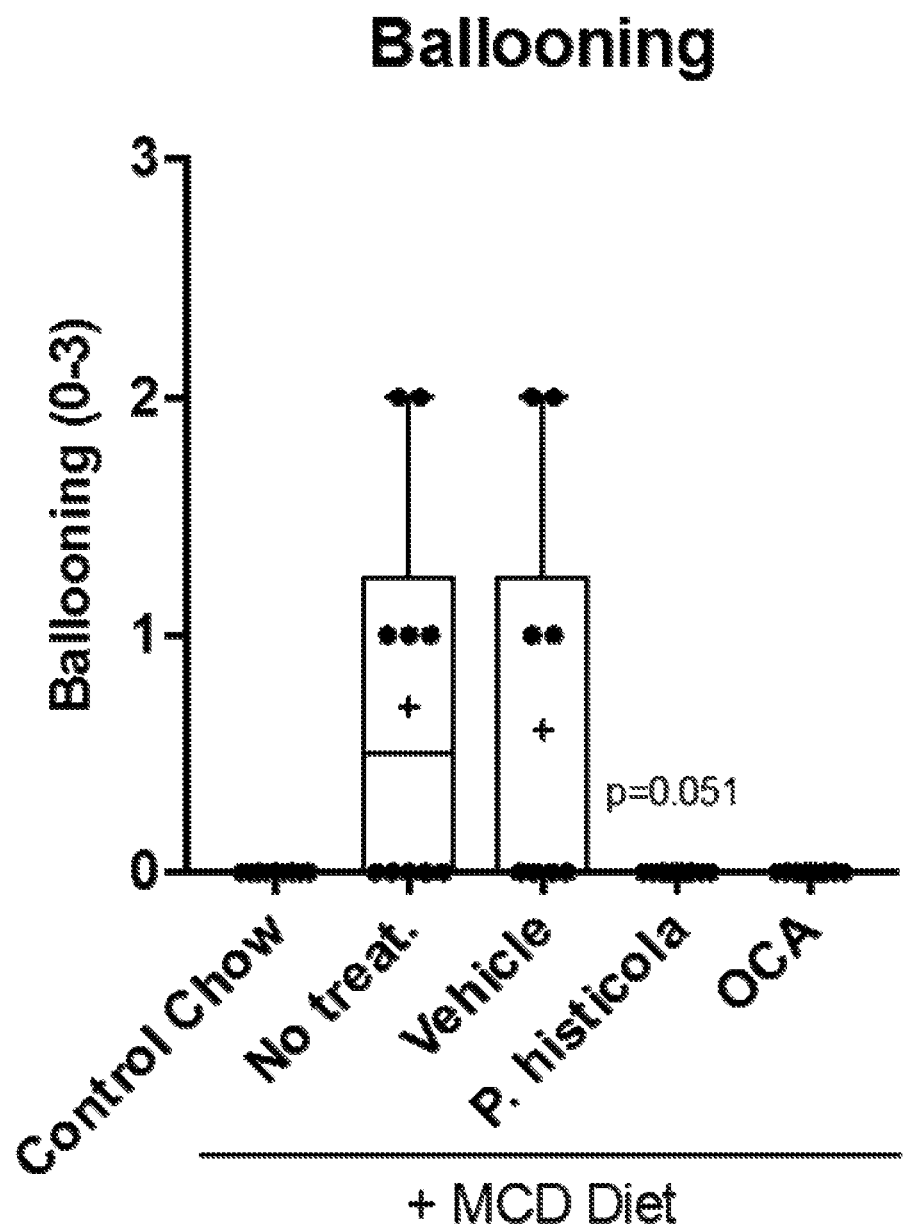
FIG. 5D shows that *P. histicola* reduced ballooning in mice that were fed an MCD diet.
Figure 6:
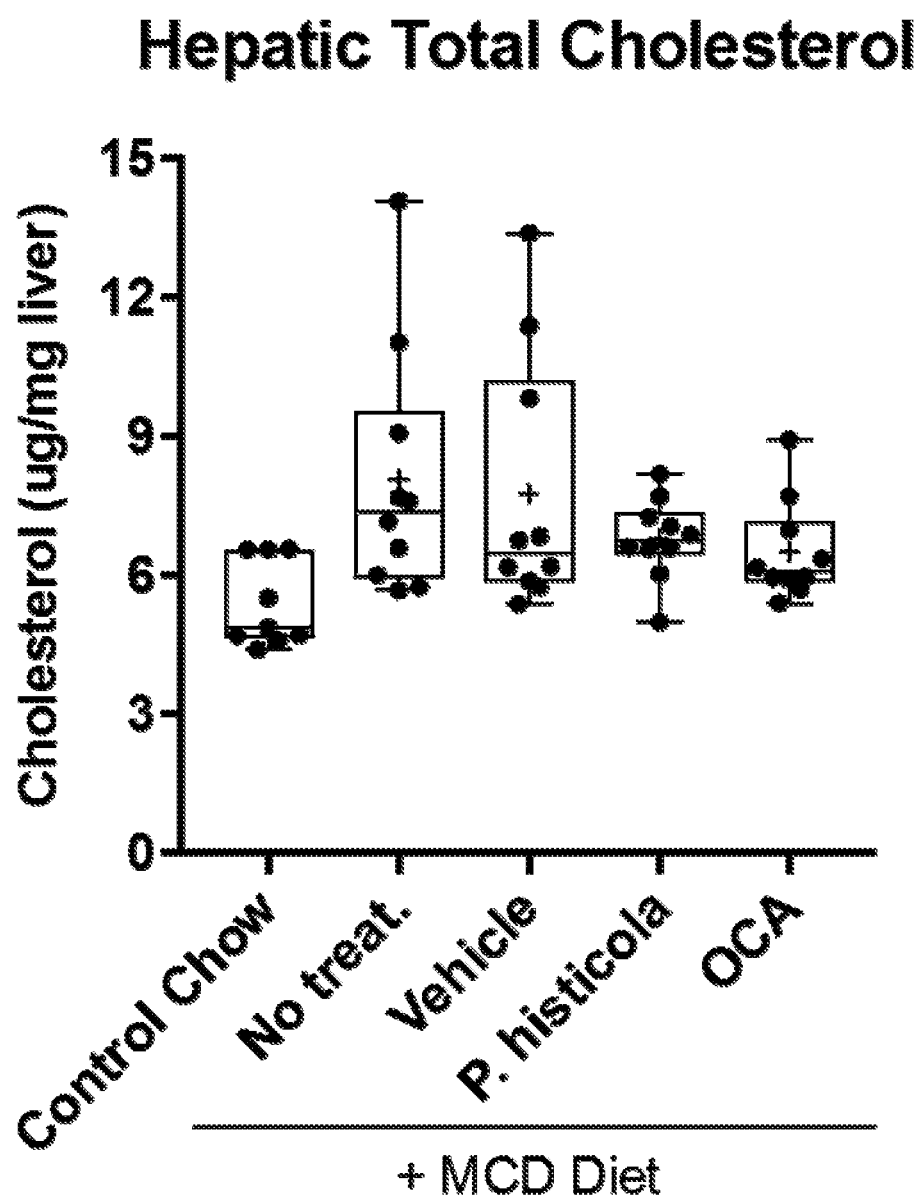
FIG. 6 shows that *P. histicola* reduced hepatic total cholesterol in mice that were fed an MCD diet.
Figure 7A:
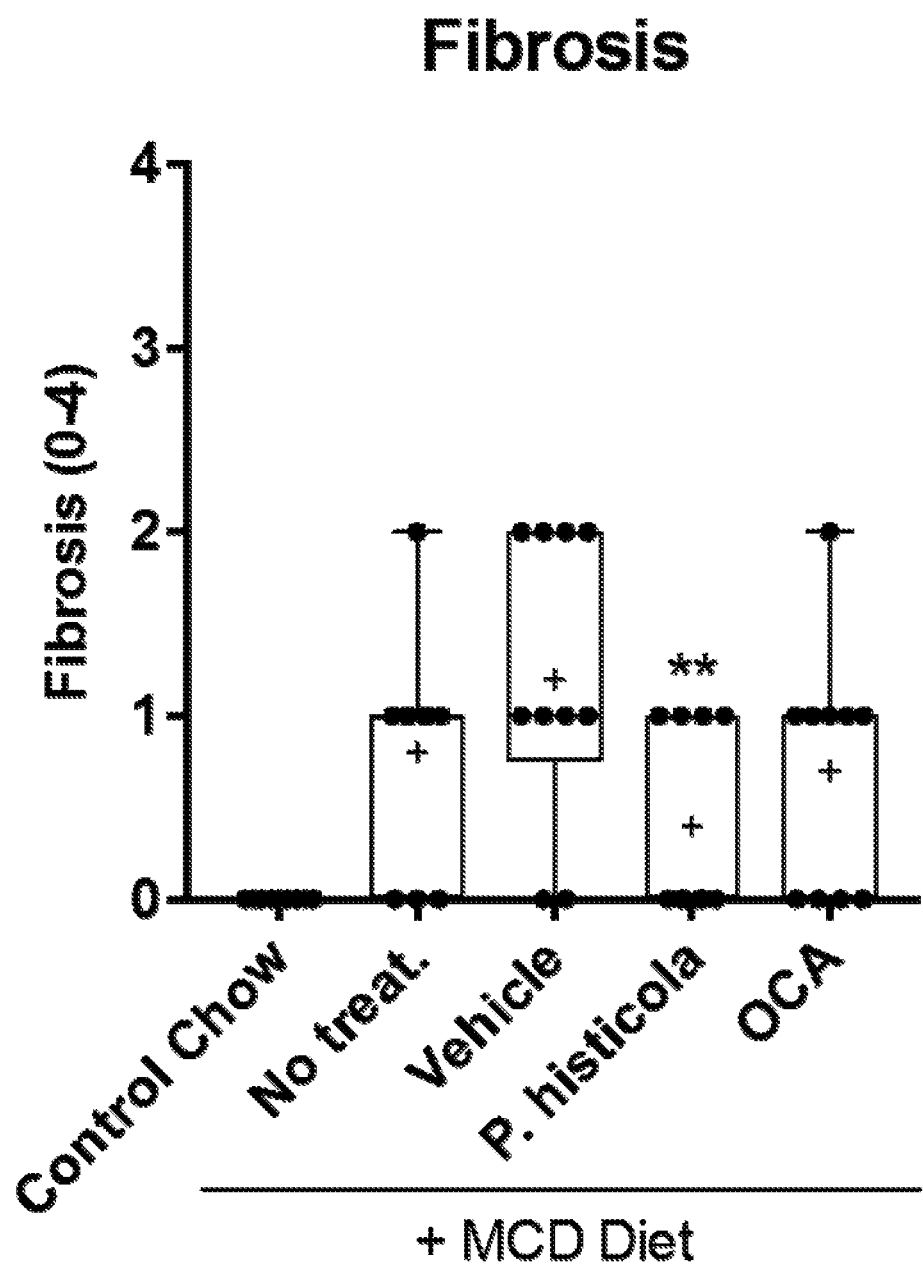
FIG. 7A and FIG. 7B show that *P. histicola* reduced the fibrosis score in mice that were fed an MCD diet.
Figure 7B:
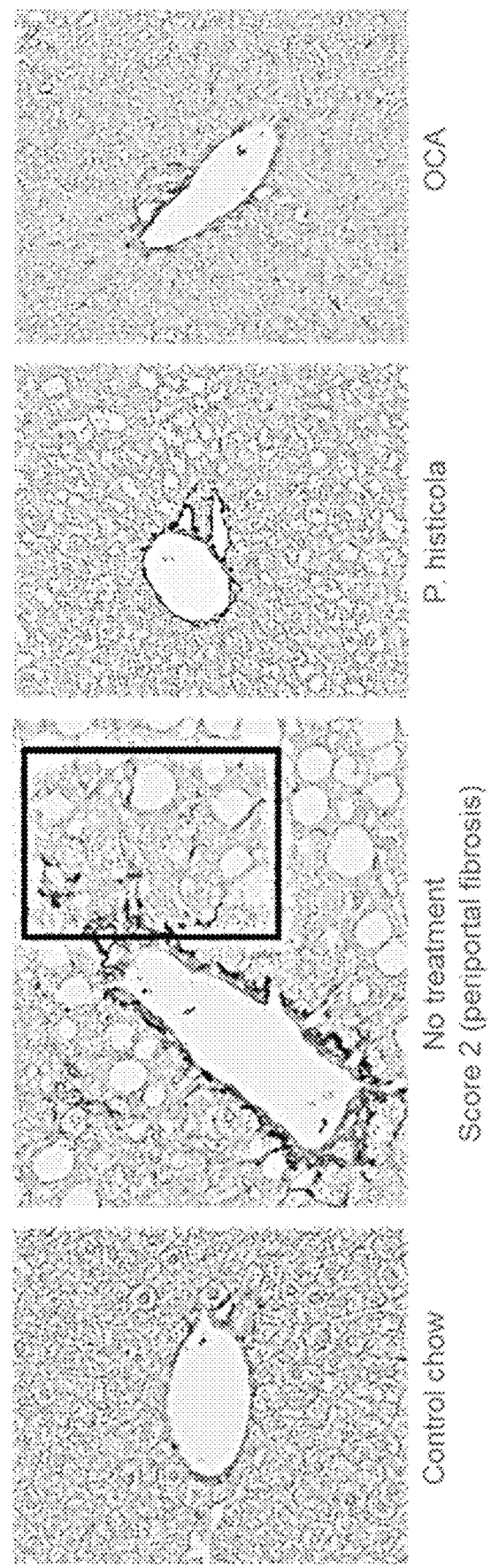

In mice receiving the MCD (NASH-inducing) diet, orally administered *P. histicola* was efficacious in reducing the NAS score compared to vehicle and no treatment groups (negative controls) (FIG. 4). *P. histicola* reduced steatosis (FIG. 5A), inflammation (FIG. 5B and FIG. 5C), and ballooning (FIG. 5D), as well as hepatic total cholesterol (FIG. 6). *P. histicola* also reduced the fibrosis score in treated mice (FIG. 7A and FIG. 7B).

Figure 9A:
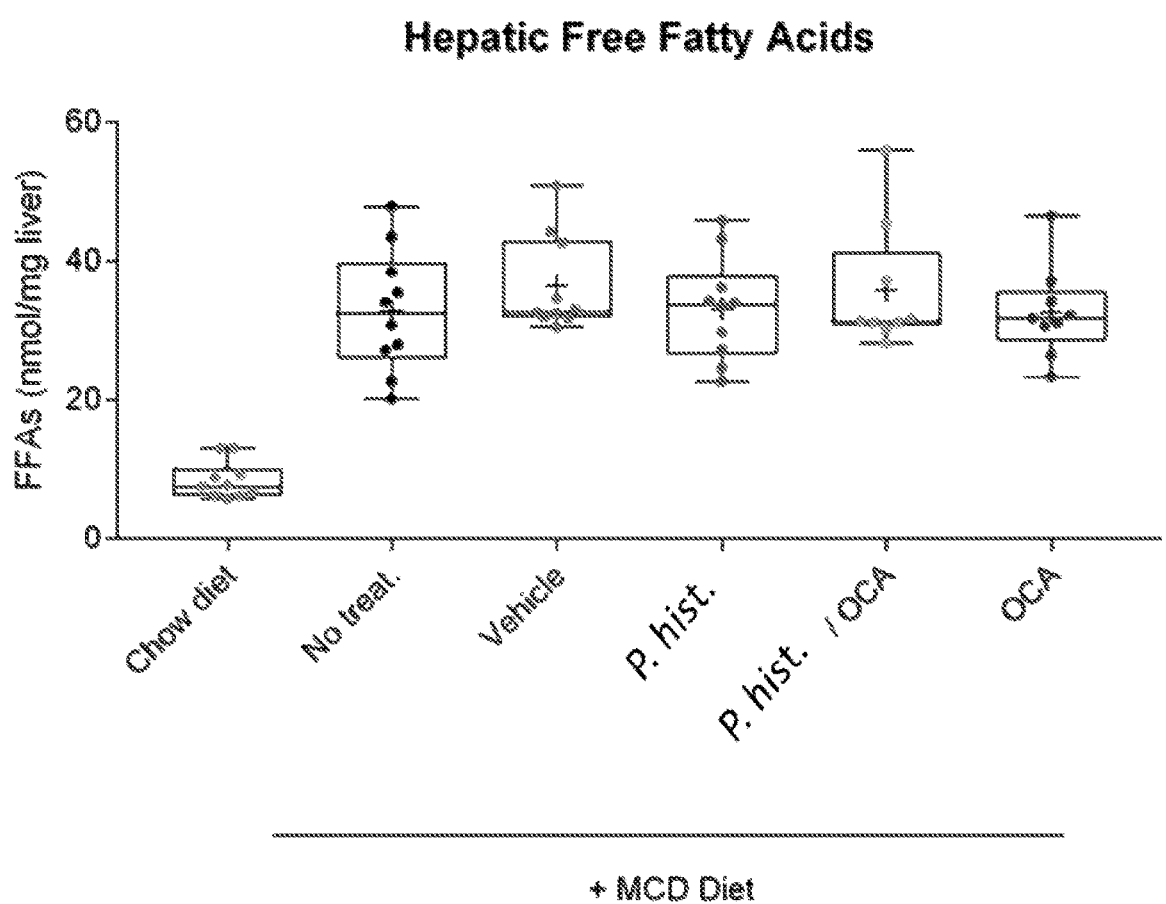
FIG. 9A shows the effect of *P. histicola* on hepatic free fatty acids in mice that were fed an MCD diet.
Figure 9B:
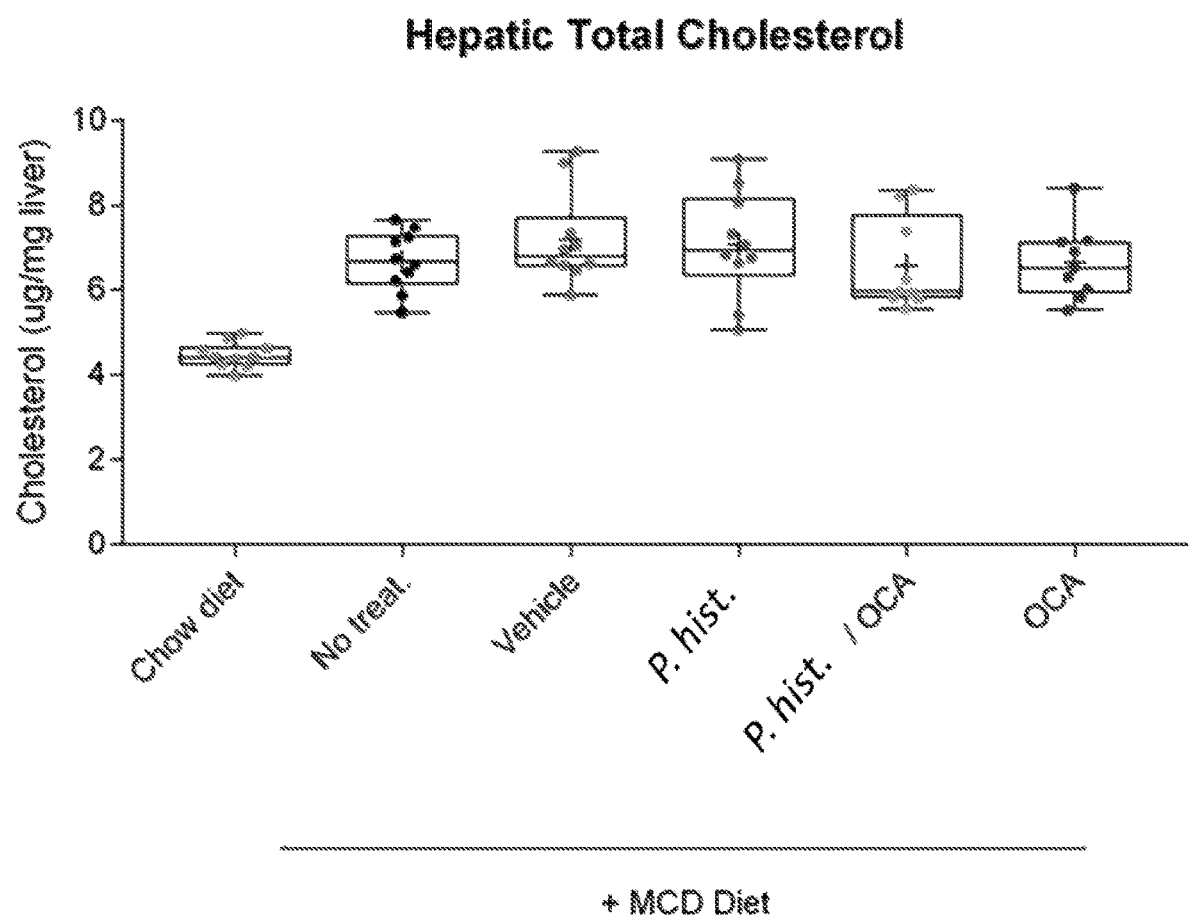
FIG. 9B shows the effect of *P. histicola* on hepatic total cholesterol in mice that were fed an MCD diet.
Figure 9C:
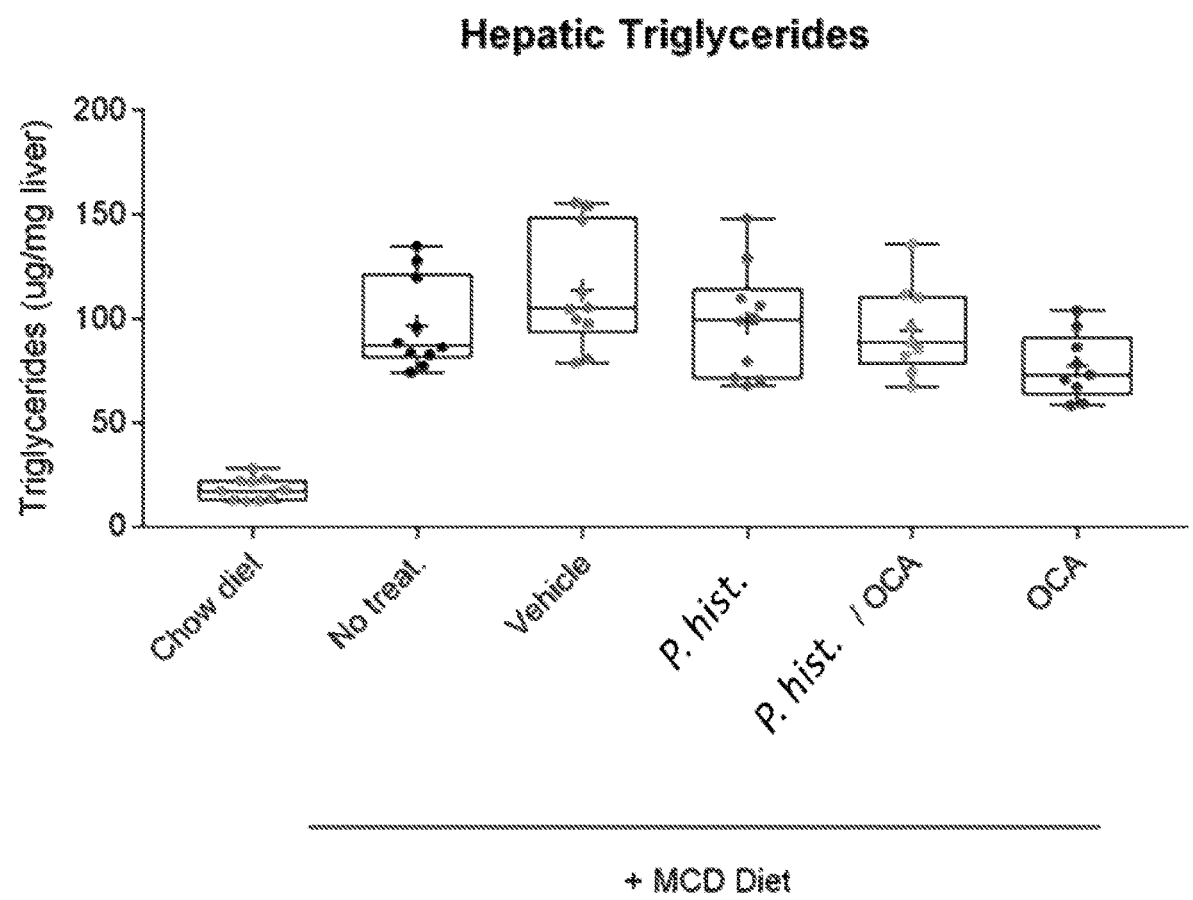
FIG. 9C shows the effect of *P. histicola* on hepatic triglycerides in mice that were fed an MCD diet.
Figure 9D:
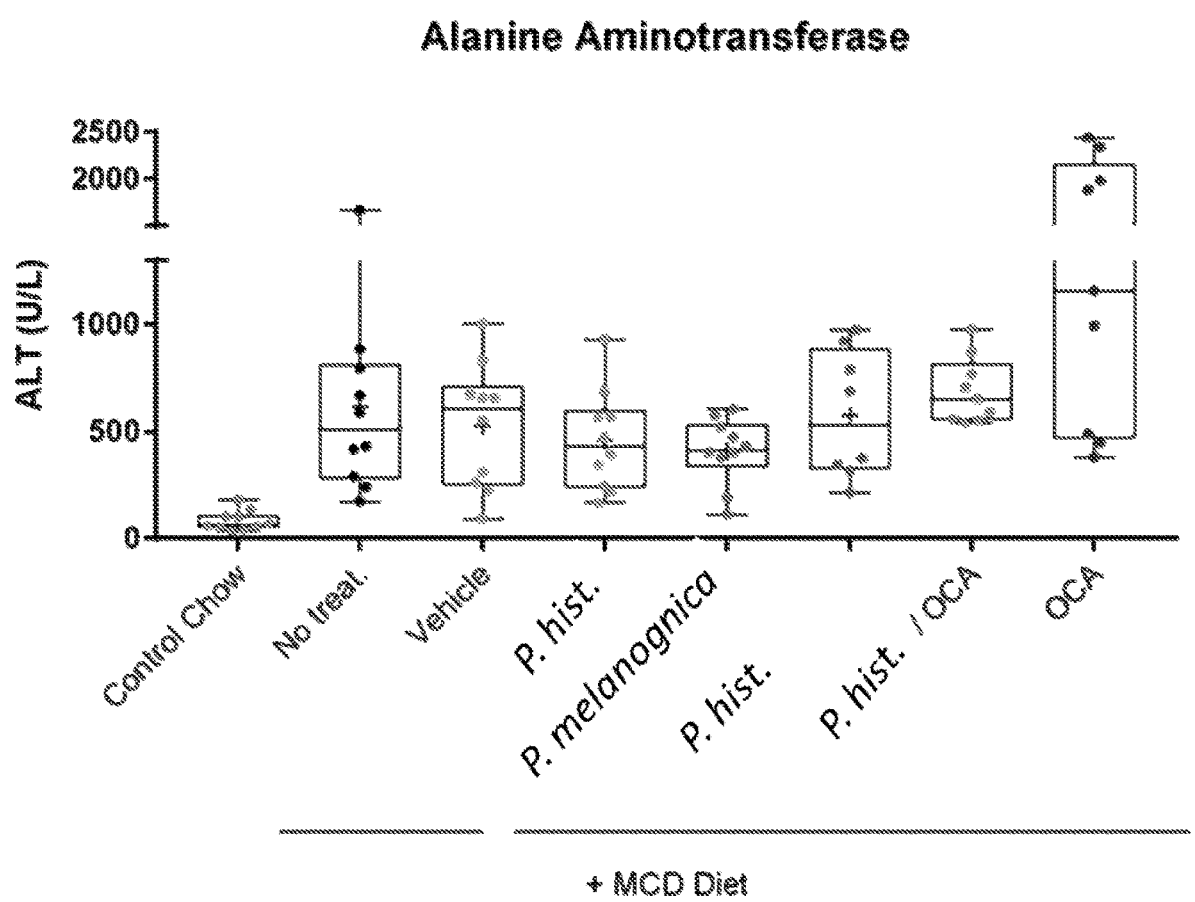
FIG. 9D shows the effect of *P. histicola* and *P. melanogenicaon* alanine aminotransferase in mice that were fed an MCD diet.
Figure 9E:
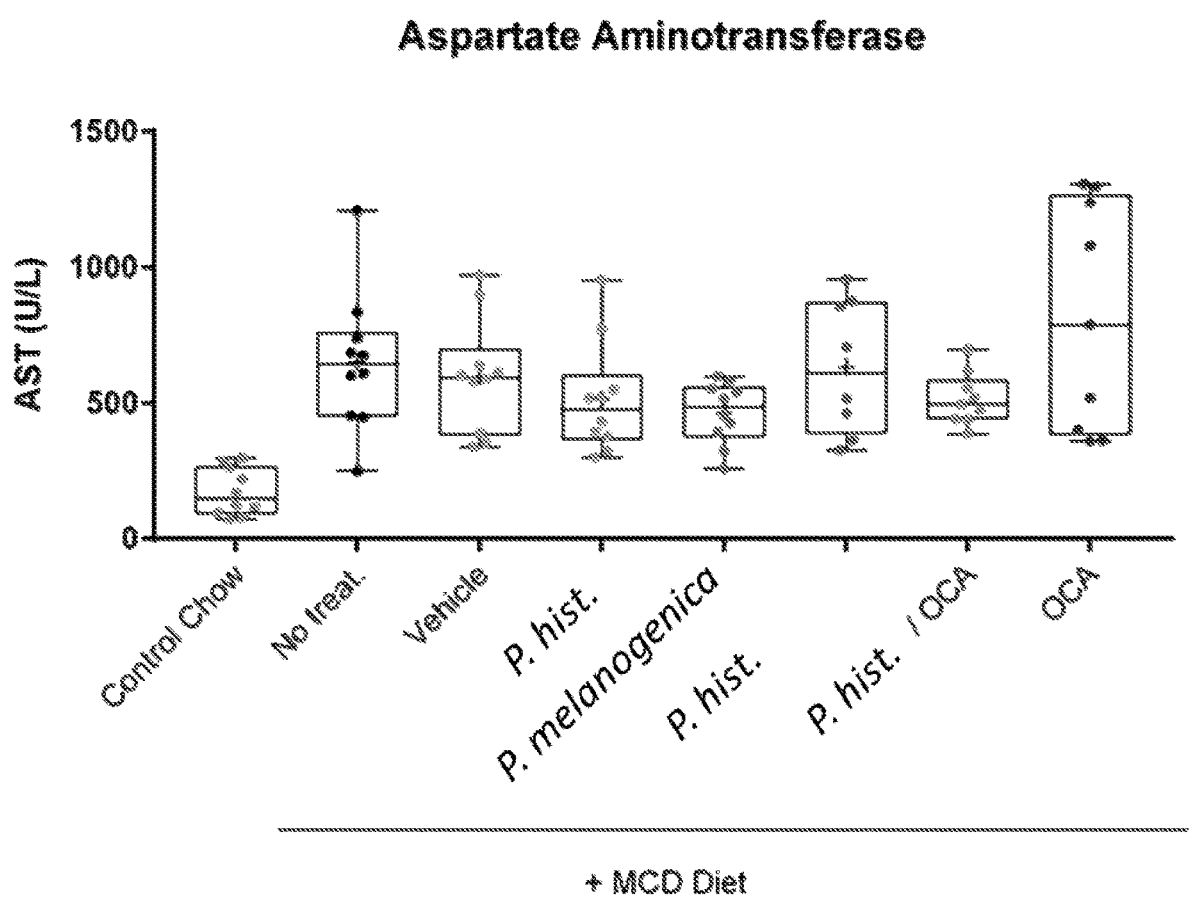
FIG. 9E shows the effect of *P. histicola* and *P. melanogenica* on aspartate aminotransferase in mice that were fed an MCD diet.

FIG. 9A shows *P. histicola* effect on hepatic free fatty acids in mice that were fed an MCD diet, FIG. 9B shows *P. histicola* effect on hepatic total cholesterol in mice that were fed an MCD diet, FIG. 9C shows *P. histicola* effect on hepatic triglycerides in mice that were fed an MCD diet, FIG. 9D shows *P. histicola* and *P. melanogenica* effect on alanine aminotransferase in mice that were fed an MCD diet, FIG. 9E shows *P. histicola* and *P. melanogenica* effect on aspartate aminotransferase in mice that were fed an MCD diet.

Figure 10A:
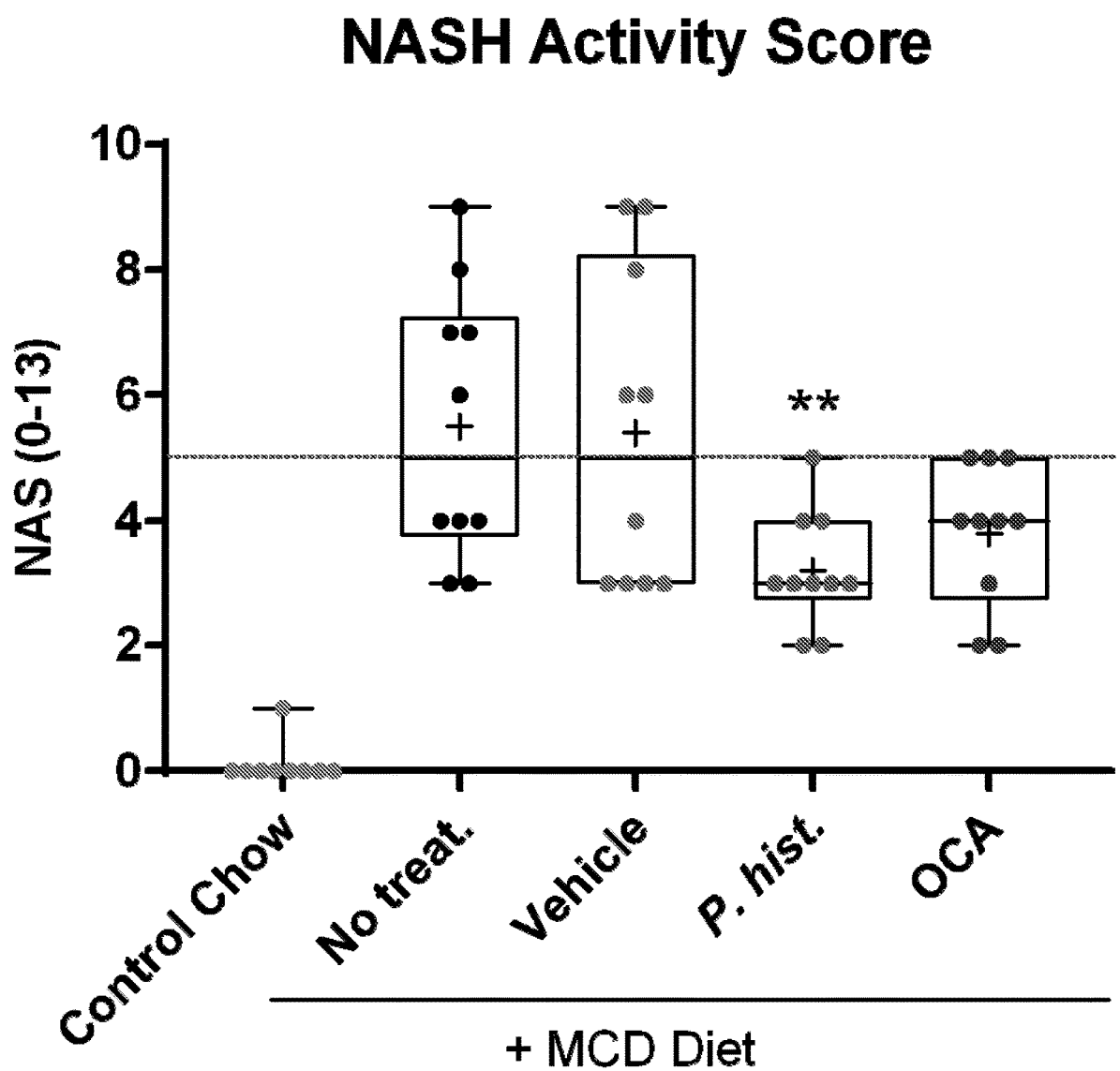
FIG. 10A shows that *P. histicola* is efficacious at reducing the NASH activity score (NAS) in mice receiving a methionine choline deficient (MCD) diet, which induces NASH symptoms.
Figure 10B:
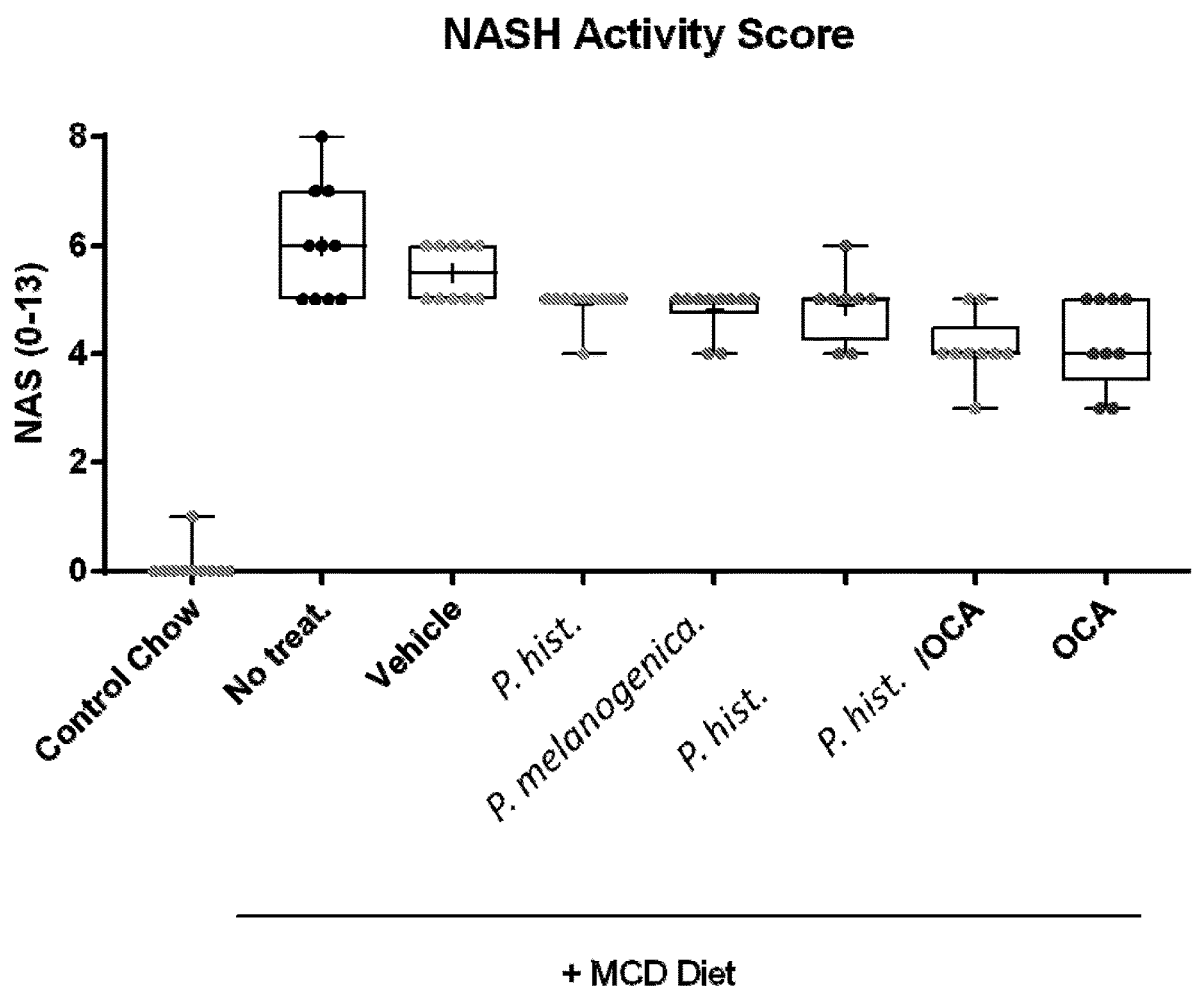
FIG. 10B shows that *Prevotella histicola, P. melanogenica, P. histicola* in combination with OCD at reducing the NASH activity score (NAS) in mice receiving a methionine choline deficient (MCD) diet, which induces NASH symptoms.

In mice receiving the MCD (NASH-inducing) diet, orally administered *P. histicola* and *P. melanogenica* was efficacious in reducing the NAS score compared to vehicle and no treatment groups (negative controls) (FIGS. 10A and 10B).

In other studies, hepatic gene expression analysis of inflammation, fibrosis, steatosis, ER stress, or oxidative stress markers may be performed by qRT-PCR using validated primers. These markers may include, but are not limited to, IL-1β, TNF-α, MCP-1, α-SMA, Col1la1, CHOP, and NRF2.

Treatment with EVs is initiated at some point, either at the beginning of the diet, or at some point following diet initiation (for example, one week after). For example, EVs may be administered starting in the same day as the initiation of the MCD diet. EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through intraperitoneal (i.p.) injection, subcutaneous (s.c.) injection, nasal route administration, oral gavage, or other means of administration. Some mice may receive EVs every day (e.g. starting on day 1), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the EV administration. As with the EVs, bacterial cell administration may be varied by route of administration, dose, and schedule. This can include oral gavage, i.v. injection, i.p. injection, or nasal route administration. Some groups of mice may be treated with additional NASH therapeutic(s) (e.g., FXR agonists, PPAR agonists, CCR2/5 antagonists or other treatment) and/or appropriate control at various timepoints and effective doses.

At various timepoints and/or at the end of the treatment, mice are sacrificed and liver, intestine, blood, feces, or other tissues may be removed for ex vivo histological, biochemical, molecular or cytokine and/or flow cytometry analysis using methods known in the art. For example, liver tissues are weighed and prepared for histological analysis, which may comprise staining with H&E, Sirius Red, and determination of NASH activity score (NAS). At various timepoints, blood is collected for plasma analysis of liver enzymes, for example, AST or ALT, using standards assays. In addition, the hepatic content of cholesterol, triglycerides, or fatty acid acids can be measured using established protocols. Hepatic gene expression analysis of inflammation, fibrosis, steatosis, ER stress, or oxidative stress markers may be performed by qRT-PCR using validated primers. These markers may include, but are not limited to, IL-6, MCP-1, alpha-SMA, Col1a1, CHOP, and NRF2. Metabolite measurements may be performed in plasma, tissue and fecal samples using established biochemical and mass-spectrometry-based metabolomics methods. Serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+bile duct-infiltrated immune cells obtained ex vivo. Finally, immunohistochemistry is carried out on liver or intestine sections to measure neutrophils, T cells, macrophages, dendritic cells, or other immune cell infiltrates.

In order to examine the impact and longevity of disease protection, rather than being sacrificed, some mice may be analyzed for recovery.

Example 23: EVs in a Mouse Model of Psoriasis

Psoriasis is a T-cell-mediated chronic inflammatory skin disease. So-called "plaque-type" psoriasis is the most common form of psoriasis and is typified by dry scales, red plaques, and thickening of the skin due to infiltration of immune cells into the dermis and epidermis. Several animal models have contributed to the understanding of this disease, as reviewed by Gudjonsson et al. (Mouse models of psoriasis. J Invest Derm. 2007. 127: 1292-1308; see also van der Fits et al. Imiquimod-induced psoriasis-like skin inflammation in mice is mediated via the IL-23/IL-17 axis. J. Immunol. 2009 May 1. 182(9): 5836-45).

Psoriasis can be induced in a variety of mouse models, including those that use transgenic, knockout, or xenograft models, as well as topical application of imiquimod (IMQ), a TLR7/8 ligand.

EVs are tested for their efficacy in the mouse model of psoriasis, either alone or in combination with whole bacterial cells, with or without the addition of other anti-inflammatory treatments. For example, 6-8 week old C57Bl/6 or Balb/c mice are obtained from Taconic (Germantown, NY), or other vendor. Mice are shaved on the back and the right ear. Groups of mice receive a daily topical dose of 62.5 mg of commercially available IMQ cream (5%) (Aldara; 3M Pharmaceuticals). The dose is applied to the shaved areas for 5 or 6 consecutive days. At regular intervals, mice are scored for erythema, scaling, and thickening on a scale from 0 to 4, as described by van der Fits et al. (2009). Mice are monitored for ear thickness using a Mitutoyo micrometer.

Treatment with EVs is initiated at some point, either around the time of the first application of IMQ, or something thereafter. For example, EVs may be administered at the same time as the subcutaneous injections (day 0), or they may be administered prior to, or upon, application. EVs are administered at varied doses and at defined intervals. For example, some mice are intravenously injected with EVs at 15, 20, or 15 ug/mouse. Other mice may receive 25, 50, or 100 mg of EVs per mouse. While some mice receive EVs through i.v. injection, other mice may receive EVs through intraperitoneal (i.p.) injection, nasal route administration, oral gavage, topical administration, intradermal (i.d.) injection, subcutaneous (s.c.) injection, or other means of administration. Some mice may receive EVs every day (e.g. starting on day 0), while others may receive EVs at alternative intervals (e.g. every other day, or once every three days). Additional groups of mice may receive some ratio of bacterial cells to EVs. The bacterial cells may be live, dead, or weakened. The bacterial cells may be harvested fresh (or frozen) and administered, or they may be irradiated or heat-killed prior to administration.

For example, some groups of mice may receive between $1\times10^4$ and $5\times10^9$ bacterial cells in an administration separate from, or comingled with, the EV administration. As with the EVs, bacterial cell administration may be varied by route of administration, dose, and schedule. This can include oral gavage, i.v. injection, i.p. injection, i.d. injection, s.c. injection, topical administration, or nasal route administration.

Some groups of mice may be treated with anti-inflammatory agent(s) (e.g. anti-CD154, blockade of members of the TNF family, or other treatment), and/or an appropriate control (e.g. vehicle or control antibody) at various timepoints and at effective doses.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some immunized mice are treated without receiving antibiotics.

At various timepoints, samples from back and ear skin are taken for cryosection staining analysis using methods known in the art. Other groups of mice are sacrificed and lymph nodes, spleen, mesenteric lymph nodes (MLN), the small intestine, colon, and other tissues may be removed for histology studies, ex vivo histological, cytokine and/or flow cytometric analysis using methods known in the art. Some tissues may be dissociated using dissociation enzymes according to the manufacturer's instructions. Cryosection samples, tissue samples, or cells obtained ex vivo are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSFIR, PD-L1, Gr-1, F4/80). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out on immune cells obtained from lymph nodes or other tissue, and/or on purified CD45+ skin-infiltrated immune cells obtained ex vivo. Finally, immunohistochemistry is carried out on various tissue sections to measure T cells, macrophages, dendritic cells, and checkpoint molecule protein expression.

In order to examine the impact and longevity of psoriasis protection, rather than being sacrificed, some mice may be studied to assess recovery, or they may be rechallenged with IMQ. The groups of rechallenged mice are analyzed for susceptibility to psoriasis and severity of response.

Example 24: Manufacturing Conditions

Enriched media is used to grow and prepare the bacterium for in vitro and in vivo use. For example, media may contain sugar, yeast extracts, plant based peptones, buffers, salts, trace elements, surfactants, anti-foaming agents, and vitamins. Composition of complex components such as yeast extracts and peptones may be undefined or partially defined (including approximate concentrations of amino acids, sugars etc.). Microbial metabolism may be dependent on the availability of resources such as carbon and nitrogen. Various sugars or other carbon sources may be tested. Alternatively, media may be prepared and the selected bacterium grown as shown by Saarela et al., *J. Applied Microbiology*. 2005. 99: 1330-1339, which is hereby incorporated by reference. Influence of fermentation time, cryoprotectant and neutralization of cell concentrate on freeze-drying survival, storage stability, and acid and bile exposure of the selected bacterium produced without milk-based ingredients.

At large scale, the media is sterilized. Sterilization may be by Ultra High Temperature (UHT) processing. The UHT processing is performed at very high temperature for short periods of time. The UHT range may be from 135-180° C. For example, the medium may be sterilized from between 10 to 30 seconds at 135° C.

Inoculum can be prepared in flasks or in smaller bioreactors and growth is monitored. For example, the inoculum size may be between approximately 0.5 and 3% of the total bioreactor volume. Depending on the application and need for material, bioreactor volume can be at least 2L, 10L, 80L, 100L, 250L, 1000L, 2500L, 5000L, 10,000L.

Before the inoculation, the bioreactor is prepared with medium at desired pH, temperature, and oxygen concentration. The initial pH of the culture medium may be different that the process set-point. pH stress may be detrimental at low cell centration; the initial pH could be between pH 7.5 and the process set-point. For example, pH may be set between 4.5 and 8.0. During the fermentation, the pH can be controlled through the use of sodium hydroxide, potassium hydroxide, or ammonium hydroxide. The temperature may be controlled from 25° C. to 45° C., for example at 37° C. Anaerobic conditions are created by reducing the level of oxygen in the culture broth from around 8 mg/L to 0mg/L. For example, nitrogen or gas mixtures (N2, CO2, and H2) may be used in order to establish anaerobic conditions. Alternatively, no gases are used and anaerobic conditions are established by cells consuming remaining oxygen from the medium. Depending on strain and inoculum size, the bioreactor fermentation time can vary. For example, fermentation time can vary from approximately 5 hours to 48 hours.

Reviving microbes from a frozen state may require special considerations. Production medium may stress cells after a thaw; a specific thaw medium may be required to consistently start a seed train from thawed material. The kinetics of transfer or passage of seed material to fresh medium, for the purposes of increasing the seed volume or maintaining the microbial growth state, may be influenced by the current state of the microbes (ex. exponential growth, stationary growth, unstressed, stressed).

Inoculation of the production fermenter(s) can impact growth kinetics and cellular activity. The initial state of the bioreactor system must be optimized to facilitate successful and consistent production. The fraction of seed culture to total medium (e.g. a percentage) has a dramatic impact on growth kinetics. The range may be 1-5% of the fermenter's working volume. The initial pH of the culture medium may be different from the process set-point. pH stress may be detrimental at low cell concentration; the initial pH may be between pH 7.5 and the process set-point. Agitation and gas flow into the system during inoculation may be different from the process set-points. Physical and chemical stresses due to both conditions may be detrimental at low cell concentration.

Process conditions and control settings may influence the kinetics of microbial growth and cellular activity. Shifts in process conditions may change membrane composition, production of metabolites, growth rate, cellular stress, etc. Optimal temperature range for growth may vary with strain. The range may be 20-40° C. Optimal pH for cell growth and performance of downstream activity may vary with strain. The range may be pH 5-8. Gasses dissolved in the medium may be used by cells for metabolism. Adjusting concentrations of $O_2$, $CO_2$, and $N_2$ throughout the process may be required. Availability of nutrients may shift cellular growth. Microbes may have alternate kinetics when excess nutrients are available.

The state of microbes at the end of a fermentation and during harvesting may impact cell survival and activity. Microbes may be preconditioned shortly before harvest to better prepare them for the physical and chemical stresses involved in separation and downstream processing. A change in temperature (often reducing to 20-5° C.) may reduce cellular metabolism, slowing growth (and/or death) and physiological change when removed from the fermenter. Effectiveness of centrifugal concentration may be influenced by culture pH. Raising pH by 1-2 points can improve effectiveness of concentration but can also be detrimental to cells. Microbes may be stressed shortly before harvest by increasing the concentration of salts and/or sugars in the medium. Cells stressed in this way may better survive freezing and lyophilization during downstream.

Separation methods and technology may impact how efficiently microbes are separated from the culture medium. Solids may be removed using centrifugation techniques. Effectiveness of centrifugal concentration can be influenced by culture pH or by the use of flocculating agents. Raising pH by 1-2 points may improve effectiveness of concentration but can also be detrimental to cells. Microbes may be stressed shortly before harvest by increasing the concentration of salts and/or sugars in the medium. Cells stressed in this way may better survive freezing and lyophilization during downstream. Additionally, Microbes may also be separated via filtration. Filtration is superior to centrifugation techniques for purification if the cells require excessive g-minutes to successfully centrifuge. Excipients can be added before after separation. Excipients can be added for cryo protection or for protection during lyophilization. Excipients can include, but are not limited to, sucrose, trehalose, or lactose, and these may be alternatively mixed with buffer and anti-oxidants. Prior to lyophilization, droplets of cell pellets mixed with excipients are submerged in liquid nitrogen.

Harvesting can be performed by continuous centrifugation. Product may be resuspended with various excipients to a desired final concentration. Excipients can be added for cryo protection or for protection during lyophilization. Excipients can include, but are not limited to, sucrose, trehalose, or lactose, and these may be alternatively mixed with buffer and anti-oxidants. Prior to lyophilization, droplets of cell pellets mixed with excipients are submerged in liquid nitrogen.

Lyophilization of material, including live bacteria, begins with primary drying. During the primary drying phase, the ice is removed. Here, a vacuum is generated and an appropriate amount of heat is supplied to the material for the ice to sublime. During the secondary drying phase, product bound water molecules are removed. Here, the temperature is raised higher than in the primary drying phase to break any physico-chemical interactions that have formed between the water molecules and the product material. The pressure may also be lowered further to enhance desorption during this stage. After the freeze-drying process is complete, the chamber may be filled with an inert gas, such as nitrogen. The product may be sealed within the freeze dryer under dry conditions, preventing exposure to atmospheric water and contaminants.

Example 25: A Mouse Melanoma Model

Female 6-8 week old C57Bl/6 mice are obtained from Taconic (Germantown, NY). 100,000 B16-F10 (ATCC CRL-6475) tumor cells are resuspended in sterile PBS containing 50% Matrigel and inoculated in a 100 μl final volume into one hind flank (the first flank) of each mouse. Treatment with *Veillonella* Strains is initiated at some point following tumor cell inoculation at varied doses and at defined intervals. For example, some mice receive between $1$-$5 \times 10^9$ CFU (100 μl final volume) per dose. Possible routes of administration include oral gavage (p.o.), intravenous injection, intratumoral injection (IT) or peritumoral or subtumoral or subcutaneous injection. In order to assess the systemic anti-tumoral effects of *Veillonella* treatment, additional mice may be inoculated with tumor cells in the contralateral (untreated, second) flank prior to IT, peritumoral, or subtumoral treatment with *Veillonella* in the first flank.

Some mice may receive *Veillonella* (p.o.) on day 1 (the day following tumor cell injection). Other mice may receive seven (7) consecutive doses of a bacterial strain (one dose per day on days 14-21). Other mice receive daily dosing or, alternatively, some mice receive dosing every other day. Alternatively, mice are randomized into various treatment groups at a defined timepoint (e.g. on day 13) or when the tumors reach a certain size (e.g. 100 mm3) and treatment is then initiated accordingly. For example, when tumor volumes reach an average of 100 $mm^3$ (approximately 10-12 days following tumor cell inoculation), animals are distributed into groups and treated with either vehicle or a bacterial strain (p.o. or IT). Some additional groups of mice may be treated with an additional cancer therapeutic or appropriate control antibody. One example of a cancer therapeutic that may be administered is an inhibitor of an immune checkpoint, for example anti-PD-1, anti-PD-L1, or other treatment that blocks the binding of an immune checkpoint to its ligand(s). Checkpoint inhibitors anti-PD-1 and anti-PD-L1 may be formulated in PBS and administered intraperitoneally (i.p.) in effective doses. For example, mice are given 100 ug of anti-PD-1 (i.p.) every four days starting on day 1, and continuing for the duration of the study.

In addition, some mice are treated with antibiotics prior to treatment. For example, vancomycin (0.5 g/L), ampicillin (1.0 g/L), gentamicin (1.0 g/L) and amphotericin B (0.2 g/L) are added to the drinking water, and antibiotic treatment is halted at the time of treatment or a few days prior to treatment. Some mice are inoculated with tumor cells without receiving prior treatment with antibiotics.

At various timepoints, mice are sacrificed and tumors, lymph nodes, or other tissues may be removed for ex vivo flow cytometric analysis using methods known in the art. For example, tumors are dissociated using a Miltenyi tumor dissociation enzyme cocktail according to the manufacturer's instructions. Tumor weights are recorded and tumors are chopped then placed in 15 ml tubes containing the enzyme cocktail and placed on ice. Samples are then placed on a gentle shaker at 37° C. for 45 minutes and quenched with up to 15 ml complete RPMI. Each cell suspension is strained through a 70 μm filter into a 50 ml falcon tube and centrifuged at 1000 rpm for 10 minutes. Cells are resuspended in FACS buffer and washed to remove remaining debris. If necessary, samples are strained again through a second 70 μm filter into a new tube. Cells are stained for analysis by flow cytometry using techniques known in the art. Staining antibodies can include anti-CD11c (dendritic cells), anti-CD80, anti-CD86, anti-CD40, anti-MHCII, anti-CD8a, anti-CD4, and anti-CD103. Other markers that may be analyzed include pan-immune cell marker CD45, T cell markers (CD3, CD4, CD8, CD25, Foxp3, T-bet, Gata3, Roryt, Granzyme B, CD69, PD-1, CTLA-4), and macrophage/myeloid markers (CD11b, MHCII, CD206, CD40, CSF1R, PD-L1, Gr-1). In addition to immunophenotyping, serum cytokines are analyzed including, but not limited to, TNFa, IL-17, IL-13, IL-12p70, IL12p40, IL-10, IL-6, IL-5, IL-4, IL-2, IL-1b, IFNy, GM-CSF, G-CSF, M-CSF, MIG, IP10, MIP1b, RANTES, and MCP-1. Cytokine analysis may be carried out immune cells obtained from lymph nodes or other tissue, and/or on purified CD45+ tumor-infiltrated immune cells obtained ex vivo. Finally, immunohistochemistry is carried out on tumor sections to measure T cells, macrophages, dendritic cells, and checkpoint molecule protein expression.

Rather than being sacrificed, some mice may be rechallenged with tumor cell injection into the contralateral flank (or other area) to determine the impact of the immune system's memory response on tumor growth.

Figure 16:
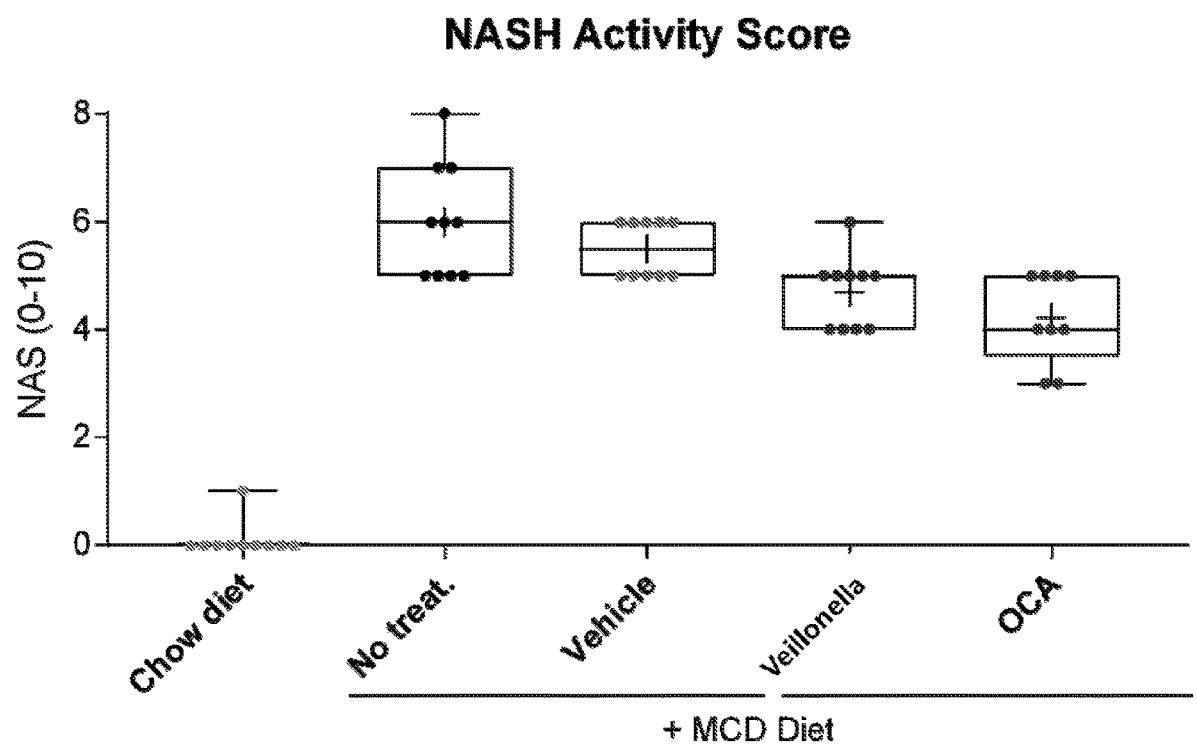
FIG. 16 shows that *Veillonella parvula* was efficacious at reducing the NASH activity score (NAS) in mice receiving a methionine choline deficient (MCD) diet, which induces NASH symptoms.
Figure 17:
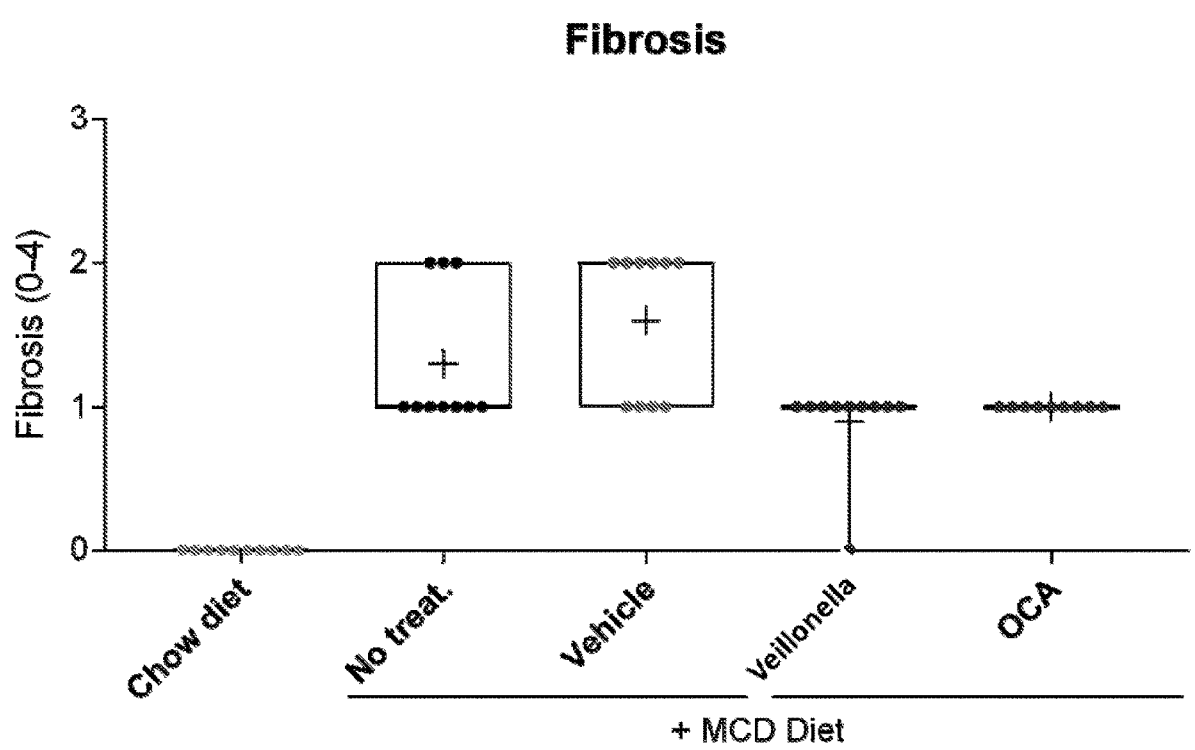
FIG. 17 shows that *Veillonella parvula* reduced Fibrosis in mice that were fed an MCD diet.
Figure 18:
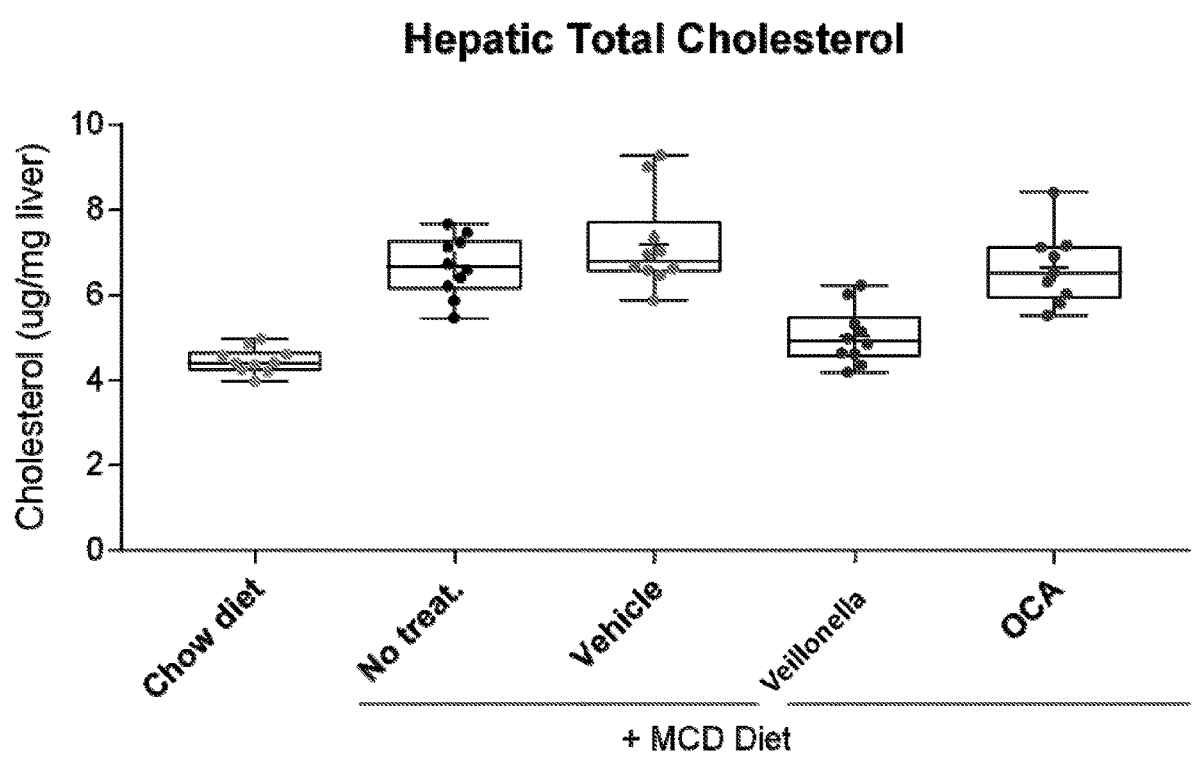
FIG. 18 shows that *Veillonella parvula* reduced Hepatic Total Cholesterol in mice that were fed an MCD diet.
Figure 19:
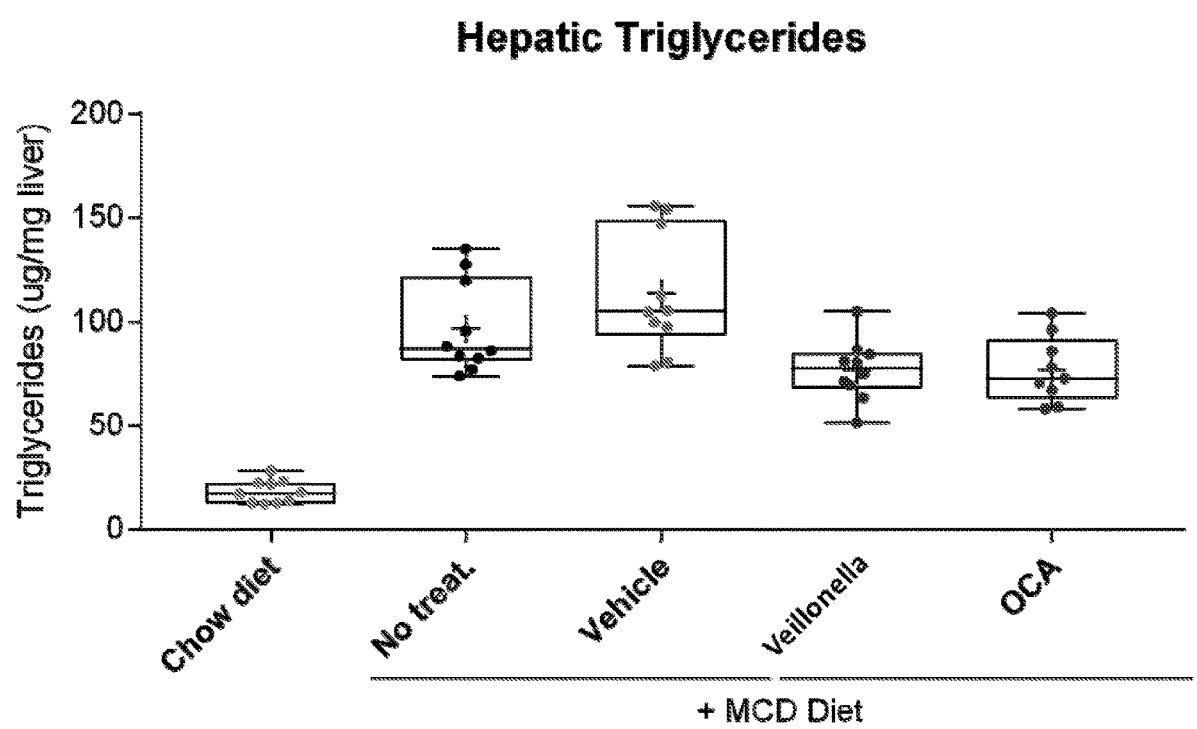
FIG. 19 shows that *Veillonella parvula* reduced Hepatic Triglycerides in mice that were fed an MCD diet

In mice receiving the MCD (NASH-inducing) diet, orally administered *Veillonella* was efficacious in reducing the NAS score compared to vehicle and no treatment groups (negative controls) (FIG. 16). *Veillonella* reduced the fibrosis score in treated mice (FIG. 17). *Veillonella* reduced hepatic total cholesterol (FIG. 18) and hepatic Triglycerides (FIG. 19).

Example 26: A Colorectal Carcinoma Model

Figure 12:
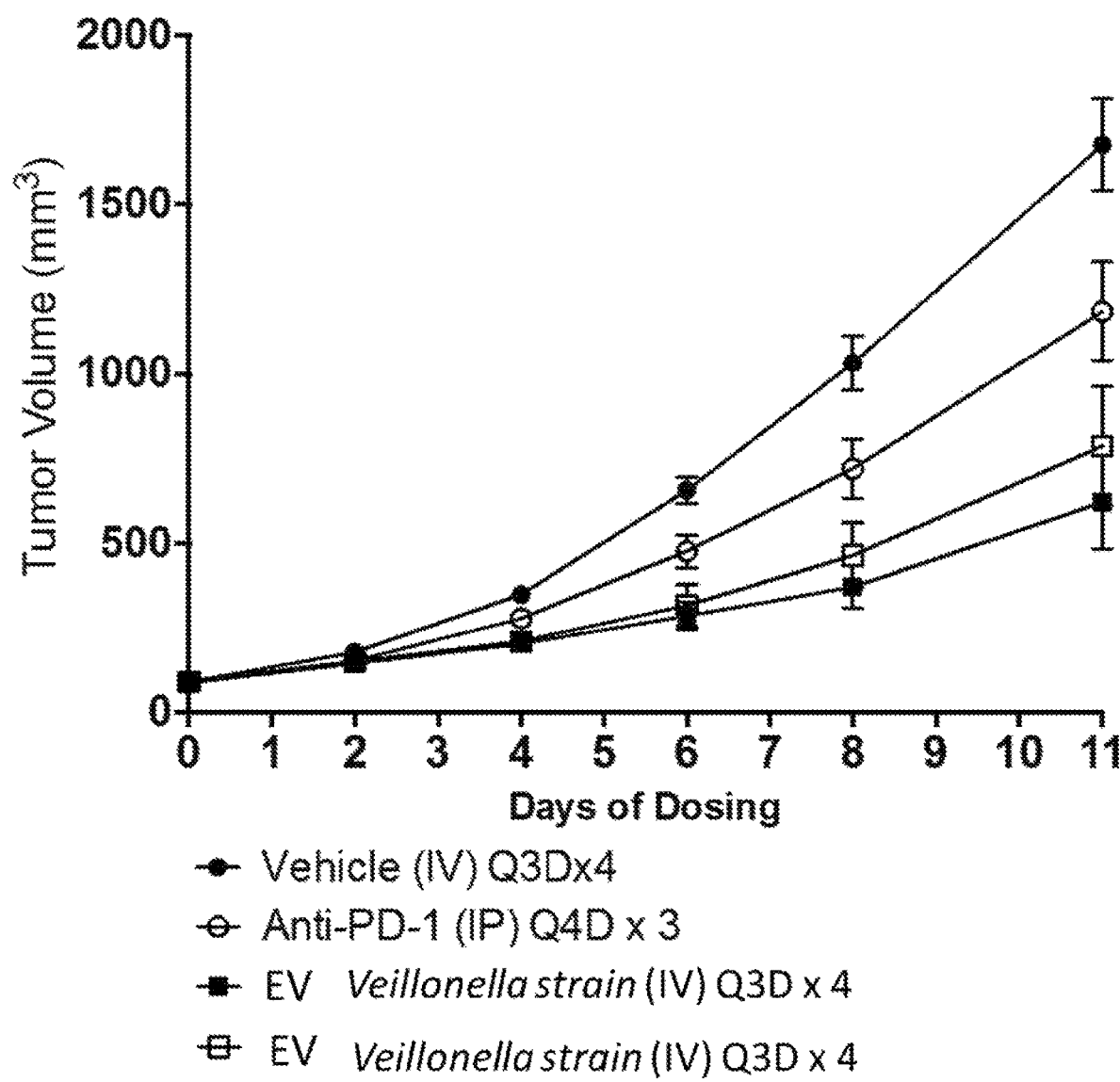
FIG. 12 shows the efficacy of EVs from two *Veillonella tobetsuensis* and *Veillonella parvula* strains compared to intraperitoneal injected (i.p.) anti-PD-1 or vehicle in a mouse colorectal carcinoma model.
Figure 13:
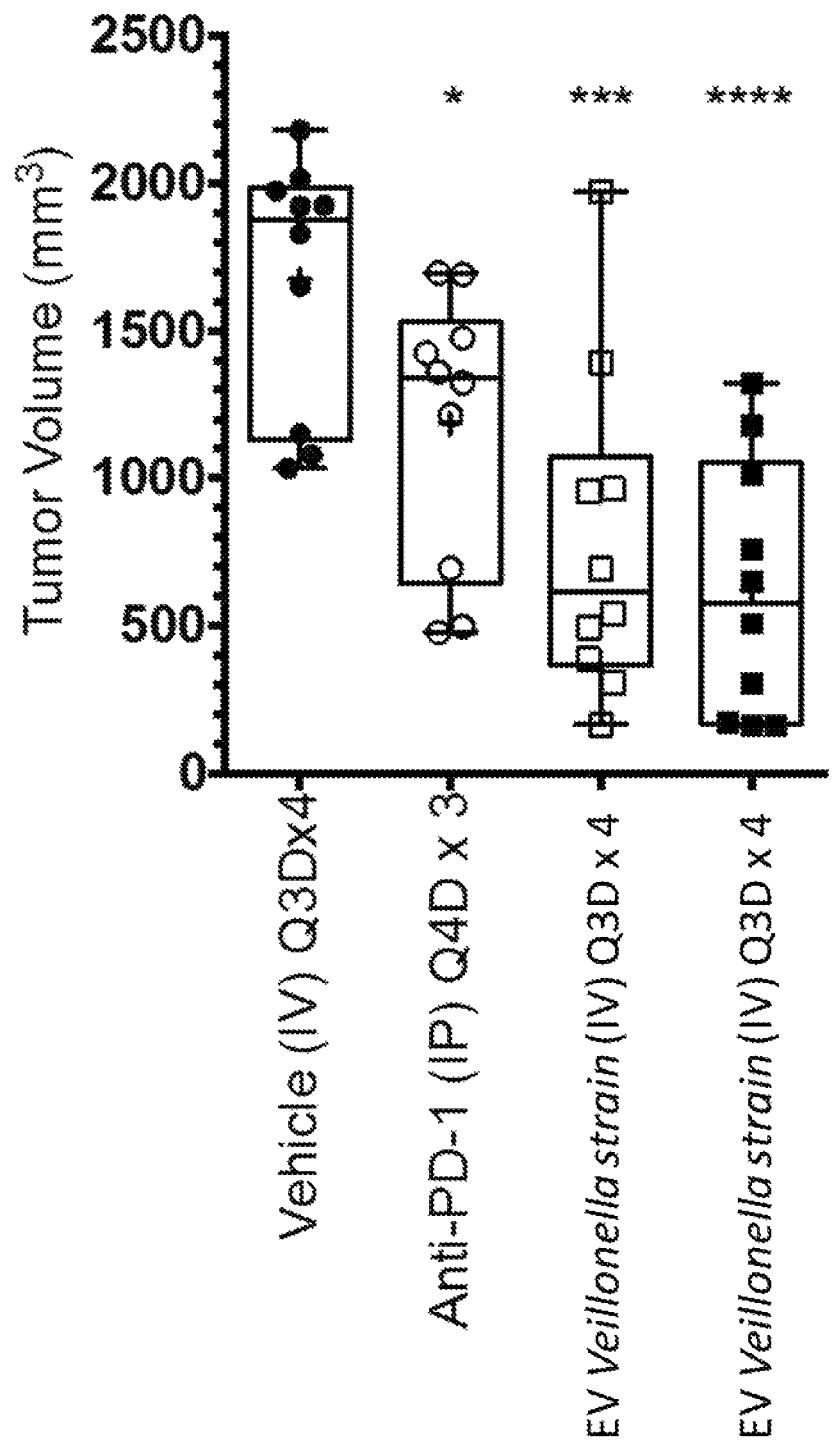
FIG. 13 shows the efficacy of EVs from *Veillonella tobetsuensis* and *Veillonella parvula* Strains compared to intraperitoneal injected (i.p.) anti-PD-1 or vehicle in a mouse colorectal carcinoma model at day 11.

Female 6-8 week old Balb/c mice were obtained from Taconic (Germantown, NY). 100,000 CT-26 colorectal tumor cells (ATCC CRL-2638) were resuspended in sterile PBS and inoculated in the presence of 50% Matrigel. CT-26 tumor cells were subcutaneously injected into one hind flank of each mouse. When tumor volumes reached an average of 100 mm$^3$ (approximately 10-12 days following tumor cell inoculation), animals were distributed into the following groups: 1) Vehicle; 2) *Veillonella* Strains 3) anti-PD-1 antibody. Antibodies were administered intraperitoneally (i.p.) at 200 µg/mouse (100 µl final volume) every four days, starting on day 1, for a total of 3 times (Q4D×3) and *Veillonella* EVs (5 µg) were intravenously (i.v.) injected every third day, starting on day 1 for a total of 4 times (Q3D×4). Both *Veillonella* groups showed tumor growth inhibition greater than that seen in the anti-PD-1 group (FIGS. 12 and 13).

Figure 20:
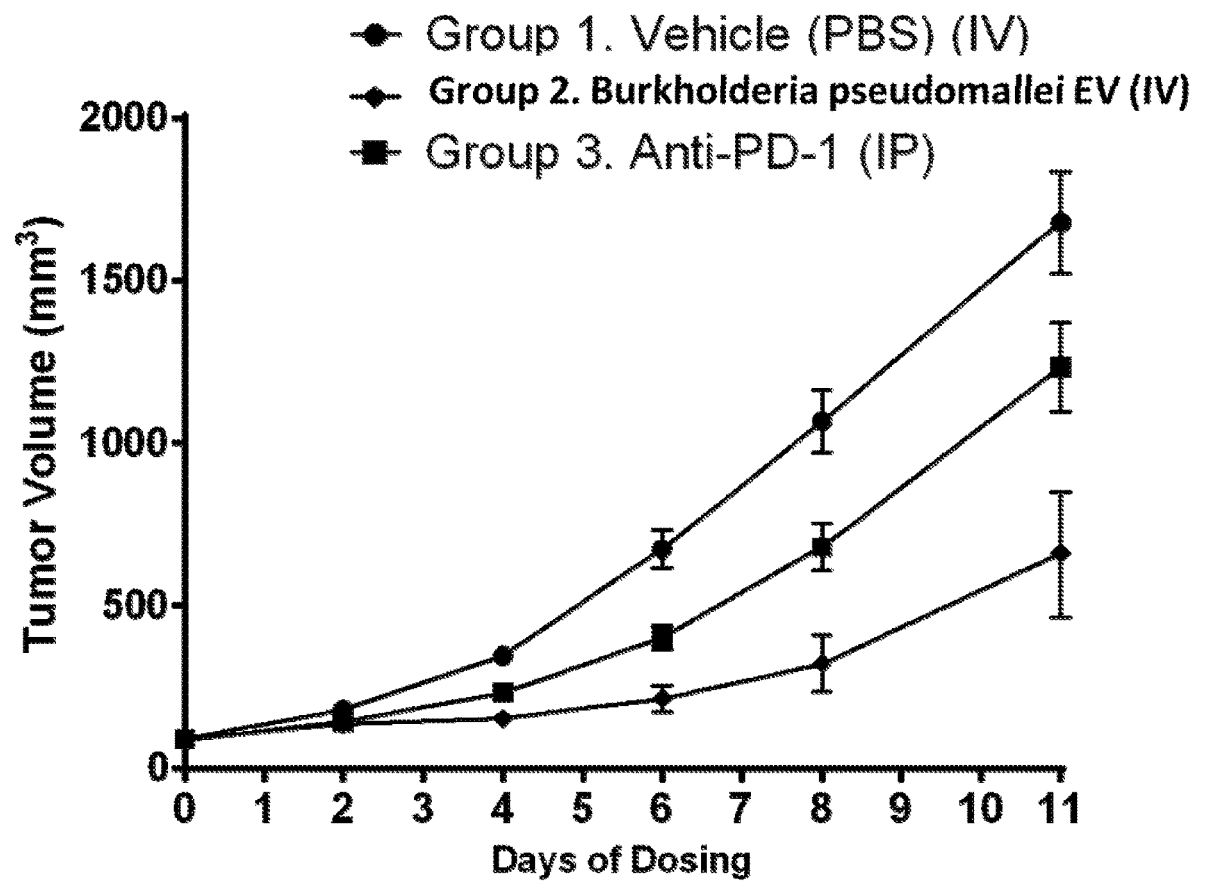
Figure 21:
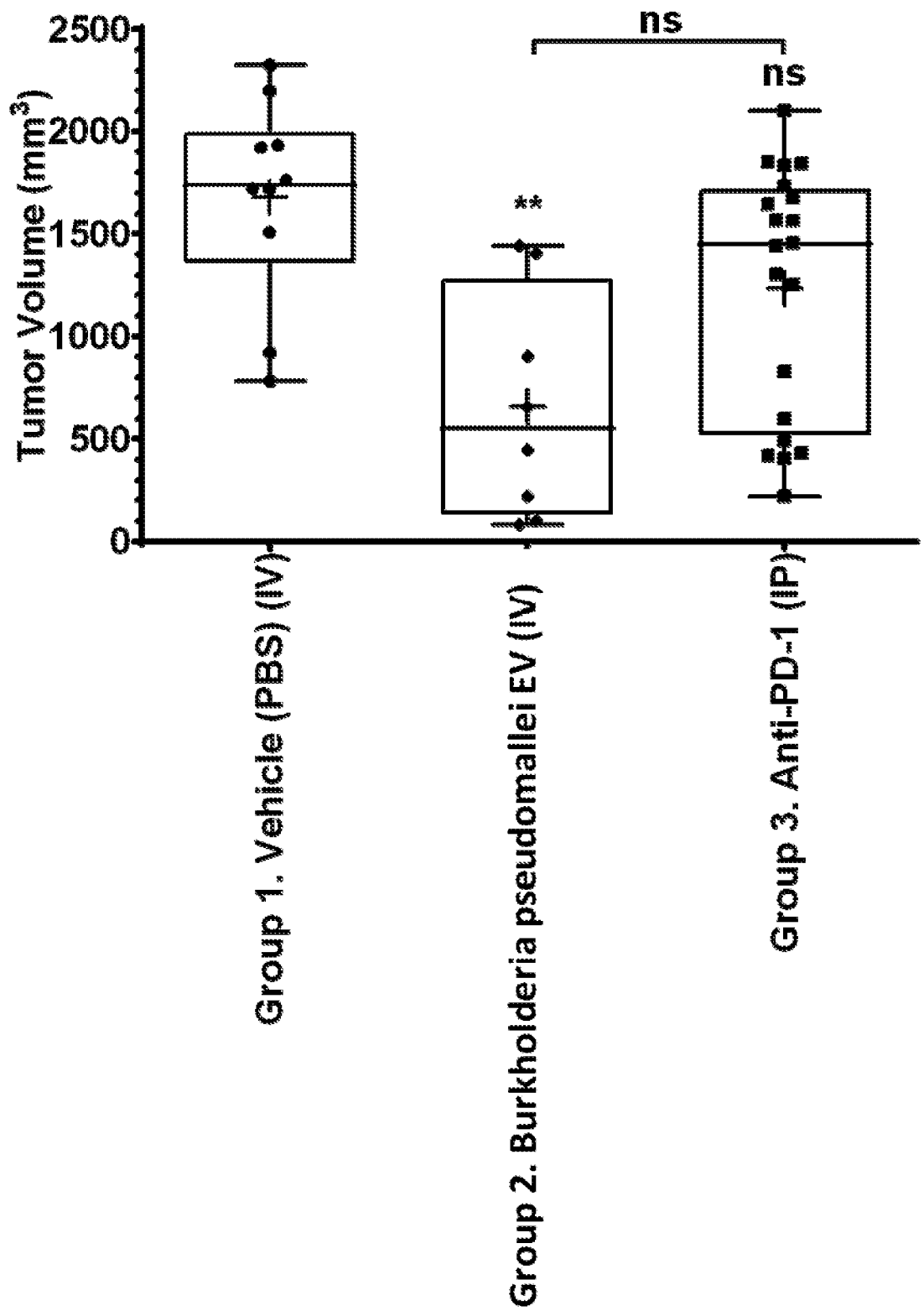
FIG. 21 shows the efficacy of *Burkholderia pseudomallei* EVs compared to intravenously (i.v.) administered anti-PD-1 or vehicle in a mouse colorectal carcinoma model at day 11. ** The difference in tumor volume in the *Burkholderia pseudomallei* EV treated group compared to vehicle control group on day 11 was highly significant, with a P-value of 0.0011 as determined by T-test (two-tailed, unpaired, welch-corrected) calculated in GraphPad.

Another example, when tumor volumes reached an average of 100 mm$^3$ (approximately 10-12 days following tumor cell inoculation), animals were distributed into the following groups: 1) Vehicle; 2) *Burkholderia pseudomallei*; and 3) anti-PD-1 antibody. Antibodies were administered intraperitoneally (i.p.) at 200 µg/mouse (100 µl final volume) every four days, starting on day 1, and *Burkholderia pseudomallei* EVs (5 µg) were intravenously (i.v.) injected daily, starting on day 1 until the conclusion of the study. The *Burkholderia pseudomallei* group showed tumor growth inhibition greater than that seen in the anti-PD-1 group (FIGS. 20, and 21).

Figure 22:
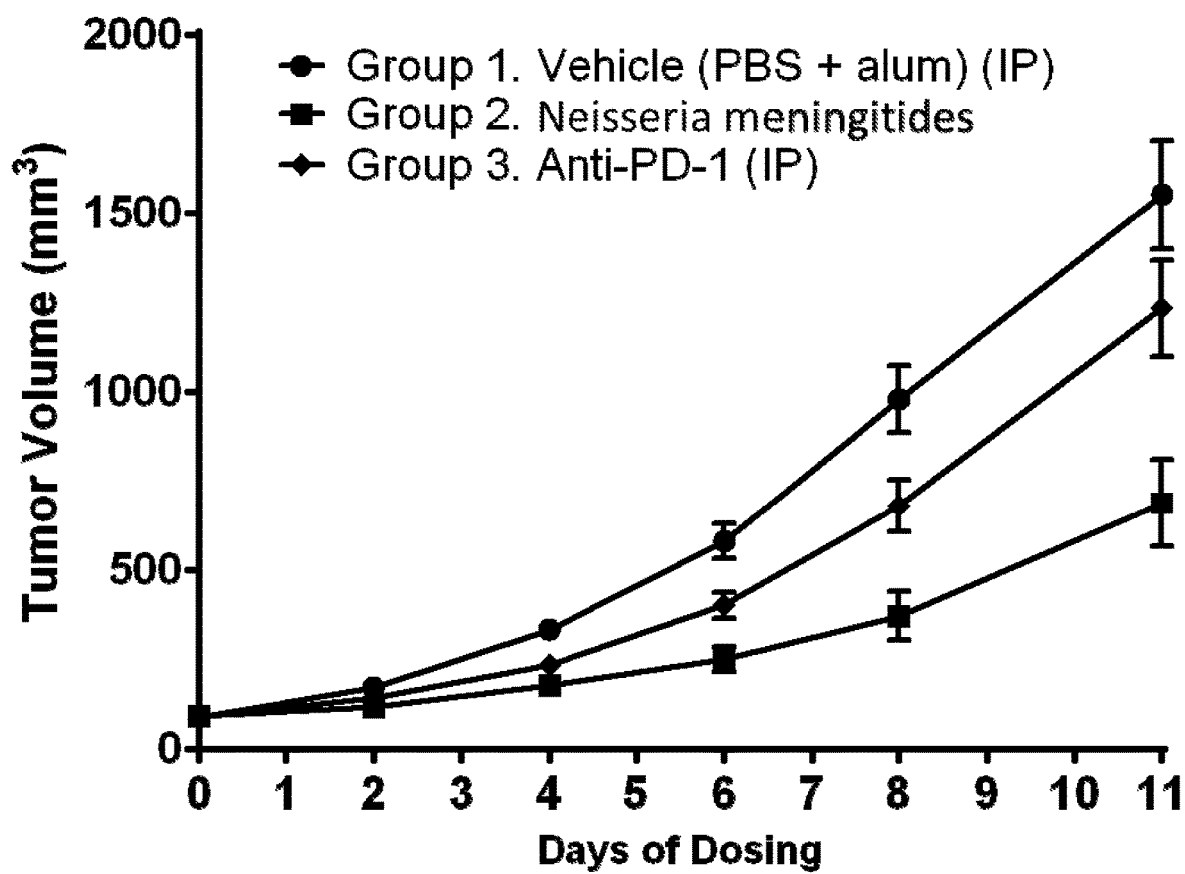
FIG. 22 shows the efficacy of *Neisseria Meningitidis* EVs compared to that of intraperitoneally (i.p.) administered anti-PD-1 or vehicle in a mouse colorectal carcinoma model.
Figure 23:
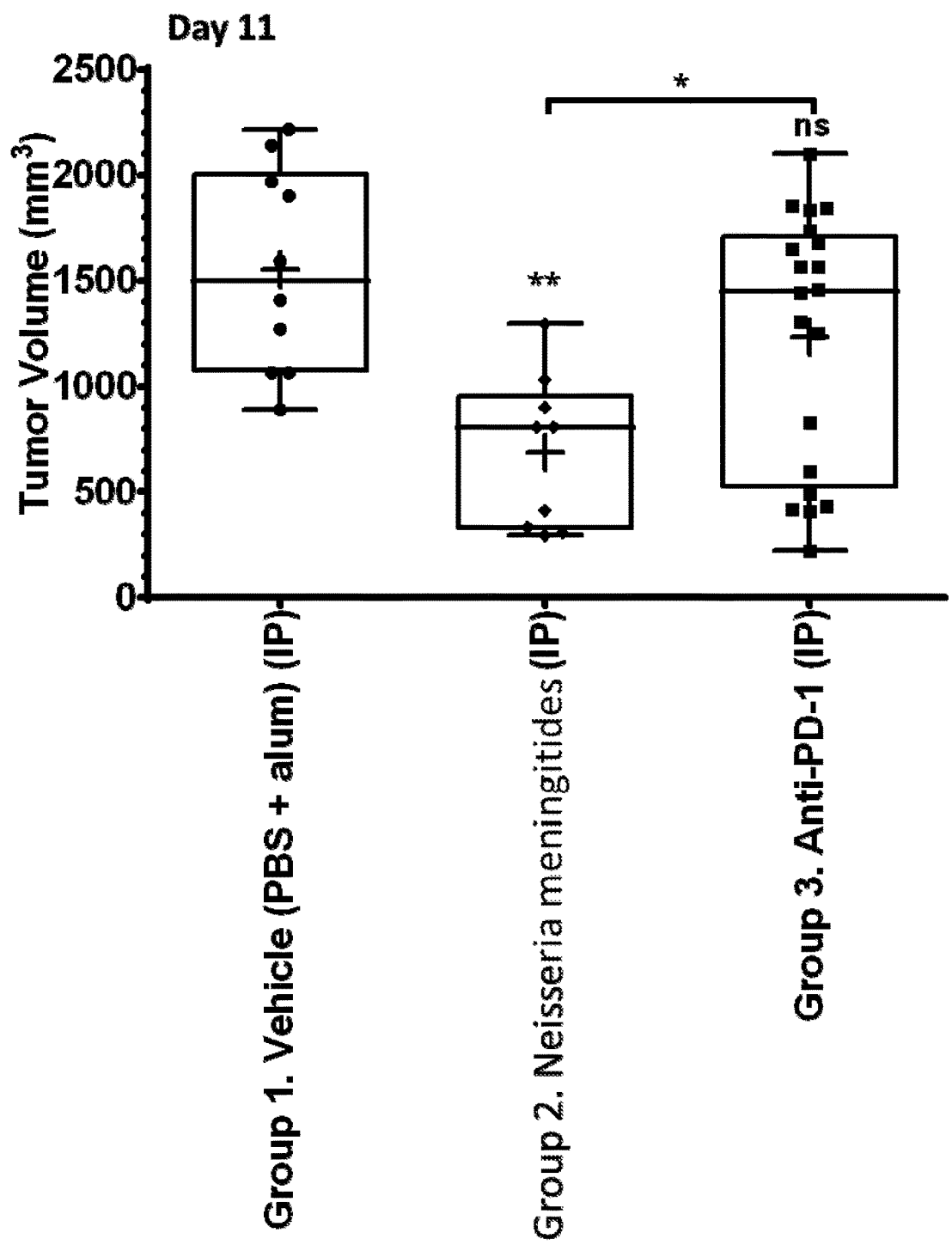
FIG. 23 shows the efficacy of *Neisseria Meningitidis* EVs compared to that of intraperitoneally (i.p.) administered anti-PD-1 or vehicle in a mouse colorectal carcinoma model at day 11.

Another example, when tumor volumes reached an average of 100 mm$^3$ (approximately 10-12 days following tumor cell inoculation), animals were distributed into the following groups: 1) Vehicle; 2) *Neisseria Meningitidis* EVs isolated from the Bexsero® vaccine; and 3) anti-PD-1 antibody. Antibodies were administered intraperitoneally (i.p.) at 200 ug/mouse (100 µl final volume) every four days, starting on day 1, and *Neisseria Meningitidis* bacteria (about 1.1×10$^2$) were administered intraperitoneally (i.p.) daily, starting on day 1 until the conclusion of the study. The *Neisseria Meningitidis* group showed tumor growth inhibition greater than that seen in the anti-PD-1 group (FIGS. 22, and 23).

TABLE 4

Significance test comparing tumor volume in treatment groups vs. control groups on day 11. T-test (two-tailed, unpaired, welch-corrected) calculated in GraphPad.

| Comparison | P value | Summary |
| --- | --- | --- |
| IP Vehicle vs. *Neisseria Meningitidis* EVs. | 0.0004 | *** |

Example 27: Efficacy of EVs Varies Based on Source Microbe, Dose, and Route of Administration Female 6-8 week old Balb/c mice were obtained from Taconic (Germantown, NY). 100,000 CT-26 colorectal tumor cells (ATCC CRL-2638) were resuspended in sterile PBS and inoculated in the presence of 50% MATRIGEL®. CT-26 tumor cells were subcutaneously injected into one hind flank of each mouse. When tumor volumes reached an average of 100 mm$^3$ (approximately 10-12 days following tumor cell inoculation), animals were distributed into the following groups as highlighted in Table 5.

TABLE 5

Treatment Groups

| Group | Treatment | Dose/Route/Schedule |
| --- | --- | --- |
| 1 | IV Vehicle (PBS) | N/A/IV/Q3Dx4 |
| 2 | PO Vehicle (sucrose) | N/A/PO/QD |
| 3 | Anti-PD-1 | 200 µg/IP/Q4Dx3 |
| 4 | *Veillonella parvula* EV | 10 µg/IV/Q3Dx4 |
| 5 | *Veillonella parvula* EV | 5 µg/IV/Q3Dx4 |
| 6 | *Veillonella parvula* EV | 2 µg/IV/Q3Dx4 |
| 7 | *Veillonella tobetsuensis* EV | 75 µg/PO. QD |
| 8 | *Veillonella tobetsuensis* EV | 5 µg/IV/Q3Dx4 |

Figure 14:
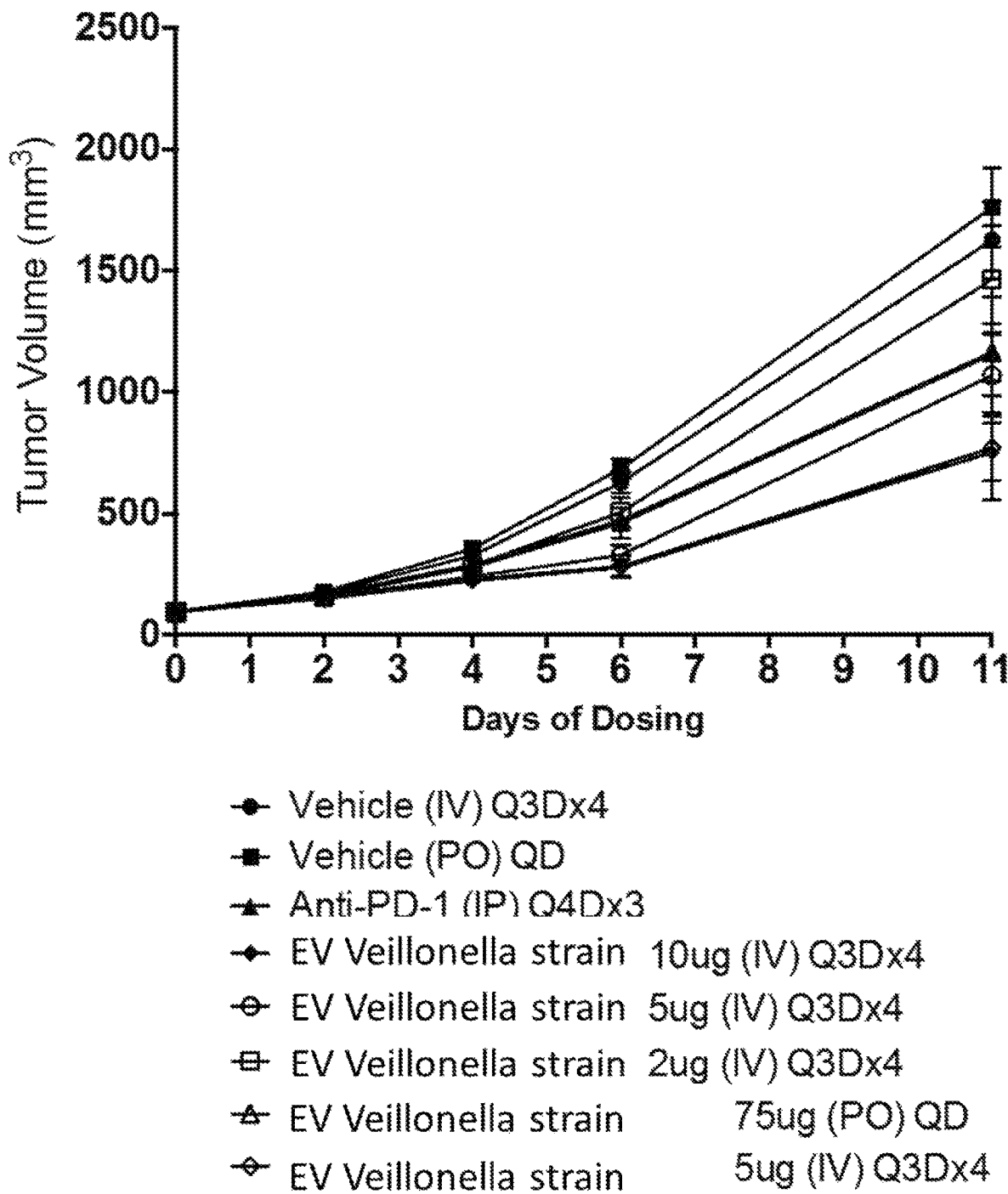
FIG. 14 shows the dose and route of administration dependent efficacy of EVs from *Veillonella tobetsuensis* and *Veillonella parvula* strains compared to intraperitoneal injected (i.p.) anti-PD-1 or vehicle in a mouse colorectal carcinoma model.
Figure 15:
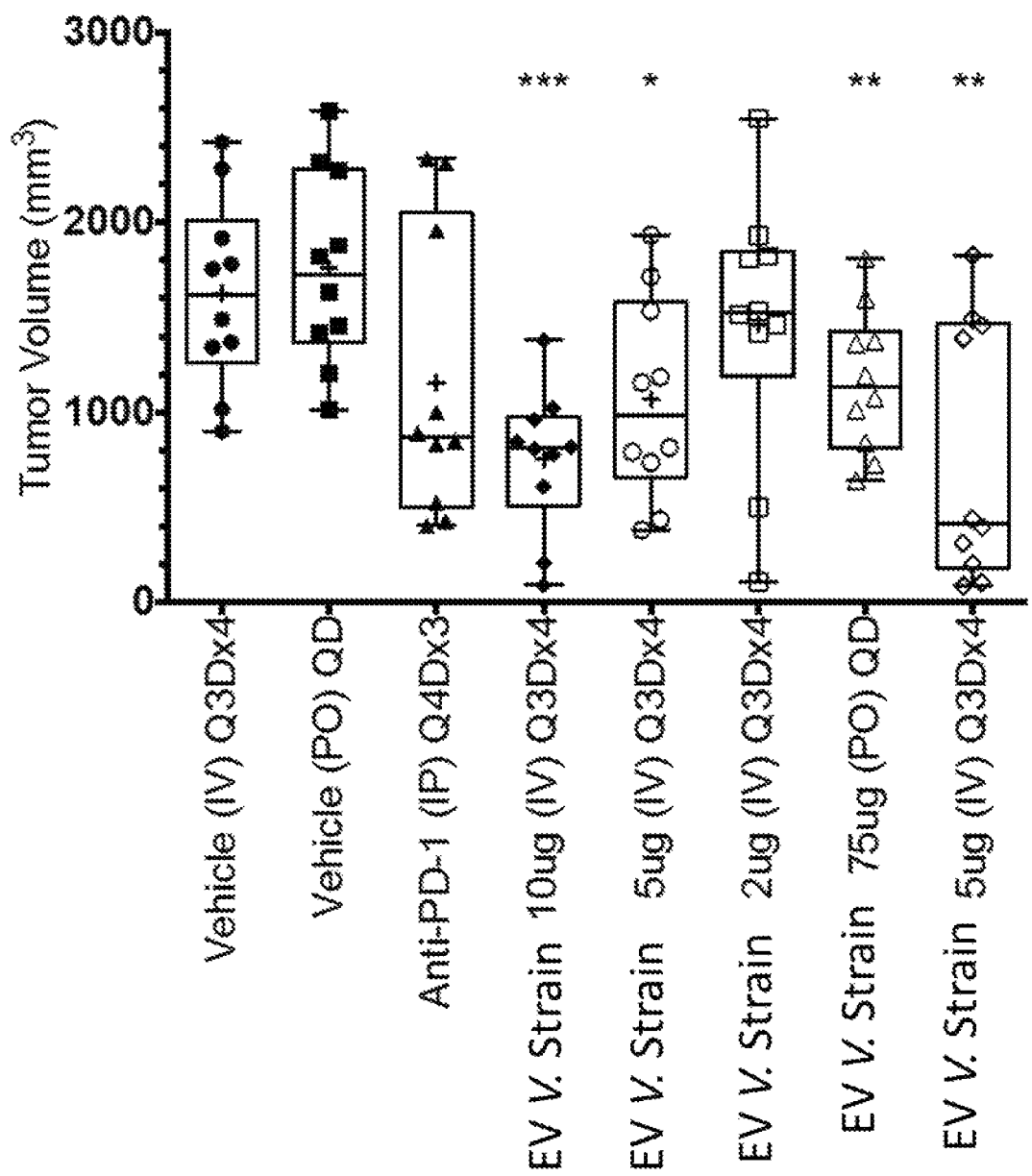
FIG. 15 shows the dose and route of administration dependent efficacy of EVs from *Veillonella tobetsuensis* and *Veillonella parvula* strains compared to intraperitoneal injected (i.p.) anti-PD-1 or vehicle in a mouse colorectal carcinoma model at day 11.

As noted in the table, antibodies were administered intraperitoneally (i.p.) at 200 µg/mouse (100 µl final volume) every four days, starting on day 1, for a total of 3 times (Q4D×3) and EVs when administered intravenously (i.v.) were injected every third day, starting on day 1 for a total of 4 times (Q3D×4). The treatment groups administered by mouth (p.o.) were administered daily (QD). Efficacy of *Veillonella* EVs varies based on source microbe, dose, and route of administration (FIGS. 14 and 15).

INCORPORATION BY REFERENCE

All publications patent applications mentioned herein are hereby incorporated by reference in their entirety as if each individual publication or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating an immune disorder in a subject comprising administering to the subject a pharmaceutical composition comprising isolated bacterial extracellular vesicles (EVs), wherein at least 90% of the total EV and bacteria particles in the pharmaceutical composition are EVs from *Prevotella* or *Veillonella* bacteria.

2. The method of claim 1, wherein the pharmaceutical composition is administered orally.

3. The method of claim 1, wherein the subject is a human.

4. The method of claim 1, wherein the pharmaceutical composition is formulated as a capsule or tablet.

5. The method of claim 1, wherein the immune disorder is psoriasis or atopic dermatitis.

6. The method of claim 1, wherein the pharmaceutical composition comprises at least $1 \times 10^6$ isolated bacterial extracellular vesicles (EVs).

7. The method of claim 1, wherein at least 95% of the total EV and bacteria particles in the pharmaceutical composition are EVs.

8. The method of claim 1, wherein no more than 1% of the total EV and bacteria particles in the pharmaceutical composition are bacteria.

9. The method of claim 1, wherein at least 95% of the total protein in the pharmaceutical composition is present in EVs.

10. The method of claim 1, wherein no more than 1% of the total protein in the pharmaceutical composition is present in bacteria.

11. The method of claim 1, wherein at least 95% of the total lipids in the pharmaceutical composition is present in EVs.

12. The method of claim 1, wherein no more than 1% of the total lipids in the pharmaceutical composition is present in bacteria.

13. The method of claim 1, wherein the pharmaceutical composition is free of bacteria.

14. The method of claim 1, wherein the pharmaceutical composition comprises at least $5 \times 10^6$ isolated EVs.

15. The method of claim 1, wherein the EVs are from a single strain of bacteria.

16. The method of claim 1, wherein the EVs are from *Prevotella histicola* bacteria.

17. The method of claim 1, wherein the EVs are from *Veillonella tobetsuensis* bacteria or *Veillonella parvula* bacteria.

18. A method of treating psoriasis or atopic dermatitis in a subject comprising orally administering to the subject a pharmaceutical composition comprising isolated bacterial extracellular vesicles (EVs), wherein at least 90% of the total EV and bacteria particles in the pharmaceutical compositions are EVs from *Prevotella histicola* bacteria.

19. A method of treating psoriasis or atopic dermatitis in a subject comprising orally administering to the subject a pharmaceutical composition comprising isolated bacterial extracellular vesicles (EVs), wherein at least 90% of the total EV and bacteria particles in the pharmaceutical compositions are EVs from *Veillonella tobetsuensis* bacteria or *Veillonella parvula* bacteria.

* * * * *